United States Patent
Achilefu et al.

(10) Patent No.: US 11,135,316 B2
(45) Date of Patent: Oct. 5, 2021

(54) IMAGING AND TREATMENT OF PATHOPHYSIOLOGIC CONDITIONS BY CERENKOV RADIATION

(71) Applicant: Washington University, St. Louis, MO (US)

(72) Inventors: Samuel Achilefu, St. Louis, MO (US); Nalinikanth Kotagiri, St. Louis, MO (US)

(73) Assignee: Washington University, St. Louis, MO (US)

(*) Notice: Subject to any disclaimer, the term of this patent is extended or adjusted under 35 U.S.C. 154(b) by 653 days.

(21) Appl. No.: 15/115,457

(22) PCT Filed: Feb. 2, 2015

(86) PCT No.: PCT/US2015/014095
§ 371 (c)(1),
(2) Date: Jul. 29, 2016

(87) PCT Pub. No.: WO2015/183346
PCT Pub. Date: Dec. 3, 2015

(65) Prior Publication Data
US 2017/0007724 A1    Jan. 12, 2017

Related U.S. Application Data

(60) Provisional application No. 61/934,073, filed on Jan. 31, 2014, provisional application No. 62/012,086, filed on Jun. 13, 2014.

(51) Int. Cl.
 A61K 49/00    (2006.01)
 A61K 41/00    (2020.01)
 A61K 51/04    (2006.01)

(52) U.S. Cl.
 CPC ...... *A61K 49/0056* (2013.01); *A61K 41/0038* (2013.01); *A61K 41/0057* (2013.01); *A61K 49/0013* (2013.01); *A61K 49/0021* (2013.01); *A61K 51/0474* (2013.01); *A61K 51/0482* (2013.01)

(58) Field of Classification Search
None
See application file for complete search history.

(56) References Cited

U.S. PATENT DOCUMENTS

| | | | |
|---|---|---|---|
| 4,551,482 A | 11/1985 | Tschang et al. | |
| 5,179,120 A | 1/1993 | Vogel et al. | |
| 5,490,840 A | 2/1996 | Uzgiris et al. | |
| 5,510,103 A | 4/1996 | Yokoyama et al. | |
| 5,574,172 A | 11/1996 | Katsuro et al. | |
| 5,651,991 A | 7/1997 | Sugiyama et al. | |
| 5,688,931 A | 11/1997 | Nogusa et al. | |
| 5,714,166 A | 2/1998 | Tomalia et al. | |
| 5,786,387 A | 7/1998 | Watanabe et al. | |
| 5,855,900 A | 1/1999 | Nobuhiko | |
| 5,858,410 A | 1/1999 | Muller et al. | |
| 5,922,356 A | 7/1999 | Koseki et al. | |
| 5,922,545 A | 7/1999 | Mattheakis et al. | |
| 5,994,392 A | 11/1999 | Shashoua | |
| 6,106,866 A | 8/2000 | Ranney | |
| 6,127,339 A | 10/2000 | Hatanaka et al. | |
| 9,974,870 B2 | 5/2018 | Achilefu et al. | |
| 2006/0019876 A1 | 1/2006 | Faulk | |
| 2007/0218049 A1 | 9/2007 | Chen et al. | |
| 2007/0292353 A1 | 12/2007 | Levy et al. | |
| 2009/0202650 A1 | 8/2009 | Hwu et al. | |
| 2009/0220430 A1 | 9/2009 | Rajopadhye et al. | |
| 2010/0209479 A1 | 8/2010 | Carroll et al. | |
| 2012/0101427 A1 | 4/2012 | Farmer et al. | |
| 2012/0220870 A1 | 8/2012 | Gambhir et al. | |
| 2012/0282185 A1 | 11/2012 | Dobson et al. | |
| 2013/0017266 A1 | 1/2013 | Ogino et al. | |
| 2013/0137916 A1 | 5/2013 | Goer | |
| 2015/0352234 A1 | 12/2015 | Achilefu et al. | |

FOREIGN PATENT DOCUMENTS

WO   2015183346 A2   12/2015

OTHER PUBLICATIONS

Office Action dated Sep. 18, 2017 from related U.S. Appl. No. 14/734,761; 24 pgs.
Shi, H. et al., "Real-Time Monitoring of Cell Apoptosis and Drug Screening Using Fluorescent Light-Up Probe with Aggregation-Induced Emission Characteristics," J. Am. Chem. Soc., 2012, pp. 17972-17981, vol. 134, American Chemical Society.
Apel, K. et al., "Reactive Oxygen Species: Metabolism, Oxidative, Stress, and Signal Transduction," Annu. Rev. Plant Biol., 2004, 373-399, vol. 55, with Figures, 2 pgs.
Augustynski, J., "The Role of the Surface Intermediates in the Photoelectrochemical Behaviour of Anatase and Rutile TIO2," Electrochimica Acta, Jan. 1993, pp. 43-46, vol. 38, No. 1, Pergamon Press Ltd., Great Britain.

(Continued)

*Primary Examiner* — Jennifer Lamberski
(74) *Attorney, Agent, or Firm* — Polsinelli PC

(57) ABSTRACT

The present disclosure discloses methods and compositions for administering Cerenkov radiation-induced therapy (CRIT). In an aspect, the invention encompasses a composition comprising at least two radiation-sensitive molecules. In another aspect, the invention encompasses a composition comprising a radiation-sensitive molecule and a targeting agent. In still another aspect, the invention encompasses a method for administering Cerenkov radiation-induced therapy (CRIT) to a target tissue in a subject. The method comprises administering to the subject an effective amount of a composition B comprising at least one radiation-sensitive molecule and administering to the subject an amount of a Cerenkov radiation (CR)-emitting radionuclide effective to activate the radiation-sensitive molecule, thereby administering CRIT to the target tissue in the subject.

15 Claims, 76 Drawing Sheets
(73 of 76 Drawing Sheet(s) Filed in Color)

(56) References Cited

OTHER PUBLICATIONS

Beattie, B. et al., "Quantitative Modeling of Cerenkov Light Production Efficiency from Medical Radionuclides," PLoS One, Feb. 2012, pp. 1-13, vol. 7, No. 2, e31402.

Boehm, H. et al., "Uber die Chemie der Oberflache des Titandioxids. I. Bestimmung des aktiven Wasserstofts, thermische Entwasserung und Rehydroxylierung," Zeitschrift für anorganische und allgemeine Chemie, (J. Inorg. General Chem.), Jul. 1967, pp. 156-167, vol. 352, Nos. 3-4, Wiley-VCH Verlag GmbH & Co. KGaA, Weinheim.

Boehm, H., "Acidic and basic properties of hydroxylated metal oxide surfaces," Discussions of the Faraday Society, 1971, pp. 264-275, Nol. 52.

Brindley, P. et al., "An ESR study of the photolysis of dicyclopentadienyltitanium dichloride," J. Organomet. Chem., Jul. 1983, pp. 247-256, vol. 250, Elsevier Sequoia S.A., Lausanne, The Netherlands.

Brown, S. et al., "The present and future role of photodynamic therapy in cancer treatment," Lancet Oncol., Aug. 2004, pp. 497-508, vol. 5.

Cai, R., et al. Induction of Cytotoxicity by Photoexcited TiO2 Particles, Cancer Res., Apr. 15, 1992, pp. 2346-2348, vol. 52, American Association for Cancer Research.

Chatterjee, D. et al., "Nanoparticles in photodynamic therapy: Ac emerging paradigm," Adv. Drug. Deliv. Rev., Dec. 14, 2008, pp. 1627-1637, vol. 60, No. 15, Elsevier B.V.

Chithrani, D. et al., "Gold Nanoparticles as Radiation Sensitizers in Cancer Therapy," Radiat. Res., 2010, pp. 719-728, vol. 173, Radiation Research Society.

Cobley, C. et al., "Gold nanostructures: a class of multifunctional materials for biomedical applications," Chem. Soc. Rev., 2011, pp. 44-56, vol. 40, The Royal Society of Chemistry.

Davidenko, N., et al., "The efficiency of titanocene as photoinitiator in the polymerization of dental formulations," J. Biomater. Sci., Polymer Edition, 2003, pp. 733-746, vol. 14, No. 7, Taylor & Francis Group.

Dolmans, D. et al., "Photodynamic therapy for cancer," Nat. Rev. Cancer, May 2003, pp. 380-387, vol. 3, Nature Publishing Group.

Ethirajan, M., et al., "The role of porphyrin chemistry in tumor imaging and photodynamic therapy," Chem. Soc. Rev., 2011, pp. 340-362, vol. 40, No. 1, The Royal Society of Chemistry.

Fabian, E., et al., "Tissue distribution and toxicity of intravenously administered titanium dioxide nanoparticles in rats," Arch Toxicol, 2008, pp. 151-157, vol. 82, Springer.

Fujishima, A. et al., "Titanium dioxide photocatalysis," J. Photochem. Photobiol. C: Photochem. Rev., 2000, pp. 1-21, vol. 1, Elsevier Science S.A.

Fung, L. et al., "Polymeric implants for cancer chemotherapy," Adv. Drug. Deliv. Rev., Jul. 1, 1997, pp. 209-230, vol. 26, Nos. 2-3, Elsevier Science B.V.

Gatter, K. et al., "Transferrin receptors in human tissues: their distribution and possible clinical relevance," J. Clin. Pathol., 1983, pp. 539-545, vol. 36.

Goldman, C. et al., "Targeted Gene Delivery to Kaposi's Sarcoma via the Fibroblast Growth Factor Receptor," Cancer Res., Apr. 15, 1997, pp. 1447-1451, vol. 57, American Association for Cancer Research.

Harada, A. et al., "Titanium dioxide nanoparticle-entrapped polyion complex micelles generate singlet oxygen in the cells by ultrasound irradiation for sonodynamic therapy," Biomater. Sci., 2013, pp. 65-73, No. 1, The Royal Society of Chemistry.

Heyne, B. et al., "Mechanism of action of sensors for reactive oxygen species based on fluorescein-phenol coupling: the case of 2-[6-(4'-hydroxy)phenoxy-3H-xanthen-3-on-9-yl]benzoic acid," Org. Biomol. Chem., 2006, pp. 802-807, vol. 4, No. 5, The Royal Society of Chemistry.

Holt, A., et al., "Transarterial Radioembolization with Yttrium-90 for Regional Management of Hepatocellular Cancer: The Early Results of a Nontransplant Center," Am. Surg., Oct. 2010, pp. 1079-1083, vol. 76, No. 10, Southeastern Surgical Congress.

Hu, Z., et al. Three-dimensional Noninvasive Monitoring Iodine-131 Uptake in the Thyroid Using a Modified Cerenkov Luminescence Tomography Approach, PLoS One, May 2012, pp. 1-12, vol. 7, No. 5, e37623.

Huang, W. et al., "Effect of polyethylene glycol on hydrophilic TiO2 films: Porosity-driven superhydrophilicity," Surf. Coat. Technol., 2010, pp. 3954-3961, vol. 204, Elsevier B.V.

Hutchinson, F., "The Distance That a Radical Formed by Ionizing Radiation Can Diffuse in a Yeast Cell," Radial Res., Nov. 1957, pp. 473-483, vol. 7, No. 5, Radiation Research Society.

Jelley, J., "Cerenkov radiation and its applications," Br. J. Appl. Phys., Jul. 1955, pp. 227-232, vol. 6, No. 7.

Ji, Z. et al., Dispersion and Stability Optimization TiO2 Nanoparticles in Cell Culture Media, Environ. Sci. Technol., 2010, pp. 7309-7314, vol. 44, No. 19, American Chemical Society.

Kaniyankandy, S. et al., "Efficient luminescence and photocatalytic behaviour in ultrafine TiO2 particles synthesized by arrested precipitation," J. Mater. Chem., 2009, pp. 3523-3528, vol. 19, No. 21, The Royal Society of Chemistry.

Kelloff, G. et al., "Progress and Promise of FDG-PET Imaging for Cancer Patient Management and Oncologic Drug Development," Clin. Cancer Res., Apr. 15, 2005, pp. 2785-2808, vol. 11, No. 8, American Association for Cancer Research.

Kotagiri, N. et al., "Activatable Probes Based on Distance-Dependent Luminescence Associated with Cerenkov Radiation," Angew. Chem. Int. Ed., Jul. 22, 2013, pp. 7756-7760, vol. 52, No. 30, Wiley-VCH Verlag GmbH & Co. KGaA, Weinheim.

Kubota, Y. et al., "Photokilling of T-24 human bladder cancer cells with titanium dioxide," Br. J. Cancer, 1994, pp. 1107-1111, vol. 70, Macmillan Press Ltd.

Lewis, J. et al., "Radiotherapy and Dosimetry of 64Cu-TETA-Tyr3-Octreotate in a Somatostatin Receptor-Positive, Tumor-Bearing Rat Model," Clin. Cancer Res., Nov. 1999, pp. 3608-3616, vol. 5, American Association for Cancer Research.

Linsebigler, A. et al., "Photocatalysis on TiO2 Surfaces: Principles, Mechanisms, and Selected Results," Chem. Rev., 1995, pp. 735-758, vol. 95, No. 3, American Chemical Society.

Liu, H., et al., "Molecular Optical Imaging with Radioactive Probes," PLoS One, Mar. 2010, pp. 1-9, vol. 5, No. 3, e9470.

Maitra, A. et al., "Pancreatic Cancer," Annu. Rev. Pathol. Mech. Dis., Feb. 28, 2008, pp. 157-188, vol. 3, Annual Reviews.

Maness, P. et al., "Bactericidal Activity of Photocatalytic TiO2 Reaction: toward an Understanding of Its Killing Mechanism," Appl. Environ. Microbiol., Sep. 1999, pp. 4094-4098, vol. 65, No. 9, American Society for Microbiology.

Manome, Y. et al., "Enhancer Sequences of the DF3 Gene Regulate Expression of the Herpes Simplex Virus Thymidine Kinase Gene and Confer Sensitivity of Human Breast Cancer Cells to Ganciclovir," Cancer Res., Oct. 15, 1994, pp. 5408-5413, vol. 54, American Association for Cancer Research.

Mathew, S. et al., "UV-Visible Photoluminescence of TiO2 Nanoparticles Prepared by Hydrothermal Method," J. Fluoresc., 2012, pp. 1563-1569, vol. 22, Springer.

Mitchell, G. et al., "In vivo Cerenkov luminescence imaging: a new tool for molecular imaging," Phil. Trans. R. Soc. A, 2011, pp. 4605-4619, vol. 369, The Royal Society.

Moghimi, S. et al., "Long-Circulating and Target-Specific Nanoparticles: Theory to Practice," Pharmacol. Rev., 2001, pp. 283-318, vol. 53, No. 2, The American Society for Pharmacology and Experimental Therapeutics.

O'Connor, K. et al., "Novel titanocene anti-cancer drugs and their effect on apoptosis and the apoptotic pathway in prostate cancer cells," Apoptosis, Aug. 2006, pp. 1205-1214, vol. 11, Springer.

Park, E-J. et al., "Oxidative stress and apoptosis induced by titanium dioxide nanoparticles in cultured BEAS-2B cells," Toxicol. Lett., Aug. 28, 2008, pp. 222-229, vol. 180, No. 3, Elsevier Ireland Ltd.

Paunesku, T. et al., "Biology of TiO2-oligonucleotide nanocomposites," Nat. Mater., May 2003, pp. 343-346, vol. 2, Nature Publishing Group.

Qian, Z. et al., "Targeted Drug Delivery via the Transferrin Receptor-Mediated Endocytosis Pathway," Pharmacol. Rev., 2002, pp. 561-587, vol. 54, No. 4, The American Society for Pharmacology and Experimental Therapeutics.

(56) References Cited

OTHER PUBLICATIONS

Robertson, R. et al., "Optical imaging of Cerenkov light generation from positron-emitting radiotracers," NIH Public Access Author Manuscript, available in PMC Aug. 21, 2010, pp. 1-13, Published in final form as: Phys. Med. Biol., Aug. 21, 2009, pp. N355-N365, vol. 54, No. 16.
Rosen, G. et al., "Detection of superoxide generated by endothelial cells," PNAS, Dec. 1984, pp. 7269-7273, vol. 81.
Rozhkova, E. et al., "A High-Performance Nano-Bio Photocatalyst for Targeted Brain Cancer Therapy," NIH Public Access Author Manuscript, available in PMC May 14, 2014, pp. 1-12, Published in final edited form as: Nano Lett., Sep. 2009, pp. 3337-3342, vol. 9, No. 9, American Chemical Society.
Schwarz, P. et al., "A New Method to Determine the Generation of Hydroxyl Radicals in Illuminated TiO2 Suspensions," J. Phys. Chem. B, 1997, pp. 7127-7134, vol. 101, No. 36, American Chemical Society.
Sies, H., "Strategies of antioxidant defense," Eur. J. Biochem., 1993, pp. 213-219, vol. 215, No. 2, FEBS.
Spinelli, A. et al., "Multispectral Cerenkov luminescence tomography for small animal optical imaging," Opt. Express, Jun. 20, 2011, pp. 12605-12618, vol. 19, No. 13, Optical Society of America.
Notice of Allowance and Examiner Initiated Interview Summary dated Jan. 23, 2018 for related U.S. Appl. No. 14/734,761; 10 pgs.
Ashkenazi et al., "Death Receptors: Signaling and Modulation," Science, Aug. 28, 1998, pp. 1305-1308, vol. 281.
Beekman et al., "The pinhole: gateway to ultra-high-resolution three-dimensional radionuclide imaging," Eur. J. Nucl. Med. Mol. Imaging, Feb. 2007, pp. 151-161, vol. 34, No. 2.
Bénard et al., "Imaging in breast cancer: Single-photon computer tomography and positron-emission tomography," Breast Cancer Research, Jul. 2005, pp. 153-162, vol. 7, No. 4.
Black et al., "Polydopamine-enabled surface functionalization of gold nanorods for cancer cell-targeted imaging and photothermal therapy," Nanomedicine, Jan. 2013, pp. 17-28, vol. 8, No. 1.
Black et al., "Bacterial Killing by Light-Triggered Release of Silver from Biomimetic Metal Nanorods," Small, Author Manuscript, Jan. 15, 2015, pp. 1-20; Small, Jan. 15, 2014, pp. 169-178, vol. 10, No. 1.
Black et al., "Radioactive 198Au-Doped Nanostructures with Different Shapes for In Vivo Analyses of Their Biodistribution, Tumor Uptake, and Intratumoral Distribution," ACS Nano., 2014, pp. 4385-4394, vol. 8, No. 5.
Boya et al., "Lysosomal membrane permeabilization in cell death," Oncogene, 2008, pp. 6434-6451, vol. 27.
Bremer et al., "In vivo molecular target assessment of matrix metalloproteinase inhibition," Nature Medicine, Jun. 2001, pp. 743-748, vol. 7, No. 6.
Bullok et al., "Biochemical and in Vivo Characterization of a Small, Membrane-Permeant, Caspase-Activatable Far-Red Fluorescent Peptide for Imaging Apoptosis," Biochemistry, 2007, pp. 4055-4065, vol. 46, No. 13.
Chau et al., Matrix metalloproteinase inhibitors—an emphasis on gastrointestinal malignancies, Critical Reviews in Oncology/Hematology, 2003, pp. 151-176, vol. 45.
Chen et al., "Radiolabeled isatin binding to caspase-3 activation induced by anti-Fas antibody," NIH Public Access Author Manuscript, Jan. 1, 2013, pp. 1-15; Nucl. Med. Biol., Jan. 2012, pp. 137-144, vol. 39, No. 1.
Choi et al., "Protease-Activated Drug Development," Theranostics, 2012, pp. 156-178, vol. 2, No. 2.
Eckelman et al., True Radiotracers: are we approaching theoretical specific activity with Tc-99m and I-123?, Nuc. Med. Biol., 2008, pp. 523-527, vol. 35.
Edwards, et al., "Multimodal Imaging of Integrin Receptor-Positive Tumors by Bioluminescence, Fluorescence, Gamma Scintigraphy and SPECT Methods Using a Cyclic RGD Peptide Labeled with a Near Infrared Fluorescent Dye and a Radionuclide," NIH Public Access Author Manuscript, Nov. 8, 2010, pp. 1-21; Mol. Imaging, 2009, pp. 101-110, vol. 8, No. 2.

Glazer et al., "SPECT/CT Evaluation of Unusual Physiologic Radio-iodine Biodistributions: Pearls and Pitfalls in Image Interpretation," RadioGraphics, Mar.-Apr. 2013, pp. 397-418, vol. 33, with Teaching Points, 1 pg.
Graham, "Clinical Molecular Imaging With Radiotracers: Current Status," Med. Princ. Pract., 2012, pp. 197-208, vol. 21.
Huang et al., "Gold Nanoparticles: interesting optical properties and recent applications in cancer diagnostics and therapy," Nanomedicine, 2007, pp. 681-693, vol. 2, No. 5.
International Search Report and Written Opinion from related International Patent Application No. PCT/US2015/014095, dated Oct. 6, 2015, 11 pgs.
Johansson et al., "Regulation of apoptosis-associated lysosomal membrane permeabilization," Apoptosis, 2010, pp. 527-540, vol. 15.
Lee et al., "Complementary optical and nuclear imaging of caspase-3 activity using combined activatable and radiolabeled multimodality molecular probe," NIH Public Access Author Manuscript, Aug. 4, 2010, pp. 1-9; J. Biomed. Opt., 2009, vol. 14, No. 4.
Luker et al., "Optical Imaging: Current Applications and Future Directions," J. Nucl. Med., 2008, pp. 1-4, vol. 49, No. 1.
Ma et al., "Targeting Chk1 in p53-deficient triple-negative breast cancer is therapeutically beneficial in human-in-mouse tumor models," J. Clinical Investigation, Apr. 2012, pp. 1541-1552, vol. 122, No. 4.
Mathis et al., "Oncolytic adenoviruses—selective retargeting to tumor cells," Oncogene, 2005, pp. 7775-7791, vol. 24.
Mebrahtu et al., "Initial characterization of a dually radiolabeled peptide for simultaneous monitoring of protein targets and enzymatic activity," Nucl. Med. Biol., 2013, pp. 190-196, vol. 40.
Ntziachristos et al., "In Vivo Tomographic Imaging of Near-Infrared Fluorescent Probes," Molecular Imaging, Apr. 2002, pp. 82-88, vol. 1, No. 2.
Olson et al., "Activatable cell penetrating peptides linked to nanoparticles as dual probes for in vivo fluorescence and MR imaging of proteases," PNAS, Mar. 2, 2010, pp. 4311-4316, vol. 107, No. 9.
Peer et al., "Nanocarriers as an emerging platform for cancer therapy," Nature Nanotechnology, Dec. 2007, pp. 751-760, vol. 2.
Solomon et al., "Detection of enzyme activity in orthotopic murine breast cancer by fluorescence lifetime imaging using a fluorescence resonance energy transfer-based molecular probe," J. Biomedical Optics, Jun. 2011, pp. 066019-1-066019-6, vol. 16, No. 6.
Van Schaijk et al., "Residualizing Iodine Markedly Improved Tumor Targeting Using Bispecific Antibody-Based Pretargeting," J. Nucl. Med., Jun. 2005, pp. 1016-1022, vol. 46.
Wang et al., "A Comparison Study of Gold Nanohexapods, Nanorods, and Nanocages for Photothermal Cancer Treatment," NIH Public Access Author Manuscript, Mar. 26, 2014, pp. 1-20; ACS Nano., Mar. 26, 2013, pp. 2068-2077, vol. 7, No. 3.
Wang et al., "Roles of caspases in apoptosis, development, and cytokine maturation revealed by homozygous gene deficiencies," J. Cell Science, 2000, pp. 753-757, vol. 113.
Wang et al., "Evaluating the Pharmacokinetics and in vivo Cancer Targeting Capability of Au Nanocages by Positron Emission Tomography Imaging," NIH Public Access Author Manuscript, Jul. 24, 2013, pp. 1-17; ACS Nano., Jul. 24, 2012, pp. 5880-5888, vol. 6, No. 7.
Wang et al., "Radioluminescent Gold Nanocages with Controlled Radioactivity for Real-time In Vivo Imaging," NIH Public Access Author Manuscript, Feb. 13, 2014, pp. 1-10; Nano Lett., Feb. 13, 2013, pp. 581-585, vol. 13, No. 2.
Yang et al., "Anticancer Therpay and Apoptosis Imaging," Exp. Oncol., Sep. 2012, pp. 269-276, vol. 34, No. 3.
Zeng et al., "Cu Core-labeled Nanoparticles with High Specific Activity via Metal-Free Click Chemistry," NIH Public Access Author Manuscript, Jun. 26, 2013, pp. 1-25; ACS Nano., Jun. 26, 2012, pp. 5209-5219, vol. 6, No. 6.
Zhang et al., "Actiavtable Molecular Systems Using Homologous Near-Infrared Fluorescent Probes for Monitoring Enzyme Activities in Vitro, in Cellulo, and in Vivo," Molecular Pharmaceutics, Aug. 5, 2008, pp. 416-427, vol. 6, No. 2.

(56) References Cited

OTHER PUBLICATIONS

Zhao et al., "Copper-64-Alloyed Gold Nanoparticles for Cancer Imaging: Improved Radiolabeled Stability and Diagnostic Accuracy," Angew. Chem. Int. Ed., 2014, pp. 156-159, vol. 53.

Spring, B. et al., "Selective treatment and monitoring of disseminated cancer micrometastases in vivo using dual-function, activatible immunoconjugates," PNAS, Feb. 26, 2014, pp. E933-E942, vol. 111, No. 26.

Thorek, D. et al., "Quantitative imaging of disease signatures through radioactive decay signal conversion," Nat. Med., Oct. 2013, pp. 1345-1350, vol. 19, No. 10, Nature America, Inc.

Thurn, K. et al., "Endocytosis of titanium dioxide nanoparticles in prostate cancer PC-3M cells," Nanomedicine: NBM, 2011, pp. 123-130, vol. 7, Elsevier Inc.

Turchi, C. et al., "Photocatalytic Degradation of Organic Water Contaminants: Mechanisms Involving Hydroxyl Radical Attack," J. Catalysis, 1990, pp. 178-192, vol. 122, Academic Press, Inc.

Vaupel, P. et al., "Blood Flow, Oxygen and Nutrient Supply, and Metabolic Microenvironment of Human Tumors: A Review," Cancer Res., Dec. 1, 1989, pp. 6449-6465, vol. 49, American Association for Cancer Research.

Wang, S. et al., "Nanomaterials and singlet oxygen photosensitizers: potential applications in photodynamic therapy," J. Mater. Chem., 2004, pp. 487-493, vol. 14, The Royal Society of Chemistry.

Wold, A., "Photocatalytic Properties of $TiO_2$," Chem. Mater., 1993, pp. 280-283, vol. 5, No. 3, American Chemical Society.

Xu, S. et al., "Active oxygen species ($1O_2$, $O_2-$) generation in the system of $TiO_2$ colloid sensitized by hypocrellin B," J. Photochem. Photobiol. B: Biol., May 2002, pp. 64-70, vol. 67, No. 1, Elsevier Science B.V.

Yamaguchi, S. et al., "Novel Photodynamic Therapy Using Water-dispersed $TiO_2$-Polyethylene Glycol Compound: Evaluation of Antitumor Effect on Glioma Cells and Spheroids In Vitro," Photochem. Photobiol., 2010, pp. 964-971, vol. 86.

Yu, B., "Cellular Defenses Against Damage From Reactive Oxygen Species," Physiol. Rev., Jan. 1994, pp. 139-162, vol. 74, No. 1, American Physiological Society.

Zhao, J. et al., "Titanium Dioxide ($TiO_2$) Nanoparticles Induce JB6 Cell Apoptosis Through Activation of the Caspase-8/Bid and Mitochondrial Pathways," J. Toxicol. Environ. Health, Part A, 2009, pp. 1141-1149, vol. 72, No. 19, Taylor & Francis Group, LLC.

Cherry, S. et al., "PET: Physics, Instrumentation, and Scanners," Physics of Positron Emission and Annihilation, pp. 1-117, ISBN 978-0-387-34946-6, Springer Science+Business Media, LLC, 2006.

Grisham, M., "Reactive Metabolites of Oxygen and Nitrogen in Biology and Medicine," 1992, ISBN 187970224X, 104 pgs., Landes.

Halliwell, B. et al., "Free radicals in biology and medicine," 1985, ISBN 9780198541370, 346 pgs., Oxford: Clarendon Press, New York.

Rajh, T. et al., "Biofunctionalized $TiO_2$-Based Nanocomposites," Handbook of Nanophysics, 2010, pp. 1-28, ISBN 978-1-4200-7552-6, CRC Press.

Wilson, B. (Dubowski, J. & Tanev, S. eds.), "Photonic and Non-Photonic Based Nanoparticles in Cancer Imaging and Therapeutics," Photon-based Nanoscience and Nanobiotechnology, 2006, pp. 121-157, vol. 239, ISBN 9781402055232, Springer Science & Business Media.

Office Action dated Mar. 23, 2017 from related U.S. Appl. No. 14/734,761; 12 pgs.

Notice of Allowance dated Jan. 15, 2021 from related U.S. Appl. No. 15/959,982; 9 pgs.

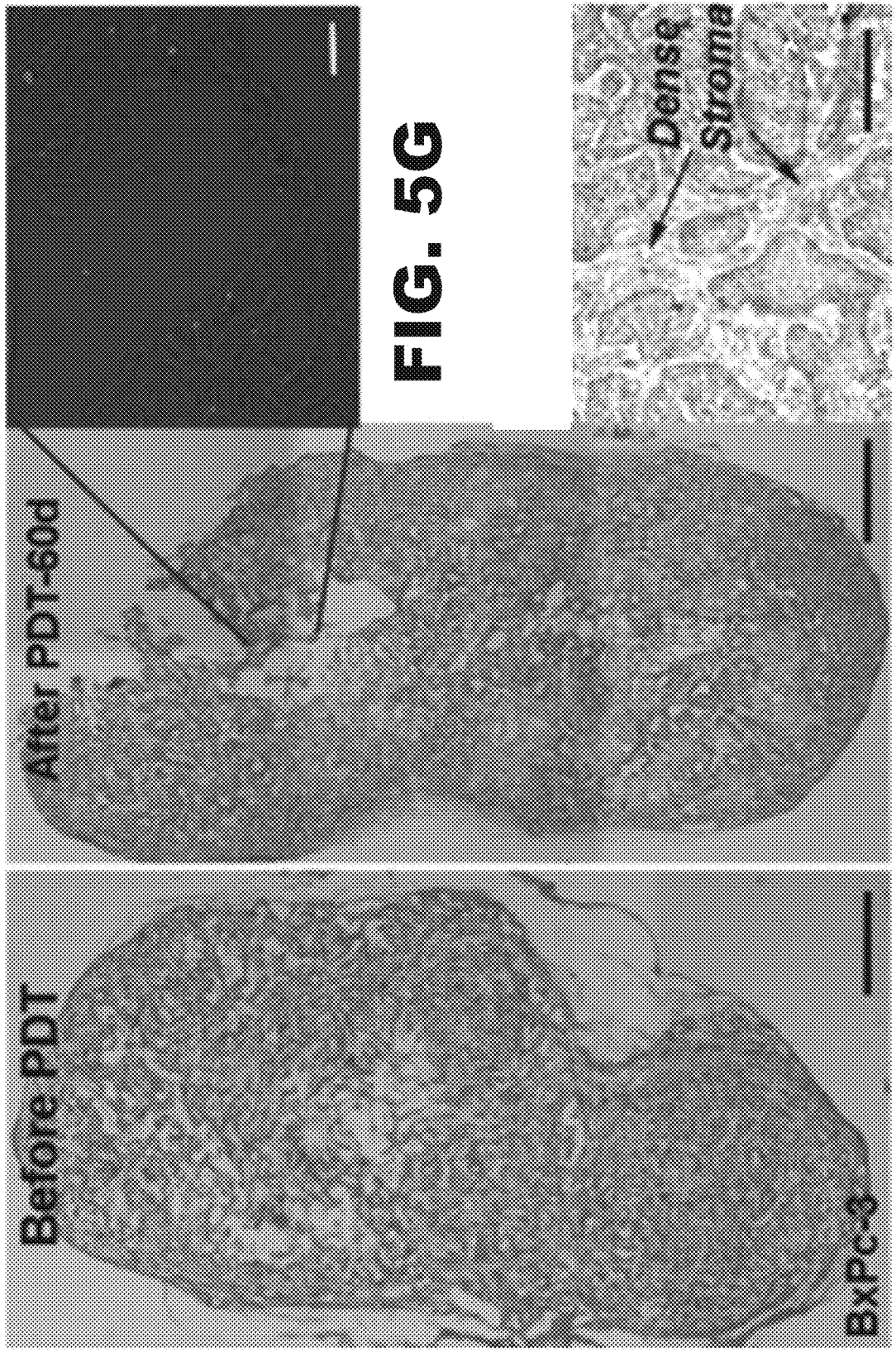

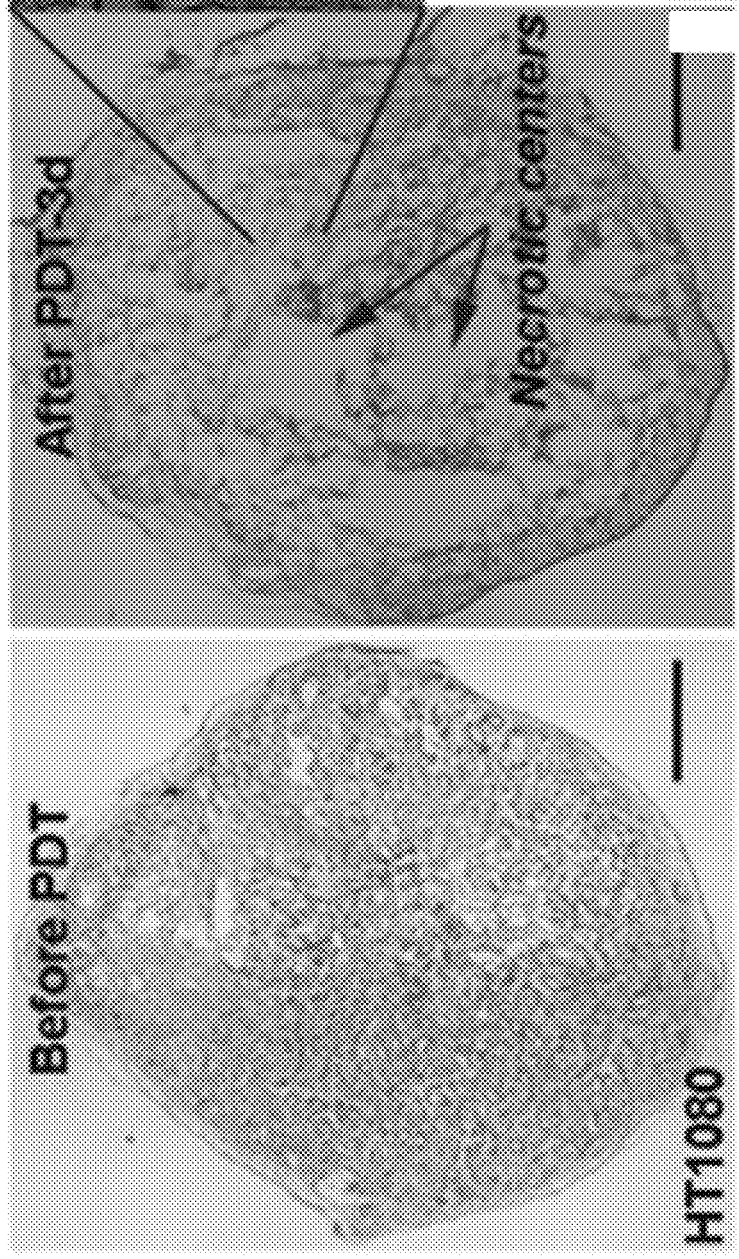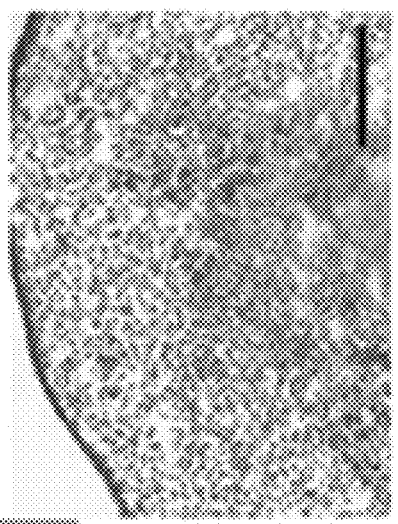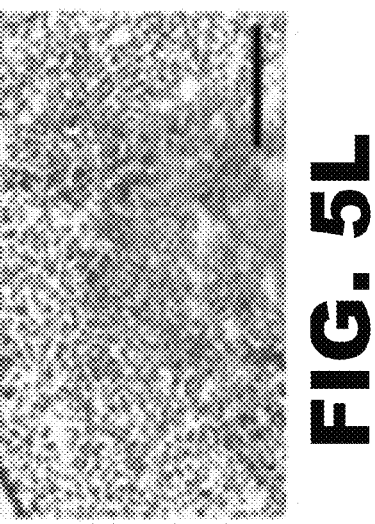
FIG. 5I  FIG. 5J  FIG. 5K  FIG. 5L

FIG. 14A
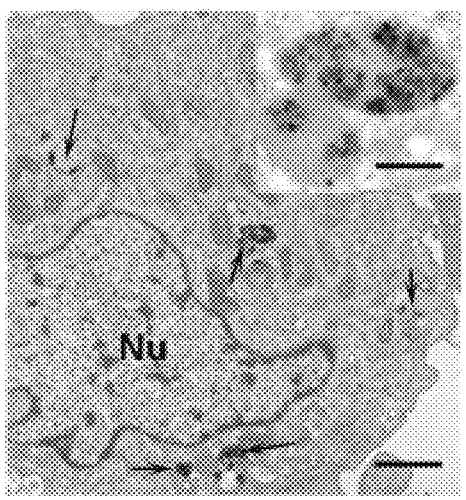
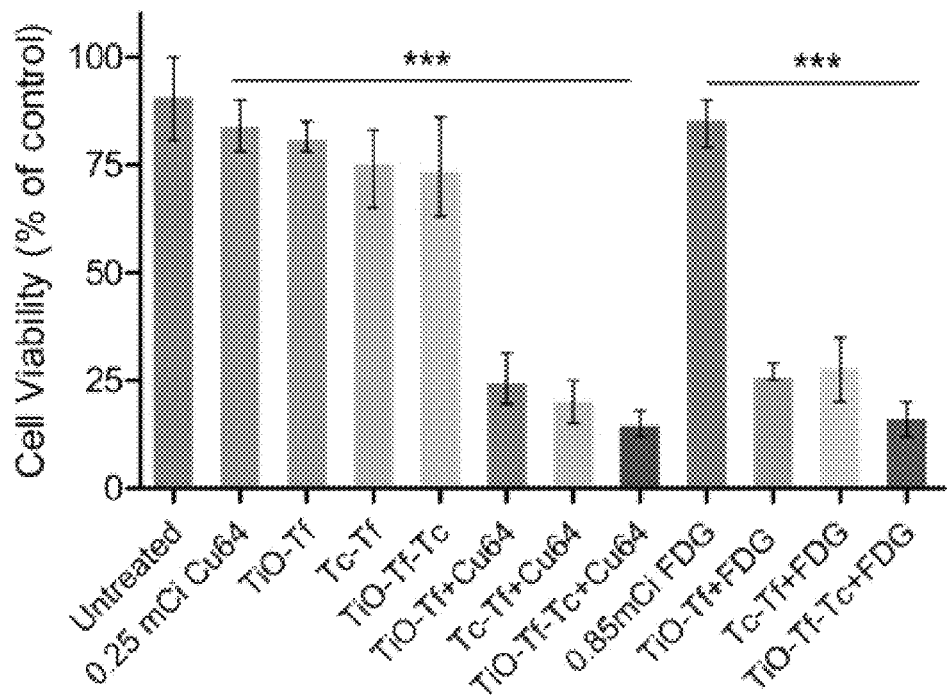
FIG. 14B
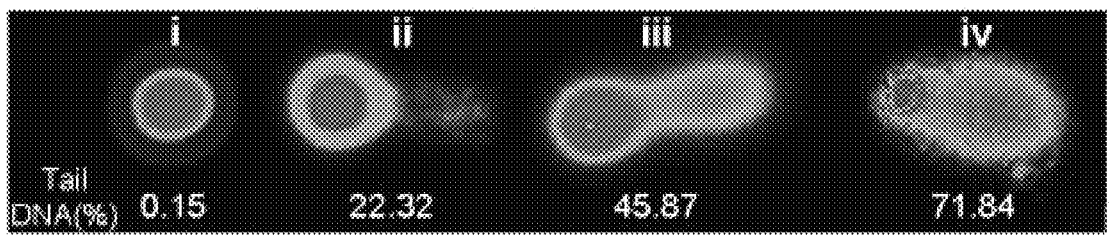
FIG. 14C

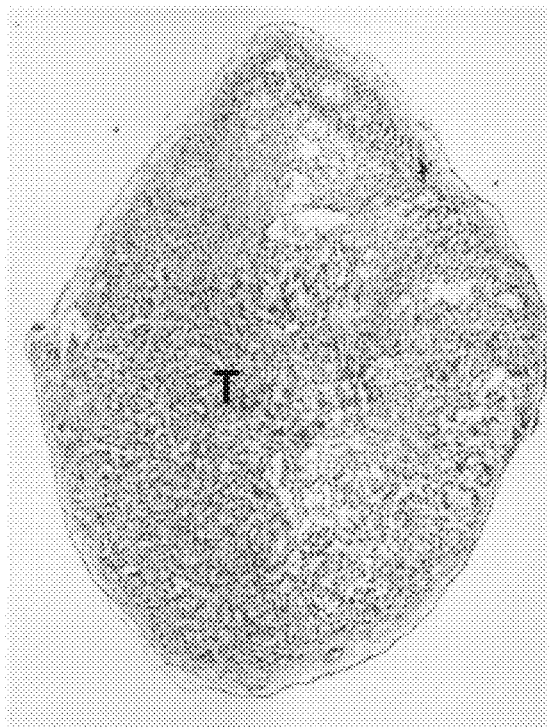
FIG. 15C
FIG. 15D
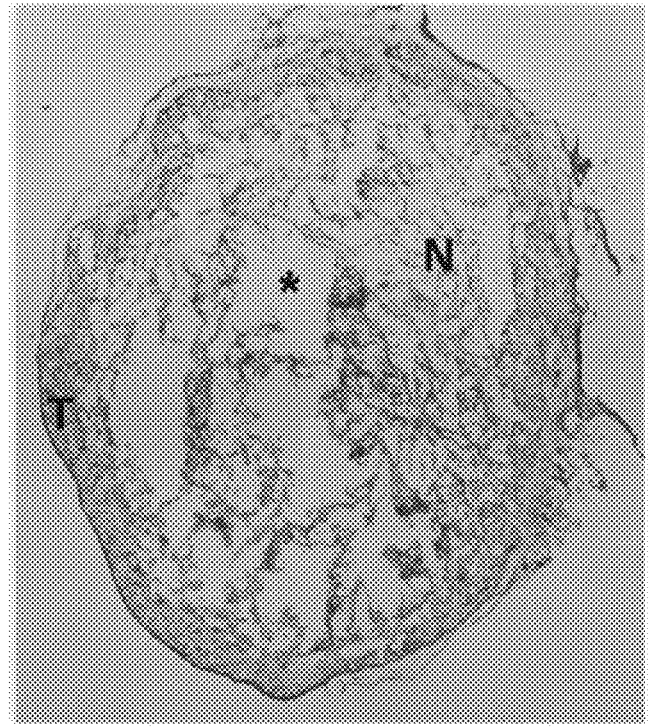

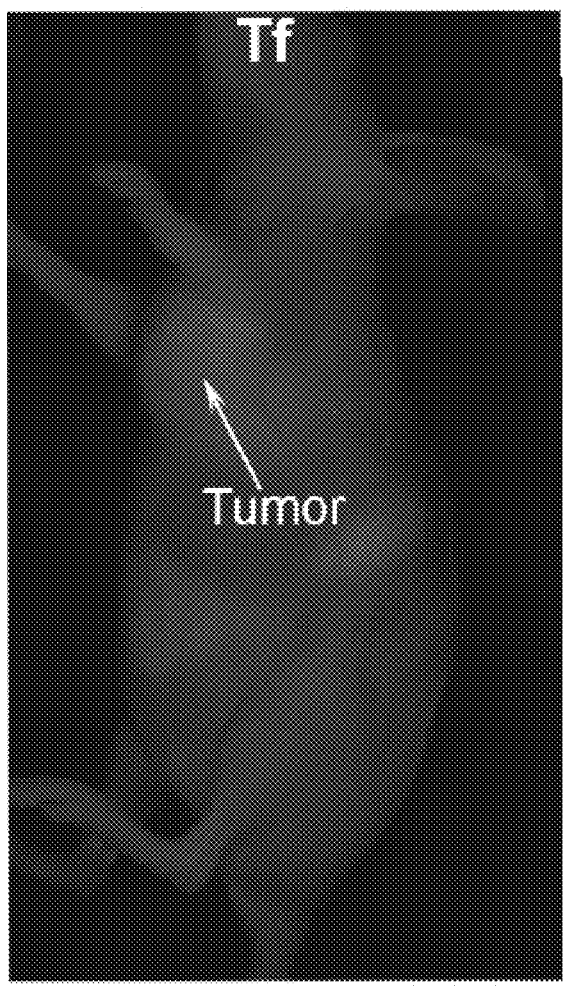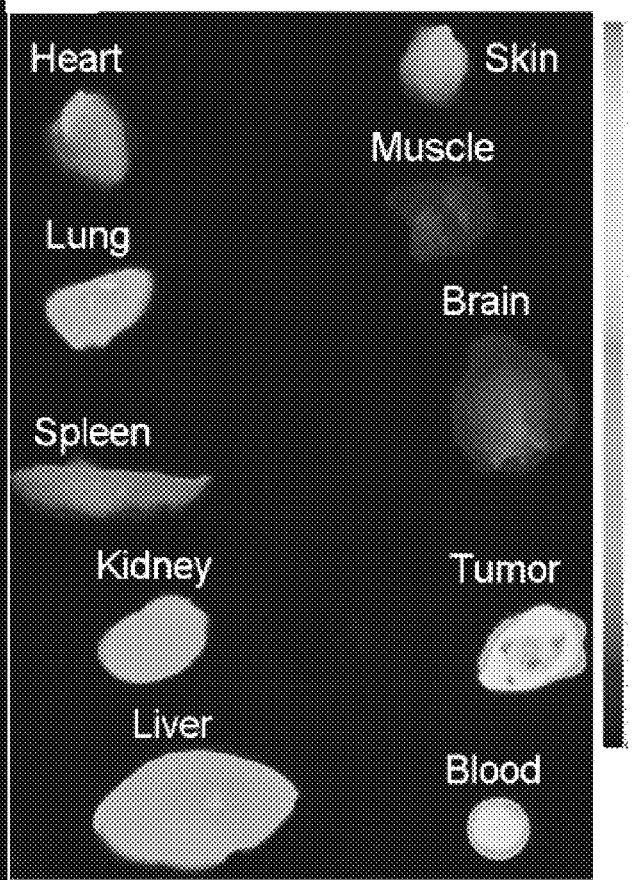
FIG. 19A  FIG. 19B

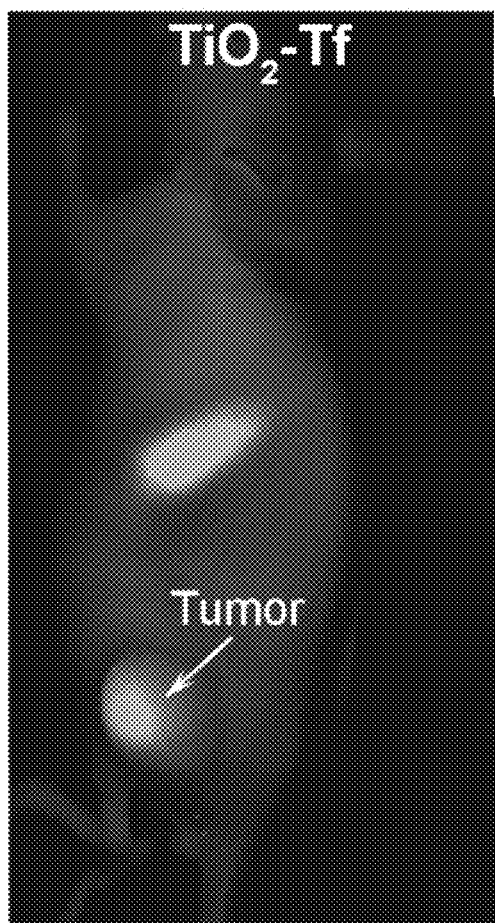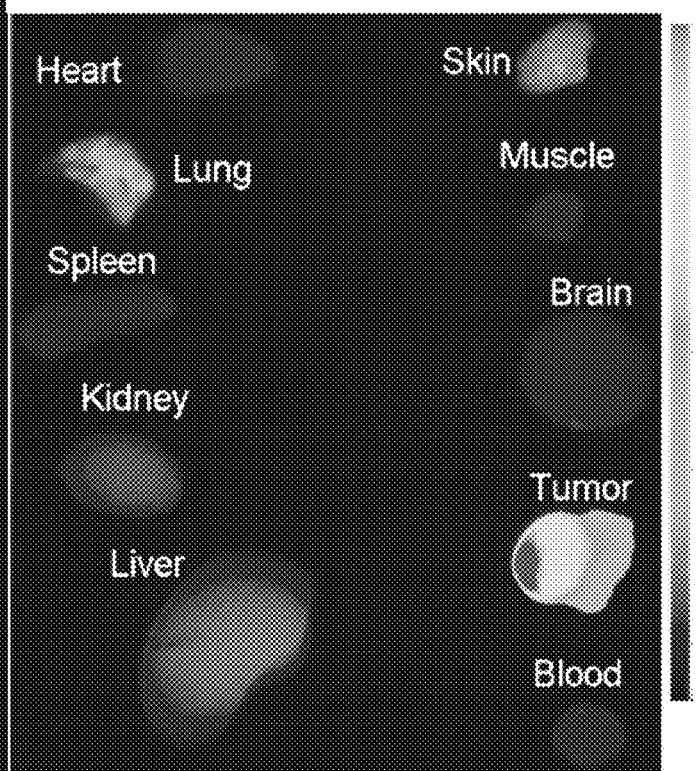
FIG. 19C   FIG. 19D

Untreated

CRIT

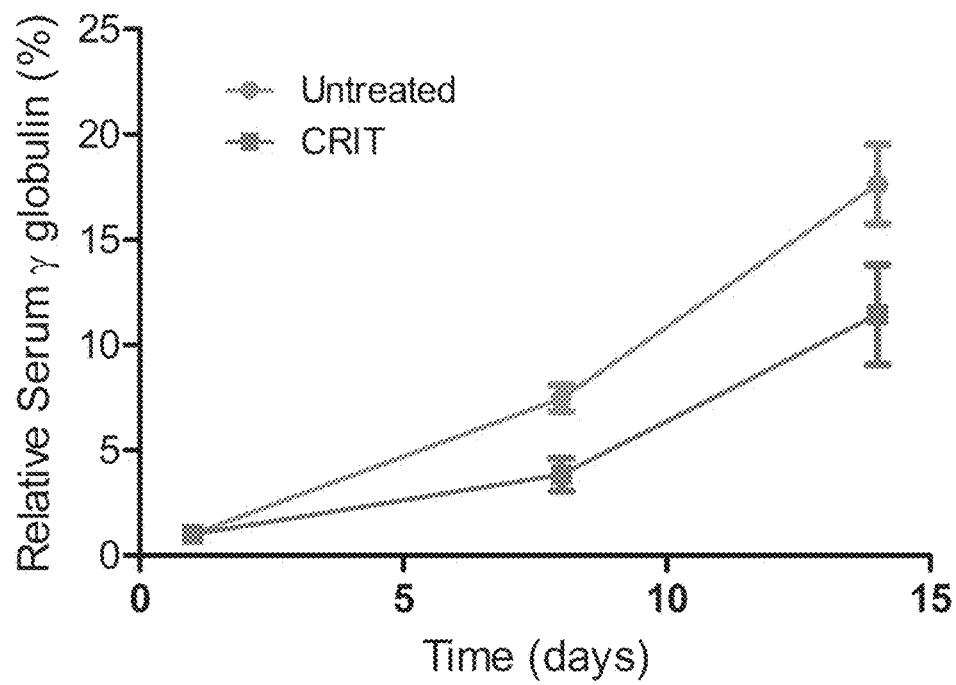
FIG. 34C
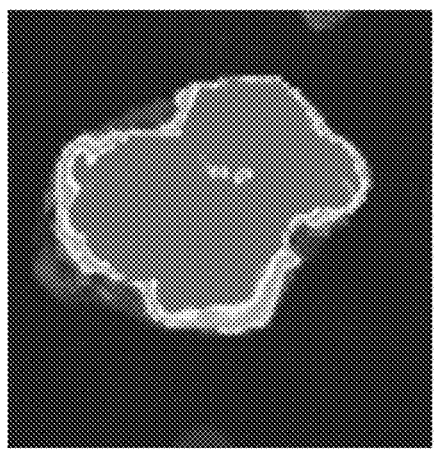 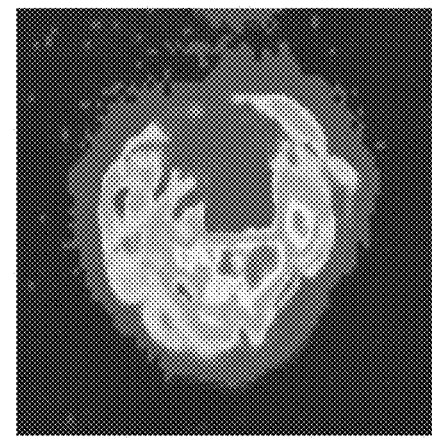
FIG. 34D  FIG. 34E

 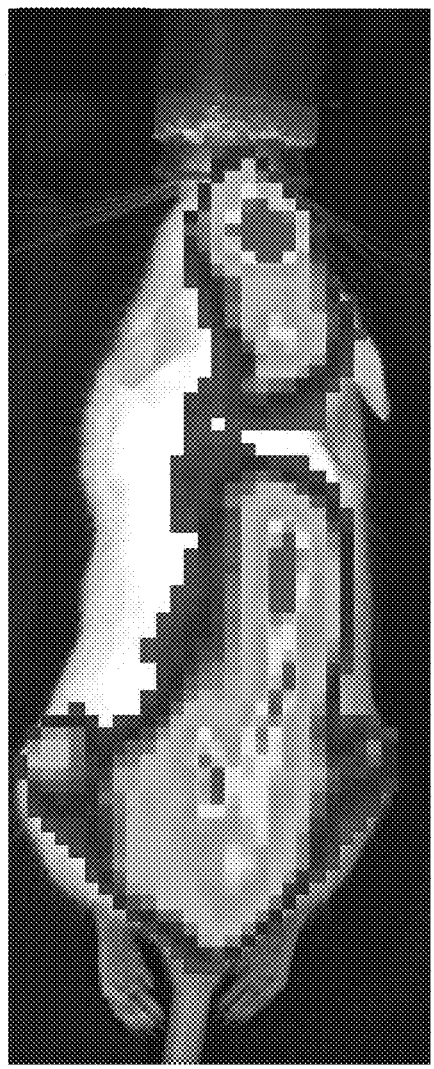 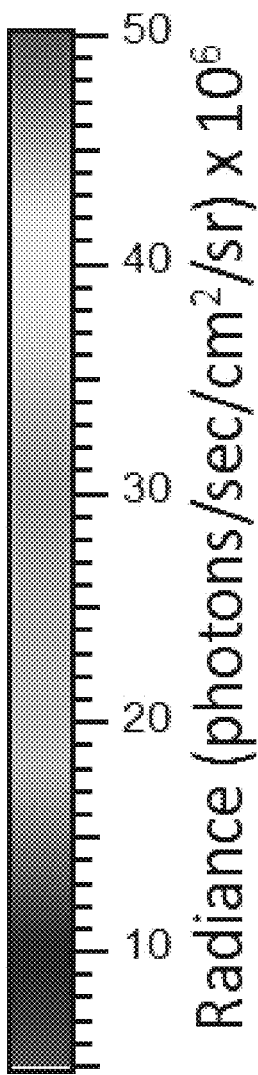
FIG. 40A FIG. 40B

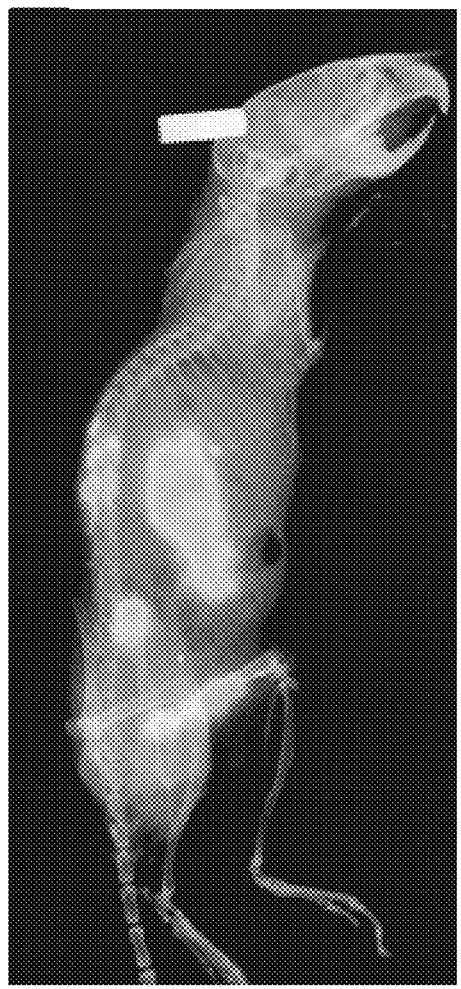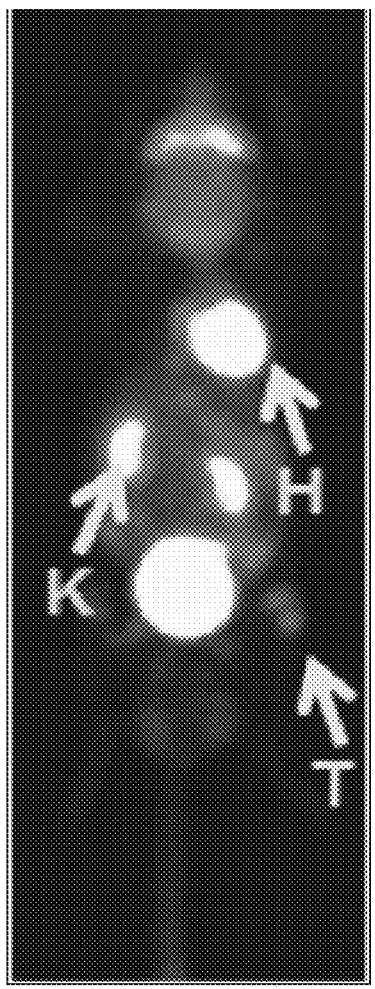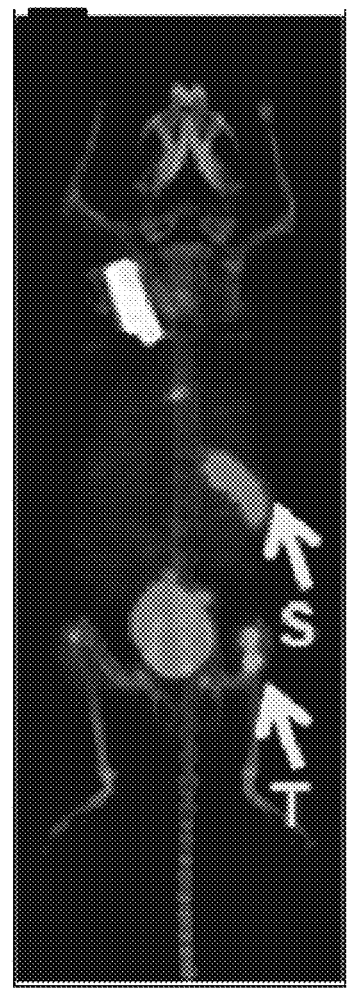
FIG. 40C    FIG. 40D  FIG. 40E

IMAGING AND TREATMENT OF PATHOPHYSIOLOGIC CONDITIONS BY CERENKOV RADIATION

CROSS REFERENCE TO RELATED APPLICATIONS

This application claims the benefit of PCT Application PCT/US2015/014095, filed Feb. 2, 2015, which claims the benefit of U.S. provisional application No. 61/934,073, filed Jan. 31, 2014, and U.S. provisional application No. 62/012,086, filed Jun. 13, 2014, each of the disclosures of which is hereby incorporated by reference in its entirety.

GOVERNMENTAL RIGHTS

This invention was made with government support under EB008111, CA171651, RR031625 and CA199092 awarded by the National Institutes of Health and CCF0963742 awarded by the National Science Foundation. The government has certain rights in the invention.

FIELD OF THE INVENTION

The present disclosure discloses methods and compositions for administering Cerenkov radiation-induced therapy (CRIT).

BACKGROUND OF THE INVENTION

Photodynamic Therapy (PDT) is a therapeutic procedure to destroy tissue, preferably pathological tissue, for example, cancer tissue or tissue in blood vessels that occur in disorders characterized by hypervascularization or proliferation of neovascular networks. In cancer, PDT can be locally administered as a primary therapy for early stage disease, palliation of late stage disease, or as a surgical adjuvant for tumors that show loco-regional spread.

In PDT, a photosensitizing agent (termed a "photosensitize") is delivered to the target tissue and then radiation, most usually light of wavelengths between 250-1000 nm is applied to the target tissue. Thus, photosensitizing agents are activated by electromagnetic (EM) radiation. This activation results in the photochemical transfer of the energy by the photosensitizer-molecules to a variety of other molecules in the tissue, resulting in the generation of reactive radical species including, amongst others, singlet oxygen, the superoxide radical, and peroxides and peroxide radicals. The activation of the photosensitizing agent in the tissue leads to, amongst other processes, the generation of radicals and, ultimately, the destruction of the target tissue, or the initiation of biological processes that result in the desired effect upon the target tissue.

However, the limited penetrability of light in tissues remains a large limiting factor in the use of PDT for the treatment of cancer, specifically cancers located within deeper tissue. Therefore, there is a need for methods of PDT, and phototherapy in general, that improve the tissue depth of penetration producing clinical benefits in deep tumors. Furthermore, there is a need to reduce the level of radiation needed to decrease the toxicity associated with PDT.

SUMMARY OF THE INVENTION

In an aspect, the invention encompasses a composition comprising at least two radiation-sensitive molecules.

In another aspect, the invention encompasses a composition comprising a radiation-sensitive molecule and a targeting agent.

In still another aspect, the invention encompasses a method for administering Cerenkov radiation-induced therapy (CRIT) to a target tissue in a subject. The method comprises administering to the subject an effective amount of a composition comprising at least one radiation-sensitive molecule and administering to the subject an amount of a Cerenkov radiation (CR)-emitting radionuclide effective to activate the radiation-sensitive molecule, thereby administering CRIT to the target tissue in the subject.

In still another aspect, the invention encompasses a method of detecting a tumor in a subject. The method comprises administering to the subject an effective amount of a composition comprising at least one radiation-sensitive molecule, administering to the subject an amount of a Cerenkov radiation (CR)-emitting radionuclide effective to activate the radiation-sensitive molecule, and imaging the subject for a signal corresponding to the radiation-sensitive molecule, wherein a signal corresponding to the radiation-sensitive molecule indicates detection of the tumor.

In still yet another aspect, the invention encompasses a method for treating a tumor in a subject. The method comprises administering to the subject an effective amount of a composition comprising at least one radiation-sensitive molecule; and an amount of a Cerenkov radiation (CR)-emitting radionuclide effective to activate the radiation-sensitive molecule, thereby treating the tumor.

BRIEF DESCRIPTION OF THE FIGURES

The application file contains at least one drawing executed in color. Copies of this patent application publication with color drawing(s) will be provided by the Office upon request and payment of the necessary fee.

(FIG. 1A-FIG. 1C) Schematic of (FIG. 1A) $TiO_2$ nanoparticles, (FIG. 1B) $TiO_2$ nanoparticles coated with PEG (MW: 400 Da) and (FIG. 1C) $TiO_2$ nanoparticles coated with dextran (MW: 5,000 Da) moieties (not to scale). (FIG. 1D-FIG. 1F) Transmission electron microscopy images of $TiO_2$ aggregates (FIG. 1D; scale bar, 400 nm), $TiO_2$-PEG (FIG. 1E; scale bar, 100 nm) and $TiO_2$-dextran (FIG. 1F; scale bar, 100 nm). (FIG. 1G-FIG. 1I) Dynamic light scattering intensity plot showing the distribution of hydrodynamic diameter of $TiO_2$ (FIG. 1G), $TiO_2$-PEG (FIG. 1H) and $TiO_2$-dextran (FIG. 1I).

(FIG. 2A) Comparison of cytotoxicity of $TiO_2$, $TiO_2$-dextran and $TiO_2$-PEG on BxPC-3 cells after incubation with 0.5 mCi of $^{64}Cu$ for 72 h. Values are means±s.e.m. (experiments for each group were run in triplicates). (FIG. 2B) In vitro CR-PDT comparing the cytotoxicity of 0.1, 0.25, 0.5, 1 mCi of $^{64}Cu$ on BxPC-3 cells loaded with 2.5 μg/ml $TiO_2$-PEG using MTS assay after 72 h. Values are means±s.e.m. (experiments for each group were run in triplicates). (FIG. 2C) Plot showing the relative change in hydroxyl and superoxide radicals generated by BxPC-3 cells with 2.5 μg/ml $TiO_2$-PEG and 0.05, 0.1, 0.25, 0.5, 1 mCi of $^{64}Cu$, using HPF and Mitosox dye, respectively. Values are means±s.e.m. (experiments for each group were run in triplicates). (FIG. 2D, FIG. 2E) Confocal microscopy image of merged bright-field and fluorescence images of Matrigel™ suspended BxPC-3 cells with extracellular $TiO_2$-PEG (FIG. 2D) and intracellular $TiO_2$-PEG (FIG. 2E), with 0.25 mCi $^{64}$Cu. Live/Dead® cell viability stain was used to distinguish live cells (green) from dead cells (red). Scale bar, 100 μm. (FIG. 2F) Schematic of $^{64}$Cu generated CR mediating PDT on internalized $TiO_2$ (not to scale).

(FIG. 3A) Absorption spectrum of $TiO_2$. (FIG. 3B) Fluorescence spectrum of $TiO_2$ and tumor cell internalized $TiO_2$, excited at 275 nm. CPS, counts per second. (FIG. 3C) Epifluorescence microscopy images of BxPC-3 cells loaded with 60 μg/ml of $TiO_2$-PEG, taken using DAPI, FITC and Cy5 filters. Scale bar, 50 pm. (FIG. 3D) Confocal microscopy images of BxPC-3 cells loaded with 60 μg/ml of $TiO_2$-PEG. Scale bar, 100 pm (FIG. 3E) Magnified confocal image of a single BxPC-3 cell showing the crystalline $TiO_2$ particles in the cytoplasm. Scale bar, 15 pm. (FIG. 3F) A 3D slice of the same cell visualized in the z-plane showing the uniform distribution of $TiO_2$ in the cytoplasm.

(FIG. 4A) Luminescence spectra of CR from $^{64}$Cu. (FIG. 4B) Luminescence spectra of 60, 125, 250, 500 pg/ml of $TiO_2$ admixed with 0.25 mCi of $^{64}$Cu in vitro, recorded in different channels: GFP (515-575 nm), DsRed (575-650 nm), Cy5.5 (685-770 nm), and ICG (810-875 nm). Values are means±s.e.m. (experiments for each group were run in triplicates). (FIG. 4C) In vivo luminescence images of subcutaneous tumor mimics in Balb/c mice, created by mixing Matrigel™ with different titrations of $TiO_2$ (60, 125, 250, 500 pg/ml) and 0.25 mCi of $^{64}$Cu. (n=3 mice per group). Color legend bar is the same for c&d. (FIG. 4D) In vivo luminescence image of BxPC-3 tumor in Athymic nu/nu mice after injecting 250 pg/ml of $TiO_2$ and 0.25 mCi of $^{64}$Cu intratumorally. (n=3 mice per group). (FIG. 4E) In vitro phantom studies carried out with 0.1 mCi of $^{64}$Cu, 0.1 mCi $^{64}$Cu admixed with 1 mg/ml $TiO_2$, and 0.1 mCi of $^{99m}$Tc admixed with 1 mg/ml $TiO_2$, in each well.

FIG. 5A, FIG. 5B, FIG. 5C, FIG. 5D, FIG. 5E, FIG. 5F, FIG. 5G, FIG. 5H, FIG. 5I, FIG. 5J, FIG. 5K and FIG. 5L depict graphs and images of in vivo CR-PDT in pancreatic (BxPC-3) and fibrosarcoma (HT1080) solid tumor xenografts. (FIG. 5A) In vivo CR-PDT of tumor mimics: Growth of Matrigel™ suspended seed culture of BxPC-3 cells implanted subcutaneously in different groups of Athymic nu/nu mice. Values are means±s.e.m. (n=6 mice per group). (FIG. 5B) In vivo CR-PDT of solid tumors: Growth of BxPC-3 and HT1080 tumors in different groups of Athymic nu/nu mice including appropriate controls. Values are means±s.e.m. (n=4 mice per group). Inset: Change in tumor size within 10 d. (FIG. 5C) Representative photographs of BxPC-3 tumor bearing mice injected with 2.5 pg/ml of $TiO_2$-PEG and 0.25 mCi of $^{64}$Cu intratumorally at day 0, 10 and 45. Scale bar, 5 mm. (FIG. 5D) Representative photograph of HT1080 tumor bearing mice injected with 2.5 pg/ml of $TiO_2$-PEG and 0.25 mCi of $^{64}$Cu intratumorally at day 0, 3 and 45. Scale bar, 5 mm. Complete tumor elimination was achieved after PDT at day 45 (dotted circle). (FIG. 5E) Untreated H&E stained BxPC-3 tumor section showing a stromal architecture. Scale bar, 1 mm. (n=4 histological sections per group). (FIG. 5F) H&E stained BxPC-3 tumor section 60 d after commencement of PDT, showing minimal change in the tumor architecture except the top right edge that could be perhaps associated with needle entry and injection site damage. Scale bar, 1 mm. (n=4 histological sections per group). (FIG. 5G) Magnified epifluorescence image of the tumor section showing fluorescence from residual $TiO_2$ particles entrapped in the stroma. Scale bar, 200 pm. (FIG. 5H) Magnified H&E stained section of normal BxPC-3 tumors showing dense stroma surrounding islands of tumor cells. Scale bar, 200 pm. (FIG. 5I) H&E stained HT1080 tumor section before PDT showing typical herringbone architecture of fibrosarcoma. Scale bar, 1 mm. (n=4 histological sections per group). (FIG. 5J) H&E stained HT1080 tumor section 3 d after commencement of PDT showing extensive necrotic centers and destruction of the tumor architecture. Scale bar, 1 mm. (n=4 histological sections per group). (FIG. 5K) Magnified epifluorescence image of the HT1080 tumor section showing localization and enrichment of $TiO_2$ in the tumor architecture. Scale bar, 200 pm. (FIG. 5L) Magnified H&E stained section of normal HT1080 tumors. Notice the relative absence of stroma and the arrangement of tumor cells. Scale bar, 200 pm.

(FIG. 7A) MTS cytotoxicity assay quantifying concentration of Tc-Tf, $TiO_2$-Tf and $TiO_2$-PEG effecting cell viability. The control group was considered to be 100% viable. (FIG. 7B) MTS cytotoxicity assay quantifying concentration of $^{64}$Cu and FDG effecting cell viability. HT1080 cells were used and the values are means±s.e.m. (experiments for each group were run in triplicates).

(FIG. 12A) Fluorescence spectrum of $TiO_2$ with excitation at 488 nm. (FIG. 12B) Fluorescence spectrum of $TiO_2$ with excitation at 633 nm.

(FIG. 13A) Schematic of CR mediated excitation of $TiO_2$ nanoparticles to generate cytotoxic hydroxyl and superoxide radicals from water and dissolved oxygen, respectively, through electron-hole pair generation. CR is generated by PET radionuclides (not to scale). (FIG. 13B) Schematic of CR mediated excitation of Tc to generate a cyclopentadienyl radical and a titanium-centered radical through photofragmentation (not to scale). In aerated media, the radicals transform into more potent peroxyl radicals. (FIG. 13C) Schematic illustrating the development of TiO$_2$-PEG,TiO$_2$-Tf by coating TiO$_2$ with Tf and subsequent generation of TiO$_2$-Tf-Tc construct by simple addition of Tc, which docks into the iron binding site of Tf (not to scale). Below (left to right) are the Transmission electron microscopy images of TiO$_2$-PEG, TiO$_2$ aggregates, TiO$_2$-Tf and TiO$_2$-Tf-Tc (right). Scale bar, 50 nm.

FIG. 14A, FIG. 14B, FIG. 14C, FIG. 14D, FIG. 14E, FIG. 14F, FIG. 14G, FIG. 14H, FIG. 14I, FIG. 14J, FIG. 14K and FIG. 14L depict cellular uptake of photoagents and in vitro CRIT assessment. (FIG. 14A) Electron microscope image of a HT1080 tumor cell showing internalized and endo-lysosomal localization of the TiO$_2$-Tf constructs (arrows). Scale bar, 2 µm. Inset shows two lysosomal compartments with TiO$_2$-Tf. Scale bar, 400 nm. (FIG. 14B) Cell viability assay comparing the TiO$_2$-Tf, Tc-Tf and TiO$_2$-Tf-Tc constructs with and without exposure to $^{64}$Cu and FDG on HT1080 cells. Values are means±s.e.m. (experiments for each group were run in triplicates). *P<0.001. (FIG. 14C) Examples of alkaline comet assay results. The images show undamaged and damaged DNA as a result of free radical damage and apoptosis. Image marked (i) is representative of undamaged DNA, from the controls, including untreated cells and either exposed to NPS or radionuclide alone. Notice there is negligible DNA in the tail (0.15%). In comparison, cells treated with the NPS and radionuclide, show considerable DNA damage as shown in (ii, iii, iv). Cells in the same treatment group exhibited variable DNA damage, such as 22.32%, 45.87% and 71.84% DNA in the tail. The fluorescence intensity is represented in pseudocolor. (FIG. 14D) Cells undergoing CRIT demonstrated an overall higher percent of damaged DNA. 100 cells were counted from each group. Values are means±s.e.m. P<0.01. (FIG. 14E) EM image of a normal HT1080 cell. Scale bar, 3 µm. (FIG. 14F) EM image showing a necrotic cell that was treated with TiO$_2$-Tf (arrows) and FDG. Notice loss of cell membrane integrity and highly vacuolated cytoplasm. Scale bar, 2 µm. (FIG. 14G) EM image showing an apoptotic cell that was treated with TiO$_2$-Tf (arrows) and FDG. Notice surface blebbing and condensed chromatin. Scale bar, 1.4 µm. (FIG. 14H) EM image of an apoptotic cell that was treated with Tc-Tf and FDG. Notice nuclear fragmentation and chromatin margination. Scale bar, 1.4 µm. (FIG. 14I) Confocal laser scanning microscopy images of HT1080 cells comparing the difference in propidium iodide uptake between TiO$_2$-Tf and FDG treated cells and Tc-Tf and FDG treated cells. The mostly necrotic TiO$_2$-Tf treated cells show a high uptake of PI and classical nuclear staining. The oncotic cells in Tc-Tf treated samples show light nuclear staining in comparison. Scale bar, 20 µm. (J) The percentage of cells which show positive PI staining of nuclei are much lower in Tc-Tf and FDG treated cells. Values are means±s.e.m. (experiments for each group were run in triplicates). *P<0.05. (FIG. 14K) Comparison between HT1080 cells not undergoing and undergoing CRIT with TiO$_2$-Tf and Tc-Tf show higher output of free radicals such as hydroxyl, superoxide and peroxyl species as measured using HPF and Mitosox fluorescent dyes. Values are means±s.e.m. (experiments for each group were run in triplicates). (FIG. 14L) Confocal microscopy image of merged bright-field and fluorescence images of Matrigel™ suspended cells with extracellular TiO$_2$ (left) and intracellular TiO$_2$ (right), with 0.5 mCi/0.1 ml $^{64}$Cu. Live/Dead® cell viability stain was used to distinguish live cells (green) from dead cells (red). Scale bar, 20 µm.

FIG. 15A, FIG. 15B, FIG. 15C and FIG. 15D depict CRIT through intratumoral administration of TiO$_2$ and $^{64}$Cu. (FIG. 15A) In vivo CRIT through a one-time intratumoral administration of PEGylated TiO$_2$ and $^{64}$Cu in HT1080 tumor bearing Athymic nu/nu mice. Toxicity through elemental Cu was eliminated by using non-radiactive CuCl$_2$, with and without TiO$_2$-PEG. Values are means±s.e.m. (n=4 mice per group). (FIG. 15B) Representative photographs at day 1, 3 & 45 of HT1080 tumor bearing mice injected with a single dose of 2.5 µg/ml of TiO$_2$-PEG and 0.5 mCi/0.1 ml of $^{64}$Cu intratumorally at day 1. Scale bar, 5 mm. Complete tumor elimination was achieved after PDT at day 45 (dotted circle). (FIG. 15C) H&E stained HT1080 tumor section before PDT showing typical herringbone architecture of fibrosarcoma. Scale bar, 1 mm. (n=4 histological sections per group). (FIG. 15D) H&E stained HT1080 tumor section 3 d after commencement of PDT showing extensive necrotic centers and destruction of the tumor architecture. Scale bar, 1 mm. (n=4 histological sections per group).

(FIG. 16A) In vivo biodistribution of TiO$_2$-Tf and Tf alone using Alexa 680 labeled holo-Tf in HT1080 tumor bearing Athymic nu/nu mice over a period of 24 h. Values are means±s.e.m. (n=5 mice per group). (FIG. 16B) In vivo CRIT through a one-time systemic administration of the constructs and FDG in HT1080 tumor bearing Athymic nu/nu mice. Values are means±s.e.m. (n=6 mice per group). P<0.01, *P<0.001. (FIG. 16C) Kaplan-Meier survival curves representing treatment with 0.87 mCi/0.1 ml FDG. * P<0.001. (FIG. 16D) Survival curves representing treatment with 0.14 and 0.43 mCi/0.1 ml FDG (n=4 mice per group). P<0.01. (FIG. 16E) FDG-PET images of untreated (left) mouse with bilateral HT1080 tumors and after CRIT (30 d), imaged by administering 0.19 mCi/0.1 ml FDG i.v. Notice the right tumor in mouse undergoing CRIT displays a necrotic zone. (FIG. 16F) Standard Uptake value of FDG is considerably low in mouse that underwent CRIT. ***P<0.001. (FIG. 16G) Histological analysis of H&E stained HT1080 tumor sections from an untreated mouse are compared to mice that underwent CRIT. Normal tumor tissue is marked as T, necrotic tissue as N, and denuded areas suggesting macrophage assisted clearance is marked as *. Magnified images show tumor infiltrating lymphocytes in the treated tumor sections.

(FIG. 17A) Absorption spectrum of TiO$_2$ in water. (FIG. 17B) Absorption spectrum of Tc in water/DMSO (95/5%). (FIG. 17C) Emission spectrum of CR from $^{64}$Cu. (FIG. 17D) Fluorescence spectrum of TiO$_2$, excited at 275 nm. CPS, counts per second. (FIG. 17E) In vitro luminescence studies carried out with 0.1 mCi/100 µl of $^{64}$Cu, 0.1 mCi/100 µl $^{64}$Cu admixed with 1 mg/ml TiO$_2$, and 0.1 mCi/100 µl of $^{99m}$Tc admixed with 1 mg/ml TiO$_2$, in each well. Images were captured in the GFP (515-575 nm) channel.

(FIG. 18A) MTS cytotoxicity assay comparing viability of tumor cells incubated with TiO$_2$-Tf and gold nanoparticles along with FDG. No change in metabolic profile and proliferation rate of cells incubated with gold nanoparticles was noticed. Values are means±s.e.m. **P<0.01. (FIG. 18B) Propidium iodide uptake assay comparing untreated, TiO$_2$-Tf and gold nanoparticles along with FDG. Minimal uptake of PI was observed, suggesting no damage to the cell membrane due to radiosensitization of cells. Values are means±s.e.m. (experiments for each group were run in triplicates).

FIG. 19A, FIG. 19B, FIG. 19C and FIG. 19D depict the biodistribution of Tf and TiO$_2$-Tf. (FIG. 19A) In vivo biodistribution profile of Alexa 680 labeled Tf in HT1080 tumor bearing Athymic nude mice at 24 h following tail vein injection (n=5). (FIG. 19B) Ex vivo fluorescence image of dissected organs from (A). Notice the high fluorescence from blood suggesting circulating Tf. (FIG. 19C) In vivo biodistribution profile of Alexa 680 labeled TiO$_2$-Tf in HT1080 tumor bearing Athymic nude mice at 24 h following tail vein injection (n=5). (FIG. 19D) Ex vivo fluorescence image of dissected organs from (FIG. 19C). Fluorescence imaging was performed using an excitation and emission wavelength of 685 nm and 720 nm, respectively.

(FIG. 24A) EDX spectra of unprocessed TiO$_2$ with the peaks labelled as Ti for titanium, 0 for oxygen and C for carbon. (FIG. 24B) EDX spectra of TiO$_2$-Tf with a pronounced C peak suggesting presence of the protein Tf on the surface of TiO$_2$. (FIG. 24C) Electron diffraction of unprocessed TiO$_2$ with ring measurements matching the crystal pattern of anatase form of TiO$_2$, from diffraction file: 21-1272. (FIG. 24D) Electron diffraction pattern of TiO$_2$-Tf with ring measurements and crystal structure identical to that of TiO$_2$.

(FIG. 25A) Comparison of fluorescence intensity between TiO$_2$—AlexaTf NPS incubated in foetal bovine serum for 24 h and untreated samples (ns: not significant). (FIG. 25B) Comparison of unlabelled TiO$_2$-Tf and unprocessed TiO$_2$ incubated with Alexa 680 labelled albumin. Values are means±s.e.m. (experiments for each group were run in triplicates). **P<0.01.

(FIG. 26A) In cellulo uptake of TiO$_2$-Tf labelled with Alexa 680 dye and successful blocking with holo-Tf suggesting Tf receptor mediated internalization as the mechanism of uptake. Scale bar, 20 μm. (FIG. 26B) Quantitation of successful blocking of TiO$_2$-Tf internalization by saturating doses of holo-Tf in HT1080 cells. Values are means±s.e.m. (experiments for each group were run in triplicates and replicated 2×). **P<0.01. Tf receptor mediates endocytosis of Tf-coated NPS in tumour cells.

(FIG. 27A) Organ biodistribution of TiO$_2$—AlexaTf. (FIG. 27B) Organ biodistribution of TiO$_2$—AlexaTf after administration of holo-Tf to block Tf receptors. (FIG. 27C) Comparison of biodistribution of TiO$_2$—AlexaTf with and without blocking.

(FIG. 30A) TEM image of tumour sections showing localization of the TiO$_2$-Tf-Tc constructs (arrow) in tumour cells after i.v. administration. Scale bar, 500 nm. (FIG. 30B) TEM image of tumour sections of mice injected with TiO$_2$-PEG showing absence of TiO$_2$ in the tumour cells. Scale bar, 1 μm. High tumour uptake and retention of Tf-coated NPS relative to non-tumour tissues demonstrate the feasibility of CRIT via i.v. administration of CR source following selective retention of the NPS in tumours.

(FIG. 31A) TEM image of tumour section extracted from untreated mice showing healthy cells. Scale bar, 3 μm (FIG. 31B) TEM image of tumour section extracted from mice that underwent CRIT showing majority of cells are apoptotic. Scale bar, 3 μm. (FIG. 31C) Magnified TEM image of (i) showing internalized NPS (arrows) in apoptotic tumour cells. Scale bar, 500 nm. (FIG. 31D) TEM image of tumour section from necrotic region showing necrotic cells with internalized NPS (arrows). Scale bar, 2 μm.

FIG. 34A, FIG. 34B, FIG. 34C, FIG. 34D and FIG. 34E depict graphs and images showing in vivo CRIT in U266 multiple myeloma tumor model. (FIG. 34A) In vivo CRIT in U266 Multiple myeloma tumor model grown in NSG mice. (FIG. 34B) Kaplan-Meier survival curves showing increase in median survival by ~8 d in targeted CRIT. (FIG. 34C) Serum protein electrophoresis analysis showing serum γ-globulin levels were lower in targeted CRIT. Ex vivo fluorescence images of (FIG. 34D) untreated and (FIG. 34E) CRIT-treated tumors using filter for GFP (Ex/Em: 488/535 nm).

(FIG. 35A) Flow cytometry of MM1.S cell line using CD71 antibodies showing high expression of TfR (99%). (FIG. 35B) Flow cytometry on T cells with CD71 and CD4 antibodies showing low expression of TfR (2%). (FIG. 35C) Flow cytometry of B cells with CD71 and CD19 antibodies showing low expression of TfR (25%).

(FIG. 38A) Schematic of lipid micellar nanoparticle with titanocene dichloride and VLA-4 homing ligands. (FIG.

38B) TEM image of micelles alone. Scale bar, 50 nm. (FIG. 38C) TEM image of micelle incorporated with Tc in the membrane as well as center. Scale bar, 50 nm.

FIG. 40A, FIG. 40B, FIG. 40C, FIG. 40D and FIG. 40E depict MM animal models. (FIG. 40A) Ventral and (FIG. 40B) dorsal view of bioluminescence imaging of NSG mice injected with MM1.S luciferase expressing cells showing the proliferation of MM in the joints and skeletal tissue. (FIG. 40C) In vivo fluorescence imaging of GFP-5TGM1 Cells in KaLwRij mice showing in the spleen and bone marrow of the femur. (FIG. 40D) Metabolic PET imaging of 5TGM1 distribution in KaLwRij mice using $^{18}$FDG. (FIG. 40E) PET imaging of VLA-4 receptor positive 5TGM1 cells in KaLwRij mice using $^{64}$Cu-CB-TE1A1P-LLP2A. K, kidney; H, heart; S, spleen; T, MM tumor.

(FIG. 41A) Pharmacokinetics of micelle+Tc using ICP OES. Half-life is 123.4 min. (FIG. 41B) Biodistribution of targeted micelle+Tc in vivo showing highest uptake and retention in tumors (STGM subcutaneous xenografts) 24 h post injection.

(FIG. 42A) Kaplan-Meier survival curves showing increase in median survival by 7 d in targeted CRIT. (FIG. 42B) Ex vivo fluorescence image of untreated tumor using filter for GFP (Ex/Em: 488/535 nm). (FIG. 42C) Ex vivo fluorescence image of treated tumor.

DETAILED DESCRIPTION OF THE INVENTION

Figure 1A:
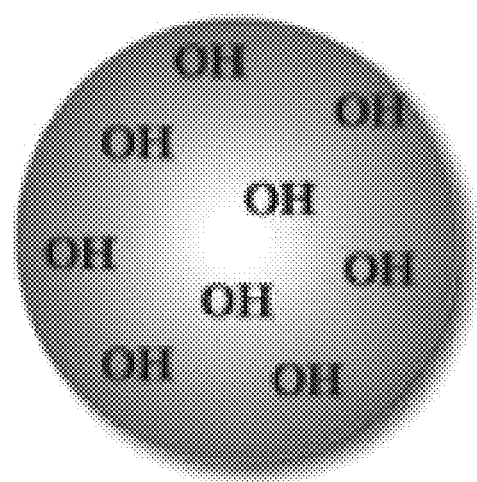
FIG. 1A, FIG. 1B, FIG. 1C, FIG. 1E, FIG. 1F, FIG. 1G, FIG. 1H and FIG. 1I depict illustrations, images and graphs of coated photocatalytic $TiO_2$ as photosensitizers for CR-PDT.

Photodynamic therapy (PDT) is based on the use of light-sensitive molecules. When light-sensitive molecules are activated by light at specific wavelengths, they cause a variety of active forms of oxygen to be created, the main one of which is singlet oxygen. The process involves absorption of photons by the light-sensitive molecule to produce an excited state which, ultimately, transfers its energy to available surrounding oxygen to produce a molecular excited state of oxygen in the singlet stage. This reaction is common to essentially all light-sensitive molecules currently being studied for possible applications in PDT. The formation of singlet oxygen in cell membranes, cytoplasm or organelles results in peroxidative reactions that cause cell damage and death. Administration of the light-sensitive molecule, followed, at the appropriate time, by light treatment using a wavelength that activates the light-sensitive molecule, may result in effective ablation of the targeted tissue. However, PDT is limited to superficial tissue and is unable to penetrate depper into tissues.

A method of administering Cerenkov-radiation induced therapy (CRIT) that overcomes the limitation of use in deeper tissues has been developed. Using a method of the invention, it is possible to perform CRIT on deeper tissues by using Cerenkov radiation (CR)-emitting radionuclides to activate at least one radiation-sensitive molecule thereby eliminating the need for an external light source. Advantageously, CR-induced therapy of the invention may allow the amount of radiation administered to be 100-fold less than the currently administered amount of radiation in clinical and nuclear radiotherapy. By activating radiation-sensitive molecules using CR-emitting radionuclides, methods of the invention also provide means for imaging a tumor and monitoring tumor progression in a subject.

I. Components of CR-PDT

A. Composition

In an aspect, the invention encompasses a composition comprising at least one electromagnetic radiation-sensitive molecule. As used herein, "electromagnetic radiation" and "radiation" are used interchangeably. In an embodiment, a composition may comprise at least two electromagnetic radiation-sensitive molecules. For example, a composition may comprise 2, 3, 4, or 5 or more electromagnetic radiation-sensitive molecules. Electromagnetic radiation may include radiowaves, microwaves, near-infrared radiation, infrared radiation, visible light, ultraviolet radiation, X-ray and gamma rays. In a specific embodiment, the electromagnetic radiation is light. Non-limiting examples of light may include ultraviolet (UV), visible, infrared, and near infrared (NIR).

In an embodiment, an electromagnetic radiation-sensitive molecule may be a light-sensitive molecule. A light-sensitive molecule may be a photosensitizer, a photocatalyst, and/or a photoinitiator. A light-sensitive molecule may be both a photosensitizer and a photocatalyst. Additionally, a light-sensitive molecule may be both a photosensitizer and a phototinitiator. As used herein, the term "photosensitizer" refers to a molecule capable of the photochemical conversion of an irradiating energy into radical and cytotoxic species. A photosensitizer may also be a photoinitiator or a photocatalyst. As used herein a "photoinitiator" is a chemical compound that decomposes into free radicals when exposed to electromagnetic radiation. All photoinitiators have bonds that cleave via photolysis. A photoinitiator converts absorbed electromagnetic radiation into chemical energy in the form of initiating species, e.g. free radicals or cations. In a specific embodiment, a photoinitiator converts light inot chemical energy. Non-limiting examples of light may include UV, visible, near infrared and infrared. As used herein a "photocatalyst" is a substance which can modify the rate of chemical reaction using electromagnetic radiation, preferably light. Generally speaking, photocatalysis is a reaction which uses light to activate a substance which modifies the rate of a chemical reaction without being involved itself.

In an embodiment, a composition may comprise one or more photosensitizers. In another embodiment, a composition may comprise one or more photoinitiators. In still another embodiment, a composition may comprise one or more photocatalysts. In a different embodiment, a composition may comprise one or more photosensitizer and one or more photoinitiators. In another different embodiment, a composition may comprise one or more photosensitizers and one or more photocatalysts. In still another different embodiment, a composition may comprise one or more photosensitizers, one or more photoinitiators, and one or more photocatalysts. In still yet another different embodiment, a composition may comprise one or more photocatalysts and one or more photoinitiators. In a specific embodiment, a composition may comprise a photosensitizer and a photoinitiator, hi another specific embodiment, a composition may comprise a photosensitizer and a photocatalyst. In still another specific embodiment, a composition may comprise a photosensitizer, a photoinitiator, and a photocatalyst. In still yet another specific embodiment, a composition may comprise a photocatalyst and a photoinitiator.

A variety of molecules may be used as photosensitizers. Non-limiting examples of photosensitizers include pyrrole derived macrocyclic compounds, porphyrins, chlorins, bacteriochlorins, isobacteriochlorins, phthalocyanines, naphthalocyanines, porphycenes, porphycyanines, pentaphyrins, sapphyrins, benzochlorins, chlorophylls, azaporphyrins, the metabolic porphyrinic precusor 5-amino levulinic acid, PHOTOFRIN®, synthetic diporphyrins and dichlorins, phenyl-substituted tetraphenyl porphyrins (e.g., FOSCAN® picket fence porphyrins), indium chloride methyl pyropheophorbide (MV64013™), 3,1-meso tetrakis (o-propionamido phenyl) porphyrin, verdins, purpurins (e.g., tin and zinc derivatives of octaethylpurpurin (NT2), and etiopurpurin (ET2)), zinc naphthalocyanines, anthracenediones, anthrapyrazoles, aminoanthraquinone, phenoxazine dyes, chlorins (e.g., chlorin e6, and mono-1-aspartyl derivative of chlorin e6), benzoporphyrin derivatives (BPD) (e.g., benzoporphyrin monoacid derivatives, tetracyanoethylene adducts of benzoporphyrin, dimethyl acetylenedicarboxylate adducts of benzoporphyrin, Diels-Adler adducts, and monoacid ring "a" derivative of benzoporphyrin), low density lipoprotein mediated localization parameters similar to those observed with hematoporphyrin derivative (HPD), sulfonated aluminum phthalocyanine (Pc) (sulfonated AlPc, disulfonated (AlPcS$_2$), tetrasulfonated derivative, sulfonated aluminum naphthalocyanines, chloroaluminum sulfonated phthalocyanine (CASP)), phenothiazine derivatives, chalcogenapyrylium dyes cationic selena and tellurapyrylium derivatives, ring-substituted cationic phthalocyanines, pheophorbide alpha, hydroporphyrins (e.g., chlorins and bacteriochlorins of the tetra(hydroxyphenyl) porphyrin series), phthalocyanines, hematoporphyrin (HP), protoporphyrin, uroporphyrin III, coproporphyrin III, protoporphyrin IX, 5-amino levulinic acid, pyrromethane boron difluorides, indocyanine green, zinc phthalocyanine, dihematoporphyrin, benzoporphyrin derivatives, carotenoporphyrins, hematoporphyrin and porphyrin derivatives, rose bengal, bacteriochlorin A, epigallocatechin, epicatechin derivatives, hypocrellin B, urocanic acid, indoleacrylic acid, rhodium complexes, etiobenzochlorins, octaethylbenzochlorins, sulfonated Pc-naphthalocyanine, silicon naphthalocyanines, chloroaluminum sulfonated phthalocyanine, phthalocyanine derivatives, iminium salt benzochlorins, and other iminium salt complexes, Merocyanin 540, Hoechst 33258, and other DNA-binding fluorochromes, psoralens, acridine compounds, suprofen, tiaprofenic acid, non-steroidal anti-inflammatory drugs, methylpheophorbide-a-(hexyl-ether), and other pheophorbides, furocoumarin hydroperoxides, Victoria blue BO, methylene blue, toluidine blue, porphycene compounds described in U.S. Pat. No. 5,179,120, indocyanines, semiconductor nanoparticle photosensitizers, and any other photosensitizers noted herein, and any combination of any or all of the above.

In an embodiment, a photosensitizer may be a fullerene. A fullerene is a molecule composed entirely of carbon, in the form of a hollow sphere, ellipsoid, tube, and many other shapes. Spherical fullerenes are also called buckyballs. Cylindrical fullerenes are called carbon nanotubes or buckytubes. Types of fullerene may include buckyball clusters, nanotubes, carbon nanobuds, megatubes, polymers, nano"onions", linked "ball-and-chain" dimers, fullerene rings, and inorganic fullerenes such as $MoS_2$, $WS_2$, $TiS_2$ and $NbS_2$.

In a specific embodiment, a photosensitizer may be an inorganic nanoparticle. An inorganic nanoparticle may also be a photocatalyst. An inorganic nanoparticle may be selected from the group consisting of ZnO nanoparticles, Si nanoparticles, $TiO_2$ nanoparticles, CdSe nanoparticles, CdS nanoparticles, InP nanoparticles, PbS nanoparticles, PbSe nanoparticles, and combinations thereof. In an exemplary embodiment, the photosensitizer is $TiO_2$ nanoparticles. Traditional photosensitizers depend on molecular oxygen to generate cytotoxic singlet oxygen for PDT. However, in solid tumors hypoxic conditions prevail, limiting the therapeutic efficacy of the photosensitizer. Biocompatible inorganic nanoparticles which generate highly cytotoxic hydroxyl radicals through oxygen-independent electron-hole pair production are attractive alternatives to conventional photosensitizers. Further, biocompatible inorganic nanoparticles, are attractive photosensitizers because of their large surface area, excellent payload capacity, and high reactivity. Semiconductor nanoparticles such as $TiO_2$ and ZnO are effective photocatalysts that are capable of generating singlet oxygen for killing cancer cells and bacteria (Wang et al, Journal of Materials Chemistry, 2004, 14: 487). For example, B-chelated $TiO_2$ nanocomposite has a high efficiency of singlet oxygen generation when irradiated with visible light (Xu et al, Journal of Photochemistry and Photobiology B: Biology, 2002). $TiO_2$ is a biocompatible material, which encourages the application of $TiO_2$ nanoparticles as a PDT agent for cancer treatment. Similar to other photosensitizers, semiconductor nanoparticles such as $TiO_2$ and ZnO only have strong absorption in UV or visible ranges, which limits their application in conventional PDT. The presently disclosed methodology provides a means of circumventing the problem of light activation.

A variety of molecules may be used as photoinitiators. Photoinitiators may be divided into classes such as acetophenone, benzyl and benzoin compounds, benzophenone, cationic photoinitiators, and thioxanthones. Non-limiting examples of biocompatible photoinitiators include titanocene or titanocene dichloride, Irgacure-2959 (2-hydroxy-1-[4-(hydroxyethoxy)phenyl]-2-methyl-1-propanone; <313 nm Abs Max), Darocur-2959 (2-hydroxy-1-[4-(hydroxyethoxy)phenyl]-1-propanone; <313 nm Abs Max), Irgacure-184 (1-hydroxycyclohexane acetophenone; 326 nm Abs Max), Irgacure-651 (2,2-dymethoxy-2-phenyl acetophenone; 335 nm Abs Max), THX (thioxanthone; 378 nm Abs Max), Eosin Y (514 nm Abs Max), camphorquinone and its derivatives (200-300 nm and 467 nm), BAPO (bisacylphosphine oxide bis(2,4,6-trimethylbenzoyl) phenylphosphineoxide; visible), and HAP (hydroxyalkylphenone; <400 nm Abs Max). In an exemplary embodiment, the photoiniator is titanocene.

In a certain embodiment, a composition of the invention may comprise a coating to eliminate undesirable effects and improve biocompatibility. In its native state, a photosensitizer such as $TiO_2$ may exhibit concentration dependent cytotoxicity. To eliminate this undesirable effect and improve biocompatibility, a radiation-sensitive molecule may be coated. Non-limiting examples of potential coatings may include polyethylene glycol (PEG), dextran, pullulan, glycolipid, hyaluronic acid, orosomucoid, heparin, chitosan, pectin, or other polysaccharides. Further, there are numerous methodologies to coat a radiation-sensitive molecule. Non-limiting examples of methods to coat a radiation-sensitive molecule may include adsorption, incorporation, copolymerization, or covalent grafting. In a specific embodiment, a radiation-sensitive molecule is coated with PEG. In another specific embodiment, a radiation-sensitive molecule is coated with dextran. In an exemplary embodiment, $TiO_2$ nanoparticles are coated with PEG. In another exemplary embodiment, $TiO_2$ nanoparticles are coated with dextran.

In a specific embodiment, a composition further comprises a targeting agent. A targeting agent may promote targeting of the radiation-sensitive molecule. For example, a radiation-sensitive molecule may be coated with a targeting agent. Additionally, the targeting agent may bind a radiation-sensitive molecule with high affinity. In an embodiment, a photosensitizer is coated with a targeting agent. In another embodiment, a targeting agent binds a photoinitiator. In still another embodiment, a photosensitizer is coated with a targeting agent and the targeting agent binds a photoinitiator with high affinity.

A targeting agent can have an affinity for a cell, a tissue, a protein, DNA, RNA, an antibody, an antigen, a compound, and the like, that may be associated with a condition, disease, or related biological event, of interest. In a specific embodiment, the targeting agent has affinity for a tumor. In particular, the targeting agent can function to target specific DNA, RNA, and/or proteins of interest. In an embodiment, the targeting agent can include, but is not limited to, polypeptides (e.g., proteins such as, but not limited to, cell surface receptors and antibodies (monoclonal or polyclonal)), antigens, nucleic acids (both monomeric and oligomeric), polysaccharides, sugars, fatty acids, steroids, purines, pyrimidines, ligands, aptamers, small molecules, albumin, or combinations thereof, that have an affinity for a condition, disease, or related biological event or other chemical, biochemical, and/or biological events of the condition, disease, or biological event. In an embodiment, the targeting agent can include: aptamers, sequence-specific DNA oligonucleotides, locked nucleic acids (LNA), and peptide nucleic acids (PNA), antibodies, and small molecule protein receptors. For example, when liver targeting is desired, a composition may comprise galactose-containing copolymers which are recognized by hepatocytes. Or, for example, when tumor targeting is desired, a composition may comprise transferrin which binds to transferrin receptors which are highly overexpressed on tumors. One of skill in the art will appreciate that various targeting agents may enable targeting of a radiation-sensitive molecule to specific tissue. For example, a radiation-sensitive molecule may be conjugated to antibodies in order to provide specific delivery of the radiation-sensitive molecule to the site of a tumor. In an embodiment, a targeting agent may be transferrin. As such, a radiation-sensitive molecule coated with transferrin may be targeted to tumor cells. In an exemplary embodiment, $TiO_2$ is coated with transferrin. In another exemplary embodiment, transferrin binds titanocene. In still another exemplary embodiment, $TiO_2$ is coated with transferrin and transferrin binds titanocene with high affinity.

(i) Pharmaceutical Composition

The compositions of the present invention may further comprise a drug carrier to facilitate drug preparation and administration. Any suitable drug delivery vehicle or carrier may be used, including but not limited to a microcapsule, for example a microsphere or a nanosphere (Manome et al., 1994; Saltzman & Fung, 1997), a peptide (U.S. Pat. Nos. 6,127,339 and 5,574,172), a glycosaminoglycan (U.S. Pat. No. 6,106,866), a fatty acid (U.S. Pat. No. 5,994,392), a fatty emulsion (U.S. Pat. No. 5,651,991), a lipid or lipid derivative (U.S. Pat. No. 5,786,387), collagen (U.S. Pat. No. 5,922,356), a polysaccharide or derivative thereof (U.S. Pat. No. 5,688,931), a nanosuspension (U.S. Pat. No. 5,858,410), a polymeric micelle or conjugate (Goldman et al., 1997 and U.S. Pat. Nos. 4,551,482, 5,714,166, 5,510,103, 5,490,840, and 5,855,900), and a polysome (U.S. Pat. No. 5,922,545).

Additionally, the composition may be formulated into pharmaceutical compositions and administered by a number of different means that may deliver a therapeutically effective dose. Such compositions may be administered orally, parenterally, by inhalation spray, rectally, intradermally, transdermally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, or intrasternal injection, or infusion techniques. Formulation of drugs is discussed in, for example, Hoover, John E., Remington's Pharmaceutical Sciences, Mack Publishing Co., Easton, Pa. (1975), and Liberman, H. A. and Lachman, L., Eds., Pharmaceutical Dosage Forms, Marcel Decker, New York, N.Y. (1980).

Injectable preparations and formulations for parenteral administration may be prepared as described above. Solid dosage forms for oral administration may include capsules, tablets, pills, powders, and granules. In such solid dosage forms, the composition is ordinarily combined with one or more adjuvants appropriate to the indicated route of administration. If administered per os, the composition can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as can be provided in a dispersion of active composition of the invention in hydroxypropylmethyl cellulose. In the case of capsules, tablets, and pills, the dosage forms may also comprise buffering agents such as sodium citrate, or magnesium or calcium carbonate or bicarbonate. Tablets and pills may additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

The amount of the composition of the invention that may be combined with the carrier materials to produce a single dosage of the composition can and will vary depending upon the subject, the radiation-sensitive molecue, the formulation, and the particular mode of administration. Those skilled in the art will appreciate that dosages may also be determined with guidance from Goodman & Goldman's The Pharmacological Basis of Therapeutics, Ninth Edition (1996), Appendix II, pp. 1707-1711 and from Goodman & Goldman's The Pharmacological Basis of Therapeutics, Tenth Edition (2001), Appendix II, pp. 475-493.

In certain embodiments, a composition comprising a radiation-sensitive molecule of the invention is encapsulated in a suitable vehicle to either aid in the delivery of the compound to target cells, to increase the stability of the composition, or to minimize potential toxicity of the composition. As will be appreciated by a skilled artisan, a variety of vehicles are suitable for delivering a composition of the present invention. Non-limiting examples of suitable structured fluid delivery systems may include nanoparticles, liposomes, microemulsions, micelles, dendrimers and other phospholipid-containing systems. Methods of incorporating compositions into delivery vehicles are known in the art.

In one alternative embodiment, a liposome delivery vehicle may be utilized. Liposomes, depending upon the embodiment, are suitable for delivery of the a radiation-sensitive molecule of the invention in view of their structural and chemical properties. Generally speaking, liposomes are spherical vesicles with a phospholipid bilayer membrane. The lipid bilayer of a liposome may fuse with other bilayers (e.g., the cell membrane), thus delivering the contents of the liposome to cells. In this manner, the a radiation-sensitive molecule of the invention may be selectively delivered to a cell by encapsulation in a liposome that fuses with the targeted cell's membrane.

Liposomes may be comprised of a variety of different types of phosolipids having varying hydrocarbon chain lengths. Phospholipids generally comprise two fatty acids linked through glycerol phosphate to one of a variety of polar groups. Suitable phospholids include phosphatidic acid (PA), phosphatidylserine (PS), phosphatidylinositol (PI), phosphatidylglycerol (PG), diphosphatidylglycerol (DPG), phosphatidylcholine (PC), and phosphatidylethanolamine (PE). The fatty acid chains comprising the phospholipids may range from about 6 to about 26 carbon atoms in length, and the lipid chains may be saturated or unsaturated. Suitable fatty acid chains include (common name presented in parentheses) n-dodecanoate (laurate), n-tretradecanoate (myristate), n-hexadecanoate (palmitate), n-octadecanoate (stearate), n-eicosanoate (arachidate), n-docosanoate (behenate), n-tetracosanoate (lignocerate), cis-9-hexadecenoate (palmitoleate), cis-9-octadecanoate (oleate), cis,cis-9,12-octadecandienoate (linoleate), all cis-9, 12, 15-octadecatrienoate (linolenate), and all cis-5,8,11,14-eicosatetraenoate (arachidonate). The two fatty acid chains of a phospholipid may be identical or different. Acceptable phospholipids include dioleoyl PS, dioleoyl PC, distearoyl PS, distearoyl PC, dimyristoyl PS, dimyristoyl PC, dipalmitoyl PG, stearoyl, oleoyl PS, palmitoyl, linolenyl PS, and the like.

The phospholipids may come from any natural source, and, as such, may comprise a mixture of phospholipids. For example, egg yolk is rich in PC, PG, and PE, soy beans contains PC, PE, PI, and PA, and animal brain or spinal cord is enriched in PS. Phospholipids may come from synthetic sources too. Mixtures of phospholipids having a varied ratio of individual phospholipids may be used. Mixtures of different phospholipids may result in liposome compositions having advantageous activity or stability of activity properties. The above mentioned phospholipids may be mixed, in optimal ratios with cationic lipids, such as N-(1-(2,3-dioleolyoxy)propyl)-N,N,N-trimethyl ammonium chloride, 1,1'-dioctadecyl-3,3,3',3'-tetramethylindocarbocyanine perchloarate, 3,3'-deheptyloxacarbocyanine iodide, 1,1'-dedodecyl-3,3,3',3'-tetramethylindocarbocyanine perchloarate, 1,1'-dioleyl-3,3,3',3'-tetramethylindo carbocyanine methanesulfonate, N-4-(delinoleylaminostyryl)-N-methylpyridinium iodide, or 1,1,-dilinoleyl-3,3,3',3'-tetramethylindocarbocyanine perchloarate.

Liposomes may optionally comprise sphingolipids, in which spingosine is the structural counterpart of glycerol and one of the one fatty acids of a phosphoglyceride, or cholesterol, a major component of animal cell membranes. Liposomes may optionally, contain pegylated lipids, which are lipids covalently linked to polymers of polyethylene glycol (PEG). PEGs may range in size from about 500 to about 10,000 daltons.

Liposomes may further comprise a suitable solvent. The solvent may be an organic solvent or an inorganic solvent. Suitable solvents include, but are not limited to, dimethylsulfoxide (DMSO), methylpyrrolidone, N-methylpyrrolidone, acetonitrile, alcohols, dimethylformamide, tetrahydrofuran, or combinations thereof.

Liposomes carrying the a radiation-sensitive molecule of the invention (i.e., having at least one methionine compound) may be prepared by any known method of preparing liposomes for drug delivery, such as, for example, detailed in U.S. Pat. Nos. 4,241,046, 4,394,448, 4,529,561, 4,755,388, 4,828,837, 4,925,661, 4,954,345, 4,957,735, 5,043,164, 5,064,655, 5,077,211 and 5,264,618, the disclosures of which are hereby incorporated by reference in their entirety. For example, liposomes may be prepared by sonicating lipids in an aqueous solution, solvent injection, lipid hydration, reverse evaporation, or freeze drying by repeated freezing and thawing. In a preferred embodiment the liposomes are formed by sonication. The liposomes may be multilamellar, which have many layers like an onion, or unilamellar. The liposomes may be large or small. Continued high-shear sonication tends to form smaller unilamellar lipsomes.

As would be apparent to one of ordinary skill, all of the parameters that govern liposome formation may be varied. These parameters include, but are not limited to, temperature, pH, concentration of methionine compound, concentration and composition of lipid, concentration of multivalent cations, rate of mixing, presence of and concentration of solvent.

In another embodiment, a composition of the invention may be delivered to a cell as a microemulsion. Microemulsions are generally clear, thermodynamically stable solutions comprising an aqueous solution, a surfactant, and "oil." The "oil" in this case, is the supercritical fluid phase. The surfactant rests at the oil-water interface. Any of a variety of surfactants are suitable for use in microemulsion formulations including those described herein or otherwise known in the art. The aqueous microdomains suitable for use in the invention generally will have characteristic structural dimensions from about 5 nm to about 100 nm. Aggregates of this size are poor scatterers of visible light and hence, these solutions are optically clear. As will be appreciated by a skilled artisan, microemulsions can and will have a multitude of different microscopic structures including sphere, rod, or disc shaped aggregates. In one embodiment, the structure may be micelles, which are the simplest microemulsion structures that are generally spherical or cylindrical objects. Micelles are like drops of oil in water, and reverse micelles are like drops of water in oil. In an alternative embodiment, the microemulsion structure is the lamellae. It comprises consecutive layers of water and oil separated by layers of surfactant. The "oil" of microemulsions optimally comprises phospholipids. Any of the phospholipids detailed above for liposomes are suitable for embodiments directed to microemulsions. The composition of the invention may be encapsulated in a microemulsion by any method generally known in the art.

In yet another embodiment, a composition of the invention may be delivered in a dendritic macromolecule, or a dendrimer. Generally speaking, a dendrimer is a branched tree-like molecule, in which each branch is an interlinked chain of molecules that divides into two new branches (molecules) after a certain length. This branching continues until the branches (molecules) become so densely packed that the canopy forms a globe. Generally, the properties of dendrimers are determined by the functional groups at their surface. For example, hydrophilic end groups, such as carboxyl groups, would typically make a water-soluble dendrimer. Alternatively, phospholipids may be incorporated in the surface of a dendrimer to facilitate absorption across the skin. Any of the phospholipids detailed for use in liposome embodiments are suitable for use in dendrimer embodiments. Any method generally known in the art may be utilized to make dendrimers and to encapsulate compositions of the invention therein. For example, dendrimers may be produced by an iterative sequence of reaction steps, in which each additional iteration leads to a higher order dendrimer. Consequently, they have a regular, highly branched 3D structure, with nearly uniform size and shape. Furthermore, the final size of a dendrimer is typically controlled by the number of iterative steps used during synthesis. A variety of dendrimer sizes are suitable for use in the invention. Generally, the size of dendrimers may range from about 1 nm to about 100 nm.

B. CR-Emitting Radionuclides

According to the invention, a composition of the invention may be activated by electromagnetic radiation to generate free radicals. In a specific embodiment, a composition of the invention may be activated by low intensity light to generate free radicals. In another specific embodiment, the free radicals may be generated in an oxygen independent fashion. The lack of reliance on molecular oxygen allows activation of the composition in hypoxic regions. Many solid tumors have significant hypoxic regions. As such, the present invention overcomes the limitation of the reliance of PDT on molecular oxygen. Low intensity light may include light in the visible spectrum or light in the ultraviolet (UV) spectrum. Generally, light in the visible spectrum comprises wavelengths from about 390 nm to about 700 nm and light in the ultraviolet spectrum comprises wavelengths from about 100 nm to about 400 nm. In an embodiment, a composition may be activated by light in the UV spectrum. For example, a composition may be activated by light at wavelengths from about 250 nm to about 350 nm. Alternatively, a composition may be activated by light at wavelengths from about 350 nm to about 600 nm, or from about 400 nm to about 550 nm. In another embodiment, a composition may be activated by Cerenkov radiation (CR)-emitting radionuclides.

Cerenkov radiation (CR) is created by high-energy charged particles that momentarily exceed the speed of light in the medium in which they propagate. As the charged particle travels through the medium, it disrupts the electromagnetic field of the medium and temporarily displaces the electrons in the atoms of the medium. Photons are emitted when the displaced electrons return to the ground state after the disruption has ceased. According to the mechanism of CR, as long as these positrons have a superluminal speed in a dielectric medium, CR will be produced until interactions with the medium cause these particles to lose kinetic energy to the point that their speed drops below the speed of light in that medium.

A variety of charged particles with the appropriate energy levels can produce CR. These include high energy x-rays such as those used in radiotherapy and radionuclides that undergo radioactive decay such as β-particles, Auger electrons, positrons (β+), and α-particles. Of particular interest is the use of Positron Emission Tomography (PET) isotopes as the photon source to power in vivo light based imaging and therapeutic inventions. The Cerenkov light spectrum is continuous, in contrast to fluorescence or emission spectra that have characteristic spectral peaks. The relative intensity is proportional to frequency thus: higher frequencies (ultraviolet/blue) are most intense. At ultraviolet/blue wavelengths, Cerenkov radiation is highly absorbed by tissue components (water, hemogloblin, cytochromes, etc.).

As described herein a wide range of radionuclides may be used in the methods of the present invention. In an embodiment, the radionuclide may include radionuclides except those that are pure gamma rays-emitting radionuclides. In a particular embodiment, the radionuclides may include those that emit radionuclides that are α, β+, β−-emitters. Radionuclides (α, β+, β−, electron capture, etc.) that emit charged particles may be suitable for optical imaging. A radionuclide that produces CR may be a radionuclide following β+, β− or electron capture decay. In this regard, a radionuclide employed in the present invention may be a radionuclide that decays via β+ decay such as $^{10}C$, $^{11}C$, $^{13}O$, $^{14}O$. $^{15}O$, $^{12}N$, $^{13}N$, $^{15}F$, $^{18}F$, $^{32}Cl$, $^{33}Cl$, $^{34}Cl$, $^{43}Sc$, $^{44}Sc$, $^{45}Ti$, $^{51}Mn$, $^{52}Mn$, $^{52}Fe$, $^{53}Fe$, $^{66}Co$, $^{66}Co$, $^{58}Co$, $^{61}Cu$, $^{62}Cu$ $^{62}Zn$, $^{63}Zn$, $^{64}Cu$, $^{65}Zn$, $^{66}Ga$, $^{66}Ge$, $^{67}m$, $^{68}Ga$, $^{69}Ge$, $^{69}As$, $^{70}As$, $^{70}Se$, $^{71}As$, $^{73}Se$, $^{74}Kr$, $^{74}Br$, $^{75}Br$, $^{76}Br$, $^{77}Br$, $^{77}Kr$, $^{78}Br$, $^{78}Rb$, $^{79}Rb$, $^{79}Kr$, $^{81}Rb$, $^{82}Rb$, $^{84}Rb$, $^{84}Zr$, $^{86}Y$, $^{86}Y$, $^{87}Y$, $^{87}Zr$, $^{88}Y$, $^{89}Zr$, $^{92}Tc$, $^{93}Tc$, $^{94}Tc$, $^{96}Tc$, $^{96}Ru$, $^{96}Rh$, $^{96}Rh$, $^{97}Rh$, $^{98}Rh$, $^{99}Rh$, $^{100}Rh$, $^{101}Ag$, $^{102}Ag$, $^{102}Rh$, $^{103}Ag$, $^{104}Ag$, $^{105}Ag$, $^{106}Ag$, $^{108}In$, $^{109}In$, $^{110}In$, $^{115}Te$, $^{116}Te$, $^{117}Te$, $^{117}I$, $^{118}I$, $^{118}Xe$, $^{119}Xe$, $^{119}I$, $^{119}Te$, $^{120}I$, $^{120}Xe$, $^{121}Xe$, $^{116}Sb$, $^{117}Sb$, $^{115}Sb$, $^{121}I$, $^{122}I$, $^{123}Xe$, $^{124}I$, $^{126}I$, $^{128}I$, $^{129}La$, $^{130}La$, $^{131}La$, $^{132}La$, $^{133}La$, $^{135}La$, $^{136}La$, $^{140}Sm$, $^{141}Sm$, $^{142}Sm$, $^{144}Gd$, $^{145}Gd$, $^{145}Eu$, $^{146}Gd$, $^{146}Eu$, $^{147}Eu$, $^{147}Gd$, $^{148}Eu$, $^{150}Eu$, $^{190}Au$, $^{191}Au$, $^{192}Au$, $^{193}Au$, $^{198}Au$, $^{199}Au$, $^{193}Tl$, $^{194}Tl$, $^{194}Au$, $^{196}Tl$, $^{196}Tl$, $^{197}Tl$, $^{198}Tl$, $^{200}Tl$, $^{200}B$, $^{202}Bi$, $^{203}Bi$, $^{205}Bi$ or $^{206}Bi$, a radionuclide that decays via β− decay such as $^{3}H$, $^{14}C$, $^{35}S$, $^{32}P$, $^{131}I$, $^{59}Fe$, $^{60}Co$, $^{67}Cu$, $^{89}Sr$, $^{90}Sr$, $^{90}Y$, $^{99}Mo$, $^{133}Xe$, $^{137}CS$, $^{163}SM$, $^{177}LU$ or $^{186}Re$, or a radionuclide that decays via electron capture such as $^{111}In$, $^{123}I$, $^{125}I$, $^{201}Tl$, $^{67}Ga$, $^{51}Cr$, $^{57}Co$, $^{58}Co$, $^{62}Zn$ or $^{82}Sr$. Most specifically, it may be $^{18}F$, $^{11}C$, $^{13}N$, $^{15}O$, $^{60}Cu$, $^{64}Cu$, $^{67}Cu$, $^{124}I$, $^{68}Ga$, $^{52}Fe$, $^{58}Co$, $^{3}H$, $^{14}C$, $^{35}S$, $^{32}P$, $^{131}I$, $^{59}Fe$, $^{60}Co$, $^{89}Sr$, $^{90}Sr$, $^{90}Y$, $^{99}Mo$, $^{133}Xe$, $^{137}Cs$, $^{163}Sm$, $^{177}Lu$, $^{186}Re$, $^{123}I$, $^{125}I$, $^{201}Ti$ or $^{67}Ga$, but is not limited thereto. Since other radionuclides that do not decay via β+, β− or electron capture can also emit light, they may also be used as the radionuclide of the present disclosure if they produce CR. In a specific embodiment, the CR-emitting radionuclides are selected from the group consisting of $^{18}F$, $^{18}F$-FDG, $^{64}Cu$, $^{90}Y$, $^{124}I$, and $^{89}Zr$.

In an embodiment, the composition comprising at least one radiation-sensitive molecule and the radionuclide can be designed to have an affinity towards the same target or similar target. In another embodiment, the composition comprising at least one radiation-sensitive molecule and a targeting agent may optionally include a radionuclide in a probe. The radiation-sensitive molecule may be associated with (e.g., bonded, form a complex with, and the like) the radionuclide directly or indirectly (e.g., via a chemical or biochemical linking group of compound), many of which are known in the art. In an embodiment, the radiation-sensitive molecule and radionuclide may be positioned so that the optical energy emitted from the radionuclide is maximized. In an embodiment, the probe can be configured that upon interaction with the target, the probe undergoes a change so that the radiation-sensitive molecule and the radionuclide are brought into proximity to maximize the energy emitted by the radiation-sensitive molecule. Activation of the probe only upon contact with the targeted tissue may limit toxicity associated with off target activity.

II. Methods of Using CRIT

In an aspect, the invention provides a method for administering Cerenkov-radiation induced therapy (CRIT) to a target tissue in a subject. The method comprises administering to the subject an effective amount of a composition comprising at least one radiation-sensitive molecule and administering to the subject an amount of a Cerenkov radiation (CR)-emitting radionuclide effective to activate the radiation-sensitive molecule, thereby administering CRIT to the target tissue in the subject.

In another aspect, the present invention provides a method of detecting a tumor in a subject. The method comprises administering to the subject an effective amount of a composition comprising at least one radiation-sensitive molecule and an amount of a Cerenkov radiation (CR)-emitting radionuclide effective to activate the radiation-sensitive molecule, and subsequently imaging the subject for a signal, wherein a signal indicates detection of the tumor.

In yet another aspect, the invention provides a method for monitoring a response to treatment in a subject. The method comprises administering to the subject an effective amount of a composition comprising at least one radiation-sensitive molecule and an amount of a CR-emitting radionuclide effective to activate the radiation-sensitive molecule, imaging the subject for a signal corresponding to the radiation-sensitive molecule, repeating the aforementioned method at a later time, and subsequently comparing the images, wherein a change in signal corresponding to the radiation-sensitive molecule indicates a response to treatment.

In still yet another aspect, the invention provides a method for treating, stabilizing and/or preventing cancer and associated diseases in a subject. The method comprises administering to the subject an effective amount of a composition comprising at least one radiation-sensitive molecule and an amount of a Cerenkov radiation (CR)-emitting radionuclide effective to activate the radiation-sensitive molecule, thereby treating, stabilizing and/or preventing the cancer or the associated diseases. By "treating, stabilizing, or preventing cancer" is meant causing a reduction in the size of a tumor or in the number of cancer cells, slowing or preventing an increase in the size of a tumor or cancer cell proliferation, increasing the disease-free survival time between the disappearance of a tumor or other cancer and its reappearance, preventing an initial or subsequent occurrence of a tumor or other cancer, or reducing an adverse symptom associated with a tumor or other cancer. In a desired embodiment, the percent of tumor or cancerous cells surviving the treatment is at least 20, 40, 60, 80, or 100% lower than the initial number of tumor or cancerous cells, as measured using any standard assay (e.g., caspase assays, TUNEL and DNA fragmentation assays, cell permeability assays, and Annexin V assays). Desirably, the decrease in the number of tumor or cancerous cells induced by administration of CRIT of the invention is at least 2, 5, 10, 20, or 50-fold greater than the decrease in the number of non-tumor or non-cancerous cells. Desirably, the methods of the present invention result in a decrease of 20, 40, 60, 80, or 100% in the size of a tumor or in the number of cancerous cells, as determined using standard methods. Desirably, at least 20, 40, 60, 80, 90, or 95% of the treated subjects have a complete remission in which all evidence of the tumor or cancer disappears. Desirably, the tumor or cancer does not reappear or reappears after at least 5, 10, 15, or 20 years.

In each of the foregoing embodiments, the composition comprising at least one radiation-sensitive molecule may further comprise a targeting agent. In each of the foregoing embodiments, the composition comprising at least one radiation-sensitive molecule may comprise two radiation-sensitive molecules. In each of the foregoing embodiments, the composition comprising at least one radiation-sensitive molecule may comprise at least two radiation-sensitive molecules. In each of the foregoing embodiments, the composition comprising at least two radiation-sensitive molecule may comprise a photosensitizer and a photoinitiator. In each of the foregoing embodiments, the composition comprising at least one radiation-sensitive molecule may comprise a photosensitizer. In each of the foregoing embodiments, the composition comprising at least one radiation-sensitive molecule may comprise a photoinitiator. In each of the foregoing embodiments, the photosensitizer may be $TiO_2$ and the photoinitiator may be titanocene.

Suitable subjects include, but are not limited to, a human, a livestock animal, a companion animal, a lab animal, and a zoological animal. A subject may or may not be known to have a tumor. In one embodiment, the subject may be a rodent, e.g. a mouse, a rat, a guinea pig, etc. In another embodiment, the subject may be a livestock animal. Non-limiting examples of suitable livestock animals may include pigs, cows, horses, goats, sheep, llamas and alpacas. In yet another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In a preferred embodiment, the animal is a laboratory animal. Non-limiting examples of a laboratory animal may include rodents, canines, felines, and non-human primates. In another preferred embodiment, the subject is a human.

A. Method of Administering CRIT

In an aspect, the invention provides a method for administering CRIT to a target tissue in a subject. The method comprises administering to the subject an effective amount of a composition comprising at least one radiation-sensitive molecule and an amount of a Cerenkov radiation (CR)-emitting radionuclide effective to activate the radiation-sensitive molecule, thereby administering CRIT to the target tissue in the subject. In an embodiment where the radiation-sensitive molecule is activated by X-rays, the invention also provides a method for administering radiotherapy to a target tissue in a subject.

In CRIT, one or more (e.g., amount and/or type) radionuclides and one or more radiation-sensitive molecules (e.g., amount and/or type) are introduced into the subject. Subsequently, low energy photons generated by the one or more radionuclide are absorbed by the radiation-sensitive molecules activating the radiation-sensitive molecules thereby causing a variety of active forms of oxygen to be created, the main one of which is singlet oxygen. It is advantageous for the radiation-sensitive molecules to absorb energy from the radionuclide so that an outside energy source is not needed to excite the radiation-sensitive molecule, since the outside or external energy has limited tissue depth penetration resulting in limited radiation-sensitive molecules activation in deep tissue. Thus, in an embodiment, the method used does not need the use of an external, outside, or another source of energy to excite the radiation-sensitive molecules since the radionuclides excite the radiation-sensitive molecules. As such, Cerenkov radiation serves as a tissue depth-independent light source for CRIT.

According to the invention, if the radiation-sensitive molecule and the radionuclide are present at the area of the target, the absorption of photons generated by the radionuclide by the radiation-sensitive molecule produces an excited state which, ultimately, transfers its energy to available surrounding oxygen to produce a molecular excited state of oxygen in the singlet stage. The formation of singlet oxygen in cell membranes, cytoplasm or organelles results in peroxidative reactions that cause cell damage and death. As such, the methods of the invention may be used to treat a disease associated with the target tissue. The terms "treat", "treating" or "treatment" include prevention, attenuation, reversal, or improvement in at least one symptom or sign of symptoms associated with the disease. In one embodiment, the target tissue may be a tumor. As such, the methods of the invention may be used to treat a tumor derived from a neoplasm or a cancer. The neoplasm may be malignant or benign, the cancer may be primary or metastatic; the neoplasm or cancer may be early stage or late stage. Non-limiting examples of neoplasms or cancers that may be treated include acute lymphoblastic leukemia, acute myeloid leukemia, adrenocortical carcinoma, AIDS-related cancers, AIDS-related lymphoma, anal cancer, appendix cancer, astrocytomas (childhood cerebellar or cerebral), basal cell carcinoma, bile duct cancer, bladder cancer, bone cancer, brainstem glioma, brain tumors (cerebellar astrocytoma, cerebral astrocytoma/malignant glioma, ependymoma, medulloblastoma, supratentorial primitive neuroectodermal tumors, visual pathway and hypothalamic gliomas, breast cancer, bronchial adenomas/carcinoids, Burkitt lymphoma, carcinoid tumors (childhood, gastrointestinal), carcinoma of unknown primary, central nervous system lymphoma (primary), cerebellar astrocytoma, cerebral astrocytoma/malignant glioma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma in the Ewing family of tumors, extracranial germ cell tumor (childhood), extragonadal germ cell tumor, extrahepatic bile duct cancer, eye cancers (intraocular melanoma, retinoblastoma), gallbladder cancer, gastric (stomach) cancer, gastrointestinal carcinoid tumor, gastrointestinal stromal tumor, germ cell tumors (childhood extracranial, extragonadal, ovarian), gestational trophoblastic tumor, gliomas (adult, childhood brain stem, childhood cerebral astrocytoma, childhood visual pathway and hypothalamic), gastric carcinoid, hairy cell leukemia, head and neck cancer, hepatocellular (liver) cancer, Hodgkin lymphoma, hypopharyngeal cancer, hypothalamic and visual pathway glioma (childhood), intraocular melanoma, islet cell carcinoma, Kaposi sarcoma, kidney cancer (renal cell cancer), laryngeal cancer, leukemias (acute lymphoblastic, acute myeloid, chronic lymphocytic, chronic myelogenous, hairy cell), lip and oral cavity cancer, liver cancer (primary), lung cancers (non-small cell, small cell), lymphomas (AIDS-related, Burkitt, cutaneous T-cell, Hodgkin, non-Hodgkin, primary central nervous system), macroglobulinemia (Waldenström), malignant fibrous histiocytoma of bone/osteosarcoma, medulloblastoma (childhood), melanoma, intraocular melanoma, Merkel cell carcinoma, mesotheliomas (adult malignant, childhood), metastatic squamous neck cancer with occult primary, mouth cancer, multiple endocrine neoplasia syndrome (childhood), multiple myeloma/plasma cell neoplasm, mycosis fungoides, myelodysplastic syndromes, myelodysplastic/myeloproliferative diseases, myelogenous leukemia (chronic), myeloid leukemias (adult acute, childhood acute), multiple myeloma, myeloproliferative disorders (chronic), nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer (surface epithelial-stromal tumor), ovarian germ cell tumor, ovarian low malignant potential tumor, pancreatic cancer, pancreatic cancer (islet cell), paranasal sinus and nasal cavity cancer, parathyroid cancer, penile cancer, pharyngeal cancer, pheochromocytoma, pineal astrocytoma, pineal germinoma, pineoblastoma and supratentorial primitive neuroectodermal tumors (childhood), pituitary adenoma, plasma cell neoplasia, pleuropulmonary blastoma, primary central nervous system lymphoma, prostate cancer, rectal cancer, renal cell carcinoma (kidney cancer), renal pelvis and ureter transitional cell cancer, retinoblastoma, rhabdomyosarcoma (childhood), salivary gland cancer, sarcoma (Ewing family of tumors, Kaposi, soft tissue, uterine), Sezary syndrome, skin cancers (nonmelanoma, melanoma), skin carcinoma (Merkel cell), small cell lung cancer, small intestine cancer, soft tissue sarcoma, squamous cell carcinoma, squamous neck cancer with occult primary (metastatic), stomach cancer, supratentorial primitive neuroectodermal tumor (childhood), T-Cell lymphoma (cutaneous), testicular cancer, throat cancer, thymoma (childhood), thymoma and thymic carcinoma, thyroid cancer, thyroid cancer (childhood), transitional cell cancer of the renal pelvis and ureter, trophoblastic tumor (gestational), enknown primary site (adult, childhood), ureter and renal pelvis transitional cell cancer, urethral cancer, uterine cancer (endometrial), uterine sarcoma, vaginal cancer, visual pathway and hypothalamic glioma (childhood), vulvar cancer, Waldenström macroglobulinemia, and Wilms tumor (childhood). In an embodiment, the neoplasm or cancer is selected from the group consisting of pancreatic cancer, fibrosarcoma, multiple myeloma and lung cancer. In specific embodiments, the neoplasm or cancer is pancreatic cancer. In other specific embodiments, the neoplasm or cancer is fibrosarcoma. In still other specific embodiments, the neoplasm or cancer is multiple myeloma. In a different embodiment, the neoplasm or cancer is lung cancer.

In another embodiment, the methods of the invention may be used to treat a disease associated with diseased and/or inflamed tissues. For example, the new methods may be useful for the treatment of ophthalmologic disorders such as age-related macular degeneration, diabetic retinopathy, and choroidal neovascularization; dermatological disorders such as acne, psoriasis and scleroderma; gynecological disorders such as dysfunctional uterine bleeding; urological disorders such as condyloma virus; cardiovascular disorders such as restenosis, intimal hyperplasia, and atherosclerotic plaques; hemangioma; autoimmune diseases such as arthritis; hyperkeratotic diseases; and for hair removal. Normal or diseased tissue on any part of the body can be treated or studies with CRIT; thus, normal or abnormal conditions of the hematological system, the lymphatic reticuloendothelial system, the nervous system, the endocrine and exocrine system, the skeletomuscular system including bone, connective tissue, cartilage and skeletal muscle, the pulmonary system, the gastrointestinal system including the liver, the reproductive system, the immune system, the cardiovascular system, the urinary system, the ocular system, and the auditory and olfactory systems may be treated using the new methods.

In certain aspects, the methods of the invention may further comprise administering therapeutic agents for neoplasms and cancer. Suitable therapeutic agents for neoplasms and cancers are known in the art, and will depend upon the type and stage of cancer. Summaries of cancer drugs, including information regarding approved indications, may be found via the National Cancer Institute at the National Institutes of Health (cancer.gov) and the FDA Approved Drug Product database.

An exemplary embodiment of the present disclosure includes a method of reducing the amount of radiation administered to a subject. According to the invention, a CR-emitting radionuclide may be administered at about a 100-fold lower dose than standard treatment. For example, a CR-emitting radionuclide may be administered at about a 2-fold, about a 5-fold, about a 10-fold, about a 20-fold, about a 30-fold, about a 40-fold, about a 50-fold, about a 60-fold, about a 70-fold, about an 80-fold, about a 90-fold or about 100-fold lower dose than standard treatment. Alternatively, a CR-emitting radionuclide may be administered at greater than 100-fold lower dose than standard treatment. In a specific embodiment, a CR-emitting radionuclide may be administered at about a 2-fold. A lower dose of radionuclide may reduce radiotoxicity to a subject. For example, a standard dose of $^{18}$F-FDG may be about 10 mCi, thus the present methodology may use a dose of about 5 to about 0.01 mCi. For example, using the methodology disclosed herein the dose of $^{18}$F-FDG may be about 0.15, about 0.2, about 0.25, about 0.3, about 0.35, about 0.4, about 0.45, about 0.5, about 0.55, about 0.6, about 0.65, about 0.7, about 0.75, about 0.8, about 0.85, about 0.9, about 0.95, about 1, about 1.1, about 1.2, about 1.3, about 1.4, about 1.5, about 1.6, about 1.7, about 1.8, about 1.9, about 2, about 2.5, about 3, about 3.5, about 4, about 4.5, or about 5 mCi.

B. Method of Detecting and Monitoring a Tumor

In another aspect, the present invention provides a method of detecting a tumor in a subject. The method comprises administering to the subject an effective amount of composition comprising at least one radiation-sensitive molecule and an amount of a Cerenkov radiation (CR)-emitting radionuclide effective to activate the radiation-sensitive molecule, and subsequently imaging the subject for a signal corresponding to the radiation-sensitive molecule, wherein a signal corresponding to the radiation-sensitive molecule indicates detection of the tumor.

In yet another aspect, the invention provides a method for monitoring a tumor in a subject. The method comprises administering to the subject an effective amount of a composition comprising at least one radiation-sensitive molecule and an amount of a CR-emitting radionuclide effective to activate the radiation-sensitive molecule, imaging the subject for a signal corresponding to the radiation-sensitive molecule, repeating the aforementioned method at a later time, and subsequently comparing the images, wherein a change in signal corresponding to the radiation-sensitive molecule indicates a change in tumor.

The invention comprises, in part, imaging a subject. Non-limiting examples of modalities of imaging may include magnetic resonance imaging (MRI), ultrasound (US), computed tomography (CT), Positron Emission Tomography (PET), Single Photon Emission Computed Tomography (SPECT), and optical imaging (OI, bioluminescence and fluorescence). Radioactive molecular probes are traditionally imaged with PET, SPECT or gamma (γ) cameras, by taking advantage of the capability of these imaging modalities to detect the high energetic γ rays. In contrast, OI generally detects low energy lights (visible or near-infrared lights) emitted from bioluminescence or fluorescence probes. Each modality has its own advantages and disadvantages. For instance, nuclear imaging modalities such as PET have high sensitivity and excellent quantification capability but suffer from poor spatial resolution, which is confined to millimeter range. On the other hand, MRI features submillimeter spatial resolution but is limited by low sensitivity and the high cost of instrumentation. Much less expensive and more widely available than PET and MRI, traditional OI also features high sensitivity, short scanning time, and relatively high throughput, yet its potential has been mostly constrained to preclinical studies because of low penetration and high scattering of optical signals in living tissues. The present invention overcomes these limitations allowing optical imaging to become a new mode of in vivo imaging besides PET and SPECT. In an exemplary embodiment, the imaging is optical imaging.

Compared to conventional fluorescence and bioluminescence optical imaging, radioactive optical imaging (OI) has some unique properties. The continued emission wavelength of radioactive OI allows monitoring and imaging of a radionuclide at different wavelengths, which is a significant advantage over the conventional optical imaging modalities. And the radioactive OI signal generated by a radionuclide does not require an excitation light and is always on, which is different from fluorescence and bioluminescence probes, which typically need an outside source of energy and which may produce unwanted and complicating optical signals from other sources (e.g., skin). In an embodiment, the signal generated by a radionuclide can be used to excite a radiation-sensitive molecule so the radiation-sensitive molecule can activate without the requirement of an excitation light.

As mentioned above, an exemplary embodiment of the present disclosure includes a method of imaging a target within a subject using a radionuclide and a composition comprising at least one radiation-sensitive molecule. Initially, one or more (e.g., amount and/or type) radionuclides and one or more radiation-sensitive molecules (e.g., amount and/or type) may be introduced into the subject. Subsequently, low energy photons generated by the one or more radionuclide are detected as a signal(s) and/or the radiation-sensitive molecule absorbs the energy from the radionuclide and then the radiation-sensitive molecule emits a signal. In an exemplary embodiment, the signal is an optical signal. It is advantageous for the radiation-sensitive molecule to absorb energy from the radionuclide so that an outside energy source is not needed to excite the radiation-sensitive molecule, since the outside or external energy source can also cause other background signals (e.g., optical signals) to be generated, thereby interfering with the signal of interest. Thus, in an embodiment, the method used does not need the use of an external, outside, or another source of energy to excite the radiation-sensitive molecule since the radionuclides excite the radiation-sensitive molecule.

According to the invention, if the composition comprising at least one radiation-sensitive molecule and the radionuclide are present at the area of the target, the radiation-sensitive molecule should emit energy associated with a signal that corresponds to the radiation-sensitive molecule. The various signals can be separated based on wavelength and/or intensity to determine the area where the signal from the radiation-sensitive molecule is derived. After the signal corresponding to the radiation-sensitive molecule is obtained, the signal or data corresponding to the detected signal can be processed to provide an image of the target or the area where the target is located. In an embodiment, the image can be a planar image or can be a 3-dimensional image of the target. In particular, the signal can be used to identify an area from which the signal is produced, where the area corresponds to the location of the target. For example, measuring a signal corresponding to the radiation-sensitive molecule that is concentrated in a specific area or location is indicative that the target is present at the location of the origin of the signal.

Once the signal corresponding to the radiation-sensitive molecule is obtained, the status of the condition or disease can be evaluated or monitored by comparing the image with one or more previous images and one or more subsequent images. In an embodiment, a change in signal indicates a response to treatment. A decrease in signal may indicate a decrease in disease. For example, a decrease in signal may indicate a decrease in tumor size and therefore tumor regression. Alternatively, an increase in signal may indicate an increase in disease. For example, an increase in signal may indicate an increase in tumors size and therefore tumor progression.

The term "signal" as used herein, refers to a signal derived from a radioactive substance, a radiation-sensitive molecule, a light-sensitive molecule, a photosensitizer, a photoinitiator, a photocatalyst etc. that can be detected and quantitated with regards to its frequency and/or amplitude. The signal may be an optical signal. The signal can be generated from one or more radionuclides, radiation-sensitive molecules, or probes of the present disclosure. In an embodiment, the signal may need to be the sum of each of the individual signals. In an embodiment, the signal can be generated from a summation, an integration, or other mathematical process, formula, or algorithm, where the signal is from one or more radionuclides, radiation-sensitive molecules, probes, or the like. In an embodiment, the summation, the integration, or other mathematical process, formula, or algorithm can be used to generate the signal so that the signal can be distinguished from background noise and the like. It should be noted that signals other than the signal of interest can be processed and/or obtained in a similar manner as that of the signal of interest.

As noted above, embodiments of the present disclosure include a method for imaging a target within a subject. In an embodiment, the system can include a detection system and a signal processing system. In an embodiment, the detection system can be configured to detect low energy photons generated by one or more radionuclides as signals within the subject. In an embodiment, the signal processing system is configured to provide images based upon the signal. As described above, the signal can be processed to produce an image. As described herein, the location of the target can be obtained using the data or information corresponding to the signal. Additional details are provided in the Examples.

In an embodiment, the system can be an in vivo imaging system that can be used to visualize molecular events in an organism by detecting emitted photons. In an embodiment, the system can be an optical detection system wherein the optical detection system includes an optical fiber system (e.g., optical fiber, optics for focusing and or direction the optical energy). The optical signal is directed using the optical fiber system to a charge-coupled device camera (CCD camera) that are often utilized for capturing images and converting them into digital values to produce an image.

Embodiments of the methods of the present disclosure may be useful for radioactive optical imaging in cancer imaging and in imaging of other diseases. Radioactive optical imaging can be used in the detection, characterization and/or determination of the localization of a disease ranging from early to late stage disease. Radioactive optical imaging has, furthermore, utility in staging a disease, i.e., determining the severity of a disease, monitoring the progression (worsening) of a disease, and/or monitoring the regression (improvement). Radioactive optical imaging can also be used in the prognosis of a disease or disease conditions. Radioactive optical imaging could be very useful for cancer imaging.

In addition, radioactive optical imaging has further utility in imaging diseases that are characterized by inflammation processes such as rheumatoid arthritis, whereby the presence and location of inflammation can be imaged; cardiovascular diseases including atherosclerosis, ischemia, stroke, or thromboses, whereby plaques, areas at risk for acute occlusion as well as areas of hypoxia can be imaged; infectious diseases, whereby areas inflicted with bacterial, viral, fungal, parasitic pathogens can be imaged. Radioactive optical imaging might also be useful for imaging immune cells to aid diagnosing immunological diseases and for neuroimaging to aid diagnosing neurodegenerative diseases.

The term "molecular imaging", as used herein, relates to the in-vivo characterization and measurement of biologic processes and pathways at the cellular and molecular levels.

The term "optical imaging", as used herein, relates to the generation of images by using photons in a wavelength range (e.g., ultraviolet to infrared).

The term "radioactive optical imaging" and "radioactive molecular optical imaging" as used herein, relate to the detection of optical signals generated by radionuclides and are used interchangeably.

C. Administration

Pharmaceutical compositions for effective administration are deliberately designed to be appropriate for the selected mode of administration, and pharmaceutically acceptable excipients such as compatible dispersing agents, buffers, surfactants, preservatives, solubilizing agents, isotonicity agents, stabilizing agents and the like are used as appropriate. Remington's Pharmaceutical Sciences, Mack Publishing Co., Easton Pa., 16Ed ISBN: 0-912734-04-3, latest edition, incorporated herein by reference in its entirety, provides a compendium of formulation techniques as are generally known to practitioners.

In an embodiment, the composition comprising at least one radiation-sensitive molecule and the CR-emitting radionuclide are administered at the same time. For example, the composition comprising at least one radiation-sensitive molecule and the radionuclide may be administered as separate species. Alternatively, the composition comprising at least one radiation-sensitive molecule and the radionuclide may be administered as a probe as described in Section I(b). The radionuclide can include those described in Section I(b). The composition comprising at least one radiation-sensitive molecule can include those described in Section I(a).

In another embodiment, the composition comprising at least one radiation-sensitive molecule and the CR-emitting radionuclide are administered sequentially, wherein the composition comprising at least one radiation-sensitive molecule may be administered first, followed by administration of the CR-emitting radionuclide. For example, the CR-emitting radionuclide may be administered minutes, hours or days after administration of a composition comprising at least one radiation-sensitive molecule. Accordingly, the CR-emitting radionuclide may be administered from about 10 to about 15 minutes, or from about 15 to about 30 minutes, or from about 30 minutes to about 45 minutes, or from about 45 minutes to 60 minutes after administration of a composition comprising at least one radiation-sensitive molecule. Alternatively, the CR-emitting radionuclide may be administered from about 1 hour to about 2 hours, or from about 2 hours to about 3 hours, or from about 3 hours to about 4 hours, or from about 4 hours to about 5 hours, or from about 5 hours to about 6 hours, or from about 6 hours to about 7 hours, or from about 7 hours to about 8 hours after administration of a composition comprising at least one radiation-sensitive molecule. In another embodiment, the CR-emitting radionuclide may be administered from about 1 day to about 2 days, or from about 2 days to about 3 days, or from about 3 days to about 4 days, or from about 4 days to about 5 days, or from about 5 days to about 6 days, or from about 6 days to about 7 days after administration of a composition comprising at least one radiation-sensitive molecule.

In still another embodiment, administration of the composition and administration of the radionuclide may be repeated. For example, administration of the composition may be repeated, administration of the radionuclide may be repeated, or administration of both may be repeated. The repeating interval may be daily, bi-weekly, bi-monthly or monthly. In an embodiment, administration of the radionuclide is repeated. In an exemplary embodiment, administration of the radionuclide is repeated on days 2 and 4 following administration of the composition.

(i) Composition

Suitable methods for administration of a composition comprising at least one radiation-sensitive molecule include but are not limited to oral, intravenous, sublingual, intraperitoneal, subcutaneous, or intratumoral administration. In an exemplary embodiment, intratumoral administration is employed. In another exemplary embodiment, intravenous administration is employed.

For therapeutic applications, a therapeutically effective amount of a composition as described in Section I(a) is administered to a subject. A "therapeutically effective amount" is an amount of the composition sufficient to produce a measurable biological tumor response (e.g., an immunostimulatory, an anti-angiogenic response, a cytotoxic response, or tumor regression) upon activation by a radionuclide. Actual dosage levels of a composition can be varied so as to administer an amount of the composition that is effective to achieve the desired therapeutic response for a particular subject. The selected dosage level will depend upon a variety of factors including the properties of the composition which may include the properties of the radiation-sensitive molecule, the combination of radiation-sensitive molecules, the properties of the targeting agent, the properties of the radionuclide, the optical properties of the target tissue, formulation, route of administration, combination with other drugs or treatments, tumor size and longevity, and the physical condition and prior medical history of the subject being treated. In one embodiment, a minimal dose is administered, and dose is escalated in the absence of dose-limiting toxicity. Determination and adjustment of a therapeutically effective dose, as well as evaluation of when and how to make such adjustments, are known to those of ordinary skill in the art of medicine. In one embodiment, a therapeutically effective amount of a composition for localized application may be from about 0.5 µg/ml to about 50 µg/ml. In another embodiment, a therapeutically effective amount may be from about 1 µg/ml to about 15 µg/ml. In yet another embodiment, a therapeutically effective amount may be less than 0.5 µg/ml. In still yet another embodiment, a therapeutically effective amount may be about 0.5 µg/ml, about 1 µg/ml, about 1.5 µg/ml, about 2 µg/ml, about 2.5 µg/ml, about 3 µg/ml, about 3.5 µg/ml, about 4 µg/ml, about 4.5 µg/ml, about 5 µg/ml, about 5.5 µg/ml, about 6 µg/ml, about 6.5 µg/ml, about 7 µg/ml, about 7.5 µg/ml, about 8 µg/ml, about 8.5 µg/ml, about 9 µg/ml, about 9.5 µg/ml, about 10 µg/ml, about 11 µg/ml, about 12 µg/ml, about 13 µg/ml, about 14 µg/ml, about 15 µg/ml about 20 µg/ml, about 25 µg/ml, about 30 µg/ml, about 35 µg/ml, about 40 µg/ml, about 45 µg/ml, or about 50 µg/ml. Alternatively, a therapeutically effective amount may be less than about 0.5 µg/ml or greater than about 50 µg/ml. In an exemplary embodiment, a therapeutically effective amount of a composition is 2.5 µg/ml. For systemic administration, a therapeutically effective amount of a composition may be from about 0.1 mg/kg to about 50 mg/kg. In another embodiment, a therapeutically effective amount of a composition may be from about 0.1 mg/kg to about 10 mg/kg. In still another embodiment, a therapeutically effective amount of a composition may be from about 0.5 mg/kg to about 1.5 mg/kg. For example, a therapeutically effective amount maybe be about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, or about 1.0 mg/kg. Additionally, a therapeutically effective amount may be about 1.0 mg/kg, about 1.5 mg/kg, about 2.0 mg/kg, about 2.5 mg/kg, about 3.0 mg/kg, about 3.5 mg/kg, about 4.0 mg/kg, about 4.5 mg/kg, about 5.0 mg/kg, about 5.5 mg/kg, about 6.0 mg/kg, about 6.5 mg/kg, about 7.0 mg/kg, about 7.5 mg/kg, about 8.0 mg/kg, about 8.5 mg/kg, about 9.0 mg/kg, about 9.5 mg/kg, or about 10.0 mg/kg. Alternatively, a therapeutically effective amount may be less than about 0.1 mg/kg or greater than about 10 mg/kg.

For diagnostic applications, a detectable amount of a composition is administered to a subject. A "detectable amount" is an amount of the composition sufficient to produce a detectable signal in vivo or in vitro upon activation by a radionuclide. A "detectable signal" is a signal derived from a radioactive substance, radiation-sensitive molecule, and the like. The detectable signal is detectable and distinguishable from other background signals that are generated from the subject or sample. In other words, there is a measurable and statistically significant difference (e.g., a statistically significant difference is enough of a difference to distinguish among the detectable signal and the background, such as about 0.1%, 1%, 3%, 5%, 10%, 15%, 20%, 25%, 30%, or 40% or more difference between the detectable signal and the background) between detectable signal and the background. Standards and/or calibration curves can be used to determine the relative intensity of the detectable signal and/or the background. A detectable amount will vary according to a variety of factors, including but not limited to the activity of the composition, formulation of the composition, the radiation-sensitive molecule, the combination of radiosensitive-molecules, the route of administration, combination with other drugs or treatments, the size and longevity of the tumor or suspected tumor, the physical condition and prior medical history of the subject, the method of imaging and parameters related thereto, metabolism of the composition in the subject, the stability of the composition, and the time elapsed following administration of the composition prior to imaging. Thus, a detectable amount can vary and can be tailored to a particular application. After study of the present disclosure, and in particular the Examples, it is within the skill of one in the art to determine such a detectable amount. For localized application, in one embodiment, a detectable amount of a composition to produce a detectable signal in vivo may be from about 50 µg/ml to about 1000 µg/ml. In another embodiment, a detectable amount may be greater than 1000 µg/ml. In yet another embodiment, a detectable amount may be less than 50 µg/ml. In still yet another embodiment a detectable amount may be about 50 µg/ml, 100 µg/ml, about 150 µg/ml, about 200 µg/ml, about 250 µg/ml, about 300 µg/ml, about 350 µg/ml, about 400 µg/ml, about 450 µg/ml, about 500 µg/ml, about 550 µg/ml, about 600 µg/ml, about 650 µg/ml, about 700 µg/ml, about 750 µg/ml, about 800 µg/ml, about 850 µg/ml, about 900 µg/ml, about 950 µg/ml or about 1000 µg/ml. In an exemplary embodiment, a detectable amount of a composition is 250 µg/ml. For systemic administration, a detectable amount of a composition may be from about 0.1 mg/kg to about 50 mg/kg. In another embodiment, a therapeutically effective amount of a composition may be from about 0.1 mg/kg to about 10 mg/kg. In still another embodiment, a detectable amount of a composition may be from about 0.5 mg/kg to about 1.5 mg/kg. For example, a detectable amount maybe be about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, or about 1.0 mg/kg. Additionally, a detectable amount may be about 1.0 mg/kg, about 1.5 mg/kg, about 2.0 mg/kg, about 2.5 mg/kg, about 3.0 mg/kg, about 3.5 mg/kg, about 4.0 mg/kg, about 4.5 mg/kg, about 5.0 mg/kg, about 5.5 mg/kg, about 6.0 mg/kg, about 6.5 mg/kg, about 7.0 mg/kg, about 7.5 mg/kg, about 8.0 mg/kg, about 8.5 mg/kg, about 9.0 mg/kg, about 9.5 mg/kg, or about 10.0 mg/kg. Alternatively, a detectable amount may be less than about 0.1 mg/kg or greater than about 10 mg/kg.

(ii) Radionuclide

Suitable methods for administration of a radionuclide include but are not limited to oral, intravenous, sublingual, intraperitoneal, subcutaneous, or intratumoral administration. In an exemplary embodiment, intratumoral administration is employed. In another exemplary embodiment, intravenous administration is employed.

For therapeutic applications, a therapeutically effective amount of a radionuclide is administered to a subject. A "therapeutically effective amount" is an amount of the radionuclide sufficient to activate the radiation-sensitive molecule to produce a measurable biological tumor response (e.g., an immunostimulatory, an anti-angiogenic response, a cytotoxic response, or tumor regression). Actual dosage levels of a radionuclide can be varied so as to administer an amount of the radionuclide that is effective to achieve the desired therapeutic response for a particular subject. The selected dosage level will depend upon a variety of factors including the properties of the radionuclide, the properties of the radiation-sensitive molecule(s), the optical properties of the target tissue, formulation, route of administration, combination with other drugs or treatments, tumor size and longevity, and the physical condition and prior medical history of the subject being treated. In one embodiment, a minimal dose is administered, and dose is escalated in the absence of dose-limiting toxicity. Determination and adjustment of a therapeutically effective dose, as well as evaluation of when and how to make such adjustments, are known to those of ordinary skill in the art of medicine. In one embodiment, a therapeutically effective amount of a radionuclide may be from about 0.1 mCi to about 2 mCi. In another embodiment, a therapeutically effective amount may be from about 0.1 mCi to about 1.5 mCi. In still another embodiment, a therapeutically effective amount may be from about 0.1 mCi to about 0.5 mCi. In yet another embodiment, a therapeutically effective amount may be less than 0.1 mCi. In still yet another embodiment, a therapeutically effective amount may be about 0.1 mCi, about 0.15 mCi, about 0.2 mCi, about 0.25 mCi, about 0.3 mCi, about 0.35 mCi, about 0.4 mCi, about 0.45 mCi, about 0.5 mCi, about 0.55 mCi, about 0.6 mCi, about 0.65 mCi, about 0.7 mCi, about 0.75 mCi, about 0.8 mCi, about 0.85 mCi, about 0.9 mCi, about 0.95 mCi or about 1 mCi. Alternatively, a therapeutically effective amount may be about 1.0, about 1.1 mCi, about 1.2 mCi, about 1.3 mCi, about 1.4 mCi, about 1.5 mCi, about 1.6 mCi, about 1.7 mCi, about 1.8 mCi, about 1.9 mCi, or about 2.0 mCi. In an exemplary embodiment, a therapeutically effective amount of a radionuclide is 0.25 mCi. In another exemplary embodiment, a therapeutically effective amount of a radionuclide is 1.0 mCi. In yet another exemplary embodiment, a therapeutically effective amount of a radionuclide is 100-fold lower than the current paradigm in clinical nuclear radiotherapy. A skilled artisan will understand that different radionuclides may have different levels of standard dose used for administration.

For diagnostic applications, a detectable amount of a radionuclide is administered to a subject. A "detectable amount" is an amount of the radionuclide sufficient to activate the radiation-sensitive molecule to produce a detectable signal in vivo or in vitro. A detectable amount will vary according to a variety of factors, including but not limited to the activity of the radionuclide, the route of administration, combination with other drugs or treatments, the size and longevity of the tumor or suspected tumor, the physical condition and prior medical history of the subject, the method of imaging and parameters related thereto, metabolism of the radionuclide in the subject, the stability of the radionuclide, and the time elapsed following administration of the radionuclide prior to imaging. Thus, a detectable amount can vary and can be tailored to a particular application. After study of the present disclosure, and in particular the Examples, it is within the skill of one in the art to determine such a detectable amount. In one embodiment, a detectable amount of a radionuclide to activate a radiation-sensitive molecule in vivo may be from about 0.1 mCi to about 1.5 mCi. In another embodiment, a detectable amount may be from about 0.1 mCi to about 0.5 mCi. In yet another embodiment, a detectable amount may be less than 0.1 mCi. In still yet another embodiment, a detectable amount may be about 0.1 mCi, about 0.15 mCi, about 0.2 mCi, about 0.25 mCi, about 0.3 mCi, about 0.35 mCi, about 0.4 mCi, about 0.45 mCi, about 0.5 mCi, about 0.55 mCi, about 0.6 mCi, about 0.65 mCi, about 0.7 mCi, about 0.75 mCi, about 0.8 mCi, about 0.85 mCi, about 0.9 mCi, about 0.95 mCi or about 1 mCi. Alternatively, a detectable amount may be about 1.0, about 1.1 mCi, about 1.2 mCi, about 1.3 mCi, about 1.4 mCi, or about 1.5 mCi. In an exemplary embodiment, a detectable amount of a radionuclide is 0.25 mCi. In another exemplary embodiment, a detectable amount of a radionuclide is 1.0 mCi.

EXAMPLES

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Introduction for Examples 1-6

Photodynamic therapy (PDT) has seen tremendous advancements in recent years, with major focus on improving the tissue specificity of photosensitizers (PS) and tissue depth penetration of light. These efforts highlight the enormous potential of PDT as a viable treatment regimen, but also expose the challenges that must be overcome to realize the full benefits of this treatment paradigm. Regardless of the mechanism of action, both Type I (direct transfer of radical ions from an activated PS to biomolecules) and Type II (direct generation of singlet oxygen species by an activated PS) PDT rely on reactive oxygen product for therapeutic effect[1]. This basic assumption implies that PDT will be less efficient in hypoxic conditions such as those found in many solid tumors[2]. Therefore, an oxygen independent free radical generating photodynamic event could address this fundamental problem.

Biocompatible inorganic nanoparticles are attractive alternatives to conventional PS because of their large surface area, excellent payload capacity, and high reactivity[3,4]. Previous studies have shown that titanium dioxide ($TiO_2$) nanoparticles are excellent photocatalysts that can absorb ultraviolet (UV) light ($\lambda$<385 nm) with high efficiency and generate free radicals such as hydroxyl and superoxide species through electron-hole pair production[5]. Generation of hydroxyl radicals through electron-hole transfer to chemisorbed $H_2O$ is an oxygen-independent process, whereas superoxide radical generation requires aerated aqueous media for electron transfer to molecular oxygen[6-9]. Of these two products, the highly cytotoxic hydroxyl radicals are the key species formed during the photocatalytic oxidation on the surface of $TiO_2$ in aqueous solvents[7,9]. These features have motivated the use of $TiO_2$ as a PS to induce cell death[10-15]. However, the shallow penetration of UV light (<0.5 mm in tissue) has confined most of the previous studies to in vitro models of human diseases.

The limited penetrability of light in tissues remains the Achilles heel for realizing the full potential of light based imaging and therapeutic techniques. Technological advances in bioluminescence imaging and low light detection techniques have prompted a fresh outlook at using Cerenkov radiation (CR) as a light source for molecular imaging[16-20]. CR occurs when charged particles such as positrons or electrons travel faster than the speed of light in a given medium, emitting light ranging from 250-600 nm[21]. Positron emission tomography (PET) isotopes are an ideal source for CR because of their high positron (13$^+$) emission decay and their short half-life. 13$^+$ particles travel short distances (<1 mm) in tissues, during which CR is first emitted before they undergo annihilation[22]. These data suggest that the broad CR luminescence spectrum and the availability of many clinical PET radionuclides could overcome the difficulty of activating $TiO_2$ in the UV region for in vivo PDT. Therefore, we hypothesized that CR-mediated excitation of $TiO_2$ nanoparticles will generate hydroxyl radicals for molecular oxygen-and depth-independent PDT (CR-PDT). To test this hypothesis, we chose $^{64}Cu$ as the CR source because of its relatively short half-life (12.7 h), significant β decay (β$^+$:19%, β$^-$:39%), and availability at low cost. Using tumor cells and tumor-bearing mice, we demonstrate for the first time that the synergistic effect of low activity $^{64}Cu$ (≤0.25 mCi) and $TiO_2$ nanoparticles in tumors was sufficient to eradicate tumors in vivo through CR-mediated depth-independent PDT. We also demonstrated that the intrinsic luminescence properties of $TiO_2$ nanoparticles can provide luminescence for optical imaging, allowing these materials to effectively serve as a theranostic agent for depth-independent CR-mediated PDT and monitoring of treatment response by luminescence imaging.

Figure 1B:
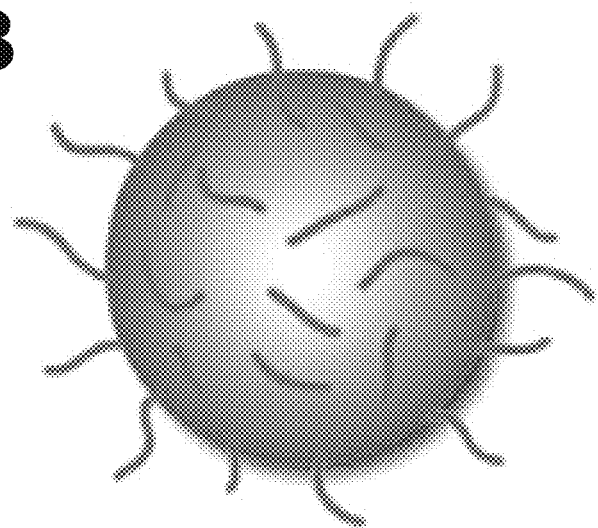
Figure 1C:
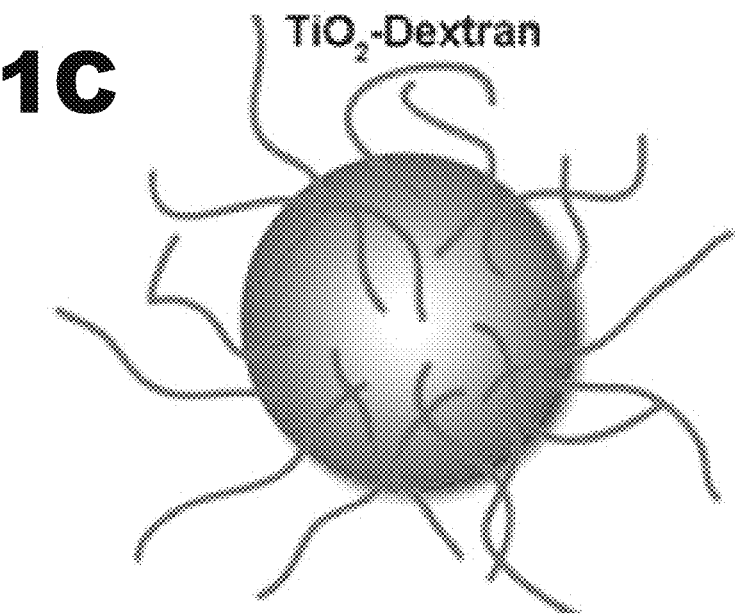
Figure 1D:
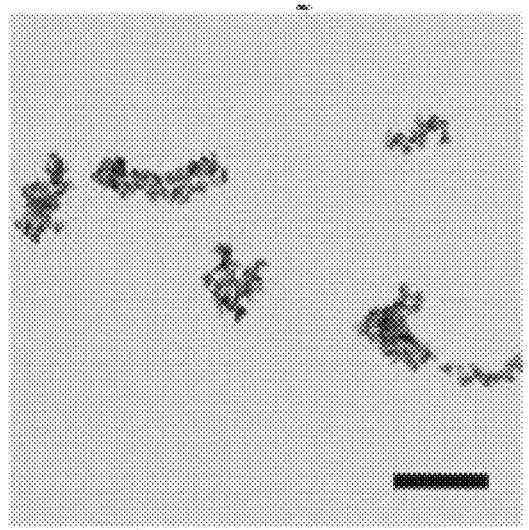
Figure 1E:
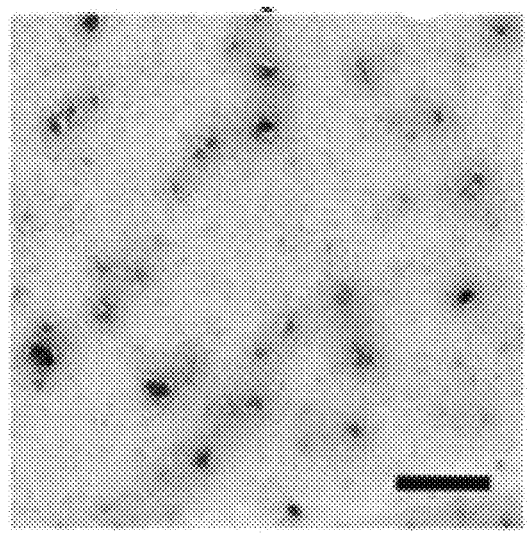
Figure 1F:
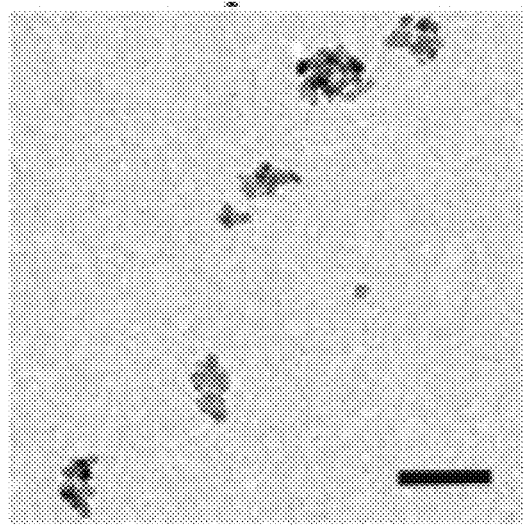
Figure 1G:
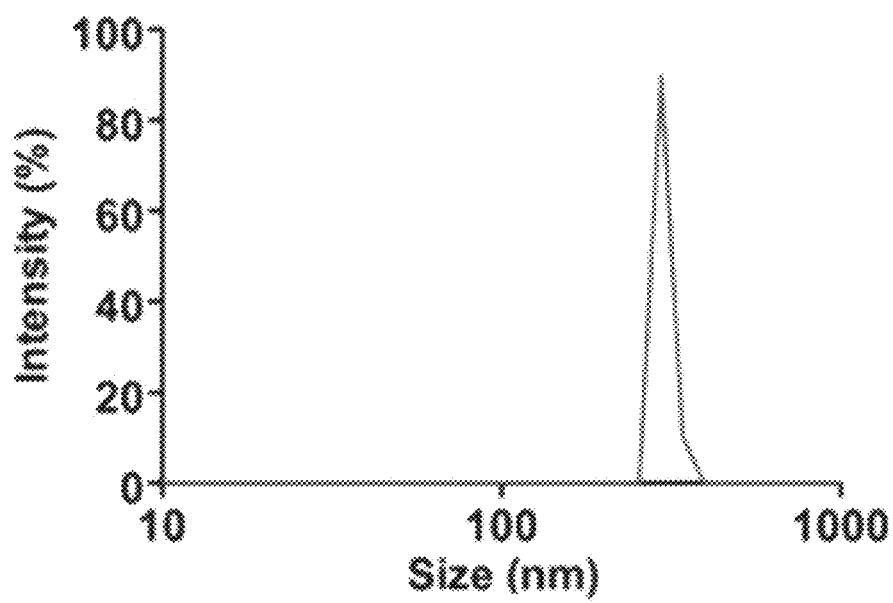
Figure 1H:
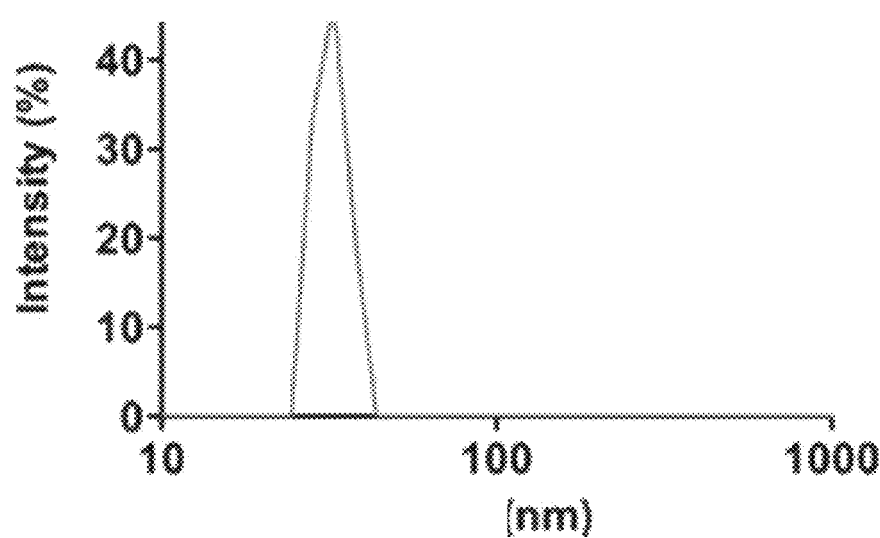
Figure 1I:
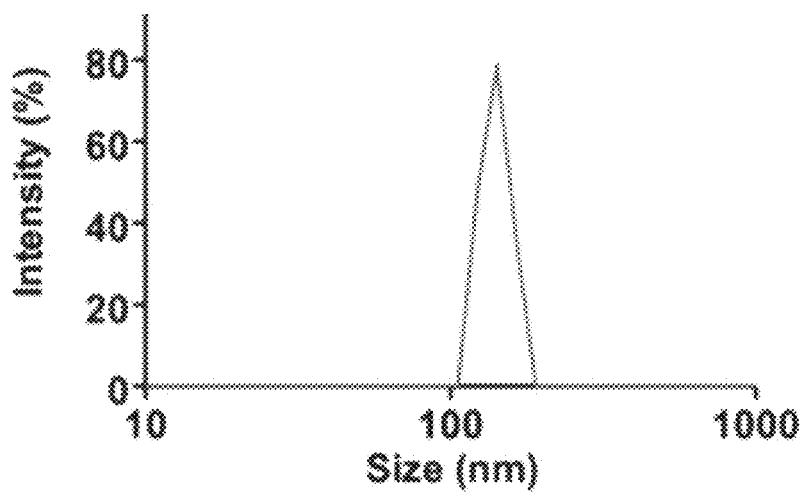

Example 1: Physical Characterization $TiO_2$ typically exists in two tetragonal forms, anatase and rutile, which differ in their crystal lattice structure[23]. We employed anatase form for CR-PDT studies because of its smaller size (<25 nm) and higher photoactivity than the rutile form. The higher photoactivity of anatase is mainly due to the extent and nature of surface hydroxyl groups that are generally associated with the surface of colloidal $TiO_2$ in water[24]. In its native state, $TiO_2$ exhibits concentration dependent cytotoxicity, and unlike PDT, this toxicity cannot be controlled[25,26]. To eliminate this undesirable effect and improve biocompatibility, we coated the nanoparticles separately with polyethylene glycol (PEG) and dextran (FIG. 1A-C). We synthesized $TiO_2$-PEG and $TiO_2$-Dextran conjugates by reacting $TiO_2$ with PEG (Molecular Weight: 400 Da) or dextran (Molecular Weight: 5,000 Da) in a sonicator to facilitate formation of Ti—O—C bonds. These bonds are a result of a combination of molecular adsorption and condensation reactions[27]. Transmission electron microscope (TEM) analysis showed that these modifications transformed the $TiO_2$ nanoparticle aggregates into monodisperse nanoparticles and small nanoclusters for PEG and dextran coatings, respectively (FIG. 1D-F). Possibly, each dextran chain, which is significantly longer than PEG, interacted with multiple $TiO_2$ particles, creating a network of $TiO_2$ nanoclusters. Solution phase characterization of nanoparticles suggests well-defined dispersions and neutral charge densities after PEG and dextran coating (FIG. 1G-I and Table 1).

TABLE 1

Physico-chemical characterization of bare and coated $TiO_2$ nanoparticles.

| Sample | Hydrodynamic Diameter (nm) | Polydispersity Index | Zeta Potential (mV) | Mobility (μmcm/Vs) |
|---|---|---|---|---|
| $TiO_2$ | 454 ± 40 | 1.00 | −17.1 ± 4.6 | −1.34 |
| $TiO_2$-Dextran (MW: 5,000) | 110 ± 23 | 0.44 | 0.6 ± 3.7 | 0.04 |
| $TiO_2$-PEG (MW: 400) | 30 ± 6 | 0.26 | 4.3 ± 3.6 | 0.33 |

The hydrodynamic size and zeta potential of the coated and uncoated $TiO_2$ nanoparticles in phosphate buffered saline (PBS) were measured using a Malvern Zetasizer. Hydrodynamic diameter was extracted by cumulant analysis of the data and Polydispersity index from cumulant fitting. Each value is the average of three experiments ± s.e.m.

Example 2: In Vitro CR-PDT

Figure 6:
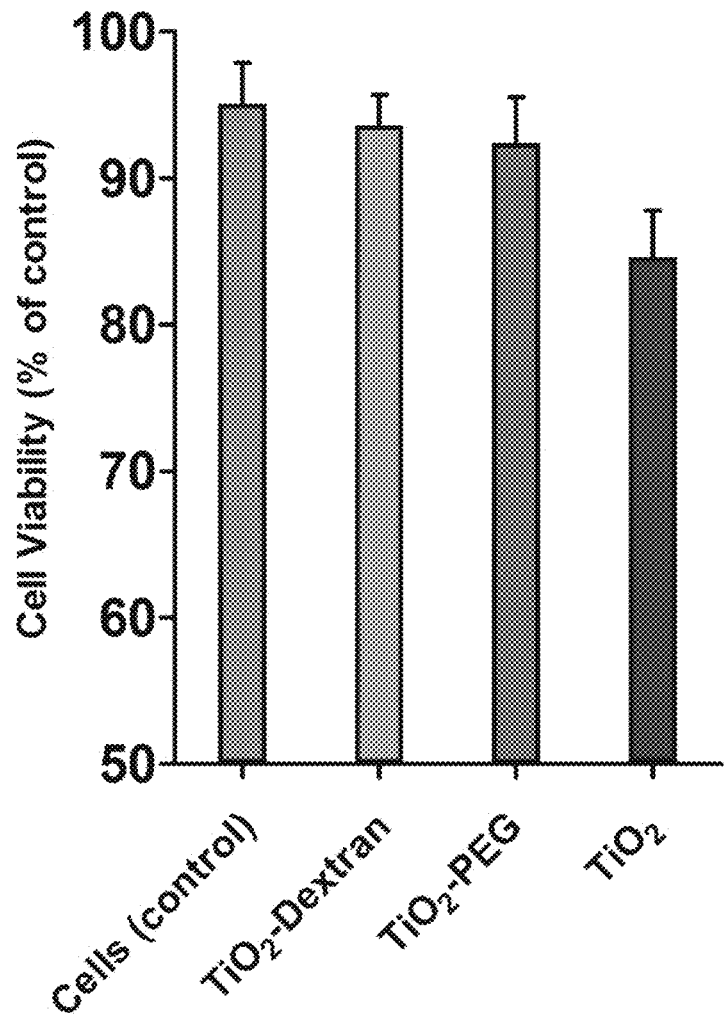
FIG. 6 depicts a comparison of cytotoxicity of 3 μg/ml $TiO_2$ and its adducts, $TiO_2$-PEG and $TiO_2$-dextran, using MTS assay.

We assessed the biocompatibility of $TiO_2$, $TiO_2$-PEG, and $TiO_2$-dextran nanoparticle (FIG. 6). $TiO_2$ particles are known to induce apoptosis in cells at concentrations exceeding 5 pg/ml through the caspase-8 (initiator) to caspase-3 (effector) pathway[28]. Hence, it is important to delineate intrinsic toxicity from CR-mediated phototoxicity.

Figure 2A:
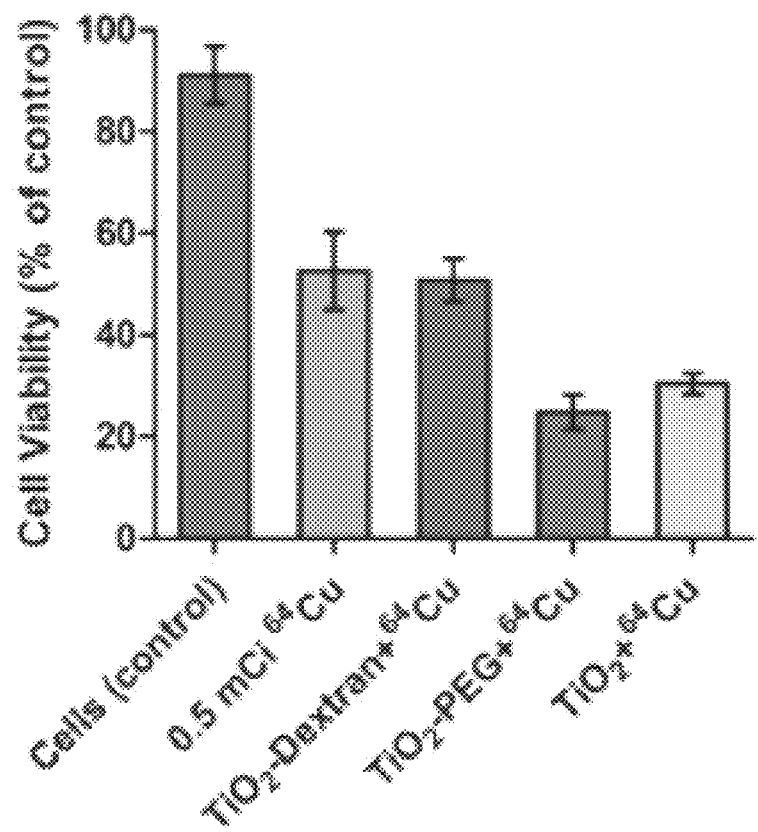
FIG. 2A, FIG. 2B, FIG. 2C, FIG. 2D, FIG. 2E and FIG. 2F depict graphs, images and an illustration of in vitro CR-PDT using $TiO_2$ and $^{64}Cu$.
Figure 7A:
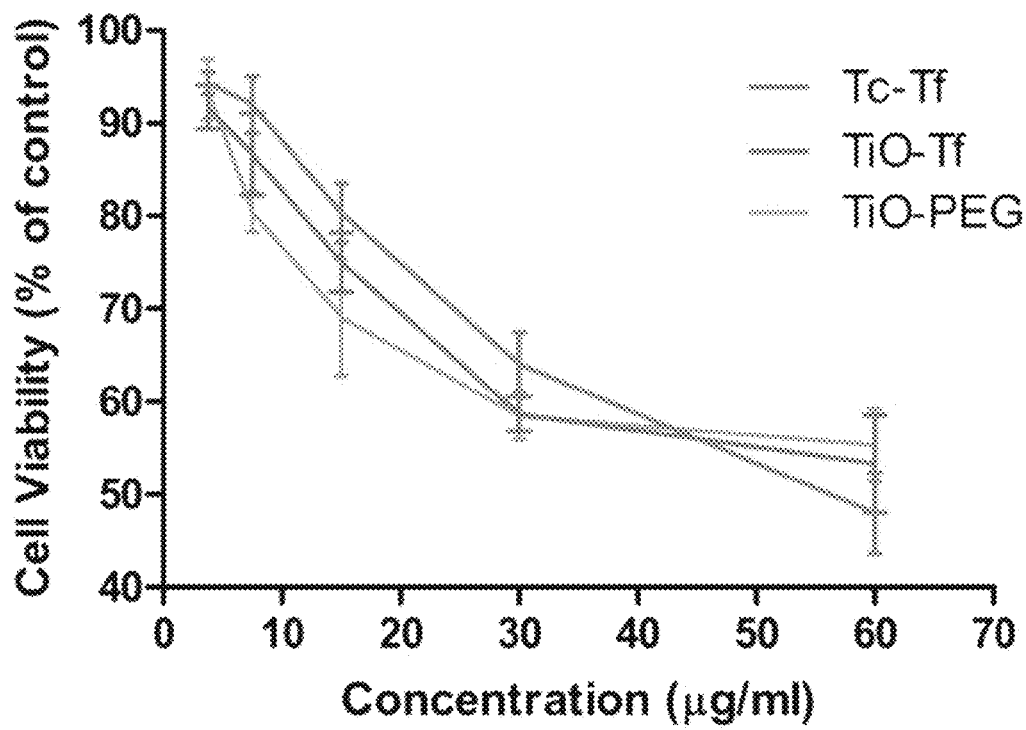
FIG. 7A and FIG. 7B depict the effect of photosensitive particles and radionuclides on cell viability.
Figure 7B:
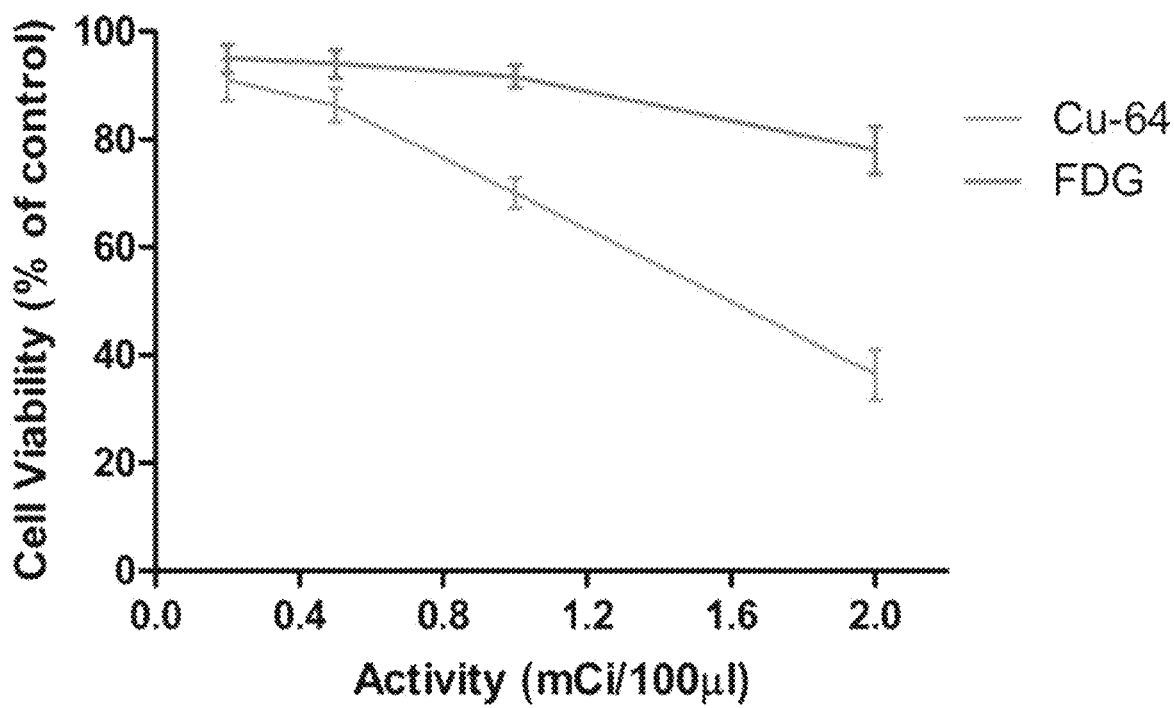
Figure 8:
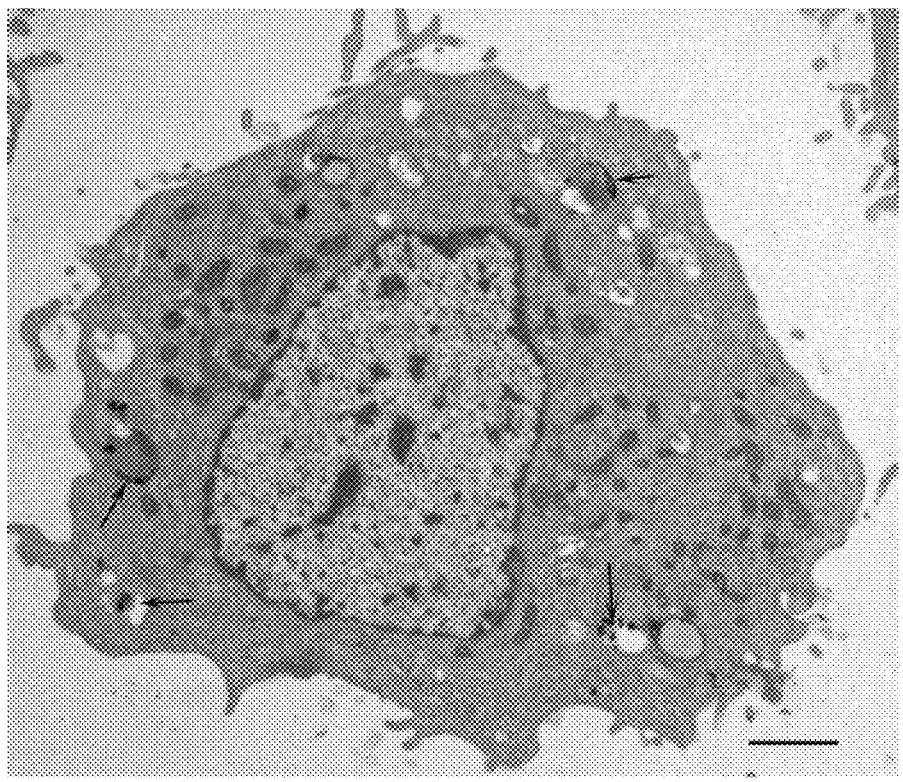
FIG. 8 depicts a TEM image of HT1080 cell with $TiO_2$-Tf in the endo-lysosomal compartments (arrows). Scale bar, 2 μm.

We found that $TiO_2$ particles did not induce apoptosis at <4 pg/ml and that $^{64}Cu$ was non-toxic at activity <0.25 mCi (FIG. 7). Therefore, we used these nontoxic doses of TiO$_2$ (2.5 pg/ml) and $^{64}$Cu activity (<0.25 mCi) to determine the effects of surface coating on PDT. Biologically inert PEG and dextran are known to prevent nonspecific uptake of nanoparticles by cells[29]. However, we observed that TiO$_2$ particles permeated into cells, irrespective of surface coating or cell type. This indiscriminate cellular uptake suggests a nonspecific endocytosis mechanism most likely through macropinocytosis, with "leaky" vesicles that are usually 500-2,000 nm in diameter[30]. Most of the nanoparticles eventually localize in the lysosomes when the macropinosomes merge into late endosomes and lysosomes (FIG. 8). When treated with $^{64}$Cu, the cell viability of TiO$_2$-Dextran and TiO$_2$-PEG loaded cells were 52% and 24%, respectively, compared to the untreated cells (FIG. 2A). The enhanced PDT effect of TiO$_2$-PEG can be attributed to the nature of surface coating. Photocatalysis is a surface phenomenon that mediates the PDT effect of TiO$_2$. Excessive adsorption of the polymers usually shields the particles from absorbing incident UV light. This phenomenon can limit the redox reaction that occurs on the surface and severely compromise the efficiency of the hydroxyl radical generation process. In contrast to TiO$_2$-PEG, the relatively higher Molecular Weight (MW) of dextran probably favored a denser surface coverage, a process that would considerably reduce the exposed TiO$_2$ surface area. This eventually translates to lower photocatalytic potential and decreased PDT effect.

Figure 2B:
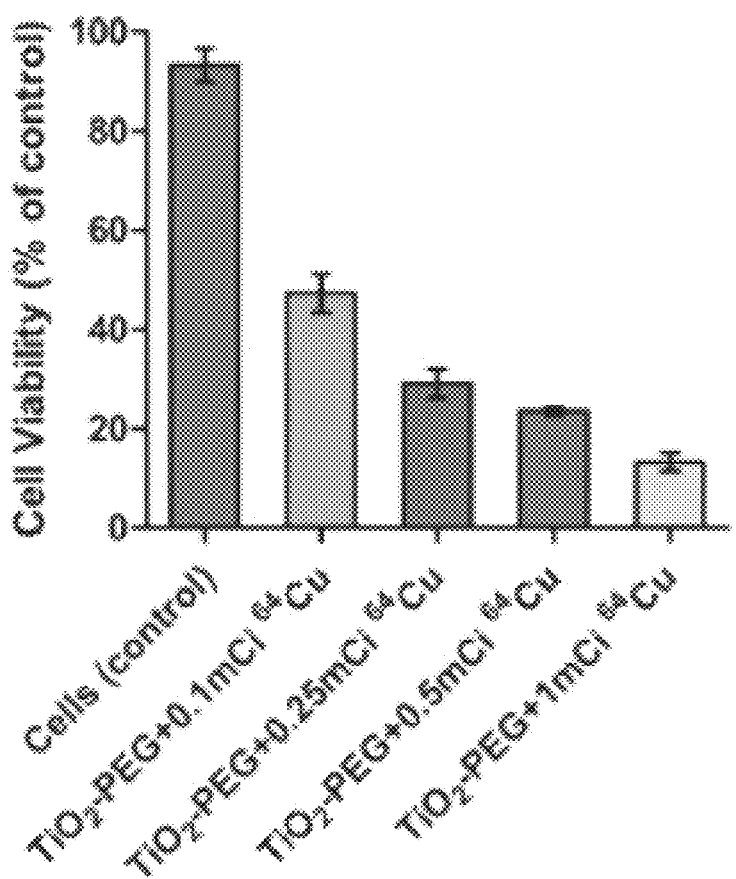
Figure 2C:
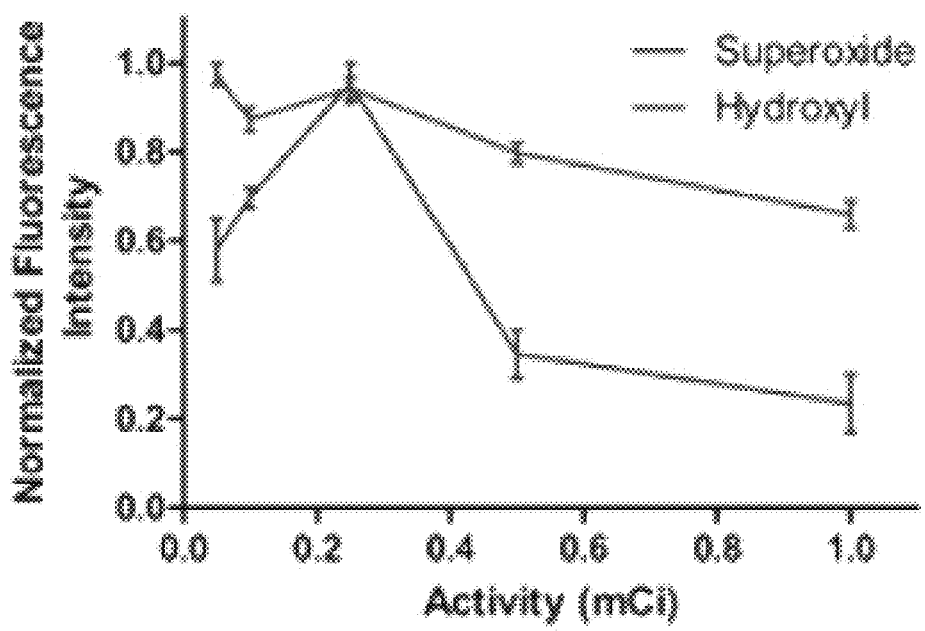
Figure 9:
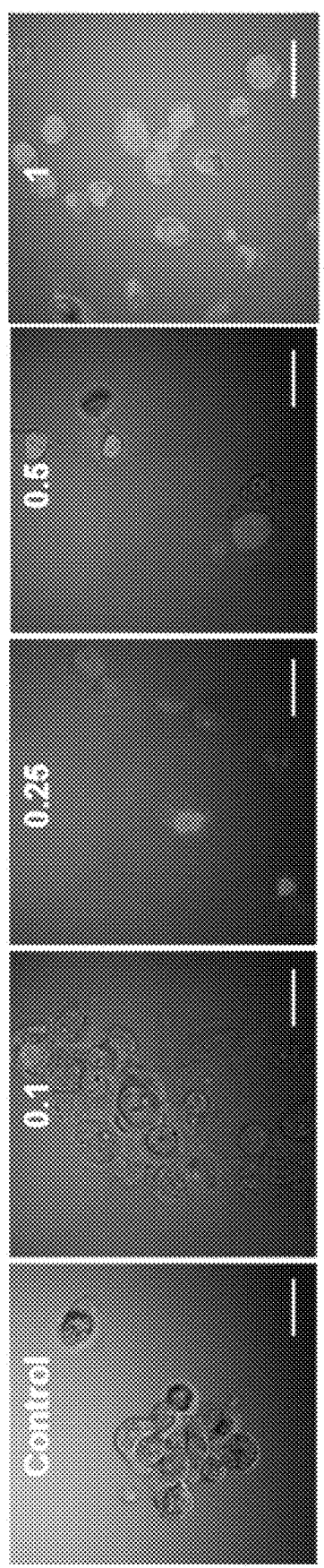
FIG. 9 depicts confocal microscopy images of merged bright-field and fluorescence images comparing the degree of necrotic cell death caused by 0.1, 0.25, 0.5, 1 mCi/100 μl of 64Cu on tumor cells with 2.5 μg/ml $TiO_2$-PEG after 72 h. PI dye was used to stain nuclei as a measure of cell viability. Majority of cells incubated with >0.1 mCi/100 μl of $^{64}$Cu stained positive with PI. Scale bar, 20 μm.
Figure 10:
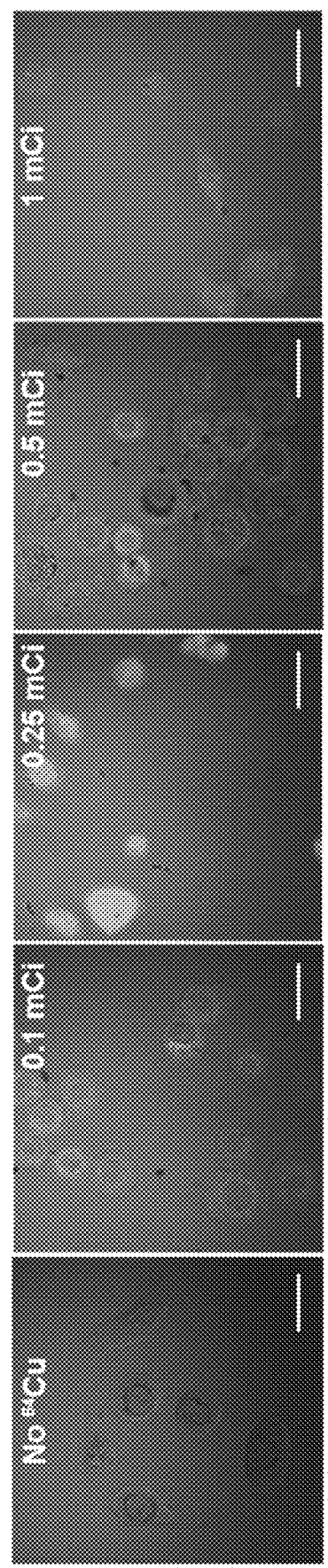
FIG. 10 depicts confocal images of merged bright-field and fluorescence images comparing the degree of hydroxyl radical generation caused by 0.1, 0.25, 0.5, 1 mCi/100 μl of $^{64}$Cu on tumor cells with 2.5 μg/ml $TiO_2$-PEG after 4 h. HPF dye was used to stain the cells. The green fluorescence from cells depicts increased hydroxyl radical generation. Highest fluorescence intensity was recorded from cells incubated with 0.25 mCi/100 μl of $^{64}$Cu. Scale bar, 20 μm.

We further characterized TiO$_2$-PEG adducts to determine the lowest activity of $^{64}$Cu required to induce optimal PDT effect. We observed significant cell death at 0.1 mCi (FIG. 2B and FIG. 9). Quantitative assays using Hydroxyphenyl fluorescein (HPF) for hydroxyl radicals and Mitosox dye for superoxide radical confirmed relatively high levels of both the species at lower (≤0.25 mCi) than higher (>0.25 mCi) $^{64}$Cu (FIG. 2C and FIG. 10). This result suggests that hydroxyl and superoxide radical generation from TiO$_2$ is highest at 0.25 mCi, which is consistent with a previous report that demonstrated maximum photocatalytic activity at low UV light intensity, caused by recombination losses occurring at higher intensities[31].

Figure 2D:
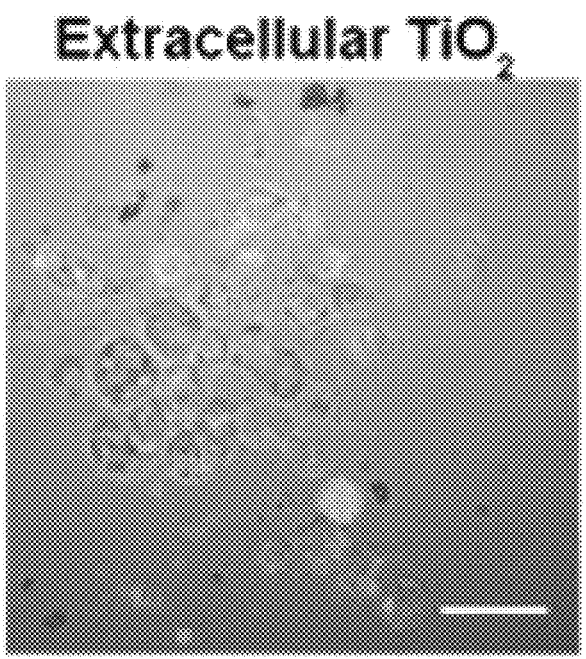
Figure 2E:
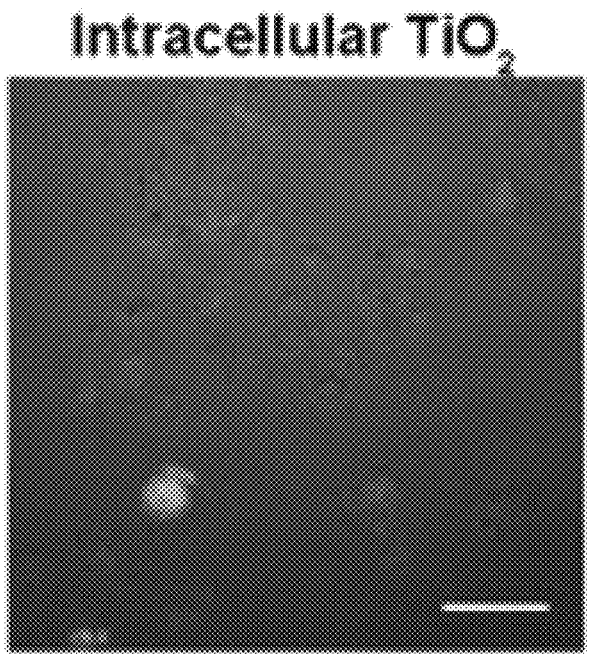
Figure 2F:
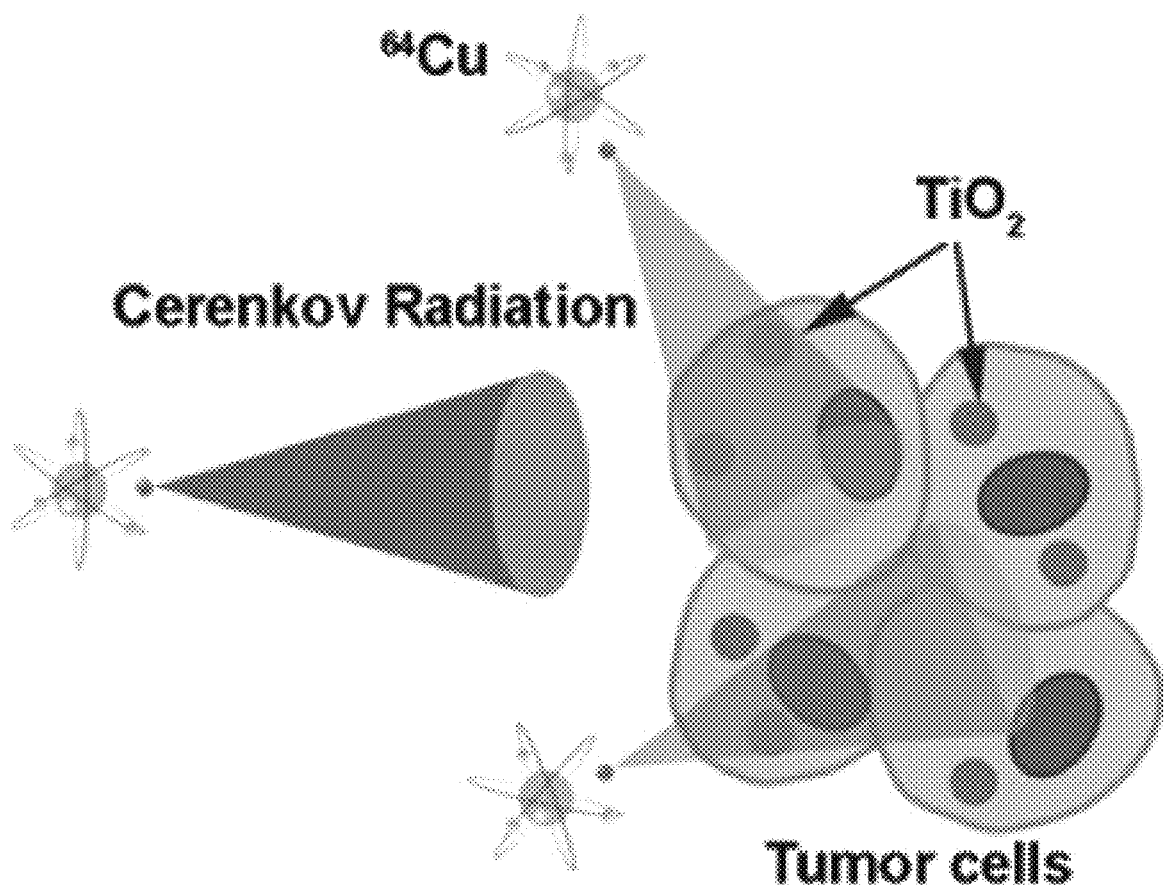

Hydroxyl radicals, which propagate within short distances (up to ~3 nm) are extremely short lived species with an in vivo half-life of $10^{-9}$ s[32,33]. They are highly reactive species, non-diffusible across cell membranes, culminating into a highly pronounced local action[34]. In contrast, superoxide radicals are more stable species that can travel across cell membranes with a long diffusion distance of ~320 nm[35]. Therefore, we evaluated the cytocidal effect of intracellular versus extracellular TiO$_2$ particles after treatment with $^{64}$Cu (0.25 mCi). We observed that a majority of the cells (>95%) with extracellular TiO$_2$ were viable (green), but cells loaded with intracellular TiO$_2$ were mostly necrotic (red) as shown in FIG. 2D,E. The minimal PDT effect on cells with extracellular TiO$_2$ strongly suggests that hydroxyl instead of superoxide radicals are responsible for the cytotoxic effect. However, the PDT outcome is less dependent on the intracellular or extracellular distribution profile of $^{64}$Cu because the UV rays produced by CR are capable of traversing cell membranes to activate the TiO$_2$ particles (FIG. 2F).

Example 3: TiO$_2$ Imaging

Figure 3A:
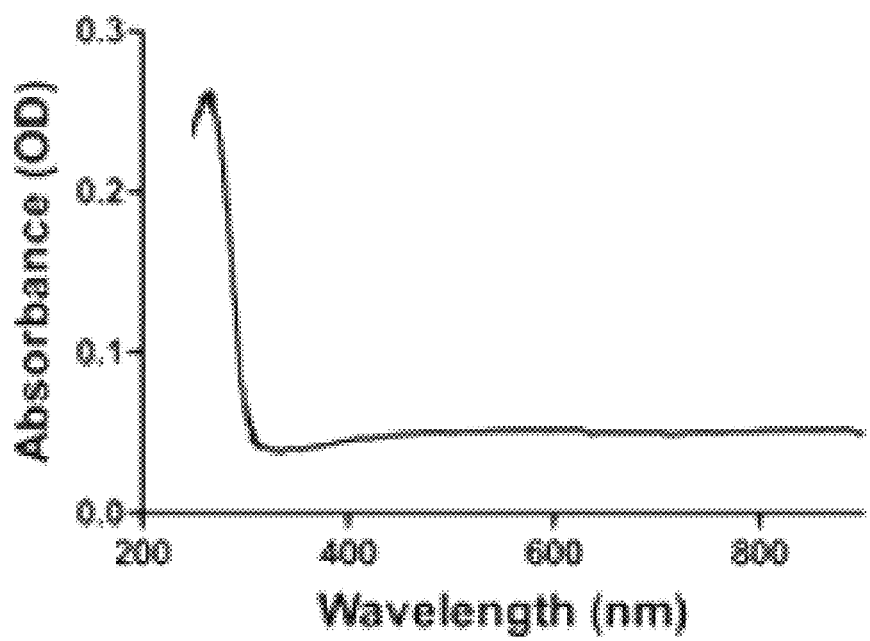
FIG. 3A, FIG. 3B, FIG. 3C, FIG. 3D, FIG. 3E and FIG. 3F depict graphs and images of in cellulo fluorescence imaging of $TiO_2$.
Figure 3B:
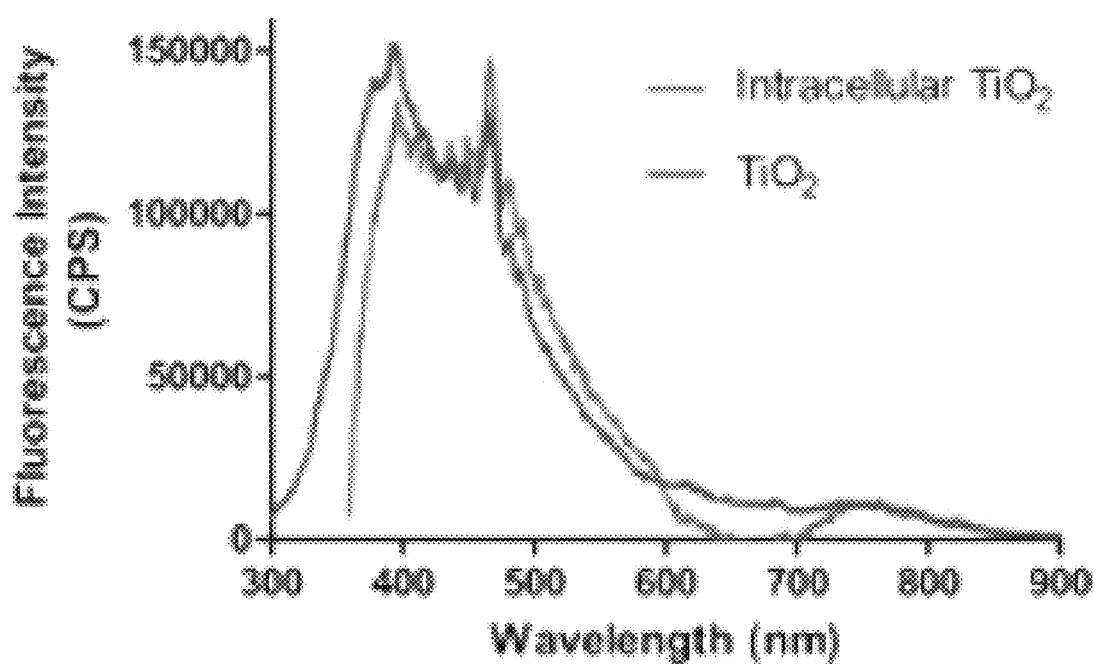
Figure 3C:
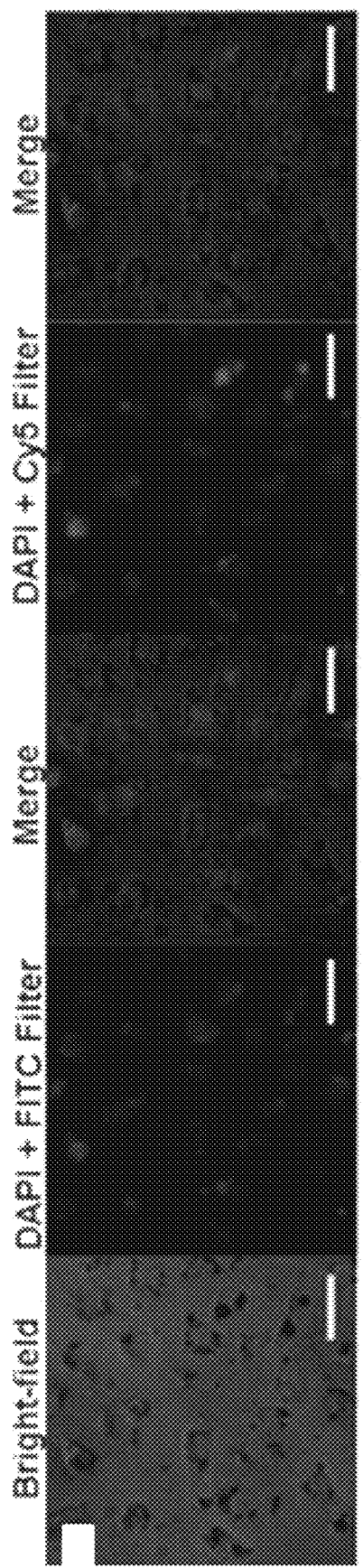
Figure 3D:
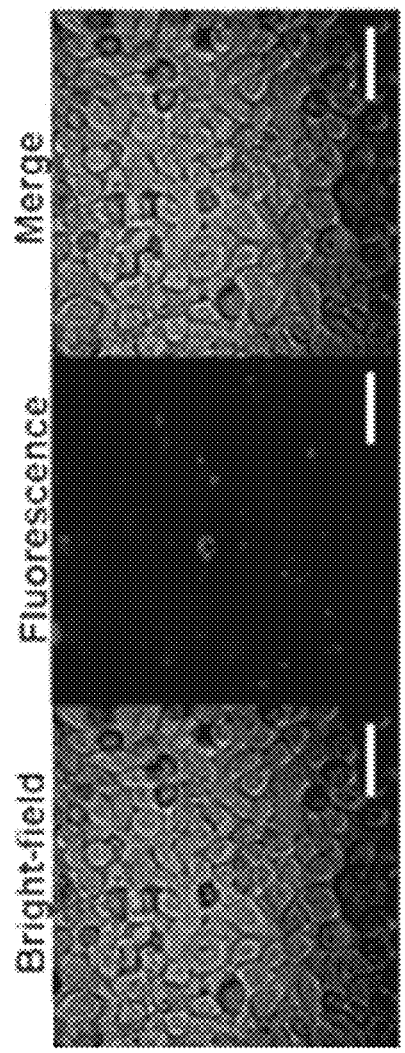
Figure 3E:
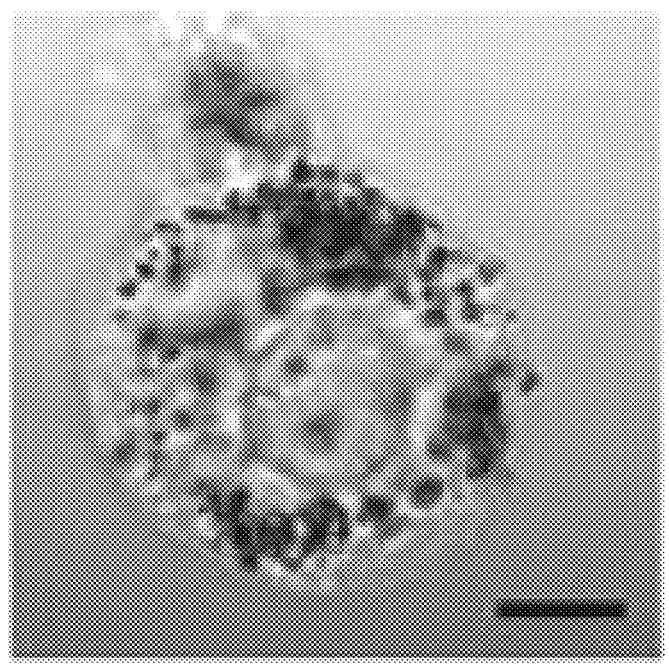
Figure 3F:
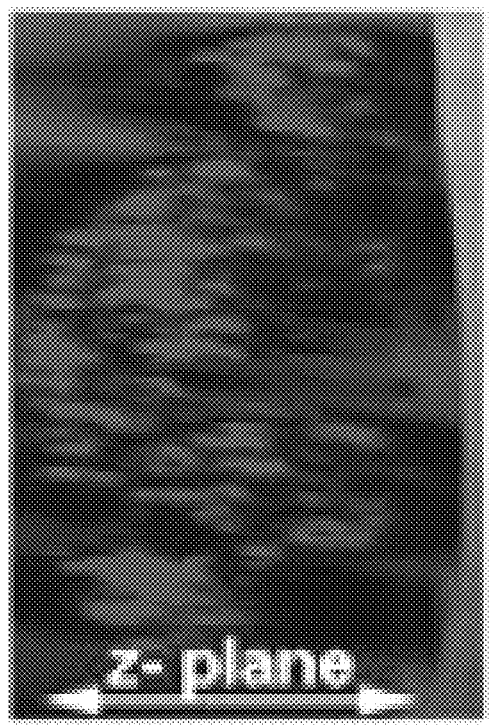
Figure 11:
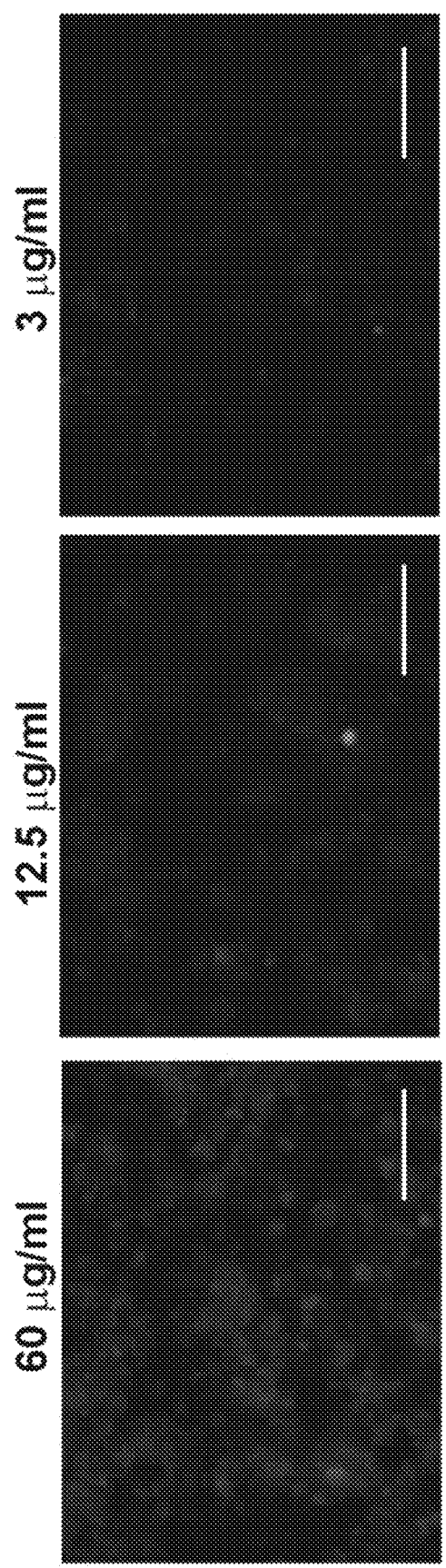
FIG. 11 depicts epifluorescence images of BxPC-3 cells with internalized $TiO_2$-PEG at various concentrations with an exposure time of 450 ms and 4×4 binning using Cy5 filter with an excitation and emission wavelength of 630 nm and 700 nm, respectively. Scale bars: 150 μm.
Figure 12A:
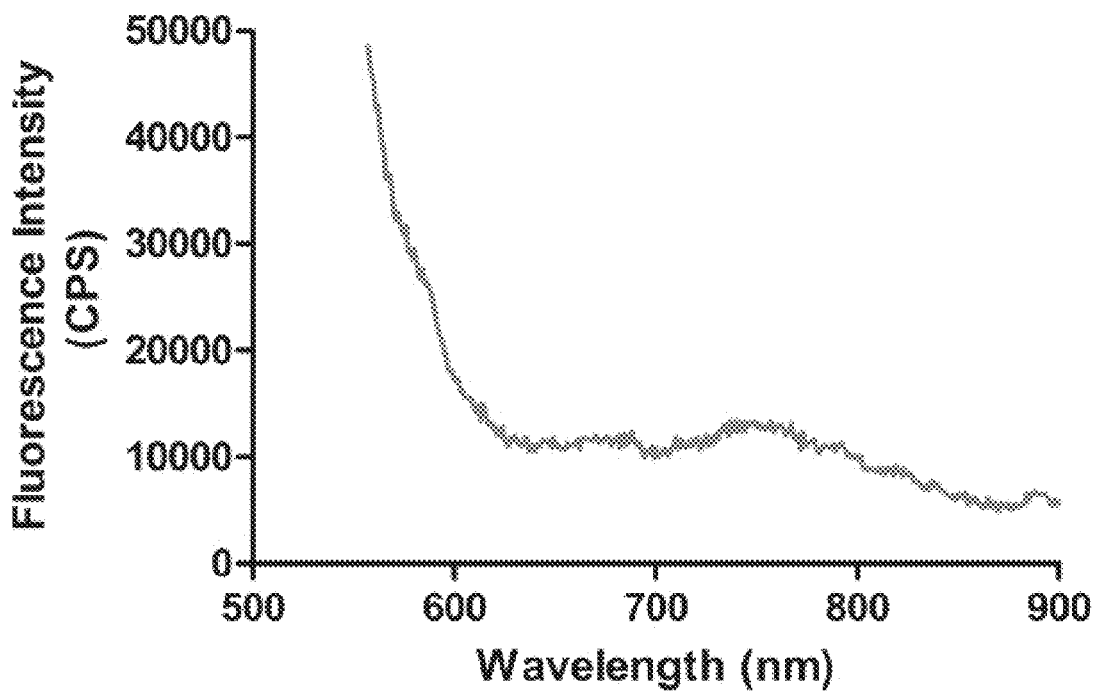
FIG. 12A and FIG. 12B depict the fluorescent spectrum of $TiO_2$ particles.
Figure 12B:
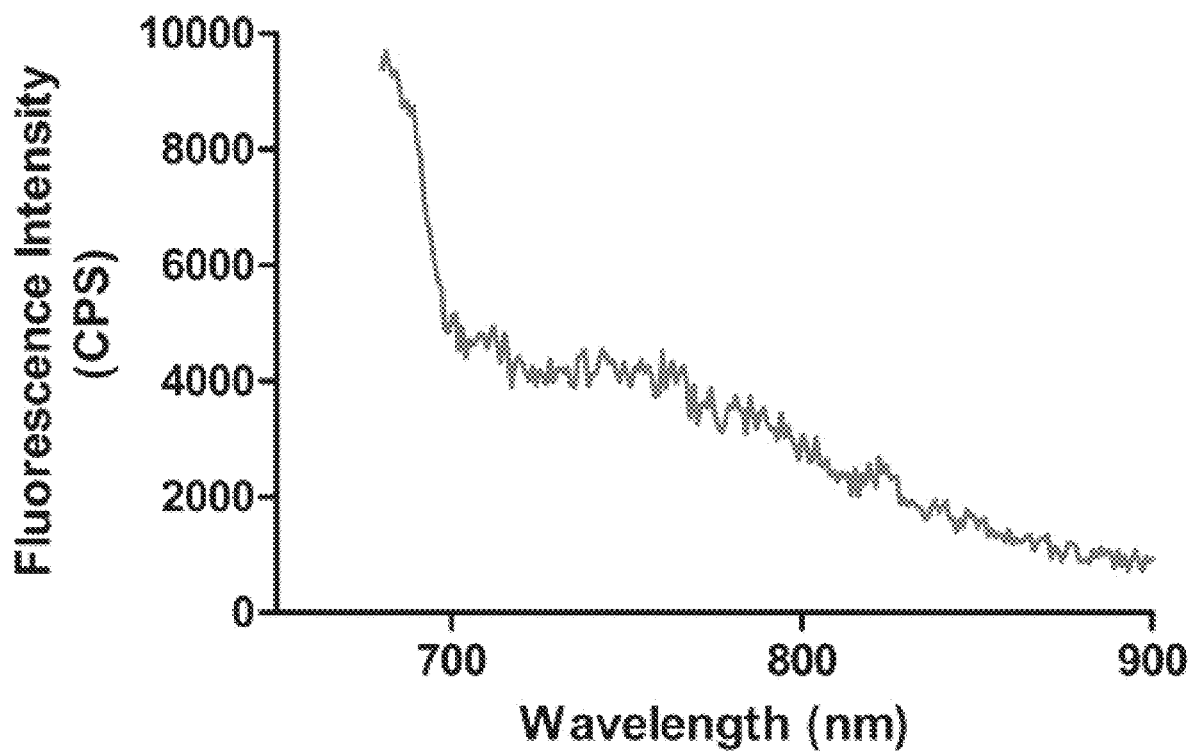

Photoluminescence of anatase TiO$_2$ as an indirect band gap semiconductor is well documented[36,37]. It is characterized by strong absorption in the UV region (λ=274 nm), relatively strong luminescence in the visible region at 391 nm and 465 nm, and weak emissions at 749 nm (FIG. 3A). However, there are no reports on exploiting the photoluminescence of TiO$_2$ for in vitro and in vivo optical imaging. In this study, we observed luminescence in cells containing TiO$_2$ with concentrations as low as 3 pg/ml (FIG. 3C and FIG. 11). This is consistent with our spectroscopic studies where no marked change in the luminescence profile of cell internalized vs. cell-free TiO$_2$ nanoparticles (FIG. 3B) was noticed. The coating of TiO$_2$ by PEG also did not alter the nanoparticles' luminescence (FIG. 3C,D). The strong luminescence of TiO$_2$ was used to determine the spatial distribution and localization of TiO$_2$ within cells and tissue. Epifluorescence microscopy revealed the broad excitability and imaging of intracellular TiO$_2$ using both FITC (Excitation/Emission: 490/545 nm) and Cy5 (Excitation/Emission: 630/710 nm) filter sets (FIG. 3C). Fluorescence spectroscopic studies also confirmed their excitability at 488 nm and 633 nm (FIG. 12). Interestingly, the cell labeling concentration of TiO$_2$ is within the limit of conventional fluorescent nanoparticles (11 ng/ml-60 μg/ml), allowing the use of this approach for routine cell imaging studies. Confocal microscopy revealed distinctly identifiable crystalline luminescent particles, evenly distributed in the cytoplasm (FIG. 3E). A z-scan 3D reconstruction of the cell shows the particles well dispersed in the cytoplasm around the nucleus (FIG. 3F).

Figure 4A:
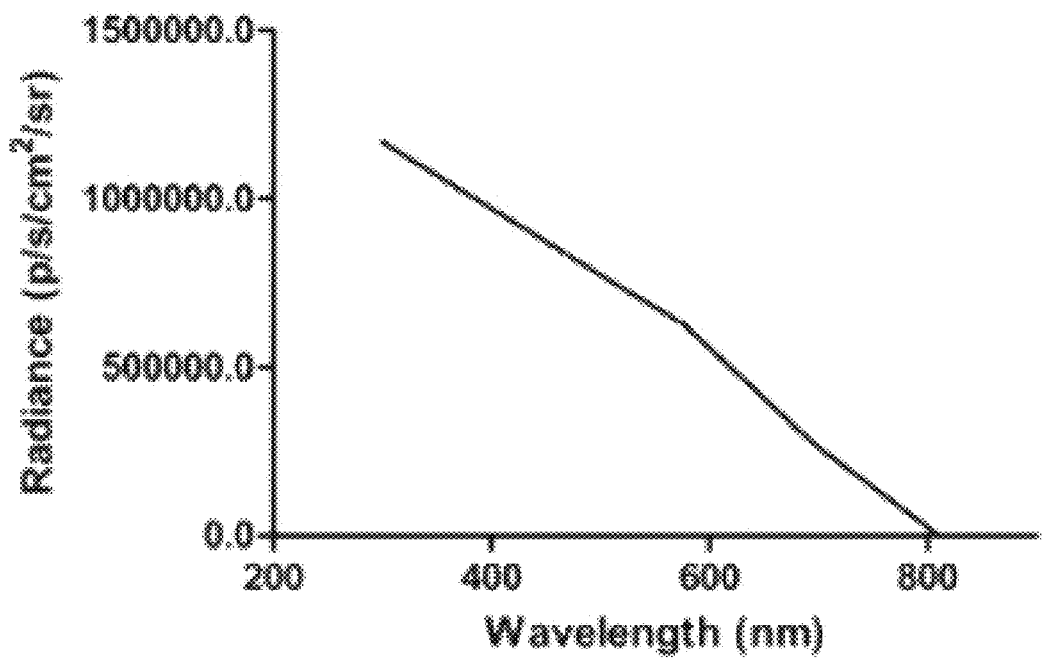
FIG. 4A, FIG. 4B, FIG. 4C, FIG. 4D and FIG. 4E depict graphs and images of in vivo luminescence imaging of $TiO_2$.
Figure 4B:
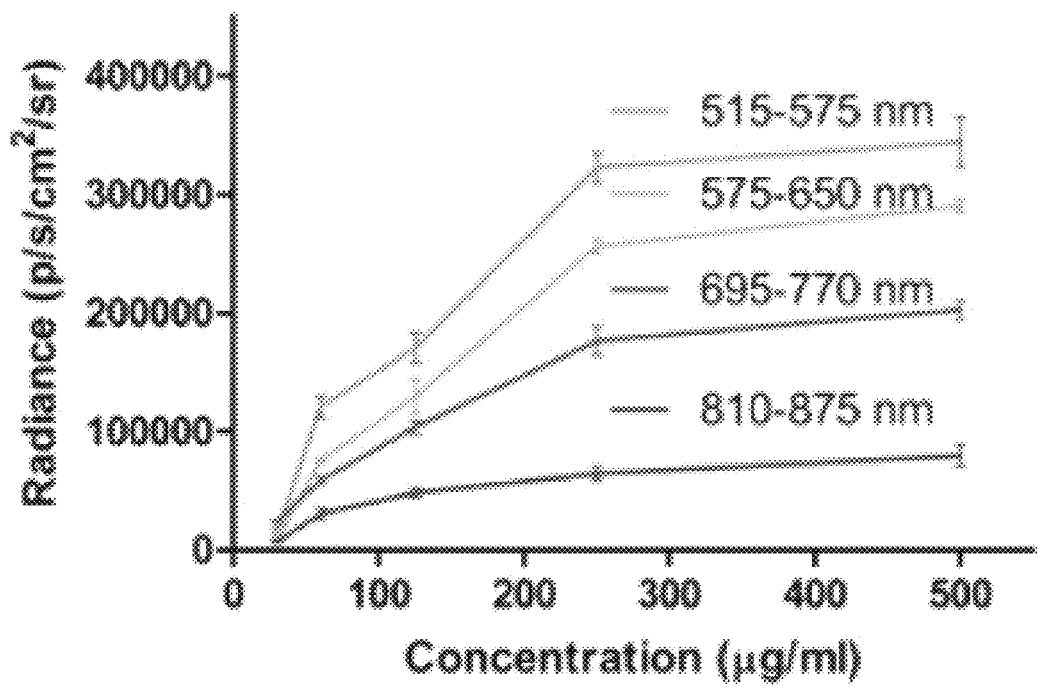
Figure 4C:
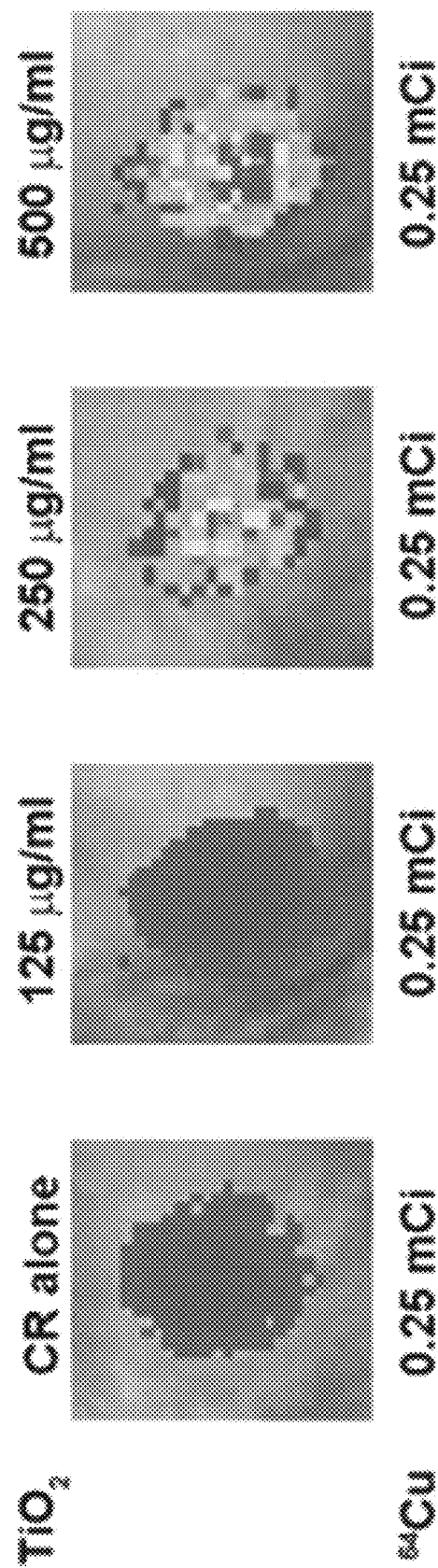
Figure 4D:
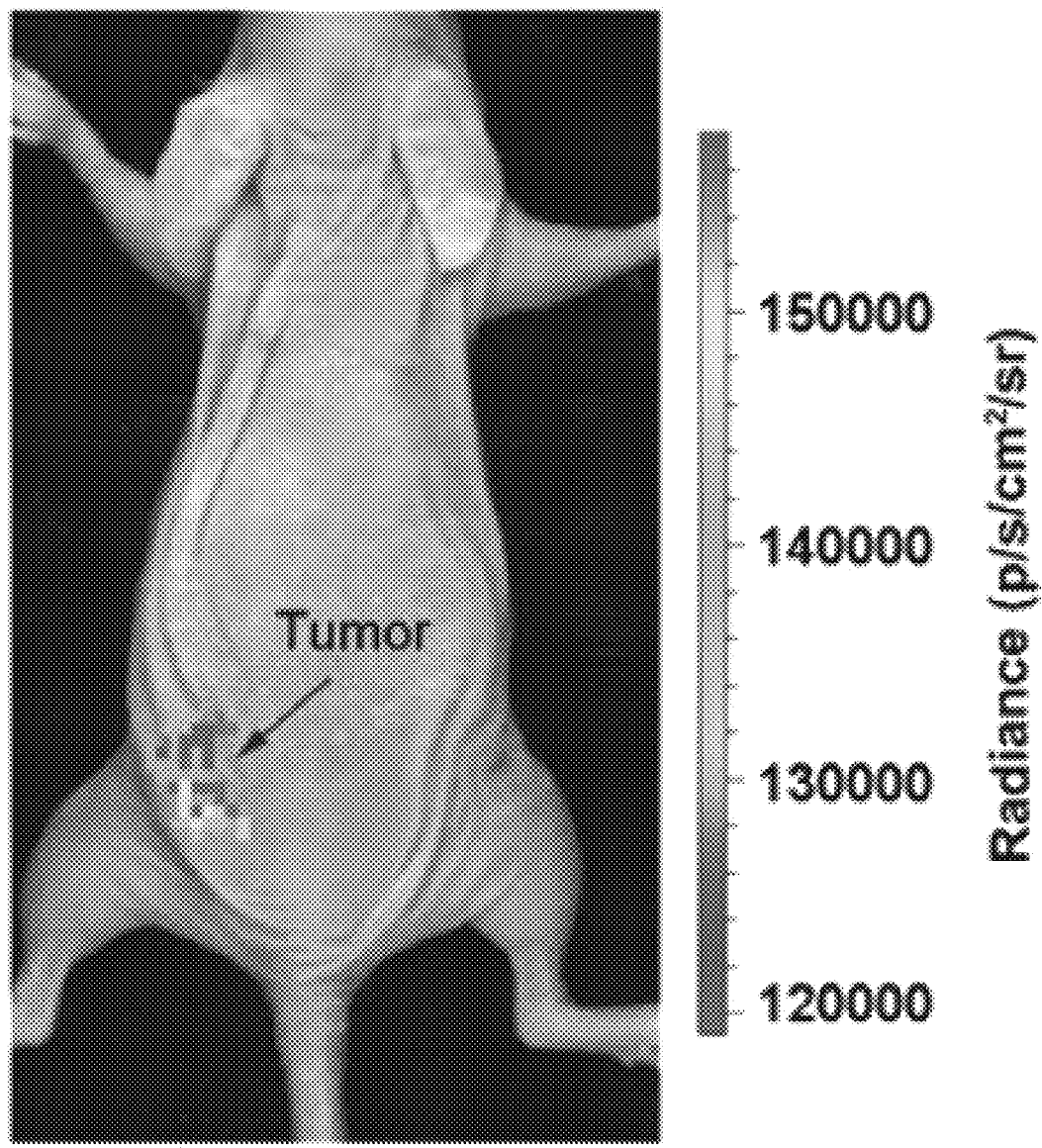
Figure 4E:
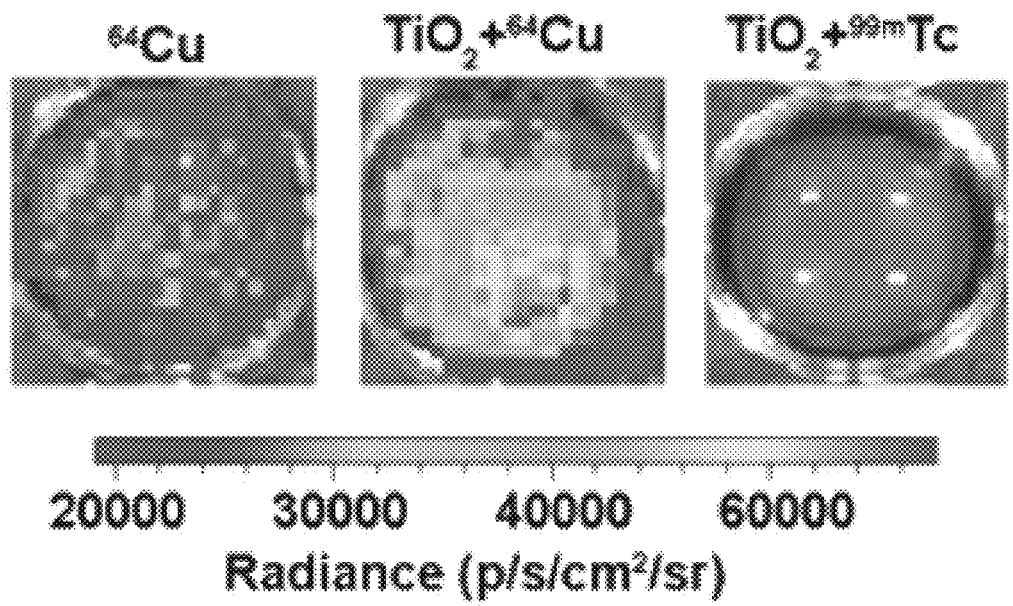

Consistent with the broad CR spectral range that tapers off from the UV to the far visible region (FIG. 4A), we observed that the luminescence of different stoichiometric amounts of TiO$_2$ decreased with increasing wavelength (FIG. 4B). Since absorption and scattering by tissues will play a major role in in vivo imaging of TiO$_2$ luminescence, the minimum detectable concentration in vivo subcutaneous tumor mimics was determined. We did not detect appreciable radiance below 250 pg/ml of TiO$_2$ (FIG. 4C). The increase in detection threshold from 3 pg/ml of TiO$_2$ in vitro to 250 pg/ml of TiO$_2$ in vivo can be ascribed to enhanced attenuation of visible light by endogenous absorbers and scattering effects of tissue. Substitution of CR with external excitation light did not result in observable luminescence. Although TiO$_2$ nanoparticles possess significant NIR luminescence, the result demonstrates that UV and visible light, which has limited penetration depth in tissue, dominates the photoactivity of TiO$_2$. Finally, we demonstrated the feasibility of using TiO$_2$ luminescence to image solid tumors in vivo following CR excitation of the nanoparticles. Similar luminosity seen in the tumor mimics was observed in the pancreatic tumor xenografts injected with 0.25 mCi of $^{64}$Cu and 250 pg/ml of TiO$_2$ (FIG. 4D). $^{64}$Cu was compared to $^{99m}$Tc, a pure γ emitter, to demonstrate that CR was the excitation source for TiO$_2$ luminescence. The result shows that only $^{64}$Cu was able to induce luminescence in TiO$_2$ (FIG. 4E). This result is consistent with the required minimum energy of 263 keV for a β particle to produce CR[38], which is not attained by the 140 keV $^{99m}$Tc γ emitter.

Example 4: In Vivo CR-PDT of Tumor Mimics

Figure 5A:
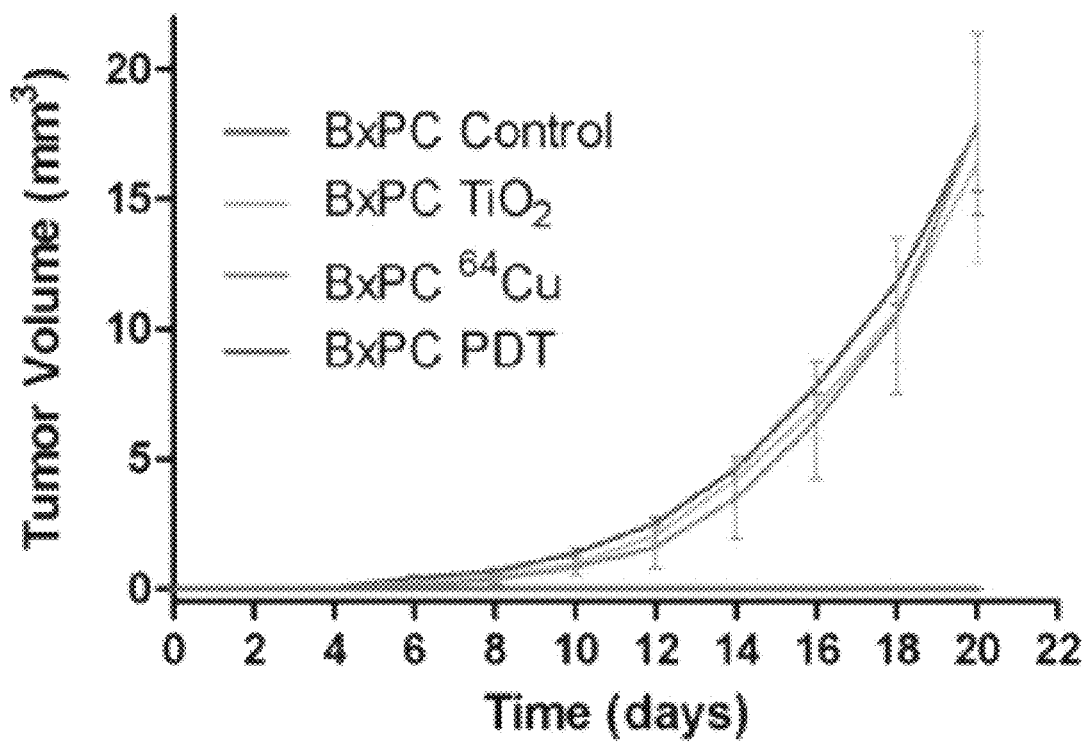

Motivated by the efficient in vitro PDT and appreciable luminescence of TiO$_2$-PEG, we explored in vivo PDT and imaging studies using subcutaneously injected cancer cells to mimic tumor mass. Pancreatic cancers are known to be extremely refractory to chemotherapy because of the extensive extracellular stromal encapsulation of the tumor cells and the low vascularity that impedes drug delivery into tumor cells[39]. Therefore, we chose the aggressive pancreatic tumor cell line, BxPC-3, for this study. The cells were loaded with TiO$_2$-PEG and $^{64}$Cu, as well as control models that include BxPC-3 cells alone, TiO$_2$-PEG loaded cells, and $^{64}$Cu-loaded cells. Tumor growth was inhibited in the mice treated with TiO$_2$-PEG and $^{64}$Cu loaded cells up to 30 days post-treatment (FIG. 5A). In contrast, tumor growth of up to 18±3 mm$^3$ was observed in all three controls within 14-16 days post-treatment. This result suggests that PDT mediated by the combined TiO$_2$-PEG and $^{64}$Cu can inhibit the progression of the initial tumor cells to form a tumor mass, thereby eradicating tumor survival. The rapid development of solid tumors from the seed cultures in the control mice indicates minimal dark toxicity of these individual components in vivo at the administered doses.

Example 5: In Vivo CR-PDT of Tumor Xenografts

Figure 5B:
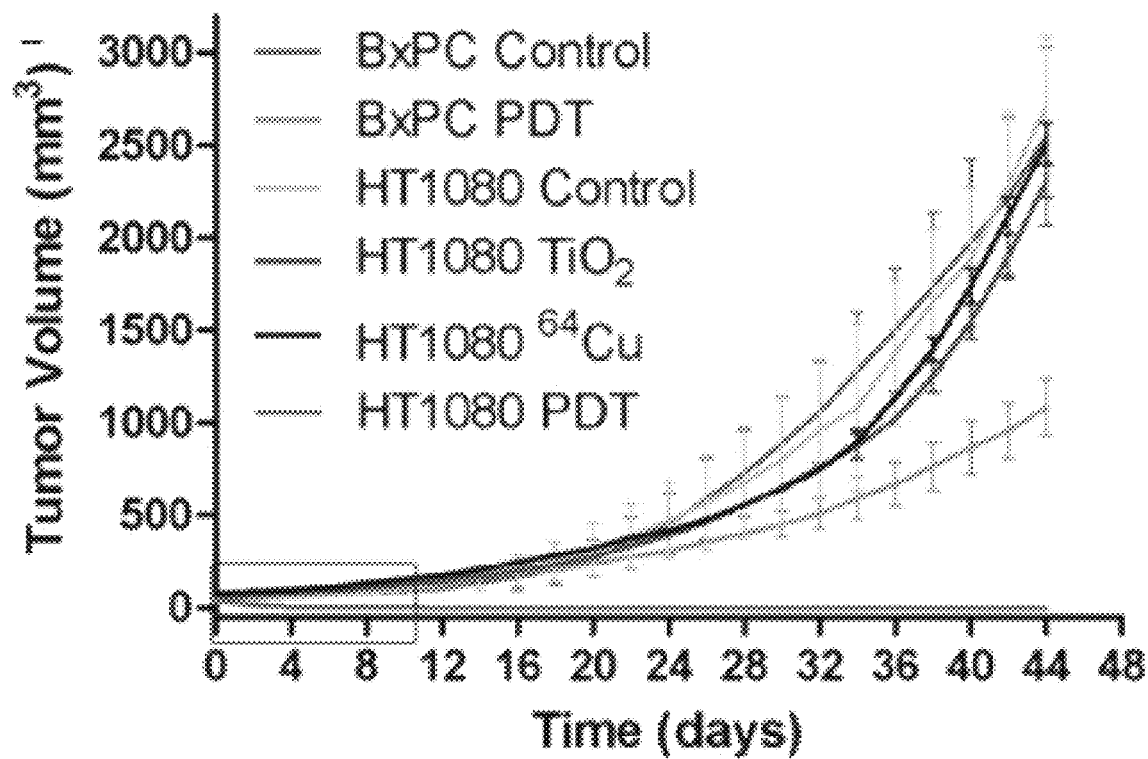
Figure 5C:
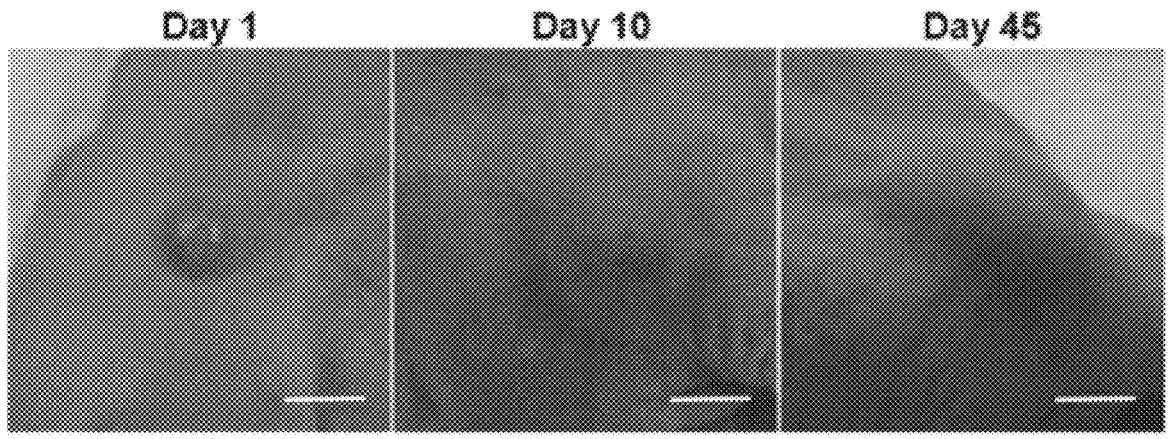
Figure 5D:
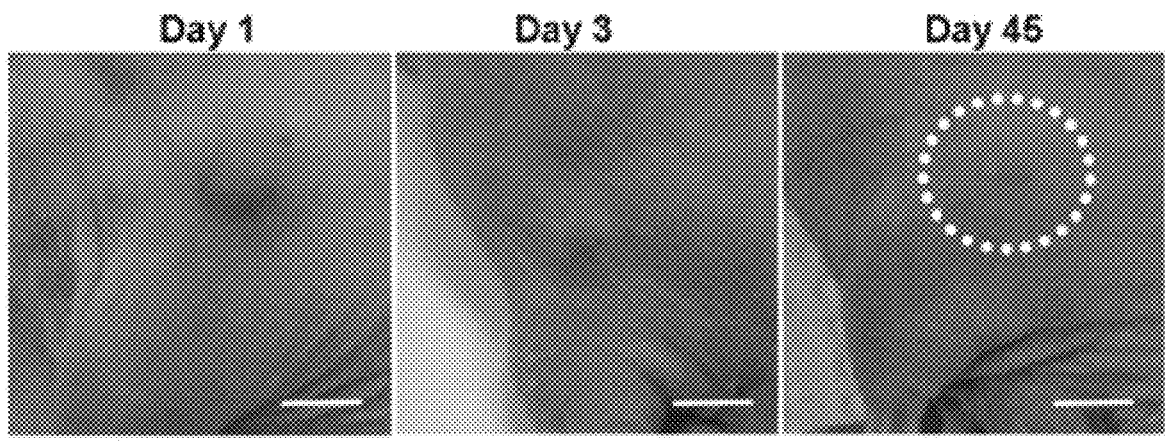

The seed culture method described above demonstrates a strong synergistic cytocidal PDT effect between TiO$_2$ and $^{64}$Cu. This led us to explore the translation of the findings to solid tumor xenografts using BxPC-3 and HT1080 fibrosarcoma cell lines. Unlike BxPC-3 cells which rapidly form solid tumors, HT1080 cells form unencapsulated tumors with relatively extensive vascularity[40]. These two distinct histopathologic tumor types provide a unique platform to assess the efficacy of TiO$_2$-$^{64}$Cu PDT in vivo. We observed shrinkage of the tumor volume (TV) by a remarkable 40±5% in HT1080 tumor bearing mice after 48 h (FIG. 5B,D). However, the mice with BxPC-3 tumors did not show any signs of regression even after 10 days (FIG. 5C). At this point, a second dose of the TiO$_2$-$^{64}$Cu cocktail was administered. The mice were observed for a total of 60 days without any measurable sign of BxPC-3 tumor regression. Nonetheless, the growth of treated BxPC-3 tumor masses progressed at a slower rate (TV at day 60=1050±150 mm$^3$) compared to untreated control tumors (2570±500 mm$^3$), extending mean survival time nearly two-fold (FIG. 5B). On the contrary, all treated mice with the HT1080 tumors showed complete regression by 45 days and did not require additional treatment to maintain this effect (FIG. 5B,D). Further monitoring of the PDT treated HT1080 tumor bearing mice for an additional 4 months demonstrated the initial tumor regression translated into complete remission without significant loss in body weight. Expectedly, the untreated HT1080 tumors did not regress.

Example 6: Histopathology

As seen in the mosaic image of the total tumor mass (FIG. 5E,F), the untreated and treated BxPC-3 tumor architecture have similar features, with only one side of the tumor margin in the treated tumor showing signs of necrosis and erosion of tumor capsule. Fluorescence image of the necrotic area shows localization of TiO$_2$-PEG at the site (FIG. 5G). On closer inspection of the cellular organization in the tumor tissue, clusters of cells are encapsulated by dense desmoplastic reaction consisting of collagen, fibroblasts and other extracellular matrix proteins (FIG. 5H). In conjunction with hypovascularity of BxPC-3 tumor, this feature prevents the particles from interacting with the proliferating tumor cells. As demonstrated in the in vitro study, TiO$_2$-PEG trapped in the basement membrane matrix is unable to cause cell death because internalization and localization in the cytoplasm are a prerequisite for an effective PDT response. Therefore, the unique tumor architecture of BxPC-3 pancreatic cancer plays a major role in the poor responsiveness to CR activatable PDT using TiO$_2$ nanoparticles. This finding suggests that the endemic resistance of pancreatic tumors to therapy could be overcome by co-administering nanotherapeutics with reagents that can disrupt desmoplasia. Interestingly, we observed extensive necrosis in the treated fibrosarcoma section at 72 h post-injection, as evidenced by the large empty pockets throughout the tumor mass (FIG. 5J). In comparison, the untreated control tumor had the typical herringbone appearance characteristic of fibrosarcomas (FIG. 5I). The fluorescence image reveals TiO$_2$-PEG is internalized by cells, apparent by the diffuse and uniform luminescence (FIG. 5K), which contrasts with the TiO$_2$-PEG distribution in the extracellular matrix as aggregates in the treated pancreatic cancer. The unencapsulated and hypervascularized tumor architecture of fibrosarcoma (FIG. 5L) probably facilitated uninhibited diffusion across the tumor milieu and subsequent cellular internalization of TiO$_2$-PEG by the proliferating tumor cells, making PDT achievable.

In summary, the successful demonstration of tumor regression and remission in a fibrosarcoma model and extending mean survival in a highly aggressive pancreatic tumor model, using $^{64}$Cu as photon source and TiO$_2$ as oxygen-independent PS, marks an important event in the applicability of CR for PDT. The short lived PET isotopes can therefore be used as a light source for both superficial and deep tissue theranostics. More importantly, lower doses of radioactivity than the current paradigm in clinical nuclear imaging and radiotherapy[41] (100-fold) are sufficient to generate effective PDT, thus reducing radiotoxicity significantly. Although the activity of PET isotopes used was low, the concentration of TiO$_2$ for in vivo imaging is 100-fold higher than that required for PDT in vitro. Replacement of $^{64}$Cu as CR source with other PET isotopes such as $^{90}$Y and $^{89}$Zr with higher CR could improve light delivery and increase the luminescence yield from TiO$_2$, thereby bridging the difference in TiO$_2$ concentration required for imaging and PDT applications. CR delimits PDT from the traditional constraints of external light beam excitation source, such as depth of penetration. The wide spectrum of CR, from UV to far visible, can also be exploited to systematically excite a range of PS. However, the low fluence of CR will be challenging to excite organic PS such as FDA approved porphyrins, due to their low molar absorption coefficients. In contrast, the high surface area and dimension of nanoparticles sufficiently generates free radicals for PDT from the low fluence of CR. The CR-mediated PDT intratumoral injection approach disclosed in this work has direct potential clinical applications. For example, transarterial radioembolization[42] has been used to treat hepatocellular carcinoma. Therefore, direct intratumoral administration of TiO$_2$ can be used for regional management of chemotherapy refractory cancers and reduce systemic toxicity. To develop a versatile strategy for deep tissue CR-mediated PDT of both primary and metastatic cancer cells, future studies will focus on improving the selectivity of nanoparticulate PS through a targeted approach, where both the radionuclide and targeting moieties are conjugated to TiO$_2$.

Methods for Examples 1-6

Synthesis of TiO$_2$-PEG and TiO$_2$-Dextran: Anatase TiO$_2$ (1 mg; Sigma Aldrich Co. St. Louis, Mo.) was suspended in deionized water (1 ml) and probe sonicated for 10 min before further processing. To a solution containing 1:1 PEG 400 (250 µl) and deionized water (250 µl), 100 µl of the sonicated TiO2 was added and sonicated for an additional 10 min at room temperature (RT). Similarly, Dextran from *Leuconostoc mesenteroides* (0.5 mg; Sigma Aldrich Co.) was added to deionized water followed by the TiO$_2$ solution and sonicated for 10 min at RT. The TiO$_2$-PEG and TiO$_2$-Dextran adducts were then filtered using a 0.22 μm membrane syringe filter to isolate the dispersed nanoparticles.

Cell Culture:

4T1, BxPC-3 and HT1080 cell lines (American Type Culture Collection —ATCC) were cultured under recommended standard conditions. 4T1 and BxPC-3 were cultured in RPMI-1640 medium containing 10% fetal bovine serum (FBS), L-glutamine (2 mM), penicillin (100 units/rip, and streptomycin (100 pg/ml), incubated at 37° C. in a humidified atmosphere of 5% CO$_2$ and 95% air. HT1080 were cultured in Dulbecco's Modified Eagle's Medium under similar conditions.

In Vitro Cell Viability Assay:

MTS (3-(4,5-dimethylthiazol-2-yl)-5-(3-carboxymethoxyphenyl)-2-(4-sulfophenyl)-2H-tetrazolium) assay, a calorimetric assay for assessing viability of cell culture, was performed using CellTiter 96®$_{AQueous}$ Non-Radioactive Cell Proliferation Assay kit (Promega Co.) according to the manufacturer's instructions.

PhiPhiLux® G$_2$D$_2$(Oncolmmunin Inc.) with a DEVDGI amino acid sequence, having the following excitation and emission peaks: $\lambda_{ex}$=552 nm and $\lambda_{em}$=580 nm was used following the manufacturer's instructions. 5×10$^5$BxPC-3 cells per well were grown in an 8 well chamber culture slide (BD Biosciences), incubated with 12.5 μg/ml, 5 μg/ml, 2.5 μg/ml and 1.25 μg/ml of TiO$_2$. The 10 μM stock of PhiPhiLux® G$_2$D$_2$ was diluted with 1:1 RPMI medium to prepare a 2× dilution working stock. 100 μl of the 5 μM substrate was added to the adherent cell monolayer after removing the medium and incubated at 37° C. in a humidified, 5% CO$_2$ atmosphere for 1 h. The substrate was gently washed away using DPBS buffer two times and imaged through confocal microscopy. Propidium iodide and Live/Dead® cell stains (Life Technologies Inc.) were used according to the manufacturer's instructions.

In Cellulo Hydroxyl and Superoxide Radical Assay:

Hydroxyphenyl fluorescein (HPF) with an excitation and emission wavelength of 490 nm and 515 nm, respectively (Life Technologies Inc.) was used according to the manufacturer's instructions. Briefly, the 5 mM stock was diluted 1,000× to 5 μM working stock in DPBS. The TiO$_2$-$^{64}$Cu treated BxPC-3 cells grown in 8 well culture slides were immersed in the HPF working stock 4 h post treatment. The cells were incubated for 1 h before the dye solution was washed away and replaced with fresh DPBS. The cells were imaged using confocal microscopy using the 488 nm Argon ion laser with emission set to 500-600 nm. Similarly, Mitosox Red (Life Technologies Inc.) with an excitation and emission wavelength of 510 nm and 580 nm, was used to detect superoxide radicals using manufacturer's instructions.

Chelation of $^{64}$Cu to DOTA:

A 1 mg/ml stock solution of DOTA (1,4,7,10-tetraazacyclododecane-1,4,7,10-tetraacetic acid) (Macrocyclics Inc.) was prepared in 50 mM ammonium acetate buffer equilibrated to pH 5.5. 50 μl of DOTA stock was added to 450 μl of ammonium acetate buffer followed by 5 mCi of $^{64}$Cu in 5 μl of Hydrochloric acid. The reaction mixture was incubated at 45° C. for 1 h in a shaker. Unchelated $^{64}$Cu was removed from the chelated DOTA-$^{64}$Cu using a Waters HPLC purification system. The flow rate was set to 1 ml/min. The solvents were A-0.1% Trifluoroacetic acid (TFA) in water and B-0.1% TFA in Acetylnitrile. After 5 min hold at 5% B the gradient was programed linearly to 100% B at 40 min. The sample was collected for 2 min at 6 min time points corresponding to the peak in the radiometer and UV detector. The sample was then dried in a rotary shaker to remove TFA and acetylnitrile, for 4 h before resuspending in DPBS.

Characterization:

Transmission electron microscopy images were acquired using a FEI Tecnai Spirit Transmission Electron Microscope operating at an acceleration voltage of 200 kV. Dynamic light scattering measurements were taken using a Malvern Zetasizer Nano ZS instrument equipped with a 633 nm laser. All sizes reported were based on intensity average. Fluorescence images were acquired using an Olympus BX51 epifluorescence microscope. Fluorescence/reflectance cell images were taken with a 40× objective using the mercury lamp of the microscope as the excitation source and Cy5 filter set with an excitation and emission range of 620±60 nm and 700±75 nm, respectively. Confocal microscopy images were acquired using an Olympus FV1000 confocal microscope. Fluorescence/reflectance cell images were taken with a 60× objective using He:Ne 633 nm excitation laser and emission range of dichroic mirrors set to 655-755 nm.

In Vivo Tumor Model:

Balb/c and Athymic nu/nu mice were purchased from Frederick Cancer Research and Development Center. All studies were conducted in compliance with Washington University Animal Welfare Committee's requirements for the care and use of laboratory animals in research. The 4T1 tumors were generated by subcutaneous injection of 4×10$^6$ cells in 100 μl of DPBS in Balb/c mice. Likewise, BxPC-3 and HT1080 tumors were generated by subcutaneous injection of 4×10$^6$ cells in 100 μl of DPBS in Athymic nu/nu mice.

In Vivo Imaging

Matrigel™ (BD Biosciences) was thawed at 4° C. and added to an equal volume of TiO$_2$-PEG solutions with the following stoichiometries—500 μg/ml, 250 μg/ml, 120 μg/ml and 60 μg/ml and 0.25 mCi $^{64}$Cu in each vial. After reformulation the final titrations of TiO$_2$-PEG was 500 μg/ml, 250 μg/ml, 120 μg/ml, 60 μg/ml and 30 μg/ml, respectively. Balb/c mice (n=3×4) were injected with 100 μl of the formulation subcutaneously in their flank region. Additionally, BxPC-3 tumor bearing Athymic nu/nu mice (n=3) were injected with 250 μg/ml of TiO$_2$ admixed with 0.25 mCi $^{64}$Cu in 50 μl of DPBS directly into the tumor. The mice were imaged using the IVIS Lumina XR multimodal imaging system (PerkinElmer Inc.) immediately pi. Fluorescence imaging was performed using an excitation and emission wavelength of 640 nm and 700 nm, respectively, 60 s exposure with 2×2 binning. Luminescence images were acquired with LivingImage software using a 695-770 nm emission filter, 3 min exposure and 4×4 binning. Region of interest (ROI) analyses were performed using LivingImage or ImageJ software. Luminescence intensity expressed as Radiance was recorded and normalized to controls. Statistical significance was calculated using Graph Pad Prism software.

Photodynamic Therapy:

CR-PDT of tumor mimic: BxPC-3 cells were treated with 2.5 pg/ml of TiO$_2$-PEG and incubated overnight to facilitate internalization. The cells were centrifuged at 3500 rpm for 5 min and resuspended in DPBS to get rid of non-internalized TiO$_2$-PEG. This cycle was repeated three times. 8×10$^6$ cells in 50 μl of DPBS were suspended in an equal volume of Matrigel™ along with 0.25 mCi of $^{64}$Cu. The gel was injected subcutaneously in the flank region of Athymic nu/nu mice (n=6). Three control groups, TiO$_2$-PEG loaded BxPC-3 cells in Matrigel™ (n=6), 0.25 mCi of $^{64}$Cu in Matrigel™ (n=6), and BxPC-3 cells in Matrigel™ (n=3), were also similarly injected into the mice. The animals were monitored for 30 days. The growing tumors were measured with calipers every two days and tumor volume calculated using the equation: TV=(length×width$^2$)/2. The TV was plotted versus time to analyze PDT effect on the seed culture.

CR-PDT of Solid Tumors:

BxPC-3 tumors in Athymic nu/nu mice (n=4) were injected with 2.5 pg/ml TiO$_2$-PEG and 0.25 mCi $^{64}$Cu cocktail in 50 μl of DPBS. Two diametrically opposite injection sites were chosen and 25 μl of the cocktail was delivered at each site. An untreated group (n=4) served as control. HT1080 tumors in Athymic nu/nu mice (n=4) were also treated similarly. Three groups, TiO$_2$-PEG treated mice (n=4), $^{64}$Cu treated mice (n=4), and untreated mice (n=4), served as controls. The mice were monitored for 60 days with tumor volume measurements taken every two days using calipers. The weight and any physical signs for distress were also monitored closely. The tumor volume calculation and analysis of PDT effect on solid tumors was conducted as described above. The mice with regressing tumors were monitored for an additional four months to determine whether the cancer was in remission.

Histology:

The BxPC-3 tumor bearing mice in the treatment and control groups were sacrificed sixty days after injection of TiO$_2$-$^{64}$Cu cocktail. Likewise, for HT1080 tumor bearing mice, the mice were sacrificed three days after injection of TiO$_2$-$^{64}$Cu cocktail. The tumors were harvested and snap-frozen in OCT media for routine staining with hematoxylin and eosin (H&E). 10 μm tumor sections were made and imaged using epi-fluorescence microscopy at 4× and 20× magnification. Brightfield images of H&E stained sections at 4× were stitched together to generate a composite image of the entire tumor volume using MicroSuite software. Fluorescence images were taken at 20× magnification using Cy5 filter set.

References for Examples 1-6

1. Dolmans, D. E., Fukumura, D. & Jain, R. K. Photodynamic therapy for cancer. *Nat Rev Cancer* 3, 380-387 (2003).
2. Vaupel, P., Kallinowski, F. & Okunieff, P. Blood flow, oxygen and nutrient supply, and metabolic microenvironment of human tumors: a review. *Cancer Res* 49, 6449-6465 (1989).
3. Wilson, B. PHOTONIC AND NON-PHOTONIC BASED NANOPARTICLES IN CANCER IMAGING AND THERAPEUTICS. in *Photon-based Nanoscience and Nanobiotechnology*, Vol. 239 (eds. Dubowski, J. & Tanev, S.) 121-157 (Springer Netherlands, 2006).
4. Chatterjee, D. K., Fong, L. S. & Zhang, Y. Nanoparticles in photodynamic therapy: an emerging paradigm. *Adv Drug Deliv Rev* 60, 1627-1637 (2008).
5. Linsebigler, A., Lu, G. & Yates, J. Photocatalysis on TiOn Surfaces: Principles, Mechanisms, and Selected Results. *Chem. Rev.* 95, 735-758 (1995).
6. Schwarz, P. F., et al. A New Method To Determine the Generation of Hydroxyl Radicals in Illuminated TiO2 Suspensions. *The Journal of Physical Chemistry B* 101, 7127-7134 (1997).
7. Boehm, H. P. & Herrmann, M. Uber die Chemie der Oberfläche des Titandioxids. I. Bestimmung des aktiven Wasserstoffs, thermische Entwasserung und Rehydroxylierung. *Zeitschrift für anorganische und allgemeine Chemie* 352, 156-167 (1967).
8. Boehm, H. P. Acidic and basic properties of hydroxylated metal oxide surfaces. *Discussions of the Faraday Society* 52, 264-275 (1971).
9. Turchi, C. S. & Ollis, D. F. Photocatalytic degradation of organic water contaminants: Mechanisms involving hydroxyl radical attack. *Journal of Catalysis* 122, 178-192 (1990).
10. Cai, R., et al. Induction of cytotoxicity by photoexcited TiO2 particles. *Cancer Res* 52, 2346-2348 (1992).
11. Kubota, Y., et al. Photokilling of T-24 human bladder cancer cells with titanium dioxide. *Br J Cancer* 70, 1107-1111 (1994).
12. Maness, P. C., et al. Bactericidal activity of photocatalytic TiO(2) reaction: toward an understanding of its killing mechanism. *Appl Environ Microbiol* 65, 4094-4098 (1999).
13. Yamaguchi, S., et al. Novel photodynamic therapy using water-dispersed TiO2-polyethylene glycol compound: evaluation of antitumor effect on glioma cells and spheroids in vitro. *Photochem Photobiol* 86, 964-971 (2010).
14. Rozhkova, E. A., et al. A High-Performance Nanobio Photocatalyst for Targeted Brain Cancer Therapy. *Nano Letters* 9, 3337-3342 (2009).
15. Harada, A., Ono, M., Yuba, E. & Kono, K. Titanium dioxide nanoparticle-entrapped polyion complex micelles generate singlet oxygen in the cells by ultrasound irradiation for sonodynamic therapy. *Biomaterials Science* 1, 65-73 (2013).
16. Robertson, R., et al. Optical imaging of Cerenkov light generation from positron-emitting radiotracers. *Phys Med Biol* 54, 0031-9155 (2009).
17. Liu, H., et al. Molecular optical imaging with radioactive probes. *PLoS One* 5, 0009470 (2010).
18. Spinelli, A. E., et al. Multispectral Cerenkov luminescence tomography for small animal optical imaging. *Opt Express* 19, 12605-12618 (2011).
19. Hu, Z., et al. Three-dimensional noninvasive monitoring iodine-131 uptake in the thyroid using a modified Cerenkov luminescence tomography approach. *PLoS One* 7, 22 (2012).
20. Kotagiri, N., Niedzwiedzki, D. M., Ohara, K. & Achilefu, S. Activatable Probes Based on Distance-Dependent Luminescence Associated with Cerenkov Radiation. *Angew Chem Int Ed Engl* 13, 201302564 (2013).
21. Jelley, J. V. Cerenkov radiation and its applications. *British Journal of Applied Physics* 6, 227 (1955).
22. Cherry, S. R. & Phelps, M. E. *Pet: Physics, Instrumentation, and Scanners*, (Springer Science+Business Media, LLC, 2006).
23. Wold, A. Photocatalytic properties of titanium dioxide (TiO2). *Chemistry of Materials* 5, 280-283 (1993).
24. Augustynski, J. The role of the surface intermediates in the photoelectrochemical behaviour of anatase and rutile TiO2. *Electrochimica Acta* 38, 43-46 (1993).
25. Park, E. J., et al. Oxidative stress and apoptosis induced by titanium dioxide nanoparticles in cultured BEAS-2B cells. *Toxicol Lett* 180, 222-229 (2008).
26. Fabian, E., et al. Tissue distribution and toxicity of intravenously administered titanium dioxide nanoparticles in rats. *Arch Toxicol* 82, 151-157 (2008).
27. Huang, W., Lei, M., Huang, H., Chen, J. & Chen, H. Effect of polyethylene glycol on hydrophilic TiO2 films: Porosity-driven superhydrophilicity. *Surface and Coatings Technology* 204, 3954-3961 (2010).

28. Zhao, J., et al. Titanium dioxide (TiO2) nanoparticles induce JB6 cell apoptosis through activation of the caspase-8/Bid and mitochondrial pathways. *J Toxicol Environ Health A* 72, 1141-1149 (2009).
29. Moghimi, S. M., Hunter, A. C. & Murray, J. C. Long-circulating and target-specific nanoparticles: theory to practice. *Pharmacol Rev* 53, 283-318 (2001).
30. Thurn, K. T., et al. Endocytosis of titanium dioxide nanoparticles in prostate cancer PC-3M cells. *Nanomedicine* 7, 123-130 (2011).
31. Fujishima, A., Rao, T. N. & Tryk, D. A. Titanium dioxide photocatalysis. *Journal of Photochemistry and Photobiology C: Photochemistry Reviews* 1, 1-21 (2000).
32. Hutchinson, F. The distance that a radical formed by ionizing radiation can diffuse in a yeast cell. *Radiat Res* 7, 473-483 (1957).
33. Sies, H. Strategies of antioxidant defense. *European Journal of Biochemistry* 215, 213219 (1993).
34. Grisham, M. B. *Reactive Metabolites of Oxygen and Nitrogen in Biology and Medicine*, (Landes, 1992).
35. Halliwell, B. & Gutteridge, J. M. C. *Free radicals in biology and medicine*, (Clarendon Press, 1985).
36. Kaniyankandy, S. & Ghosh, H. N. Efficient luminescence and photocatalytic behaviour in ultrafine TiO2 particles synthesized by arrested precipitation. *Journal of Materials Chemistry* 19, 3523-3528 (2009).
37. Mathew, S., et al. UV-visible photoluminescence of TiO2 nanoparticles prepared by hydrothermal method. *J Fluoresc* 22, 1563-1569 (2012).
38. Beattie, B. J., et al. Quantitative Modeling of Cerenkov Light Production Efficiency from Medical Radionuclides. *PLoS ONE* 7, e31402 (2012).
39. Maitra, A. & Hruban, R. H. Pancreatic cancer. *Annual review of pathology* 3, 157 (2008).
40. Michaels, L. & Hellquist, H. B. *Ear, Nose and Throat Histopathology*, (Springer, 2001).
41. Lewis, J. S., et al. Radiotherapy and dosimetry of 64Cu-TETA-Tyr3-octreotate in a somatostatin receptor-positive, tumor-bearing rat model. *Clin Cancer Res* 5, 3608-3616 (1999).
42. Holt, A., et al. Transarterial radioembolization with Yttrium-90 for regional management of hepatocellular cancer: the early results of a nontransplant center. *Am Surg* 76, 10791083 (2010).

Introduction for Examples 7-10

The combination of light and photosensitizers offers a high degree of control for selective treatment of human diseases, eradication of contagious microbes, and understanding the molecular basis of drug resistance[1,2]. Despite the promise of phototherapeutic interventions, such as photodynamic therapy (PDT), the shallow penetration of light in tissue, use of high light power to activate photosensitizers, and reliance on tissue oxygenation to generate cytotoxic radicals confine PDT to superficial or endoscope accessible lesions[1]. Here, we report a two-prong approach that uses tissue depth independent Cerenkov radiation (CR) from radionuclides ($^{18}$F or $^{64}$Cu), as well as low radiance and an oxygen independent photocatalyst, titanium dioxide (TiO$_2$) nanophotosensitizer (NPS), for CR-induced therapy (CRIT). We demonstrate that administration of tumor-targeted transferrin coated TiO$_2$ and radionuclides in tumor-bearing mice remarkably increased median survival or achieved complete tumor remission. This work reveals a new paradigm for harnessing low radiance-sensitive NPS to achieve efficient depth-independent CR-mediated therapy.

Breakthroughs in light-based diagnostic and therapeutic interventions have transformed medicine and biology, as evidenced by recent advances in multiphoton microscopy, photoacoustic technology, targeted photoablation of tissue, photothermal therapies, PDT, and image guided surgeries. Regardless of the method employed, light-based interventions suffer from the rapid attenuation of light in tissue, confining phototherapy to superficial lesions[3], unless a fiber light source[4] is used to access deep organs.

CR, a broad spectrum light (250-600 nm) produced by many clinical grade radionuclides[5], could serve as a depth-independent light source for photo-induced therapy. Several studies have demonstrated the use of CR for molecular imaging[6-8], but the low radiance of CR is less effective in activating conventional photosensitizers used in PDT. In this work, we demonstrate that a photocatalyst, TiO$_2$ NPS, can efficiently harvest the predominant UV light from CR for a therapeutic effect. Unlike some conventional photosensitizers which largely rely on tissue molecular oxygen to generate cytotoxic reactive oxygen species[9], the oxygen-independent radical generation by TiO$_2$ NPS potentially extends PDT to the treatment of hypoxic lesions, such as solid tumors[10]. By incorporating a photoinitiator into the NPS, we demonstrate that CRIT is an effective therapeutic paradigm using low light power and low concentrations of NPS.

Example 7: Titanium Dioxide and Titanocene Photoagents for CRIT

Figure 13A:
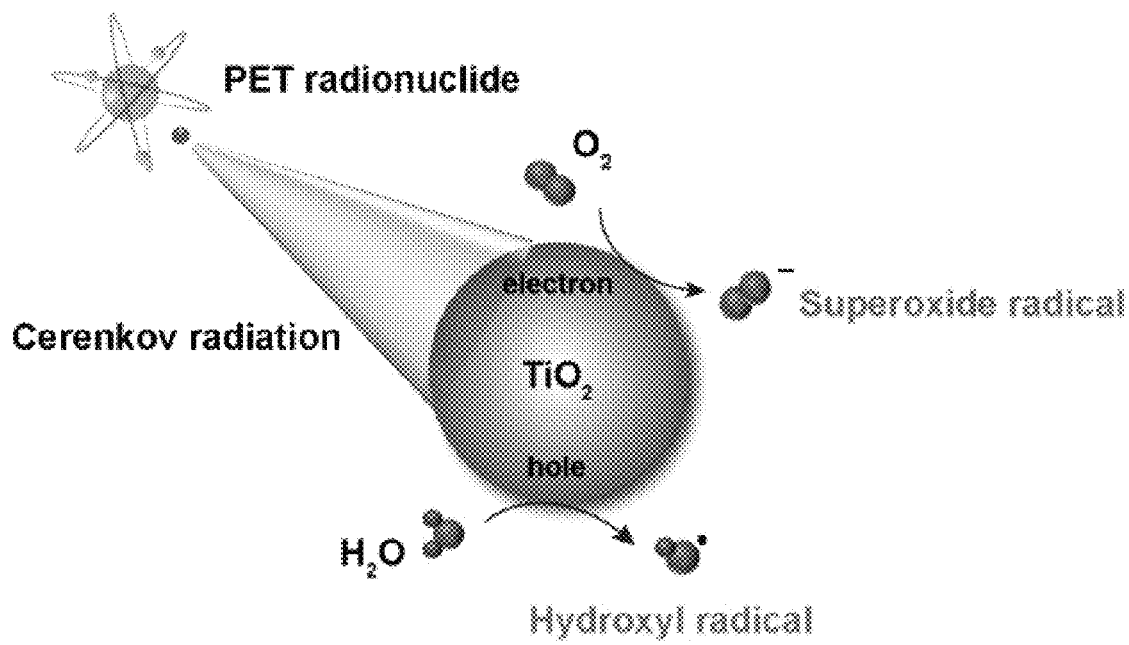
FIG. 13A, FIG. 13B and FIG. 13C depict titanium dioxide and titanocene photoagents for CRIT.

TiO$_2$ NPS is a regenerative photocatalyst that produces predominantly hydroxyl radicals (FIG. 13A) through electron-hole transfer to chemisorbed H$_2$O in an oxygen-independent process[11-13]. Because of their large surface area for efficiently harvesting UV light[14], where CR quantum efficiency is highest[15], and their ability to generate free radicals at low CR radiance for localized cytotoxicity[14], we explored the use of TiO$_2$ NPS for CRIT. Three types of stable TiO$_2$ NPS were synthesized for this study. The first, TiO$_2$-PEG NPS, was prepared by ultrasonicating TiO$_2$ with PEG (Molecular Weight: 400 Da), which transformed the TiO$_2$ nanoparticle aggregates into small nanoclusters (FIG. 13C and Table 2)[16]. Due to the nonspecific distribution of this NPS, it was used to determine tumor response to CRIT via an intra-tumoral administration route.

Figure 13B:
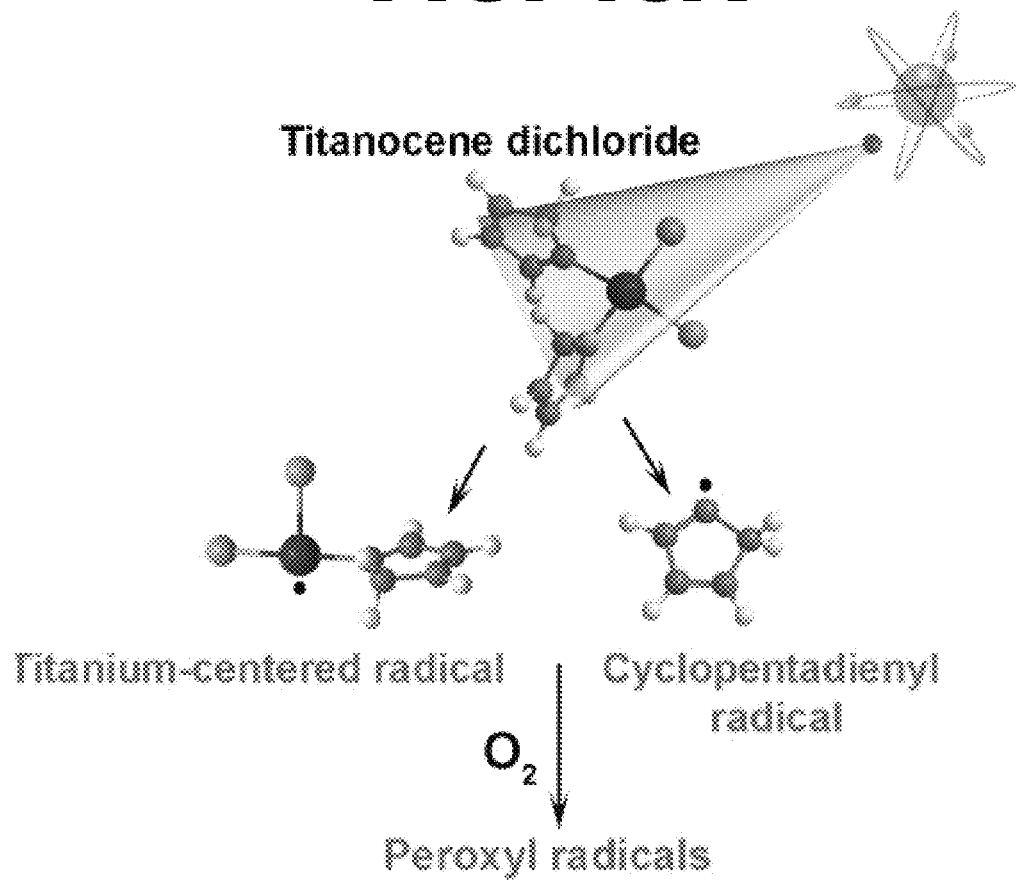
Figure 13C:
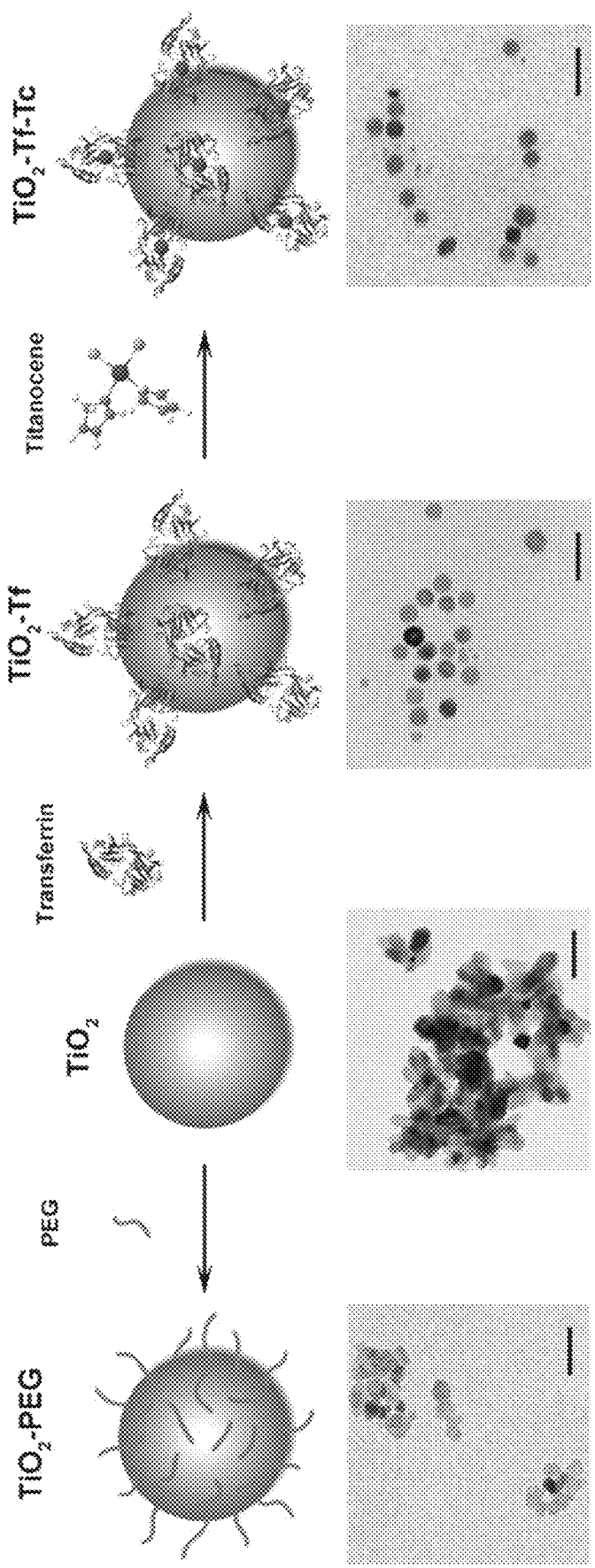

The second NPS was designed for intravenous injection (i.v.) administration. Because of the high demand for iron by rapidly proliferating cells, many tumors overexpress transferrin (Tf) receptors[17]. We discovered that treatment of TiO$_2$ nanoclusters (FIG. 13C) with Tf produces monodispersed TiO$_2$ NPS (FIG. 13C). Under neutral pH, sonication of high concentrations of Tf facilitates adsorption of the negatively charged Tf (isoelectric point=5.5) onto TiO$_2$ (isoelectric point=5.8), which stabilizes the monodispersed NPS through protein-protein electrostatic repulsions. Although bovine serum albumin was previously used to prepare stable suspensions of TiO$_2$ nanoclusters in protein rich media[18], our new method allows Tf to serve simultaneously as a TiO$_2$ monodispersant, stabilizer and a tumor targeting moiety.

An inherent flaw of receptor-mediated targeting strategies is that low concentrations of materials are delivered to the target tissue. For therapy, this could lead to suboptimal effects. To overcome this challenge, we prepared the third NPS by incorporating titanocene (Tc) into the tumor-targeted NPS to amplify the therapeutic effect of CRIT at low NPS concentrations in tissue. Tc is a photoinitiator that can be activated by UV light to generate free radicals (FIG. 13B) through photofragmentation[19]. The cyclopentadienyl and titanium-centered radicals from Tc fragmentation are generated in an oxygen independent fashion[20]. Similar to $TiO_2$ ($A_{max}$ 274 nm), the excitation energy for Tc ($A_{max}$ 250 nm) is in the UV spectrum (FIG. 17)[14,19], which favors CRIT. Importantly, apo-Tf (Tf devoid of iron) binds Tc with high affinity at the iron-chelating epitope[21], such that Tc-$TiO_2$-Tf can be synthesized by simply adding Tc to a solution of $TiO_2$-Tf (FIG. 13C).

Figure 17A:
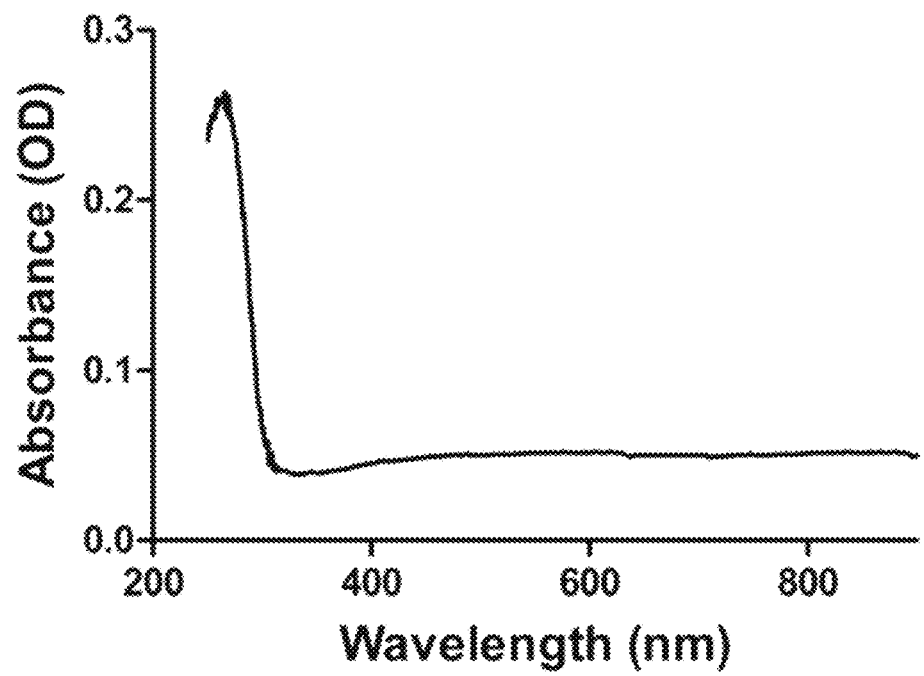
FIG. 17A, FIG. 17B, FIG. 17C, FIG. 17D and FIG. 17E depict spectral characterization of TiO$_2$ and Tc.
Figure 17B:
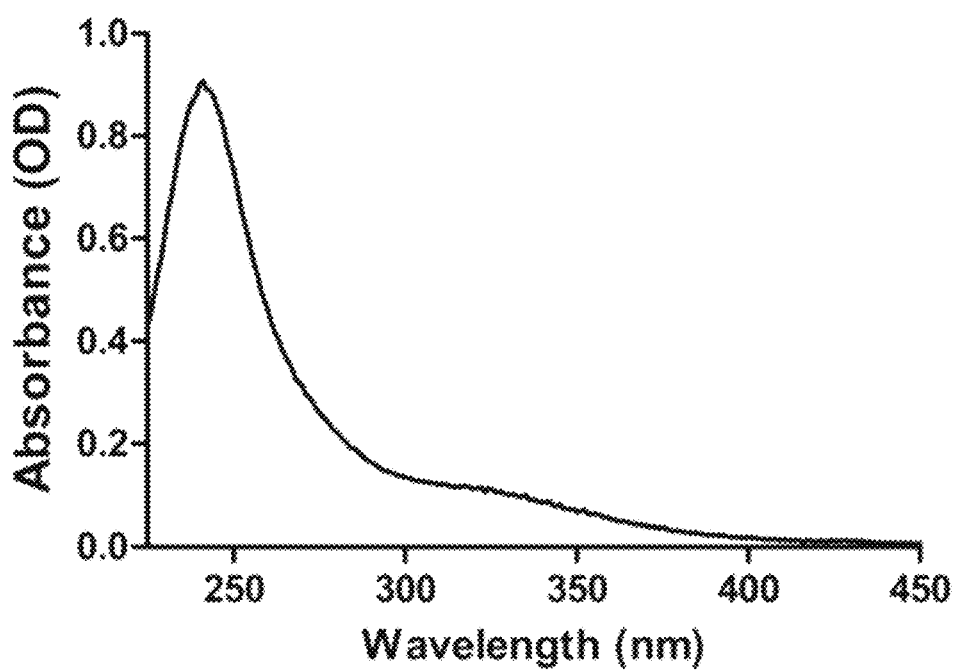
Figure 17C:
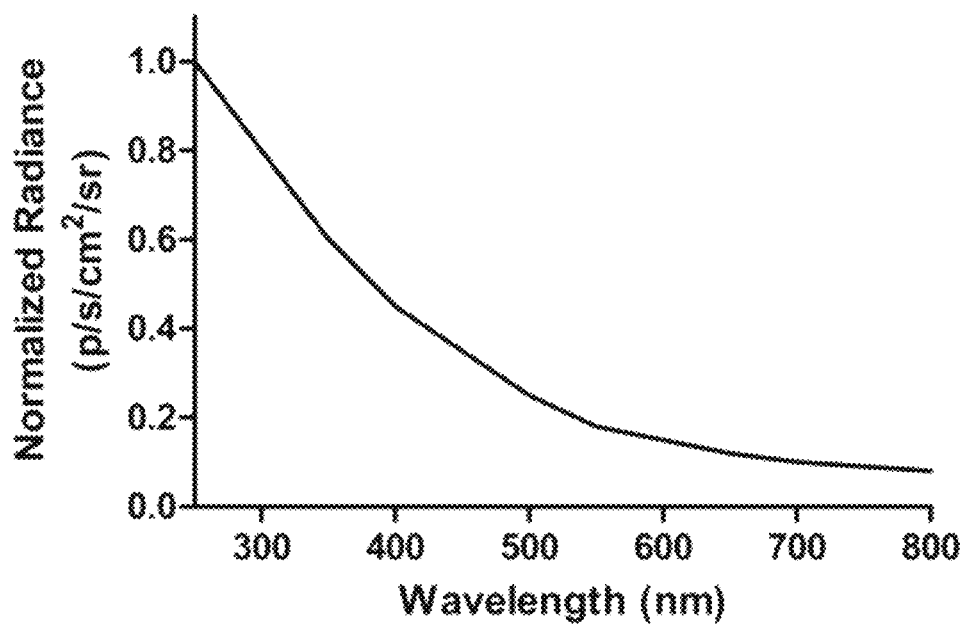
Figure 17D:
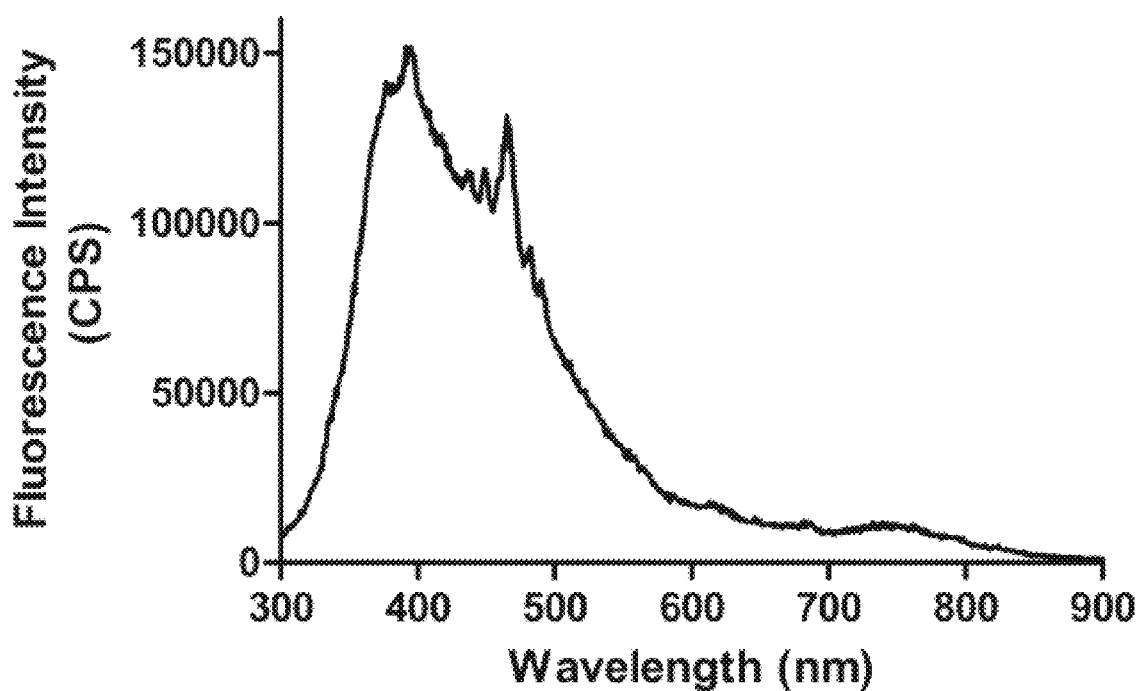
Figure 17E:
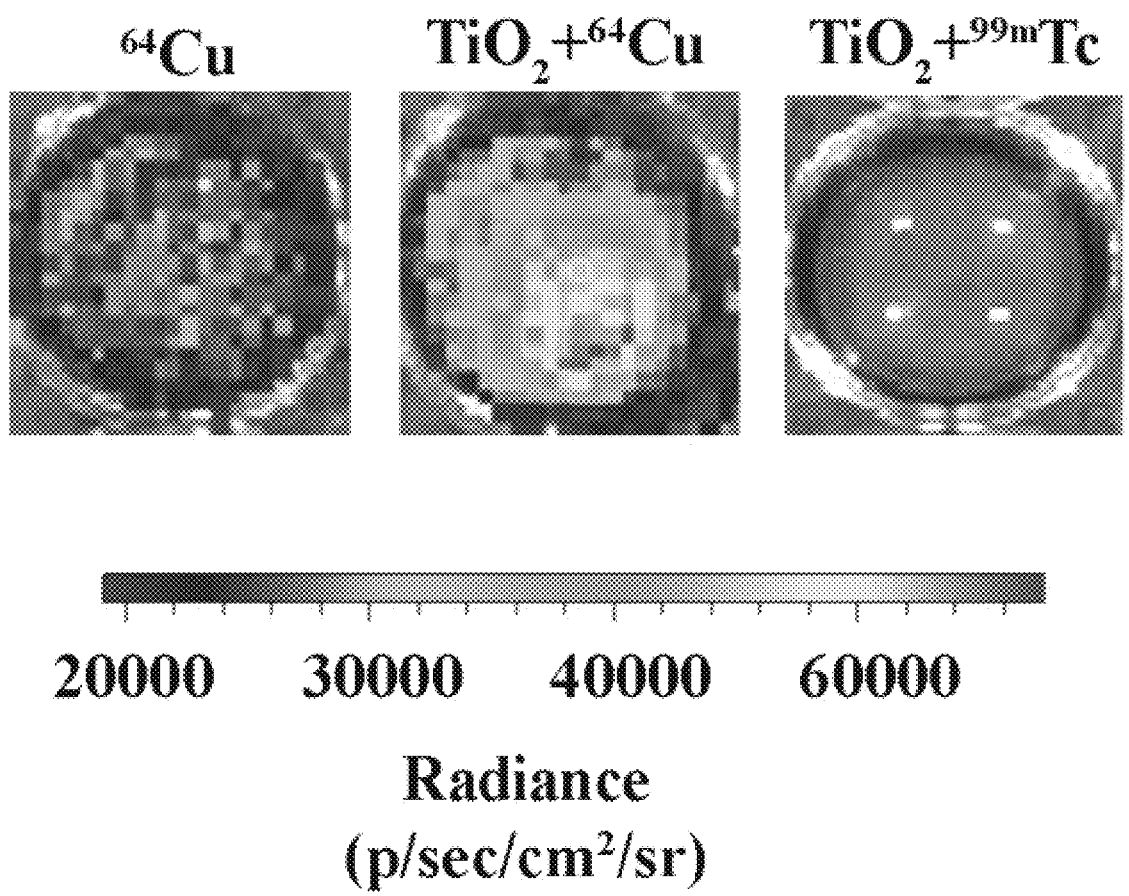

TEM and DLS analyses show monodispersed (polydispersity index=0.08) $TiO_2$-Tf and $TiO_2$-Tf-Tc nanoparticles with an average size distribution of 18±3 nm and a hydrodynamic diameter of 106±18 nm, respectively (Table 2). Using the strong luminescence of $TiO_2$ in the visible region (FIG. 17D), we observed CR-mediated $TiO_2$ luminescence in $^{64}Cu$ (a β particle emitter) treated samples, but not in $^{99m}Tc$ (a pure γ emitter) treated samples, demonstrating that CR was the excitation source for $TiO_2$ luminescence (FIG. 17E). This finding is supported by a previous study that shows CR from $^{32}P$ can excite $TiO_2$ and cleave DNA[22] in similar manner as activation with white light[23].

TABLE 2

Physico-chemical characterization of $TiO_2$-PEG, $TiO_2$-Tf and $TiO_2$-Tf-Tc constructs.

| Sample | Hydrodynamic Diameter (nm) | Polydispersity Index | Zeta Potential (mV) | Mobility (μmcm/Vs) |
|---|---|---|---|---|
| $TiO_2$ | 454 ± 40 | 1.00 | −17.1 ± 4.6 | −1.34 |
| $TiO_2$-PEG | 268 ± 26 | 0.23 | 4.28 ± 1.9 | 0.33 |
| $TiO_2$-Tf | 106 ± 18 | 0.08 | −7.77 ± 3.7 | −0.61 |
| $TiO_2$-Tf-Tc | 108 ± 13 | 0.09 | −7.36 ± 3.6 | −0.57 |

The hydrodynamic size and zeta potential of the $TiO_2$ based constructs in phosphate buffered saline (PBS) were measured using a Malvern Zetasizer. Hydrodynamic diameter was extracted by cumulant analysis of the data and polydispersity index from cumulant fitting. Each value is the average of three experiments ± s.e.m.

Example 8: Cellular Uptake of Photoagents and In Vitro CRIT Assessment

Using an electron microscope (EM), we demonstrated sub-cellular localization of the $TiO_2$-Tf NPs in the endo-lysosomal compartment of HT1080 tumor cells. NPS-free Tf successfully inhibited the endocytosis, suggesting internalization is mediated by the Tf receptor (FIG. 14A). $TiO_2$ NPS and Tc are known to induce apoptosis in cells at concentrations≥5 μg/ml and 12.5 μg/ml, respectively[24,25]. To delineate the intrinsic from CR-mediated toxicity, we used $TiO_2$-Tf, Tc-Tf, and $TiO_2$-Tf-Tc NPS, as well as two radionuclides, $^{18}F$ and $^{64}Cu$. With a half-life of 1.83 h and predominantly β decay (β+: 97%), the widely used PET imaging agent 2'-deoxy-2'-($^{18}F$)fluoro-D-glucose (FDG) is suitable for systemic administration, where its high specific activity and tumor-targeting capability[26] combine to deliver rapid and localized CR for CRIT without prolonged exposure of healthy tissue to radioactivity. For intra-tumoral injection, where rapid regression of tumor growth is needed, we used $^{64}Cu$, which has a half-life of 12.7 h and significant β decay (β+:19%, β−:39%). Our cytotoxicity analysis showed that cell viability in $^{64}Cu$ (<0.5 mCi (18.5 MBq)/0.1 ml) and FDG (1 mCi (37 MBq)/0.1 ml) treated cells was >95% relative to untreated controls (FIG. 7B). Similarly, $TiO_2$ NPS or Tc did not induce apoptosis at <4 μg/ml and <10 μg/ml, respectively (FIG. 7A). Therefore, we used doses below the toxicity threshold to determine efficacy of CRIT in vitro.

Figure 14D:
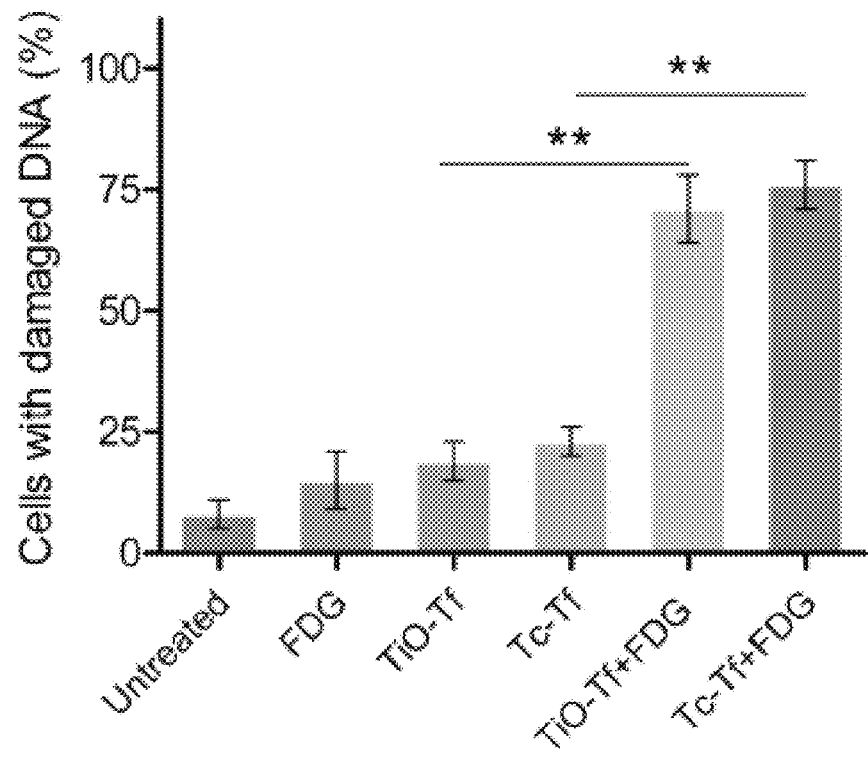
Figure 14E:
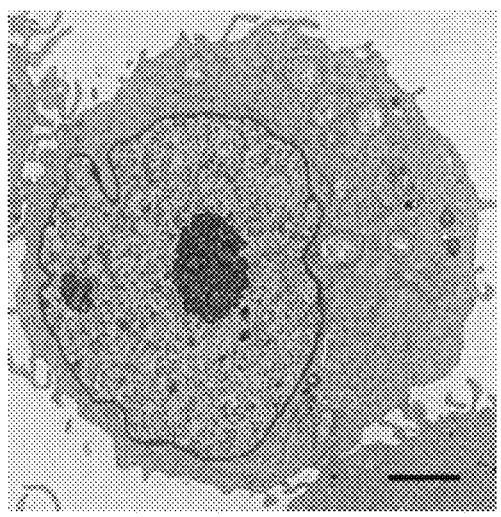
Figure 14F:
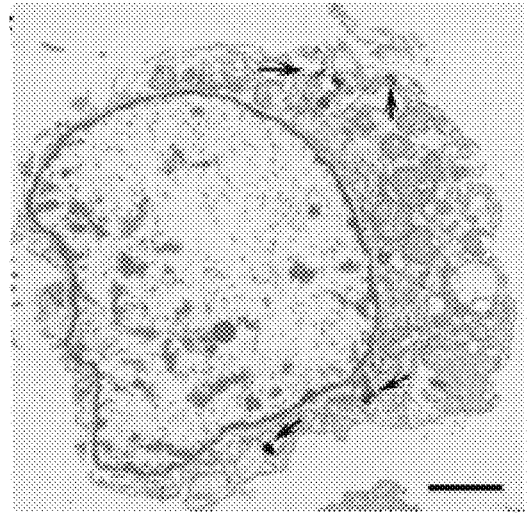
Figure 14G:
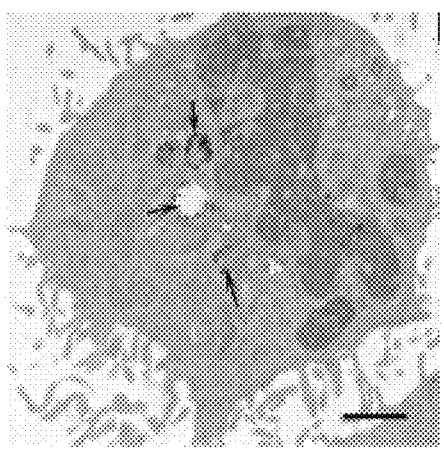
Figure 14H:
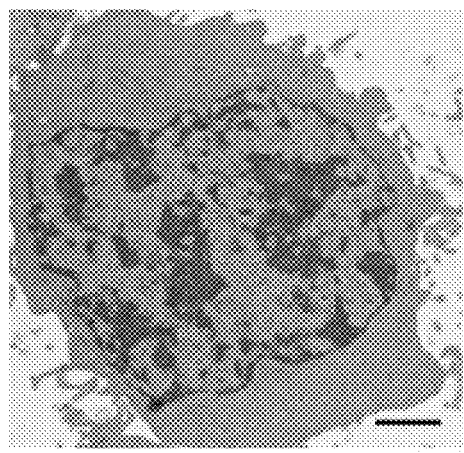
Figure 14I:
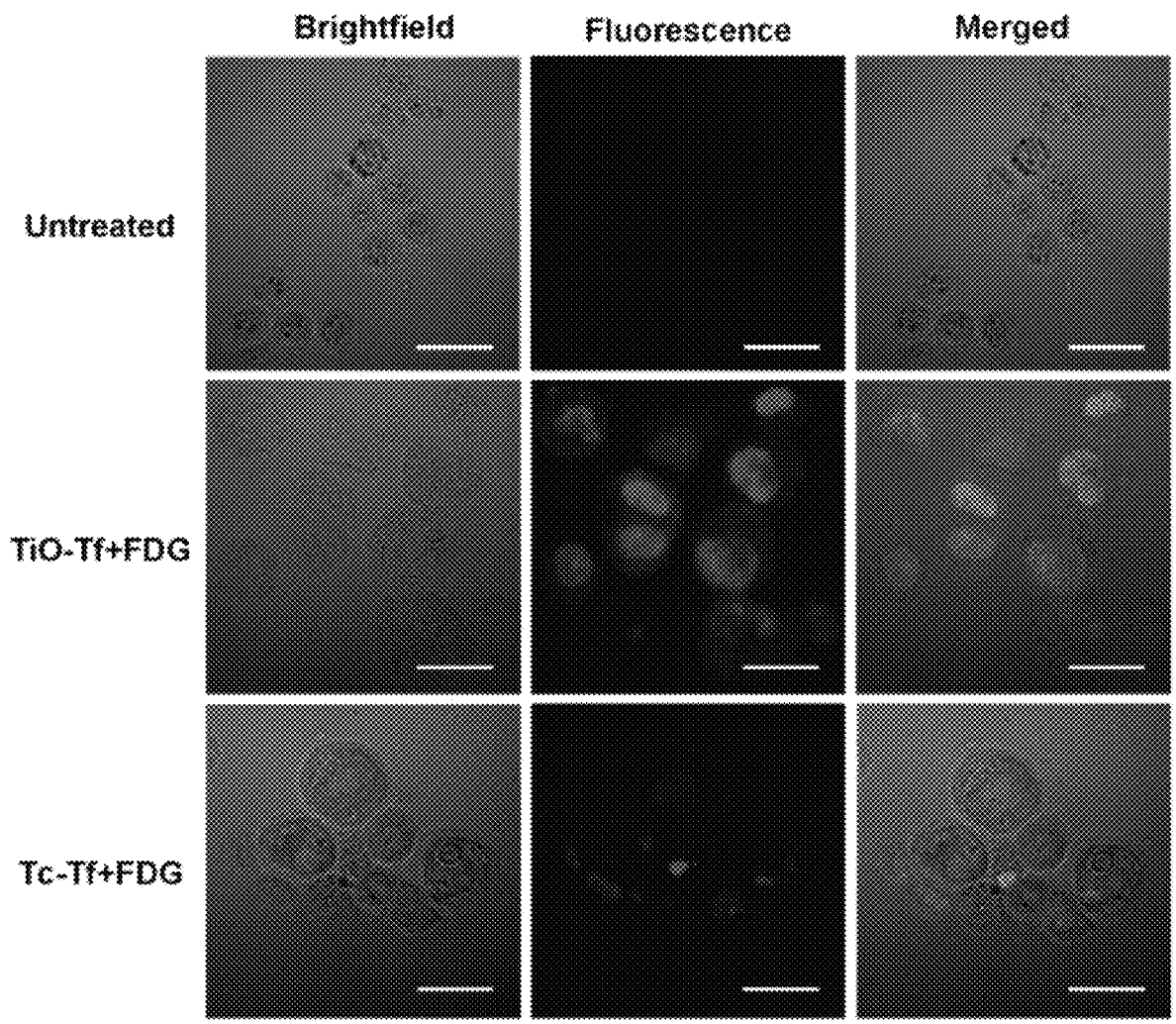
Figure 14J:
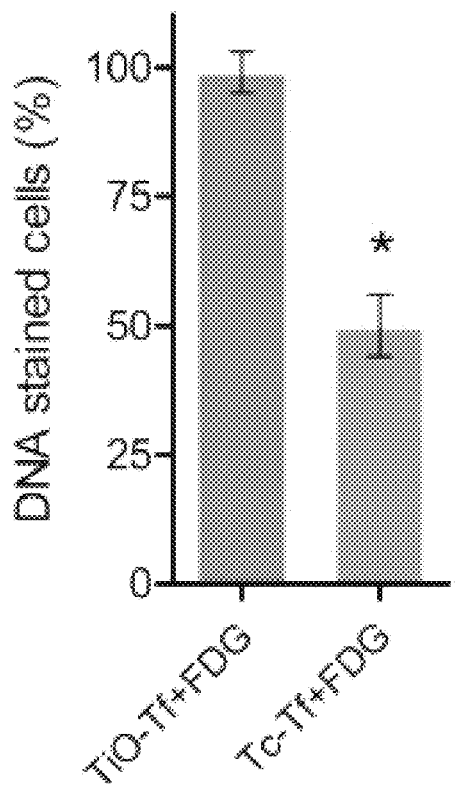

When treated with FDG and $^{64}Cu$, the viability of tumor cells preloaded with NPS significantly decreased (FIG. 14B), suggesting low metabolic activity and attenuated proliferation. Cellular analysis with the alkaline Comet Assay show various degrees of DNA mobility outside the nucleus (FIG. 14C) and that a significant percentage of treated cells exhibited DNA damage, which correlated with the viability studies (FIG. 14D). Compared to untreated cells (FIG. 14E), EM images of cells loaded with TiO2-Tf after treatment with FDG revealed features associated with both necrosis, such as loss of cell membrane integrity and a vacuolated cytosol (FIG. 14F), and apoptosis, such as dense nuclei, chromatin margination, and excessive surface blebbing (FIG. 14G). However, cells treated with Tc-Tf and FDG exhibited predominantly apoptotic features (FIG. 14H). Propidium iodide staining demonstrated oncotic cells with high uptake (FIG. 14I, middle) and low uptake (FIG. 14I, bottom) of the stain in $TiO_2$-Tf+FDG and Tc-Tf+FDG treated cells, respectively (see TiO2-PEG+$^{64}Cu$ related information in FIG. 9 and FIG. 10). Loss of cell membrane integrity and disruption of the signal transduction pathway leading to apoptosis and cell death is a hallmark of oxidative cell damage mediated by peroxyl, hydroxyl, and superoxide radicals via lipid peroxidation of the cell membrane[27]. Peroxyl, cyclopentadienyl and metal-centered radicals are known to be less disruptive than hydroxyl radicals[28], which is consistent with the observation of oncotic cells with lightly stained nuclei, indicating a lower degree of cellular damage and that the cells are in late stages of apoptosis (FIG. 14J).

Figure 14K:
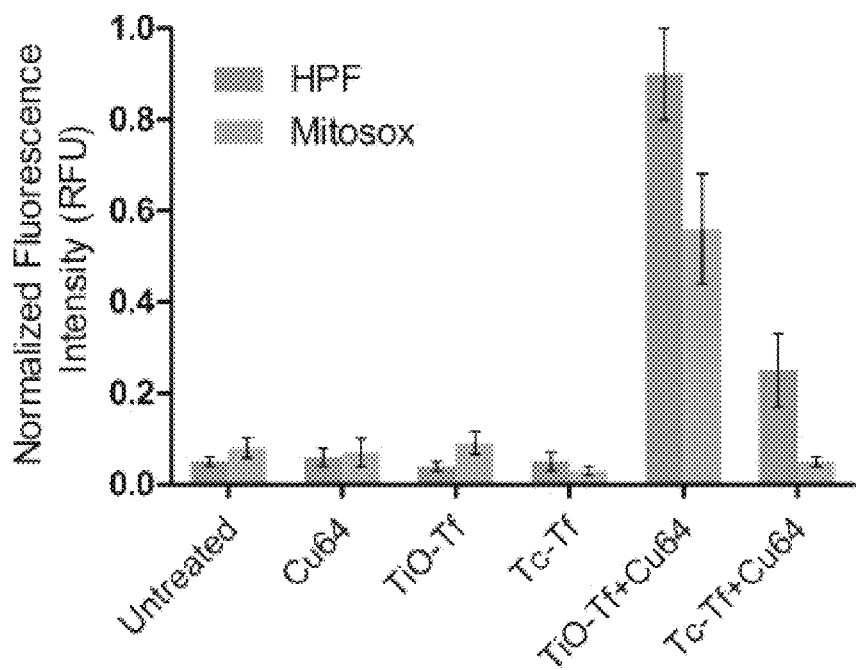
Figure 14L:
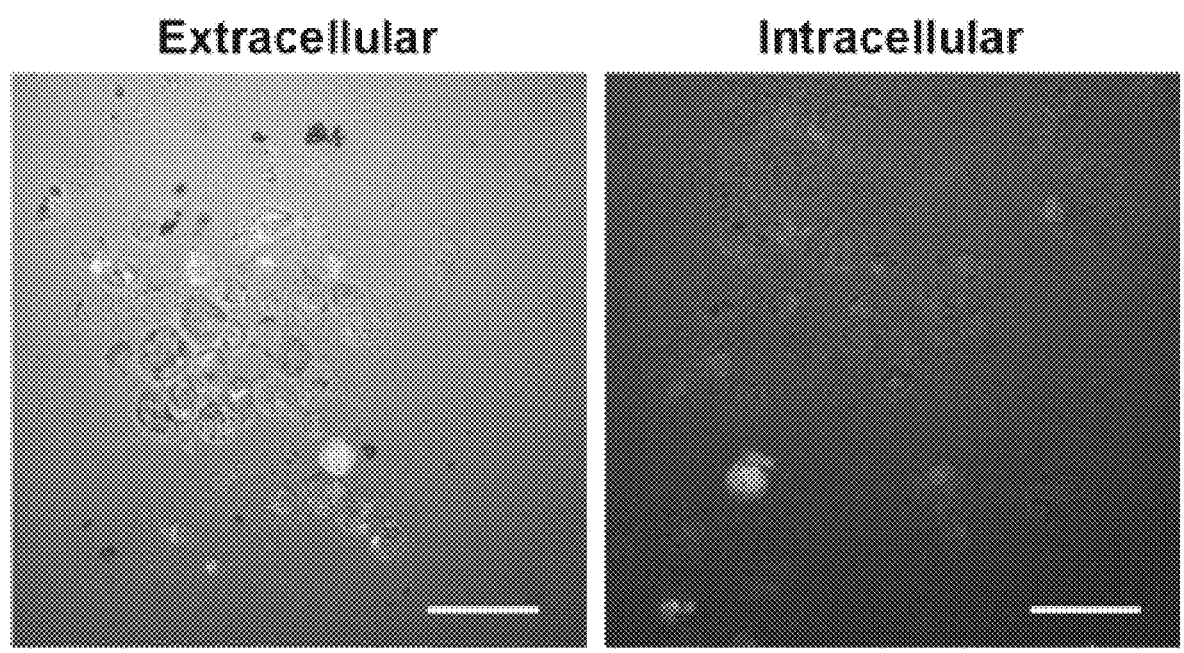
Figure 18A:
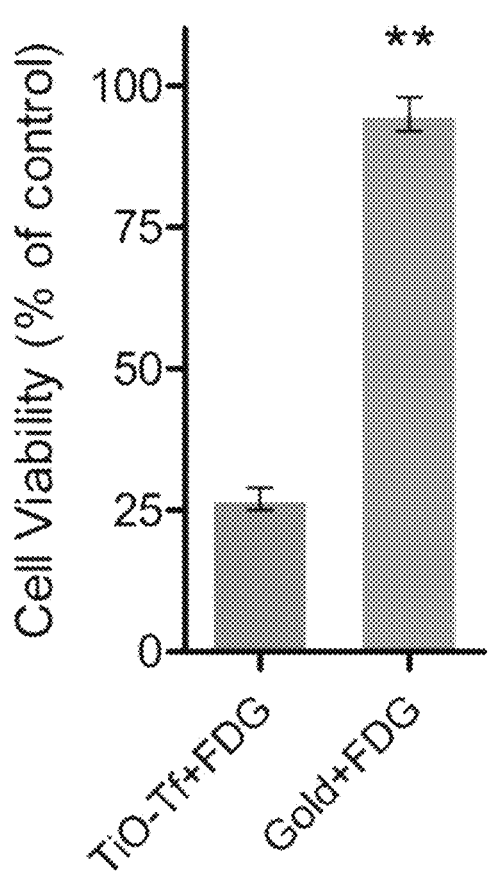
FIG. 18A and FIG. 18B depict cytoxicity and apoptosis observed with photosensitizer nanoparticles versus gold nanoparticles.
Figure 18B:
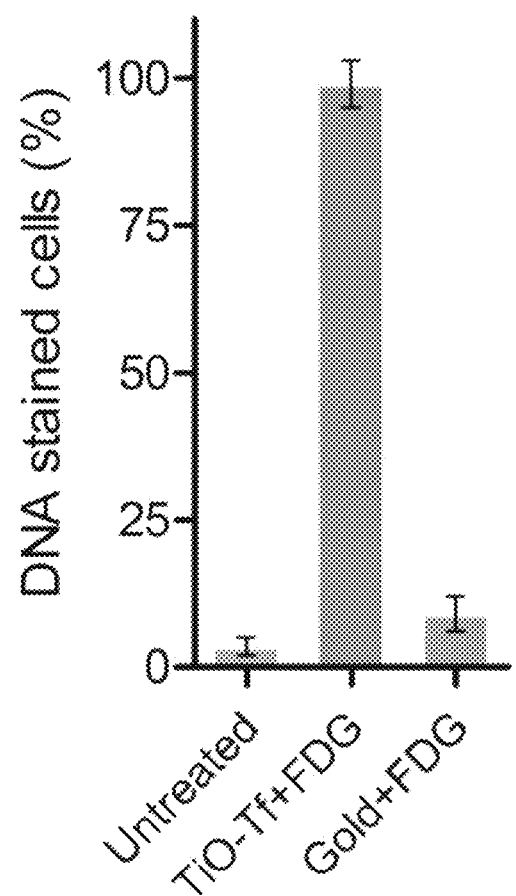

Using dyes that are sensitive to hydroxyl and peroxyl radicals (hydroxyphenyl fluorescein, HPF)[29], and superoxide radicals (Mitosox), we demonstrated that cells treated with $TiO_2$-Tf and FDG exhibited high levels of both HPF and mitosox fluorescence (FIG. 14K). These results suggest the involvement of both hydroxyl and superoxide species in CRIT. Hydroxyl radicals are a highly reactive species and non-diffusible across cell membranes, culminating in a highly pronounced local action[30]. In contrast, superoxide radicals are a more stable species that can travel across cell membranes with a long diffusion distance of ~320 nm[31]. Because CR can traverse cell membranes to activate intra-cellular and extracellular $TiO_2$ NPS, we used differences in the propagation kinetics of the two radicals to delineate the contributions of each radical species to CRIT. FIG. 14L shows that a majority of the cells (>95%) treated with extracellular $TiO_2$ and $^{64}Cu$ (0.5 mCi/0.1 ml) were viable, suggesting that the hydroxyl, and not the superoxide, radicals play a major role in CRIT. Although the interaction of beta particles or gamma rays with $TiO_2$ NPS can mediate CRIT, this effect was not observed under our experimental conditions. We did not observe CRIT after treatment of $TiO_2$ NPS with the pure gamma emitter ($^{99m}Tc$) or after FDG treatment of gold nanoparticles, which are radiosensitizers known to generate photoelectrons and auger electrons upon interacting with ionizing radiation and X-rays[32] (FIG. 18).

Example 9: CRIT Through Intratumoral Administration of $TiO_2$ and $^{64}Cu$

Figure 15A:
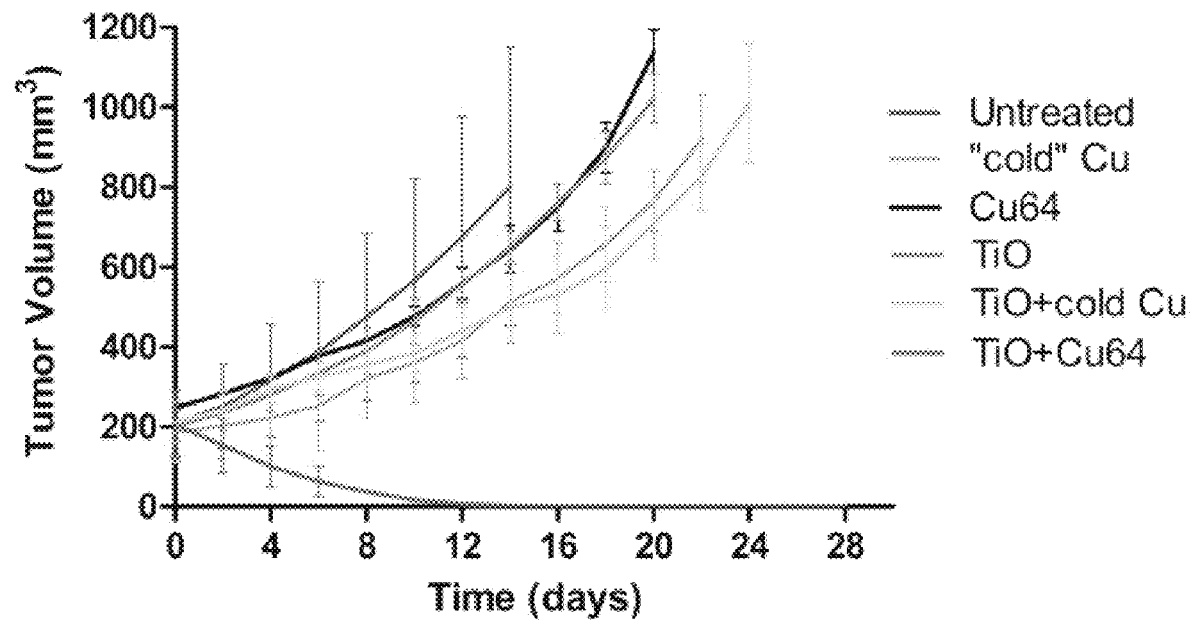
Figure 15B:
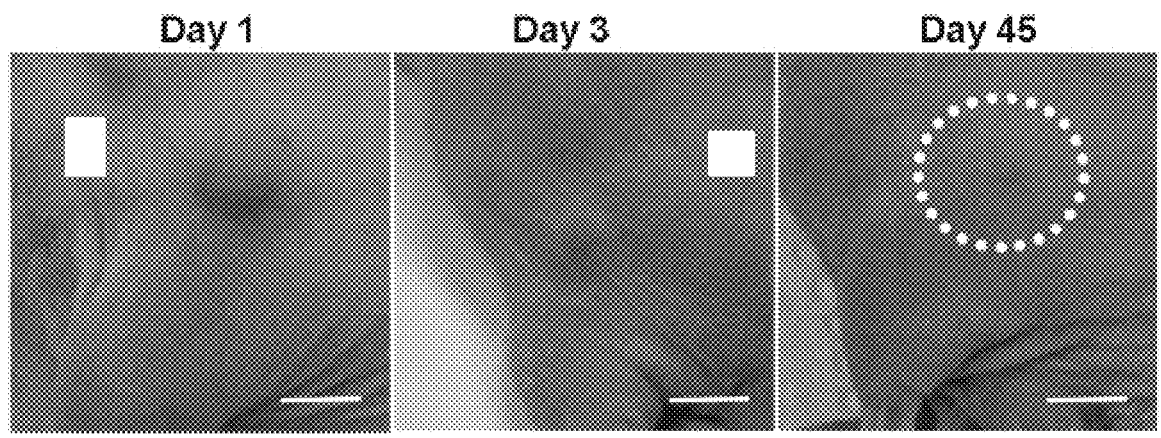

To demonstrate the in vivo application of CRIT, we administered a single sub-cytotoxic dose of $TiO_2$-PEG NPS (2.5 pg/ml) and $^{64}Cu$ (0.5 mCi/0.1 ml) into mice bearing the aggressive HT1080 tumor model. We observed a remarkable shrinkage in tumor volume (40±5%) within 3 days of CRIT initiation (FIG. 15A,B). Complete tumor regression was achieved by 30 days (FIG. 15B), translating into complete remission without significant loss in body weight up to 4 months post treatment. In contrast, the untreated HT1080 tumors grew rapidly and the mice were euthanized by day 15. Histologic analysis showed that untreated tumors had the typical herringbone appearance characteristic of fibrosarcomas (FIG. 15C), but treated tumors revealed extensive necrosis at 72 h post-injection, as evidenced by the large denuded areas throughout the tumor mass (FIG. 15D). Although intra-tumoral administration of drugs is a viable adjuvant therapy for a variety of tumors such as liver (radionuclide therapy through chemoembolization) or brain cancer, we expanded the potential application of the system to i.v.-based CRIT.

Figure 16A:
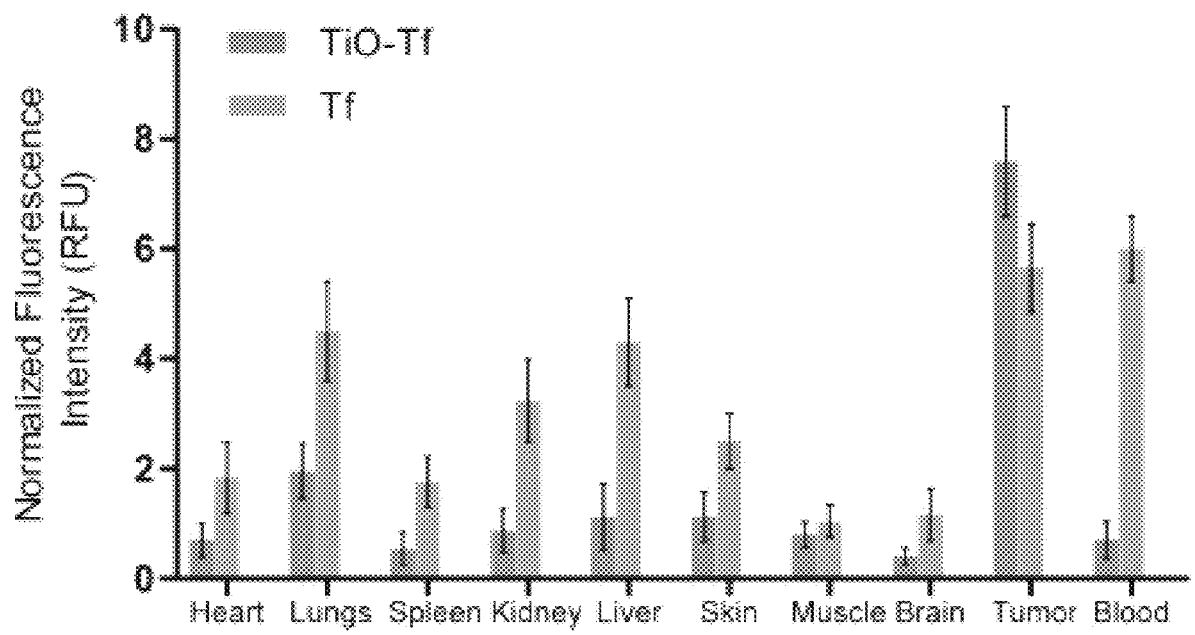
FIG. 16A, FIG. 16B, FIG. 16C, FIG. 16D, FIG. 16E, FIG. 16F and FIG. 16G depict in vivo biodistribution and CRIT through systemically administered photoagents and FDG.
Figure 16B:
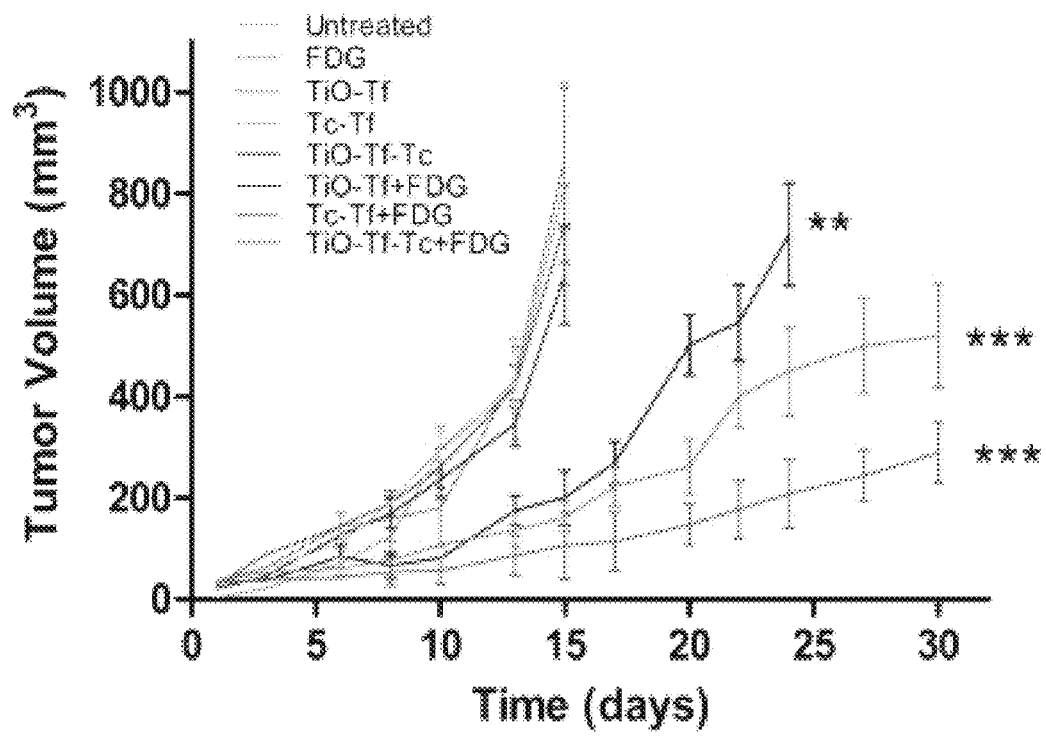
Figure 16C:
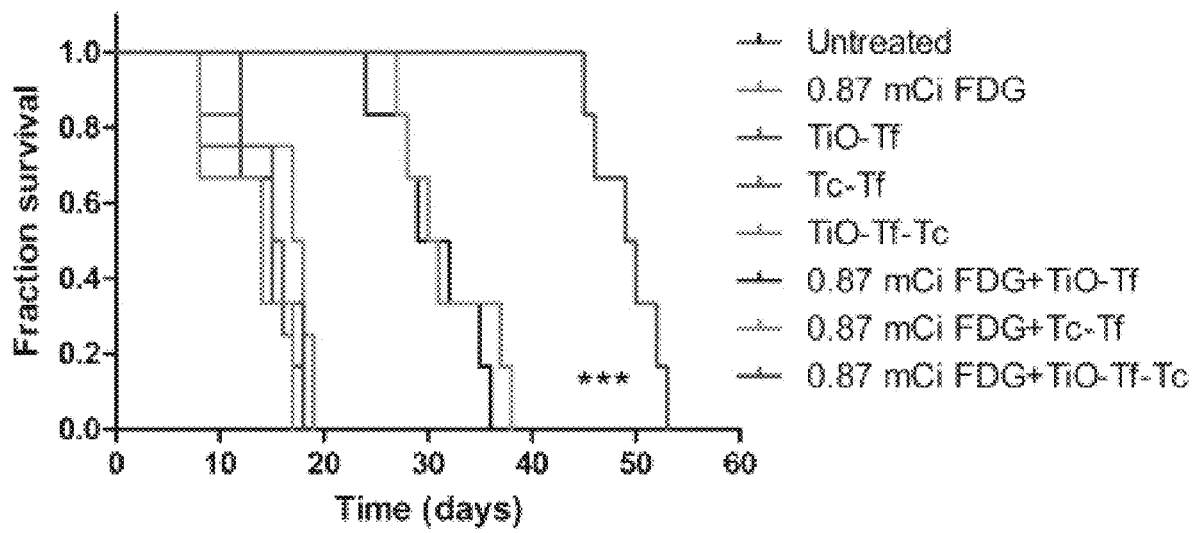
Figure 16D:
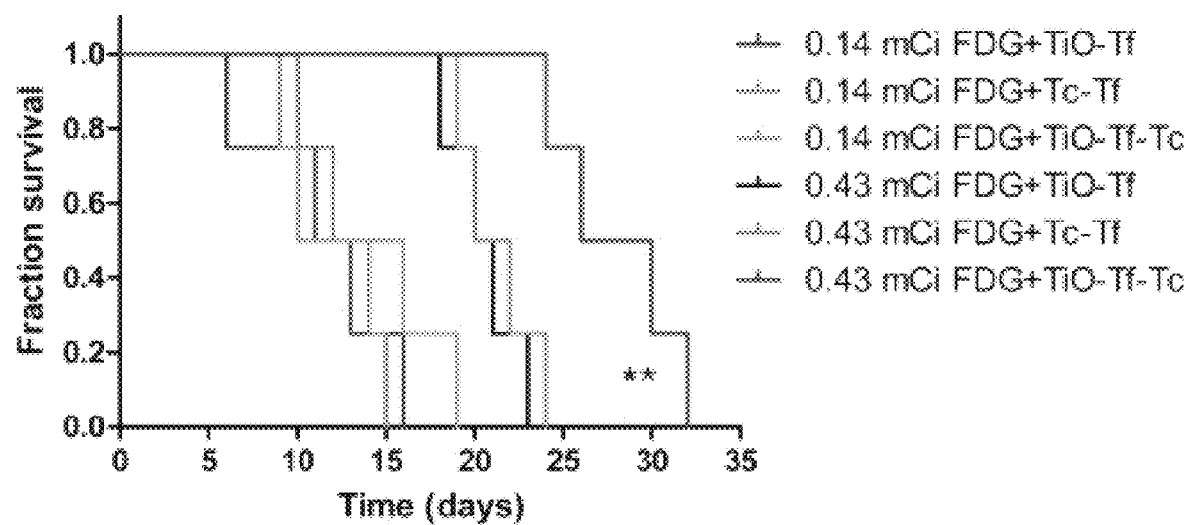

Example 10: In Vivo Distribution and CRIT Through Systemically Administered Photoagents and FDG Labeling Tf with the dye Alexa 680 allowed us to determine the in vivo distribution and tumor uptake of the NPS. For $TiO_2$-Tf, the uptake was highest in tumors (FIG. 16A) relative to other organs, an outcome that is rare for most nanoparticles (see FIG. 19 for additional information). The tumor to muscle ratio for $TiO_2$-Tf (9.5) is higher than that of Tf alone (5.3), which could be attributed to additional uptake due to enhanced permeability and retention effect. Inspired by this result, we intravenously administered a one-time dose of each $TiO_2$-Tf, Tc-Tf or $TiO_2$-Tf-Tc (1 mg/kg body weight) in different mice, followed by two doses of FDG (0.87 mCi (32.19 MBq)/0.1 ml) within 72 h. The animals were monitored over 45 days (FIG. 16B). We observed that the tumor growth rate for mice undergoing CRIT was considerably slower than in untreated or other control mice. The average tumor volume for mice treated with $TiO_2$-Tf or Tc-Tf and FDG was four-fold smaller than the corresponding controls at day 15, when the control groups had to be euthanized before the tumors attained 2 cm limit imposed by our protocol. Importantly, mice treated with $TiO_2$-Tf-Tc and FDG showed superior response to CRIT, with an eight-fold smaller average tumor volume compared to the control groups. Median survival increased from 15±2 d, for the untreated and control groups, to 30.5 d for $TiO_2$-Tf+FDG, 31 d for Tc-Tf+FDG, and a remarkable 50 d for $TiO_2$-Tf-Tc+ FDG (FIG. 16C) treated mice. This result suggests a complementary effect of $TiO_2$ and Tc in the presence of FDG, leading to an additive effect in growth inhibition. We also observed the attenuation of tumor growth and a significant increase in median survival to 21 d for $TiO_2$-Tf+FDG, 22 d for Tc-Tf+FDG, and 29 d for $TiO_2$-Tf-Tc+FDG, when mice were treated with lower dose of FDG (0.43 mCi (15.91 MBq)/0.1 ml) (FIG. 16D). However, administration of trace amounts of FDG (0.14 mCi (5.18 MBq)/0.1 ml activity) did not induce CRIT (FIG. 16D). Taken together, the systemic and intra-tumoral CRIT data suggest a positive correlation between in vivo cell death and the intensity of CR. Clearly other factors such as duration of exposure, administered dose, and the type of radionuclide used will influence CRIT outcomes.

Figure 16E:
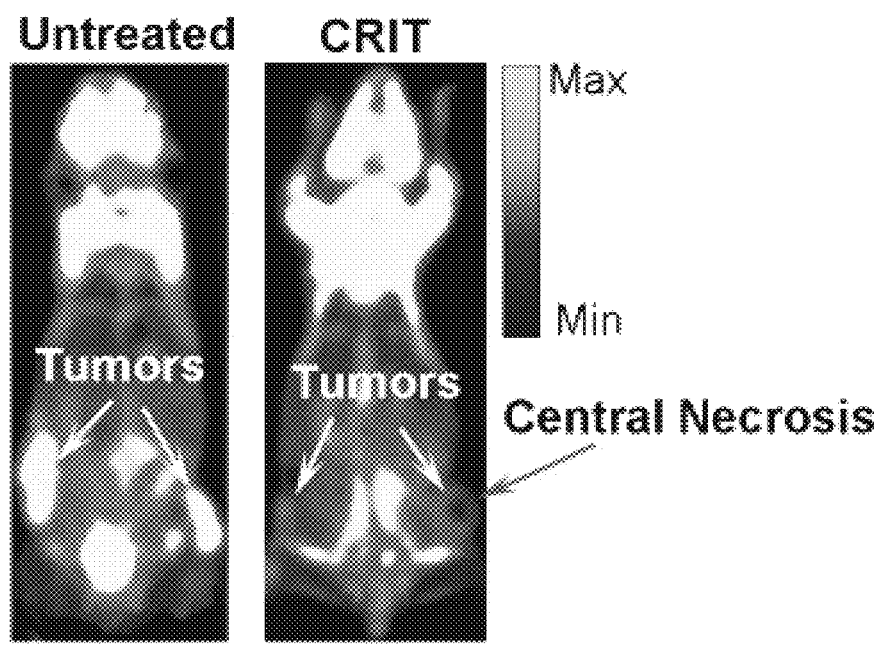
Figure 16F:
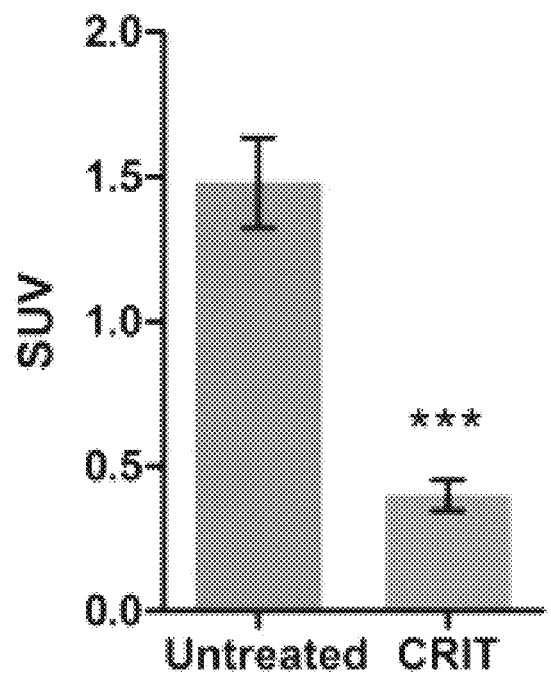
Figure 16G:
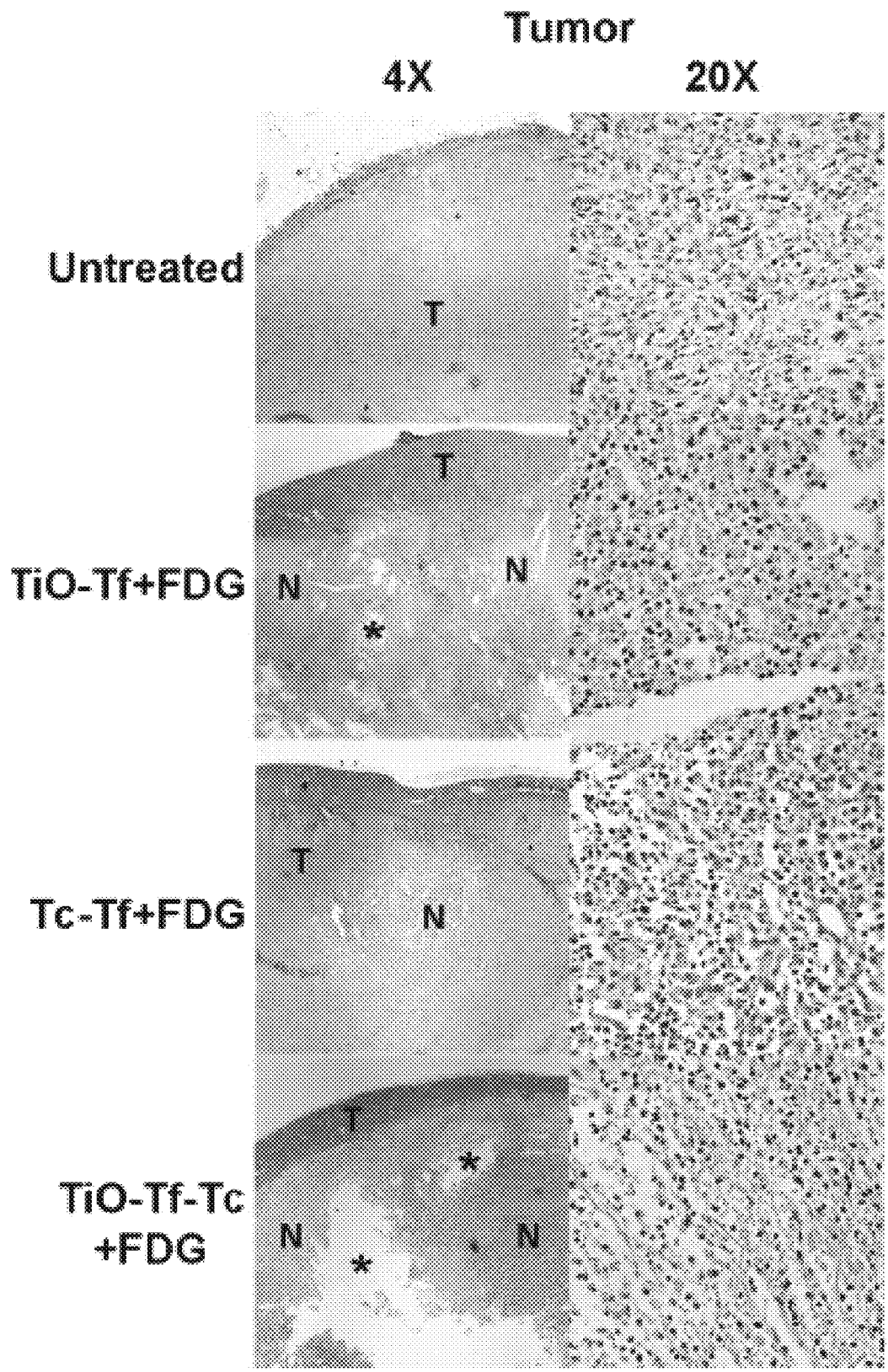

The high specific activity of FDG provided excellent images of tumors before and after CRIT using positron emission tomography (PET). At trace levels, FDG serves as an imaging agent without inducing CRIT (FIG. 16E,F). After increasing the injected dose to >0.4 mCi (15.91 MBq)/0.1 ml per mouse to trigger CRIT, FDG-PET imaging clearly demonstrates a remarkable decrease in FDG uptake in tumors that responded to CRIT. Image analysis shows selective destruction of proliferating cells in the tumor region, with one tumor revealing necrotic centers (FIG. 16E,F). Histological analysis of tumor sections of $TiO_2$-Tf and $TiO_2$-Tf-Tc treated mice reveals pronounced necrotic zones occupying approximately 30% and 40% of the tumor mass, respectively (FIG. 16G). A significantly high number of tumor infiltrating lymphocytes (TIL), primarily neutrophils, and macrophages were observed among the necrotic cells. Large areas of the tumor exhibited loss of cellular architecture, probably due to scavenging of the necrotic debris by macrophages, as evidenced by large denuded pockets. However, in Tc-Tf and FDG treated tumors, only 15% of the tumor mass was necrotic, with a high TIL population and a significantly higher distribution of apoptotic foci. These findings suggest that in addition to free radical mediated direct damage to cells, activation of the immune system against the tumor cells triggered neutrophil and macrophage recruitment. As observed in our in vitro studies, it appears that necrosis is the dominant feature of $TiO_2$ based CRIT, while apoptosis mediated cell death when the Tc based constructs were used. The extended median survival in $TiO_2$-Tf-Tc treated mice resulted from the additive bimodal cell death mechanism through the combined effects of different radicals generated by the photocatalyst and photoinitiator.

Figure 20:
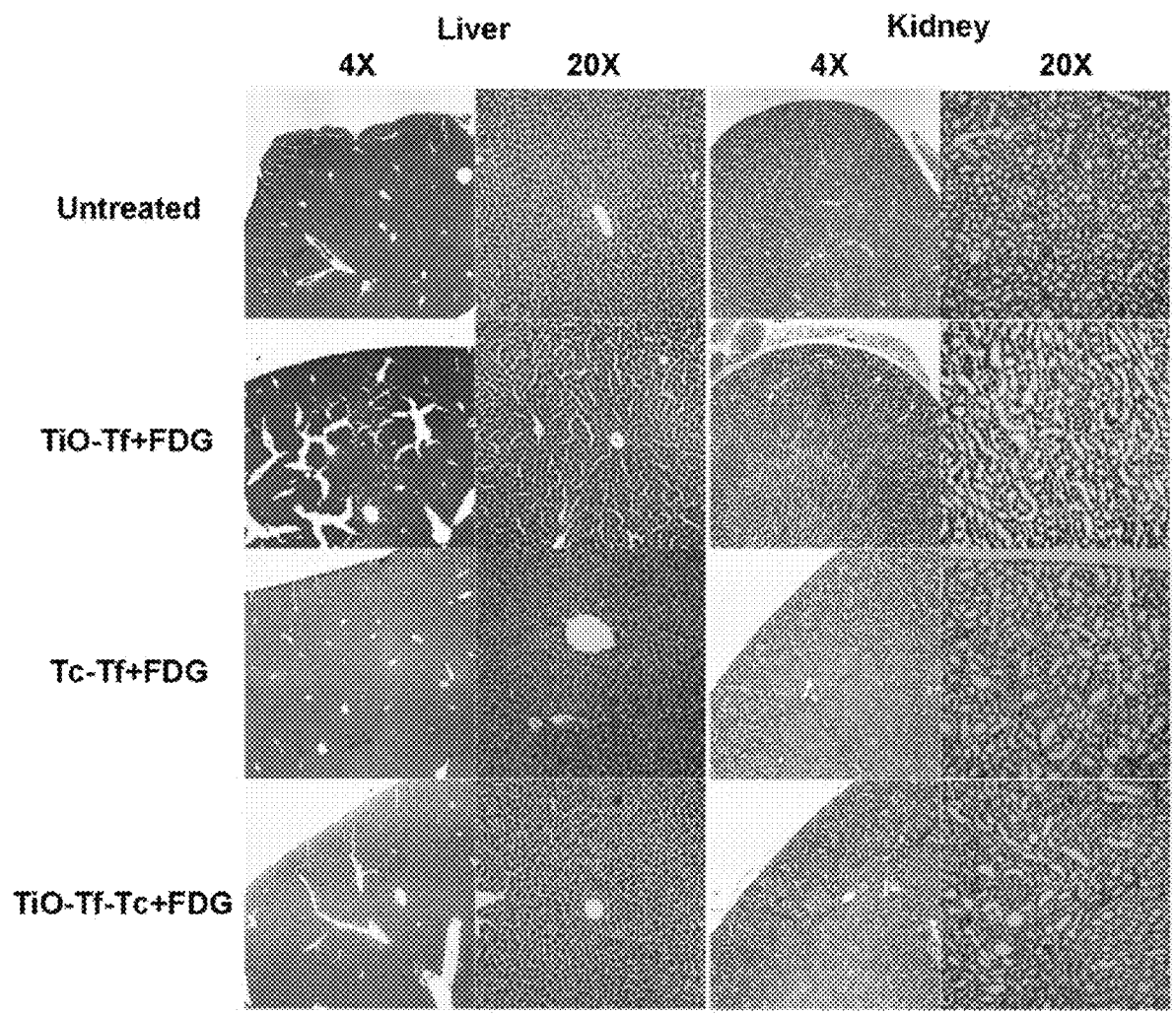
FIG. 20 depicts images of histological analysis of H&E stained liver and kidney sections before and after treatment are shown to demonstrate no significant lesions in these organs indicating absence of systemic toxicity due to CRIT.

Off-target toxicity is a concern for i.v. based CRIT. This is particularly important in the liver and kidneys, which are the main elimination route for the materials. These organs are also sensitive indicators of systemic toxicity caused by therapeutic interventions. Histological analysis of the liver and kidneys following CRIT did not show any significant lesions in the organs, indicating CRIT was selective for proliferating tumor cells (FIG. 20).

Conclusions for Examples 7-10

In this study, we have demonstrated a new approach for the use of low radiance CR for phototherapy by designing NPS that are susceptible to sub-therapeutic doses of radioactivity. Additive effects of complementary radical generation mechanisms of photocatalysts (hydroxyl radicals) and photoinitiators (photofragmentation) enabled effective CRIT using tumor targeted NPS, where the tumor concentration is conventionally low. The astute use of Tf as a tumor-targeting agent a Tc chaperone, a $TiO_2$ chelator, a linker, and a dispersant to prevent nanoparticle aggregation, ushers in a modular approach for NPS design and efficient tumor-targeted CRIT in vivo. Optimization of the dosing regimen could lead to complete tumor remission using i.v. administration of the agents. Because of the established biocompatibility of all components used in the study, our work creates a clear path to human translation. Although we focused on tumor therapy, the approach described in this study is versatile, opening the possibility of treating a variety of lesions in a depth-and oxygen-independent manner, thus overcoming the Achilles heel of phototherapeutic interventions.

Methods for Example 7-10

Synthesis of $TiO_2$-PEG, $TiO_2$-Tf, Tc-Tf and $TiO_2$-Tf-Tc. Anatase $TiO_2$ (1 mg; Sigma Aldrich Co.) was suspended in deionized water (1 ml) to prepare a working stock solution. PEG 400 (100 μl) was added to the $TiO_2$ solution and sonicated using a probe sonicator for 10 min at room temperature (RT). The mixture was then dialyzed overnight against Dulbecco's Phosphate Buffered Saline (DPBS) using a 3000 Da molecular weight cutoff (MWCO) Slide- A-Lyzer MINI Dialysis Device (Thermo Fisher Scientific Inc.) to remove excess PEG. Working stock solutions of Tf were prepared by dissolving 5 mg of human apo-Tf (Sigma Aldrich Co.) in 1 ml DPBS, pH 7.4. To prepare $TiO_2$-Tf, a 1:1 (v/v) solution of $TiO_2$ and Tf was mixed and probe sonicated in continuous mode for 5 min. The solution was then immediately passed through a 0.45 µm syringe filter to isolate monodisperse nanoparticles. To prepare Tc-Tf, five-fold molar excess of Tc (Sigma Aldrich Co.) was added to human apo-Tf and incubated in a shaker for 2 h at room temperature (RT). A working stock of Tc was initially prepared in DMSO due to the low solubility of Tc in water and aqueous buffers. The mixture was then dialyzed overnight against DPBS using a 3000 Da molecular weight cutoff (MWCO) Slide-A-Lyzer MINI Dialysis Device to remove excess Tc. $TiO_2$-Tf-Tc was similarly prepared by incubating Tc with $TiO_2$-Tf conjugates and thereafter dialyzing to remove excess Tc.

Physicochemical Characterization.

Transmission electron microscopy images were acquired using a FEI Tecnai Spirit Transmission Electron Microscope (FEI) operating at an acceleration voltage of 200 kV. Dynamic light scattering measurements were taken using a Malvern Zetasizer Nano ZS (Malvern Instruments Ltd.) instrument equipped with a 633 nm laser. Three measurements were conducted for each sample with at least 10 runs, each run lasting 10 s. All sizes reported were based on intensity average. Absorption spectra of TiO2 and Tc were recorded on a Beckman Coulter DU 640 UV-visible spectrophotometer (Beckman Coulter Inc.) and analyzed using Graphpad Prism statistical software. Fluorescence spectra of $TiO_2$ were recorded on a Fluorolog-3 spectrofluorometer (Jobin Yvon Horiba). The sample was placed in a quartz cuvette and measurements recorded in triplicates.

Cell Culture.

HT1080 fibrosarcoma cells (American Type Culture Collection —ATCC) were cultured in Dulbecco's Modified Eagle's Medium (DMEM) containing 10% fetal bovine serum (FBS), L-glutamine (2 mM), penicillin (100 units/rip, and streptomycin (100 µg/ml) at 37° C. in a humidified atmosphere of 5% $CO_2$ and 95% air. For cytotoxicity studies, concentration of 2.5 pg/ml of the $TiO_2$-Tf, Tc-Tf, and $TiO_2$-Tf-Tc NPS as well as 0.5 mCi/0.1 ml of FDG and $^{64}Cu$ were used.

TEM Analysis of Cells with $TiO_2$-Tf and Tc-Tf.

For ultrastructural analysis, cells were fixed in 2% paraformaldehyde/2.5% glutaraldehyde (Polysciences Inc.) in 100 mM cacodylate buffer, pH 7.2 for 1 h at room temperature. Samples were washed in cacodylate buffer and postfixed in 1% osmium tetroxide (Polysciences Inc.) for 1 h. Samples were then rinsed extensively in distilled water prior to en bloc staining with 1% aqueous uranyl acetate (Ted Pella Inc.) for 1 h. Following several rinses in water, samples were dehydrated in a graded series of ethanol and embedded in Eponate 12 resin (Ted Pella Inc.). Sections of 95 nm were cut with a Leica Ultracut UCT ultramicrotome (Leica Microsystems Inc.), stained with uranyl acetate and lead citrate, and viewed on a JEOL 1200 EX transmission electron microscope (JEOL USA Inc.) equipped with an AMT 8 megapixel digital camera (Advanced Microscopy Techniques).

In Vitro Cell Viability Assays.

The MTS (3-(4,5-di methylthiazol-2-yl)-5-(3-carboxymethoxyphenyl)-2-(4-sulfophenyl)-2H-tetrazolium) assay, a colorimetric assay for assessing cell viability was performed using the CellTiter 96® AQueous Non-Radioactive Cell Proliferation Assay kit (Promega Co.) according to the manufacturer's instructions. The cells were incubated with the constructs and FDG for 48 h before analysis.

The alkaline Comet Assay (Cell Biolabs Inc.) was performed using the manufacturer's protocol. Briefly, treated and untreated control cells were removed from the flask by scraping. The cell suspension was centrifuged and washed with ice-cold DPBS two times and resuspended at $1 \times 10^5$ cells/ml in ice-cold DPBS. Cells were embedded in low melt Comet agarose and plated on provided microscope slides. The cells were then lysed with lysis buffer and treated with alkaline solution. The slides were electrophoresed in alkaline solution at 1 Volt/cm with a setting of 300 mAmp for 30 minutes. The slides were stained with Vista Green DNA dye after washing and drying. Fluorescence images were acquired using an Olympus BX51 epifluorescence microscope equipped with a CCD camera. % Tail DNA was estimated using the OpenComet (v1.3) plugin for Image J software.

Propidium iodide stain (Life Technologies Inc.) was used according to the manufacturer's instructions. Fluorescence/reflectance cell images were taken with a 40× objective using the mercury lamp of the microscope as the excitation source. FITC and Cy5 filter sets with an excitation/emission range of 480±40/535±50 nm and 620±60/700±75 nm, respectively, were used. Confocal microscopy images were acquired using an Olympus FV1000 confocal microscope. Fluorescence/reflectance cell images were taken with a 60× objective using He:Ne 488 and 633 nm excitation lasers and an emission range of dichroic mirrors set to 455-575 nm and 655-755 nm, respectively. Fluorescence and reflectance image overlay with false color was performed using Fluoview FV10-ASW software from Olympus (Center Valley, Pa.).

In Cellulo Hydroxyl and Superoxide Radical Assay.

Hydroxyphenyl fluorescein (HPF) with an excitation and emission wavelength of 490 nm and 515 nm, respectively (Life Technologies Inc.) was used according to the manufacturer's instructions. Briefly, the 5 mM stock was diluted to a 5 µM working stock in DPBS. Cells were grown in 8 well slides. The $TiO_2$-Tf, Tc-Tf and $TiO_2$-Tf-Tc and FDG treated HT1080 cells were immersed in the HPF working stock 4 h post treatment. The cells were incubated for 1 h before the dye solution was washed away and replaced with fresh DPBS. The cells were imaged using confocal microscopy using the 488 nm Argon ion laser with emission set to 500-600 nm. Similarly, Mitosox Red (Life Technologies Inc.) with an excitation and emission wavelength of 510 nm and 580 nm, was used to detect superoxide radicals, following the manufacturer's instructions.

Chelation of $^{64}Cu$ to DOTA.

For experiments with $^{64}Cu$, typically chelation is essential to mitigate toxicity from Cu(II) ions. A 1 mg/ml stock solution of DOTA (1,4,7,10-tetraazacyclododecane-1,4,7, 10-tetraacetic acid) (Macrocyclics Inc.) was prepared in 50 mM ammonium acetate buffer equilibrated to pH 5.5. 50 µl of DOTA stock was added to 450 µl of ammonium acetate buffer followed by 5 mCi (185 MBq) of $^{64}Cu$ in 5 µl of hydrochloric acid. The reaction mixture was incubated at 45° C. for 1 h in a shaker. Non-chelated $^{64}Cu$ was removed from the chelated DOTA-$^{64}Cu$ using a Waters HPLC purification system. The flow rate was set to 1 ml/min. The solvents were A-0.1% Trifluoracetic acid (TFA) in water and B-0.1% TFA in acetonitrile. After 5 min hold at 5% B the gradient was programed linearly to 100% B at 40 min. The sample was collected for 2 min at 6 min time points corresponding to the peaks in the radiometer and UV detector. The sample was then dried in a rotary shaker to remove TFA and acetonitrile for 4 h before re-suspending in DPBS.

Matrigel Based Cell Studies.

Matrigel™ (BD Biosciences) was thawed at 4° C., added to an equal volume of TiO2 solution, and plated on 8 well chamber slides. HT1080 cells were grown on the plated slides before $^{64}Cu$ (0.5 mCi/0.1 ml) was introduced. Matrigel is expected to prevent internalization of trapped $TiO_2$ into cells. The cells were incubated at 37° C. for 48 h. Live/Dead® cell stains (Life Technologies Inc.) were used according to the manufacturer's instructions.

In Vivo Tumor Model.

Athymic nu/nu mice were purchased from Frederick Cancer Research and Development Center. All studies were conducted in compliance with Washington University Animal Welfare Committee's requirements for the care and use of laboratory animals in research. The HT1080 tumors were generated by subcutaneous injection of $4 \times 10^6$ cells in 100 μl of DPBS in Athymic nude mice.

In Vivo Biodistribution Studies.

Athymic nude mice with a tumor volume of ~300 $mm^3$, were injected with 1 mg/ml of $TiO_2$-Tf (n=5) or Tf alone (n=5) in 100 j.il of DPBS intravenously through tail vein, where Tf was labeled with Alexa 680 dye (Life Technologies Inc.). Fluorescence imaging was performed using an excitation and emission wavelength of 685 nm and 720 nm, respectively, in a Pearl whole animal imager (Li-Cor Biosciences Inc.). The mice were sacrificed 24 h post-injection and the major organs were dissected and imaged. Mean fluorescence intensity was estimated by ROI analysis using ImageJ software. The intensity was normalized to equalize muscle fluorescence levels and plotted for all the organs using Graph Pad Prism software.

CRIT of Solid Tumors.

When tumor volume in mice reached 50 $mm^3$, which is ~7-9 days after subcutaneous implantation of cells, the mice (n=6 per group) were injected with 1 mg/ml $TiO_2$-Tf, Tc-Tf, $TiO_2$-Tf-Tc in 100 μl of DPBS intravenously and 0.87 mCi/0.1 ml of FDG also intravenously 48 h later. Control mice (n=6 per group) were administered with DPBS, the constructs, or FDG alone. The mice were starved for 6 h before administering FDG and kept in a dark room post injection, shielded by lead bricks. A second administration of FDG (0.87 mCi/0.1 ml) was given 48 h after the first FDG injection. Similarly, two additional cohorts were administered with 0.14 mCi/0.1 ml and 0.43 mCi/0.1 ml FDG (n=4 per group), respectively, and monitored over 45 d. For intra-tumoral administration, a cocktail of 2.5 pg/ml of $TiO_2$-PEG and 0.5 mCi/0.1 ml $^{64}Cu$ in 50 μl of DPBS was injected directly into the tumor mass after the tumor volume reached 200 $mm^3$ (~12-14 days after subcutaneous implantation of cells). Two diametrically opposite injection sites were chosen and 25 μl of the cocktail was delivered at each site. Four groups (n=4), $TiO_2$-PEG treated mice, $^{64}Cu$ treated mice, non-radioactive Cu (1 μM $CuCl_2$) treated mice and untreated mice, served as controls. For both, systemic and intra-tumoral studies, the mice were monitored for 45 days. The growing tumors were measured with calipers every two days and tumor volume (TV) calculated using the equation: TV=(length×$width^2$)/2. The TV was plotted versus time to analyze CRIT effect on the seed culture. Weight and any physical signs for distress were also monitored closely. Kaplan-Meir survival curves were plotted using Graph Pad Prism software. The mice with regressing tumors were monitored for an additional four months to determine whether the cancer was in remission.

FDG-PET Imaging.

After anaesthetizing the mice with 1.5-2% Isoflurane and Oxygen, 0.19 mCi (7.03 MBq)/0.1 ml FDG was administered i.v. A ten minute transition scan was performed just before the ten minute emission at 1 h post injection. The animals were placed on the microCT® in the same position to obtain anatomical imaging that was co-registered to the microPET® image. The images were acquired using a MicroPET-Inveon MultiModality scanner (Siemens Preclinical Solutions).

Histology.

The HT1080 tumor bearing mice in the control groups were sacrificed 15 d post administration of constructs or FDG, while mice that underwent CRIT with $TiO_2$-Tf or Tc-Tf were sacrificed 30 d post administration, and the group that underwent CRIT with $TiO_2$-Tf-Tc at 45 d post administration. Likewise, for HT1080 tumor bearing mice, the mice were sacrificed 3 d after intra-tumoral administration of $TiO_2$-$^{64}Cu$ cocktail. The tumors were harvested and snap-frozen in OCT media for routine staining with hematoxylin and eosin (H&E). Brightfield images of H&E stained 10 μm tumor sections were taken using the epifluorescent microscope at 4× and 20× magnifications.

Statistical Analysis.

Unless noted otherwise, all values are means and error bars are standard deviations. Statistical significance was measured by student T test using Graphpad Prism software.

References for Examples 7-10

1. Brown, S. B., Brown, E. A. & Walker, I. The present and future role of photodynamic therapy in cancer treatment. *Lancet Oncol* 5, 497-508 (2004).
2. Chatterjee, D. K., Fong, L. S. & Zhang, Y. Nanoparticles in photodynamic therapy: an emerging paradigm. *Adv Drug Deliv Rev* 60, 1627-1637 (2008).
3. Ethirajan, M., Chen, Y., Joshi, P. & Pandey, R. K. The role of porphyrin chemistry in tumor imaging and photodynamic therapy. *Chem Soc Rev* 40, 340-362 (2011).
4. Spring, B. Q., et al. Selective treatment and monitoring of disseminated cancer micrometastases in vivo using dual-function, activatable immunoconjugates. *Proc Natl Acad Sci USA* 111, 26 (2014).
5. Jelley, J. V. Cerenkov radiation and its applications. *Br J Appl Phys* 6, 227 (1955).
6. Robertson, R., et al. Optical imaging of Cerenkov light generation from positron-emitting radiotracers. *Phys Med Biol* 54, 0031-9155 (2009).
7. Kotagiri, N., Niedzwiedzki, D. M., Ohara, K. & Achilefu, S. Activatable Probes Based on Distance-Dependent Luminescence Associated with Cerenkov Radiation. *Angew Chem Int Ed* 52, 7756-7760 (2013).
8. Thorek, D. L., Ogirala, A., Beattie, B. J. & Grimm, J. Quantitative imaging of disease signatures through radioactive decay signal conversion. *Nat Med* 19, 1345-1350 (2013).
9. Dolmans, D. E., Fukumura, D. & Jain, R. K. Photodynamic therapy for cancer. *Nat Rev Cancer* 3, 380-387 (2003).
10. Vaupel, P., Kallinowski, F. & Okunieff, P. Blood flow, oxygen and nutrient supply, and metabolic microenvironment of human tumors: a review. *Cancer Res* 49, 6449-6465 (1989).
11. Schwarz, P. F., et al. A New Method To Determine the Generation of Hydroxyl Radicals in Illuminated TiO2 Suspensions. *J Phys Chem B* 101, 7127-7134 (1997).

12. Boehm, H. P. Acidic and basic properties of hydroxylated metal oxide surfaces. *Discuss Faraday Soc* 52, 264-275 (1971).
13. Turchi, C. S. & Ollis, D. F. Photocatalytic degradation of organic water contaminants: Mechanisms involving hydroxyl radical attack. *J Catal* 122, 178-192 (1990).
14. Linsebigler, A., Lu, G. & Yates, J. Photocatalysis on TiOn Surfaces: Principles, Mechanisms, and Selected Results. *Chem. Rev.* 95, 735-758 (1995).
15. Mitchell, G. S., Gill, R. K., Boucher, D. L., Li, C. & Cherry, S. R. In vivo Cerenkov luminescence imaging: a new tool for molecular imaging. *Philos Trans A Math Phys Eng Sci* 369, 4605-4619 (2011).
16. Huang, W., Lei, M., Huang, H., Chen, J. & Chen, H. Effect of polyethylene glycol on hydrophilic TiO2 films: Porosity-driven superhydrophilicity. *Surf Coat Technol* 204, 3954-3961 (2010).
17. Gatter, K. C., Brown, G., Trowbridge, I. S., Woolston, R. E. & Mason, D. Y. Transferrin receptors in human tissues: their distribution and possible clinical relevance. *J Clin Pathol* 36, 539-545 (1983).
18. Ji, Z., et al. Dispersion and stability optimization of TiO2 nanoparticles in cell culture media. *Environ Sci Technol* 44, 7309-7314 (2010).
19. Brindley, P. B., Davies, A. G. & Hawari, J. A. A. An ESR study of the photolysis of dicyclopentadienyltitanium dichloride. *J Organomet Chem* 250, 247-256 (1983).
20. Davidenko, N., Garcia, O. & Sastre, R. The efficiency of titanocene as photoinitiator in the polymerization of dental formulations. *J Biomater Sci Polym Ed* 14, 733-746 (2003).
21. Qian, Z. M., Li, H., Sun, H. & Ho, K. Targeted drug delivery via the transferrin receptor-mediated endocytosis pathway. *Pharmacol Rev* 54, 561-587 (2002).
22. Tijana, R., Nada, M. D., Adam, E. & Elena, R. Biofunctionalized TiO2-Based Nanocomposites. in *Handbook of Nanophysics* 1-28 (CRC Press, 2010).
23. Paunesku, T., et al. Biology of TiO2-oligonucleotide nanocomposites. *Nat Mater* 2, 343346 (2003).
24. Zhao, J., et al. Titanium dioxide (TiO2) nanoparticles induce JB6 cell apoptosis through activation of the caspase-8/Bid and mitochondrial pathways. *J Toxicol Environ Health A* 72, 1141-1149 (2009).
25. O'Connor, K., et al. Novel titanocene anti-cancer drugs and their effect on apoptosis and the apoptotic pathway in prostate cancer cells. *Apoptosis* 11, 1205-1214 (2006).
26. Kelloff, G. J., et al. Progress and promise of FDG-PET imaging for cancer patient management and oncologic drug development. *Clin Cancer Res* 11, 2785-2808 (2005).
27. Mylonas, C. & Kouretas, D. Lipid peroxidation and tissue damage. *In Vivo* 13, 295-309 (1999).
28. Yu, B. P. Cellular defenses against damage from reactive oxygen species. *Physiol Rev* 74, 139-162 (1994).
29. Heyne, B., Maurel, V. & Scaiano, J. C. Mechanism of action of sensors for reactive oxygen species based on fluorescein-phenol coupling: the case of 2-[6-(4'-hydroxy) phenoxy-3H-xanthen-3-on-9-yl]benzoic acid. *Org Biomol Chem* 4, 802-807 (2006).
30. Apel, K. & Hirt, H. Reactive oxygen species: metabolism, oxidative stress, and signal transduction. *Annu Rev Plant Biol* 55, 373-399 (2004).
31. Rosen, G. M. & Freeman, B. A. Detection of superoxide generated by endothelial cells. *Proc Natl Acad Sci USA* 81, 7269-73 (1984).
32. Chithrani, D. B., et al. Gold nanoparticles as radiation sensitizers in cancer therapy. *Radiat Res* 173, 719-728 (2010).

Introduction to Examples 11-14

Phototherapeutic interventions such as photodynamic therapy (PDT) are currently used in clinics for cancer treatment. The exciting combination of light and photosensitizer (PS) offers high degree of control that is typically used in different stages of cancer patient management as well as other disease states. Despite the promise of PDT, the shallow penetration of light in tissue confines its use to localized and superficial lesions. In addition, light dosimetry for effective PDT remains a challenge because of the difficulty in delivering external light uniformly to the heterogeneous contours of diseased tissues. A second level of complexity arises from the efficacy of PS. Although there has been significant progress in the development of newer and better PS drugs, other clinically and biologically relevant problems such as low sensitivity and selectivity, as well as sustained skin photosensitivity, continue to diminish the effectiveness of PDT. Another major limitation of current PS is the reliance on tissue oxygen to generate cytotoxic singlet oxygen free radicals. This feature precludes the effective application of PDT in the treatment of many solid tumors, which often have hypoxic regions.

We propose a two-prong approach that addresses the issue of shallow penetration of light by employing Cerenkov radiation (CR) and the issue of tissue oxygen dependence and suboptimal activation of PS by using previously unexplored light sensitive materials for effective CR-Induced Therapy (CRIT). CR from clinical grade radionuclides used in positron emission tomography (PET) emits predominantly a continuous spectrum of ultraviolet (UV) light. Particularly, the PET radionuclides Fluorine-18 ($^{18}F$), Copper-64 ($^{64}Cu$), and Zirconium-89 ($^{89}Zr$) emit CR suitable for molecular imaging applications by recording the weak visible light radiance of CR. In addition, the clinical applicability of CR for quantifying disease signatures was recently demonstrated. To improve PS activation, minimize reliance on molecular oxygen, overcome tissue depth dependency, and favor clinical translation, a new class of PSs capable of selective photoactivation using the low radiance from CR for CRIT is urgently needed.

Toward this goal, we have identified the light-sensitive materials, titanocene (Tc) and titanium dioxide ($TiO_2$) for CRIT. Tc is a photoinitiator that can be activated by low intensity light to generate free radicals, and titanium dioxide ($TiO_2$) is a regenerative photocatalyst that produces free radicals capable of localized cytotoxicity. There are several advantages to using Tc and $TiO_2$: 1. The predominantly hydroxyl radicals from $TiO_2$ and the photo-fragmentation products from Tc are generated in an oxygen independent fashion. 2. The excitation energy for Tc and $TiO_2$ are in the UV spectrum, where CR quantum efficiency is highest; the large surface area of $TiO_2$ nanoparticles can efficiently harvest CR. These combined features favor CRIT. 3. Radical generation mechanisms for Tc and $TiO_2$ are different, which could result in different mechanisms of cell death. Thus, a combination of both materials could synergistically enhance treatment outcomes. 4. Transferrin (Tf), a tumor targeting protein, binds Tc with high affinity. Further, $TiO_2$ nanoparticles typically form aggregates in aqueous solutions, but addition of Tf produces monodispersed and stable $TiO_2$-Tf nanoparticles. Thus, treatment of $TiO_2$ with Tf spontaneously forms $TiO_2$-Tf, which readily binds Tc to generate TiO$_2$-Tf-Tc without loss of Tf tumor targeting affinity. This provides a simple method to prepare tumor-avid materials for both photoinitiator- and photocatalyst-mediated CRIT. 5. Clinically, radiolabeled 2'-deoxy-2'-($^{18}$F)fluoro-D-glucose (FDG) is widely used to image rapidly proliferating cells, which can co-localize with TiO$_2$-Tf-Tc in tumors overexpressing Tf receptors. Our early results suggest that FDG can induce effective CRIT with TiO$_2$-Tf-Tc. This is a first demonstration of a strategy to overcome the low light intensity of CR. 6. The FDA has approved TiO$_2$ nanoparticles for use as colorant in food and as a UV protective ingredient; Tc has been used in Phase II clinical trials as a chemotherapeutic drug but was discontinued for lack of efficacy; and FDG is clinically used in PET. Therefore, the ensemble of products is clinically translatable using sublethal doses of both Tc and TiO$_2$.

This work should demonstrate the efficacy of CRIT in cancer therapy and show that photoactivation of TiO$_2$-Tf-Tc by radionuclides such as $^{18}$FDG-mediated CR will inhibit, reverse, or prevent tumor growth. This work should answer the following questions: (1) Can a tumor-targeted photoinitiator such as Tc inhibit tumor growth via CRIT? We expect that photofragmentation of Tc will produce free radicals that damage DNA, resulting in cell death. (2) Can a tumor-targeted photocatalyst such as TiO$_2$ inhibit tumor growth via CRIT? We expect cell death mediated by light-induced and oxygen-independent hydroxyl radicals generated from TiO$_2$ nanoparticles. (3) Can we achieve complementary CRIT by combing photoinitiator- and photocatalyst-cell death mechanisms via TiO$_2$-Tf-Tc nanoparticles? We expect to observe a significant inhibition or regression of tumor growth with TiO$_2$-Tf-Tc than can be achieved with tumor targeted Tc or TiO$_2$ alone. We will determine the mechanism of cell death in vitro and the rate of tumor growth or regression in vivo.

Example 11: Success and Struggles of Photodynamic Therapy (PDT)

Photodynamic therapy (PDT) is a viable treatment paradigm for cancer: PDT uses light of appropriate wavelengths to excite a photosensitizer (PS) in the tissue volume of interest. Upon light absorption, the PS can mediate PDT by Type I (direct transfer of radical ions from an activated PS to biomolecules) or Type II (transfer of PS triplet state electrons to molecular oxygen, which generates reactive singlet oxygen species), or occasionally a combination of both mechanisms. The mechanisms of PDT have been reviewed extensively. The combination of non-lethal light levels and non-toxic PS to induce highly selective and localized phototoxicity in target tissue remains an attractive feature of PDT, as reflected by its tremendous advancements over conventional cancer therapies. PDT has resulted in high cure rates for some tumors without cumulative toxicity. Examples of the diverse clinical uses of PDT include malignancies of the gastrointestinal tract, lungs, head & neck, and skin. To improve PDT efficacy, different approaches have been employed, including the conjugation of PS to carrier molecules for tumor-selective uptake, the development of new nanoparticles to amplify radical generation, the use of nonlinear activation techniques to increase treatment depth, and the design of activatable PS to selectively trigger photosensitivity in target tissue. Despite these laudable accomplishments, the broad application of PDT in clinics has been limited by several factors, some of which are summarized below.

Reliance on Molecular Oxygen for Effective PDT Precludes Application Under Hypoxic Conditions:

Regardless of the mechanism of action, both Type I and Type II PDT regimens currently used in the clinics rely on reactive oxygen products for therapeutic effect. This basic assumption implies that PDT will be less efficient under hypoxic conditions. Unfortunately, many solid tumors have significant hypoxic regions, some of which develop resistance to PDT. Moreover, most PSs require high radiant exposure to generate sufficient singlet oxygen species for PDT, which may harm sensitive healthy tissues, rapidly photobleach some PSs and possibly produce undesirable effects. Therefore, an oxygen-independent light-induced therapy could address this fundamental problem.

PDT is Largely Confined to Localized and Shallow Lesions:

The limited penetrability of light in tissues and the challenges in optimizing light dosimetry have prevented the full realization of the enormous potential of light-based imaging and therapeutic methods. Both UV and visible light (UV-vis) can only penetrate tissue from a few microns to a few millimeters from the incident light, which has confined their use to direct tissue ablation or the treatment of skin lesions. To improve the treatment depth, newer near infrared (NIR) absorbing PSs have been developed. Because NIR light can penetrate deeper in tissue than UV-vis, these agents can improve the depth of treatment. Recent studies have explored the use of multiphoton excitation of PS in the NIR wavelengths to activate PS in the visible light region. Unfortunately, this approach required PSs with high multiphoton absorption cross sections to harvest the multiphotons efficiently. Moreover, only small tissue volumes can be treated per multiphoton event. Additionally, even these improvements can only interrogate tissue depths within 10 mm when using a high intensity light source. Further, the efficiency of light delivery decreases rapidly with tissue depth, requiring different settings to optimize depth-dependent dosimetry. This limitation can be overcome by the use of depth-independent light source to activate PS. As such, we have developed a molecular oxygen- and tissue depth-independent light-induced cancer therapy, which will expand light treatment to pathologies that are currently not amenable to current phototherapeutic methods.

Titanium Based PSs can Eradicate Tumors in a Molecular Oxygen-Independent Manner:

Titanium compounds are widely used in medicine, clean energy generation, and environment remediation because of their low toxicity, redox activity, and photoactive properties. Among them, Titanocene dichloride (Tc) and titanium dioxide (TiO$_2$) have shown promise as photoinitiators and photosensitizers, respectively. Tc is derived from the family of metallocenes and has been used in phase II clinical trials as a chemotherapeutic drug. Although only mild to moderate side effects were observed at high doses, the clinical trials were discontinued due to poor treatment outcomes. Still, these studies established precedence for using Tc in humans. Apart from its use in medical oncology, it is also widely used as a photoinitiator in the plastics industry. After exposure to UV light, Tc is able to generate free radicals in the presence or absence of oxygen following photofragmentation. Because the photo-initiation process occurs even with low radiance, and its excitation maximum is in the UV region ($\lambda$=250-325 nm), photofragmentation of sub-cytotoxic doses of Tc may induce DNA damage and subsequent cell death.

In addition to being used clinically in a variety of medical and food formulations, previous studies have shown that TiO$_2$ nanoparticles are excellent photocatalysts that can absorb UV light (λmax=275 nm) with high efficiency and generate free hydroxyl and superoxide radicals through electron-hole pair production. Generation of hydroxyl radicals through electron-hole transfer to chemisorbed H$_2$O is an oxygen-independent process, whereas superoxide radical generation requires aerated aqueous media for electron transfer to molecular oxygen. Of these two products, the highly cytotoxic hydroxyl radicals are the key species formed during the photocatalytic oxidation on the surface of TiO$_2$ in aqueous solvents. These features have motivated the use of TiO$_2$ as a PS to induce cell death in vitro. Moreover, biocompatible inorganic nanoparticles are attractive alternatives to conventional PS because of their large surface area, excellent payload capacity, and high reactivity. However, the shallow penetration of UV light has confined most of the previous studies to in vitro models of human diseases. The generation of cytotoxic free hydroxyl species at low intensity UV light suggests that the low radiance of Cerenkov radiation (CR) can serve as a UV light source for depth-independent photoactivation of the nanomaterials for phototherapy.

Cerenkov Radiation can Serve as Tissue Depth-Independent Light Source for PDT:

Some clinically relevant radionuclides can produce a continuous spectrum of UV light via CR. CR occurs when charged particles such as positrons or electrons travel faster than the speed of light in a given medium, emitting predominantly UV light that tails off to the visible spectrum (250-600 nm). Positron emission tomography (PET) isotopes such as radiolabeled 2'-deoxy-2'-($^{18}$F)fluoro-D-glucose (FDG) are an ideal source for CR because of their high positron (β+) emission decay and short half-life. The β+ particles travel short distances (<1 mm) in tissues, during which CR is first emitted before they undergo annihilation. Recently, technological advances in low light detection techniques have enabled the use of CR as a light source for molecular imaging. We recently developed activatable CR probes for optical-nuclear imaging using Copper-64 ($^{64}$Cu). Clinical application of CR imaging was recently demonstrated. Despite these advancements, CR remains a low intensity light source, which limits the amount of material that can be activated, and thus requiring significant signal amplification and prolonged data acquisition times to minimize background and dark noise. Our preliminary data suggest that the low UV light threshold needed to excite photoinitiators such as Tc and photocatalysts such as TiO$_2$ nanoparticles could unleash a new paradigm in CR-Induced Therapy (CRIT).

There are several elements of innovation to this work: (1) The use of Tc and TiO$_2$ for CRIT for in vivo treatment of cancer in a depth-independent manner is new. (2) The processing of crystalline TiO$_2$ to synthesize monodispersed and tumor selective nanoparticles is new. (3) We have discovered a new and efficient method to use transferrin (Tf) as tumor-targeting agent, as well as Tc chaperone, TiO$_2$ chelator, a linker, and a dispersant to prevent nanoparticle aggregation. This approach simplifies preparation of the PS for in vivo use. (4) We discovered the synergistic effects of combining Tc and TiO$_2$ for efficient CRIT. This is the first demonstration of the use of spontaneously generated CR at low UV light intensity to inhibit tumor growth in depth-independent manner. (5) Because the components of the treatment methods are already used in humans (Tc, TiO$_2$, Tf, and $^{18}$FDG), we envisage a clear path to human translation.

Although the Examples focus on specific photoinitiators and catalysts because of the limited time and resources to demonstrate feasibility, this work uncovers a new strategy to develop tailored molecular photosensitive agents for treating cancer and other human diseases. Highly refractory tumors such as pancreatic cancer and gliomas, which typically require partial regression of tumor size before surgery, will benefit highly from this technique. For example, intratumoral administration of the photoactive agents and radionuclide cocktail will help achieve rapid tumor regression, as demonstrated in our preliminary studies. In addition, hypoxic tumors that are resistant to radiation therapy will now be sensitized for improved therapeutic outcomes because the CR from linear accelerators can activate the photoinitiators similar to PET radionuclides, opening new treatment techniques for these patients. Non-cancer diseases will also benefit from this method. For example, photoinitiators and catalysts can be targeted to bacteria to prevent infections during wound healing and minimize expensive replacement of hip replacement transplants; purge latent HIV reservoir by HIV protease activation of photoinitiators; photo-stimulate neurons to combat neurological disorders, etc. Taken together, this depth independent PDT platform can be implemented to selectively inhibit or eradicate diverse diseases at cellular and tissue levels.

This work demonstrates the feasibility of using CR and highly sensitive photosensitizers for depth-independent and highly selective CRIT. Although longer lived radionuclides with excellent CR such as $^{64}$Cu, $^{90}$Y, $^{124}$I, and $^{89}$Zr, will be explored in future, this study will focus on FDG because it is trapped in cells with high metabolism, allowing uptake in tumors without further modification. Similarly, many molecular designs for delivering Tc and TiO$_2$ nanoparticles to tumors are available, but we will focus on transferrin (Tf) for this study because it serves the triple role of generating monodispersed TiO$_2$ nanoparticles, possesses high binding affinity for Tc, and delivers its cargo to tumors that overexpress Tf receptors. Together, the use of both Tf and FDG will accelerate the proof of concept research, minimize product synthesis, and allow us to test parameters for detailed studies with more effective CR-radionuclides without loss of focus on the long-term translational goals of the project.

Example 12: Determination of CRIT Using Tc-Tf Bimolecular System

The goals of this Example are to (a) develop Tc-Tf adducts using Tf as a targeting ligand and binding site for Tc; (b) evaluate the tumor selectivity of Tc-Tf in tumor cells; (c) demonstrate CRIT effects in tumor cells; (d) determine the mechanism of cell death; (e) determine in vivo biodistribution and demonstrate tumor selectivity of Tc-Tf; and (f) demonstrate therapeutic response and long term survival in small animal tumor models. All animal and cell studies will be conducted with (i) HeLa cells, a human cervical cancer model, in which Tf receptors internalize rapidly after binding to Tf; and (ii) HT1080, a fibrosarcoma model, in which Tf receptors internalize slowly after binding to Tf. These models will allow us to determine the use of the proposed platform in more than one tumor cell line. We describe the methods for HT1080 cell line in the following sections. We used FDG activity of 32.5 MBq to ensure that sufficient amount of the radionuclide was internalized by the tumors. We will first administer different activities (2, 8 & 30 MBq) of FDG and use PET imaging to determine the optimal therapeutic dose based on the lowest injected dose to maximize FDG activity in the tumor. We expect that this activity will be closer to the imaging dose.

Development of Tc-Tf Adducts:

Tc-Tf adducts will be prepared by adding an equimolar solution of Tc to Apo-Tf. Due to the high affinity binding affinity of Tc to Tf, which is similar to Tf-Fe(III), it is expected that the Tc-Tf adducts will be stable in a neutral buffer solution. The adducts will be purified using membrane filters and characterized by UV-vis spectrophotometry. The absorption spectrum is expected to reveal both Tf ($\lambda$=280 nm) and Tc ($\lambda$=322 nm) peaks. For binding assays, commercially available Alexa 680 labeled Tf will be used to prepare the Tc-Tf adducts.

Determination of Tumor Selectivity of Tc-Tf:

Binding assays using Tc-Tf will be performed in live cells to determine the binding capacity ($B_{max}$) and equilibrium dissociation constant (Kd) values, as described in the literature. We will conduct these studies in HT1080 cells, which overexpress Tf receptors. This cell line will also be used for in vivo studies. Increasing concentrations of the fluorescent Tc-Tf constructs will be added to the confluent cells followed by incubation at 37° C. and 4° C. for 2 h. Inhibition studies with a 100-fold excess of unlabeled Tf will be used to determine non-specific binding, which will be subtracted from total binding to give Tf-specific binding. We expect that the Kd of Tf and Tc-Tf will be similar since Tc binding does not affect the binding to the Tf receptor.

Determination of Mechanism of Cell Death:

Tc is known to generate free radicals through photofragmentation on exposure to UV light and the nature of the radicals is well characterized. Since Tc is known to intercalate DNA, we hypothesize that upon UV illumination using CR, the free radicals will cause DNA strand breakage, leading to apoptosis. We will perform agarose gel electrophoresis to detect DNA fragments in lysed cells as well as a Comet assay to determine DNA damage and fragmentation in cellulo. We will also assess the cytotoxicity profiles of Tc-Tf in vitro, with and without application of FDG, at therapeutically relevant escalating doses in relation to different time intervals. Quantitative evaluation of cellular cytotoxicity will be performed using independent assays that assess various cellular parameters such as: 1. MTT, for measuring activity of cellular enzymes and mitochondria using the Vibrant® MTT Cell Proliferation Assay Kit through absorbance readings of sample cells/control cells. 2. Propidium iodide staining of cells, specific to double stranded DNA and indicative of cell membrane integrity, will be carried out using the Coulter® DNA Prep™ Reagents Kit and analyzed using flow cytometry. In addition, we will also determine the mitotic index of the respective cells, to count the number of mitotic cells as an indicator of mitotic arrest and impending cell death. 3. Detection of mono and oligonucleosomes in the cytoplasm, indicative of endogenous endonuclease activation in apoptotic cells, will be carried out using Cell Death ELISA$^{PLUS}$ kit through absorbance readings of sample cells/control cells. Dose vs. response will be plotted for these assays and data will be statistically analyzed using Graph Pad Prism software. $LD_{50}$ (dose that kills 50% of the cells) values for the constructs will be determined from a plot of percentage cell death vs. Tc-Tf concentration using fixed FDG activity. We will observe and monitor cellular parameters for apoptosis over a period of 5 days. Based on our preliminary studies, we expect $LD_{50}$ to be achieved at Tc concentration at least 4-fold lower with CR than without FDG.

Determination of CRIT in Tumor-Bearing Mice:

We will use the Alexa 680 fluorescent Tf-Tc to determine the optimal time point for CRIT by fluorescence imaging at different time points (0.5, 2, 4, 8, 24, 48 and 96 h) post-injection using the LICOR Pearl imaging system with 685/720 nm excitation/emission, as we reported previously. HT1080 tumors will be implanted subcutaneously and treatment will be initiated in three phases (1) five days post injection of tumor cells when the tumors are barely palpable, to determine the feasibility of eradicating tumors in early stages of growth; (2) when tumor mass reaches 5 mm, to assess the feasibility of regressing tumor growth; and (3) when tumor mass reaches 10 mm, to assess the feasibility of inhibiting tumor growth and defining tumor boundaries for accurate surgical tumor resection, especially in highly sensitive organs such as the brain and to minimize margin positivity, thereby minimizing patient recall rates. Based on the time point of highest tumor:liver contrast (the expected major excretion organ of Tf-Tc) in vivo, the mice will be euthanized, and major organs exhibiting Alexa 680 fluorescence will be harvested and imaged ex vivo to confirm in vivo data. Organs will then be separately homogenized and the product will be extracted with 40% DMSO in PBS for quantitative analysis of the Tf-Tc distribution. We will report the distribution as percent injected dose/g organ.

The HT1080 tumor bearing mice will be randomly assigned to two cohorts, for each phase specified above, of 5 mice per group: (i) untreated control; (ii) FDG treated control; (iii) Tc-Tf (1 mg/kg) treated control; and (iv) Tc-Tf and FDG treated group. Using the optimal time point for tumor-to-liver uptake of Tc-Tf for the different tumor sizes, we will administer Tc-Tf as a single dose intravenously. Two FDG doses will be administered on alternate days to account for the short half-life of the $^{18}$F isotope. The body weights and tumor volumes will be measured thrice a week in each group. Caliper measurements will be used to calculate tumor volumes (TV) using the equation: $V=\pi/6$ (length$\times$width$^2$). The percentage of tumor growth inhibition will be calculated as 100$\times$(mean TV of treated group)/(mean TV of untreated control group). Statistically significant differences in tumor volumes between control and drug-treated mice will be determined by the Mantel-Cox test.

The first cohort of each phase will be euthanized at day 7, after injections, to evaluate the acute therapeutic parameters such as cell proliferation (e.g. Ki67 immunohistochemistry), decreased microvascular density and apoptosis (e.g. TUNEL IHC) in tumor tissue, through histopathology. Measurement of acute inflammatory signs such as fluid accumulation and identification of neutrophils in the affected site will be carried out using histopathologic assessment. The second cohorts will be monitored for effect of therapy on long-term tumor growth. Kaplan-Meier survival analysis will be carried out to measure the fraction of mice living for a certain amount of time after treatment. Mice will be euthanized when tumor size reaches 1.5 cm maximum diameter or lose>10% body weight. Associated complications of high dose rates on all major organs and nearby tissues will be evaluated. Histochemical analysis of the tumors, including H&E staining and Ki67 immunohistochemistry, will be performed by counting the number of Ki67 positive and negative cells in ten randomly chosen areas of the tissue sections from each treatment and control group. We expect to achieve faster tumor regression for the constructs with the lower administered dose, without inducing any acute inflammatory changes to vital organs.

Histology:

Histologic validation of tumor death will be performed by histological section analysis.

In the event of unstable interaction between Tc and Tf, we will covalently link Tc to antibodies such as anti-epidermal growth factor receptor antibody and perform stability and binding studies. The use of Alexa 680 labeled Tf as a surrogate for the distribution of Tc-Tf is based on the strong binding of Tc to Tf until it dissociates within the acidic intracellular lysosomes before translocating to the nucleus. A study showed that the biodistribution of the radiolabeled Tc-Tf analogue ($^{45}$Ti-Tf) was consistent with Tf distribution. If treatment response does not correlate with the determined fluorescence biodistribution profile, we will prepare a stable scandocene analogue, which can be readily converted to radiolabeled Tc. The initial doses for Tc-Tf and FDG are based on published sub-lethal doses of Tc[19] and an exploratory dose of FDG, respectively. In the event of unappreciable tumor volume reduction, an increase in the administered doses will be considered.

Example 13: Determination of CRIT Using TiO$_2$-Tf Bimolecular System

Development of TiO$_2$-Tf Adducts:

TiO$_2$ typically exists in two tetragonal forms, anatase and rutile, which differ in their crystal lattice structure. We will employ the anatase form for CRIT studies because of its smaller size and higher photoactivity arising from the extensive surface hydroxyl groups in water. Larger or smaller-sized monodispersed nanoparticles can be obtained by starting with different sized nanocrystals. We will start with commercially available ~25 nm crystalline TiO$_2$ and use our newly discovered Tf formulation to create monodispersed nanoparticles of ~18 nm from the crystalline TiO$_2$ aggregates. In this method, a suspension of TiO$_2$ and Tf will be sonicated using a probe sonicator and immediately filtered through membranes. By using membrane filters of different pore cutoff points such as 0.1, 0.2 and 0.4 μm, we can narrow the size distribution. Membrane dialysis will be used to remove unbound Tf from the TiO$_2$-Tf adducts. UV-vis, TEM and DLS particle analysis will be performed on each batch. Determination of tumor selectivity of TiO$_2$-Tf will be as described in Example 12.

Determination of mechanism of cell death will be as described in Example 12. Assays will be performed to evaluate whether the mechanism of cell death is through apoptosis or necrosis. TiO$_2$ generates cytotoxic hydroxyl and superoxide radicals when irradiated with UV light. We will quantitatively estimate the amount of hydroxyl and superoxide radicals using fluorescent dyes such as hydroxyphenyl fluorescein and Mitosox, respectively. Blocking studies with L-Tryptophan, for hydroxyl radicals, and superoxide dismutase, for superoxide radicals, will be performed.

Determination of CRIT in Tumor-Bearing Mice:

Using Alexa 680 labeled Tf, biodistribution and tumor specificity studies of TiO$_2$-Tf adduct will be carried out as described in Example 12, as well as efficacy studies of using TiO$_2$-Tf as a photocatalyst for CRIT. Histology will be as described in Example 12.

The stability of TiO$_2$-Tf in solution and the potential for re-aggregation over time is a concern. TEM and DLS analyses performed 12-14 h after synthesis suggest minimal re-aggregation and no noticeable change in the polydispersity index. However, we plan on performing stability studies, using TEM and DLS, both in buffer solution and serum over extended periods—up to a month post-formulation. If long-term stability is a problem, we will prepare new batches after the useable shelf-life.

Example 14: Determination of CRIT Using Tc-TiO$_2$-Tf Trimolecular System

Development of TiO2-Tf-Tc:

To prepare TiO$_2$-Tf-Tc, we will use the Tc-Tf prepared in in Example 12 to prepare the monodispersed TiO$_2$-Tf-Tc following the procedure described in Example 13.

For determination of tumor selectivity of TiO$_2$-Tf-Tc, we will use similar methods as described in Example 12.

For determination of mechanism of cell death, we will use the same methods described in Example 12 for this study. We expect to observe a combination of photoinitiator- and photocatalyst-induced cell death mechanisms. We will determine if the effect is additive or synergistic by comparing the LD$_{50}$ of CRIT for TiO$_2$-Tf-Tc relative to equal concentrations of TiO$_2$-Tf and Tc-Tf under the similar conditions.

Determination of CRIT in Tumor-Bearing Mice:

We will perform CRIT with TiO$_2$-Tf-Tc using the procedure described in Example 12. We will evaluate if the treatment response is an additive (complementary) or amplified (synergistic) effect based on the inhibition of tumor growth rate relative to equal concentrations of TiO$_2$-Tf and Tc-Tf under similar conditions.

Histology:

We will use a similar method as described in Example 12.

In the event there is unstable association of Tc to TiO$_2$-Tf, we will covalently conjugate Tc directly to the surface of TiO$_2$ using suitable intracellular cleavable linkers such as disulfide bonds to allow release of Tc for subsequent translocation to the nucleus under the highly reducing intracellular environment of tumor cells.

Example 15: Systemic CR-PDT

After achieving successful tumor regression in a fibrosarcoma model through intratumoral administration of TiO$_2$ and $^{64}$Cu, we developed a clinically relevant strategy to achieve targeted CR-PDT through systemic administration of the PS and radionuclide. Synthesis of monodisperse, ultrafine spherical TiO$_2$ with narrow size distribution suitable for systemic administration using inorganic titanium salt remains a challenge. Here, we demonstrate for the first time a "green" strategy to achieve monodisperse TiO$_2$. The strategy includes development of hybrid TiO$_2$ conjugates with a targeting moiety, transferrin (Tf)—a ubiquitous iron transporter found in serum. Many tumors including HT1080 fibrosarcoma overexpress transferrin receptors due to high demand for iron by rapidly proliferating cells. TiO$_2$-Tf conjugates were further appended by a biocompatible photoinitiator, titanocene (Tc), to enhance the generation of free radicals and improve cytolytic activity of the conjugates. Tc is a visible light photoinitiator and TiO$_2$ a UV photosensitizer, therefore, consolidating their use in conjunction with CR that has a broad emission spectrum spanning UV and visible wavelengths, will only enhance the overall design. The photoinitiator-photosensitizer two component system interact through both energy transfer and electron transfer mechanisms, complementing each other and consequently exhibiting faster and higher radical generation. Like iron, Tc has high binding affinity to apo-Tf, and therefore readily forms a stable complex with TiO$_2$-Tf. TiO$_2$-Tf-Tc complexes as next-generation PDT agents, can therefore offer highly efficient radical species generation through synergistic activity of the two photoactive components and at the same time also offer targeting functionality towards Tf receptor expressing tumors.

Figure 21:
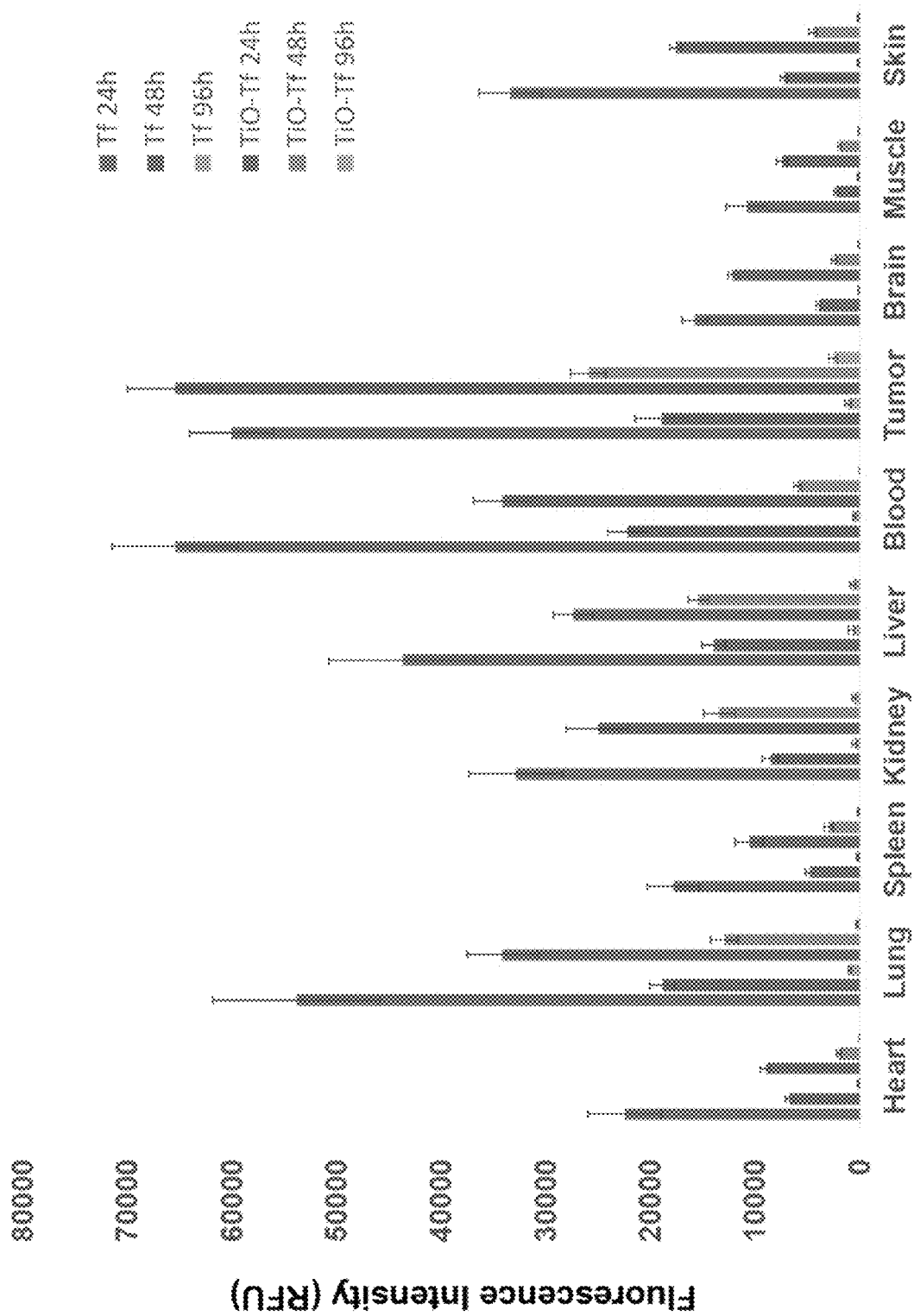
FIG. 21 depicts a graph of biodistribution studies of TiO$_2$-Tf in mice (n=3) with HT1080 tumors at various timepoints.

In vivo biodistribution studies carried out in 4T1 and HT1080 tumor bearing mice using Alexa 680 labeled Tf-TiO$_2$ conjugates, show highest uptake in the tumors (FIG. 21). The tumor:muscle ratio's registered for TiO$_2$-Tf and Tf alone were 9 and 5.5, respectively. Biodistribution studies carried out over 96h suggest gradual clearance of the conjugates through the hepatobiliary and renal system. Since the highest tumor:background contrast was obtained at 24h post injection, accordingly this was chosen as "drug-light interval". As CR source, a radionuclide with high tumor selectivity and uptake is desired to achieve optimum activation of the TiO$_2$ constructs. F-18-fluorodeoxyglucose (FDG) is ideal because of its affinity towards rapidly proliferating cells, which affords it high tumor selectivity, as well as its high energy (633 keV) positron (97%) emission which generates CR with high fluence rate. Moreover, FDG has a reasonably short half-life (109 min) that is conducive for avoiding systemic toxicity in the short term, which is a result of residual PDT occurring in non-targeted tissues. It's current clinical utility for high resolution PET imaging and monitoring therapeutic response is an added advantage.

Figure 22:
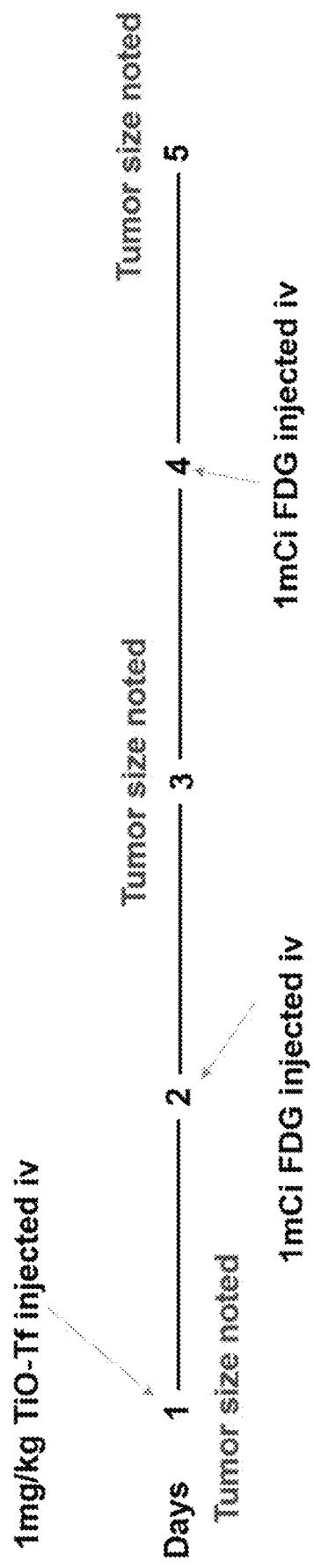
FIG. 22 depicts a schematic of the treatment plan.
Figure 23:
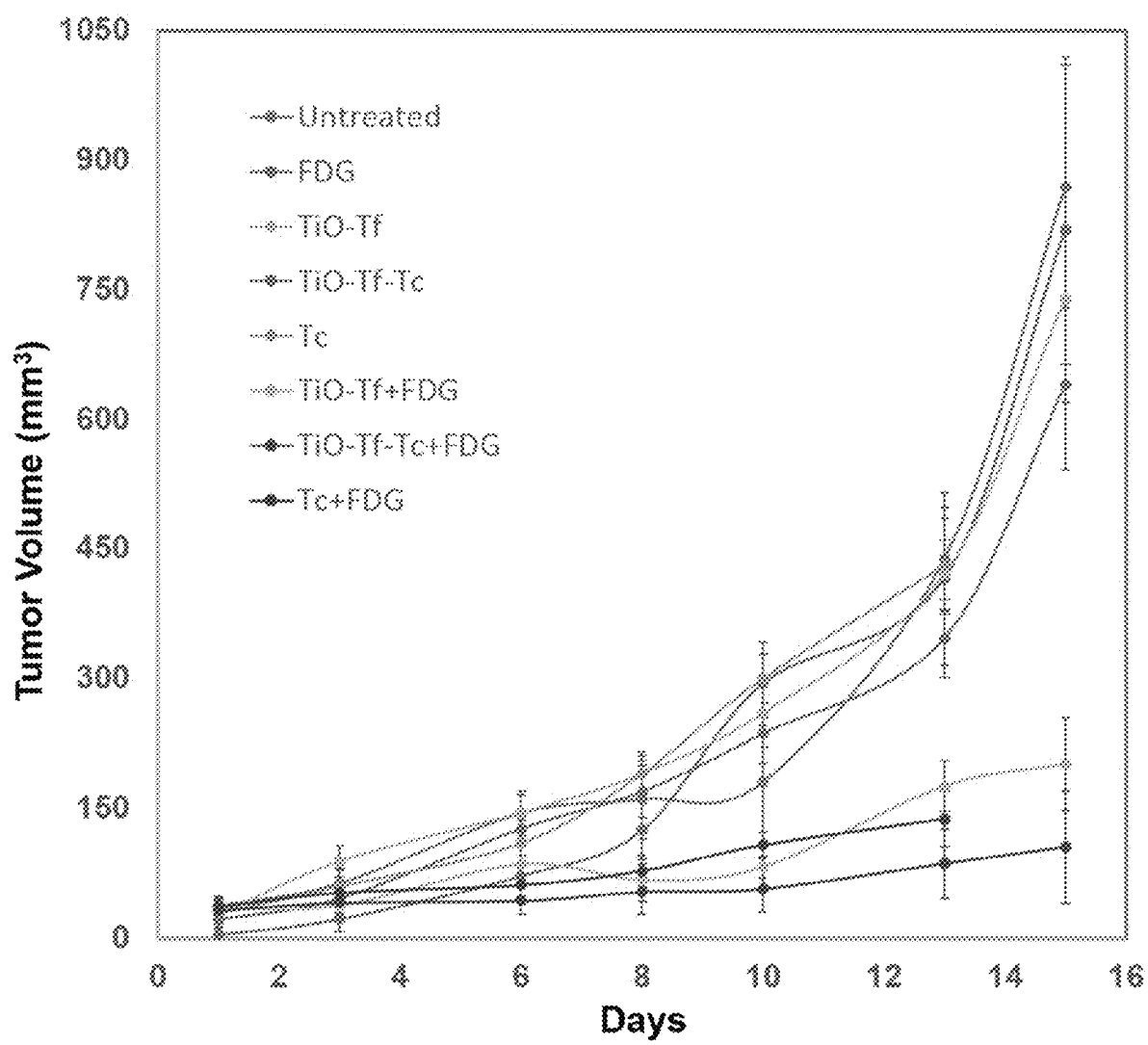
FIG. 23 depicts a graph of tumor growth curves during CR-PDT.

After intravenous administration of the TiO$_2$ constructs and FDG into mice bearing HT1080 tumors, the animals were monitored over 15 days (FIG. 22). It was observed that the tumor progression rate for the mice treated with TiO$_2$-Tf, TiO$_2$-Tf-Tc and Tc along with FDG was considerably slower in comparison to mice that were left untreated as well as treated with only the constructs or FDG, as controls (FIG. 23). The tumor volume registered for mice treated with TiO$_2$-Tf and Tc with FDG was four-fold smaller compared to the controls. Whereas, mice treated with TiO$_2$-Tf-Tc and FDG showed a superior response to the treatment with a tumor volume of eight-fold smaller compared to controls. This suggests the synergistic activity of TiO$_2$ and Tc in achieving better treatment response is a result of amplified generation of free radicals. The attenuated growth rate of tumors after systemic administration of the constructs is significant because the dose of the constructs was maintained at sublethal levels, known to not cause any dark toxicity; and activity of FDG injected was that of clinically acceptable levels routinely used in small animal imaging studies.

Methods for Example 15

Synthesis of TiO$_2$-Tf and TiO$_2$-Tf-Tc conjugates: Human transferrin from Sigma Aldrich (St. Louis, Mo.) was dissolved in PBS at a concentration of 1 mg/ml to which 500 mg/ml of TiO$_2$ was added. After brief sonication, using a probe sonicator, the solution was filtered using a 0.4 mm syringe filter to obtain TiO$_2$-Tf conjugates. The conjugates were further purified using 100 kDa MWCO membrane filters from Millipore, to remove unbound Tf. The conjugates were analyzed by UV-vis spectrophotometer before and after filtration to estimate yield of the final conjugates. A working stock solution of 5 mg/ml Titanocene dichloride from Sigma Aldrich was prepared in DMSO. To a solution of TiO$_2$-Tf, 100 mg/ml of Tc was added and incubated at RT for 1 h. Unbound Tc was removed from TiO$_2$-Tf-Tc constructs using 3k MWCO membrane filters.

Biodistribution Studies:

To track TiO$_2$-Tf conjugates, Alexa 680 labeled Tf was used. The studies were commenced when tumor volume reached 500 mm$^3$. 0.5 mg/kg of TiO$_2$-Tf was injected intravenously in mice with 4T1 (n=3) and HT1080 (n=3) tumors and monitored for 96h post injection using Li-cor Pearl animal imaging system with an Ex/Em of 680/715 nm. The animals were euthanized subsequently and major organs dissected and imaged in the same channel. Image J was used to quantitate fluorescence intensity by drawing regions of interest encompassing entire organs.

Systemic CR-PDT:

After the HT1080 tumors grew to ~20 mm$^3$, 1 mg/kg of TiO$_2$-Tf was administered intravenously. After 24h, 1mCi of FDG was administered intravenously. Tumor volume was registered every alternate day for 15 days.

Example 16: Physical Characterization of TiO$_2$-Tf

Figure 24A:
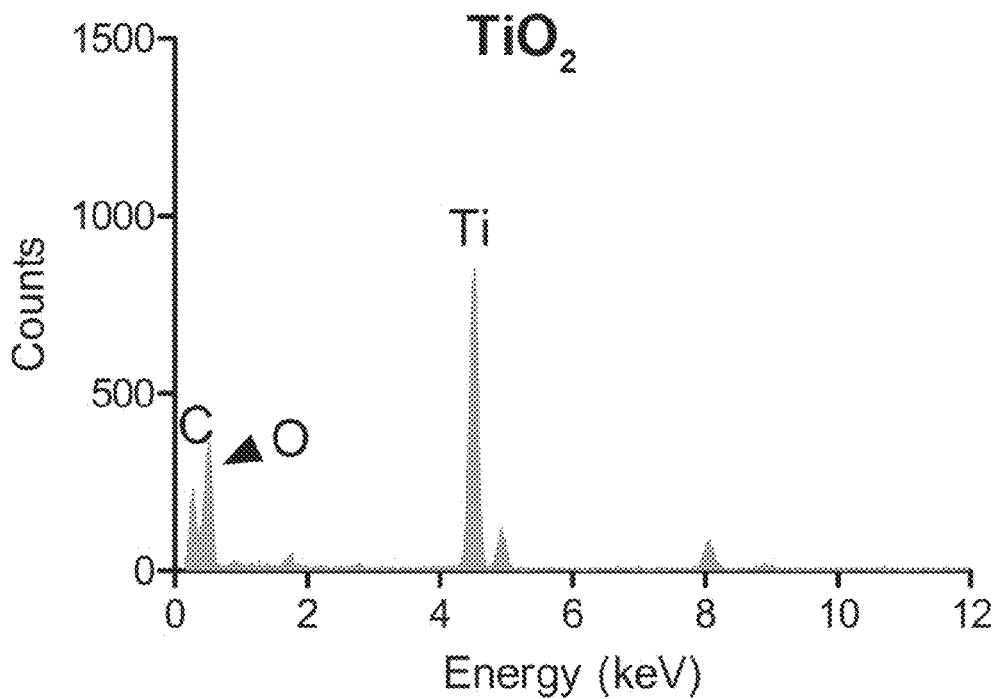
FIG. 24A, FIG. 24B, FIG. 24C and FIG. 24D depict graphs and images showing the composition and phase characterization of TiO$_2$-Tf.
Figure 24B:
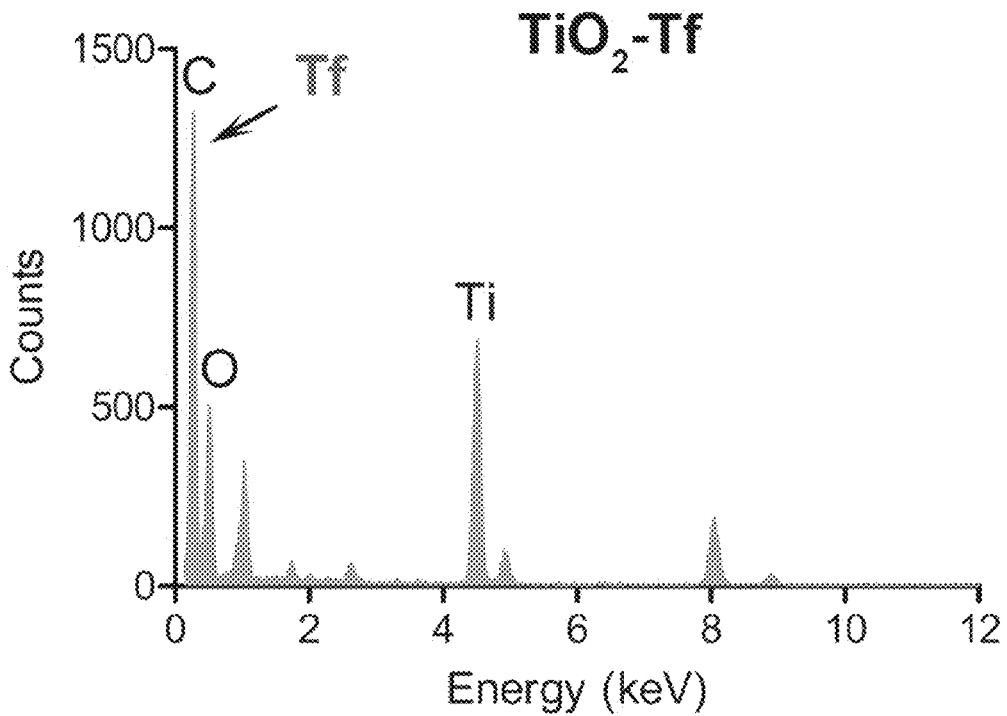
Figure 24C:
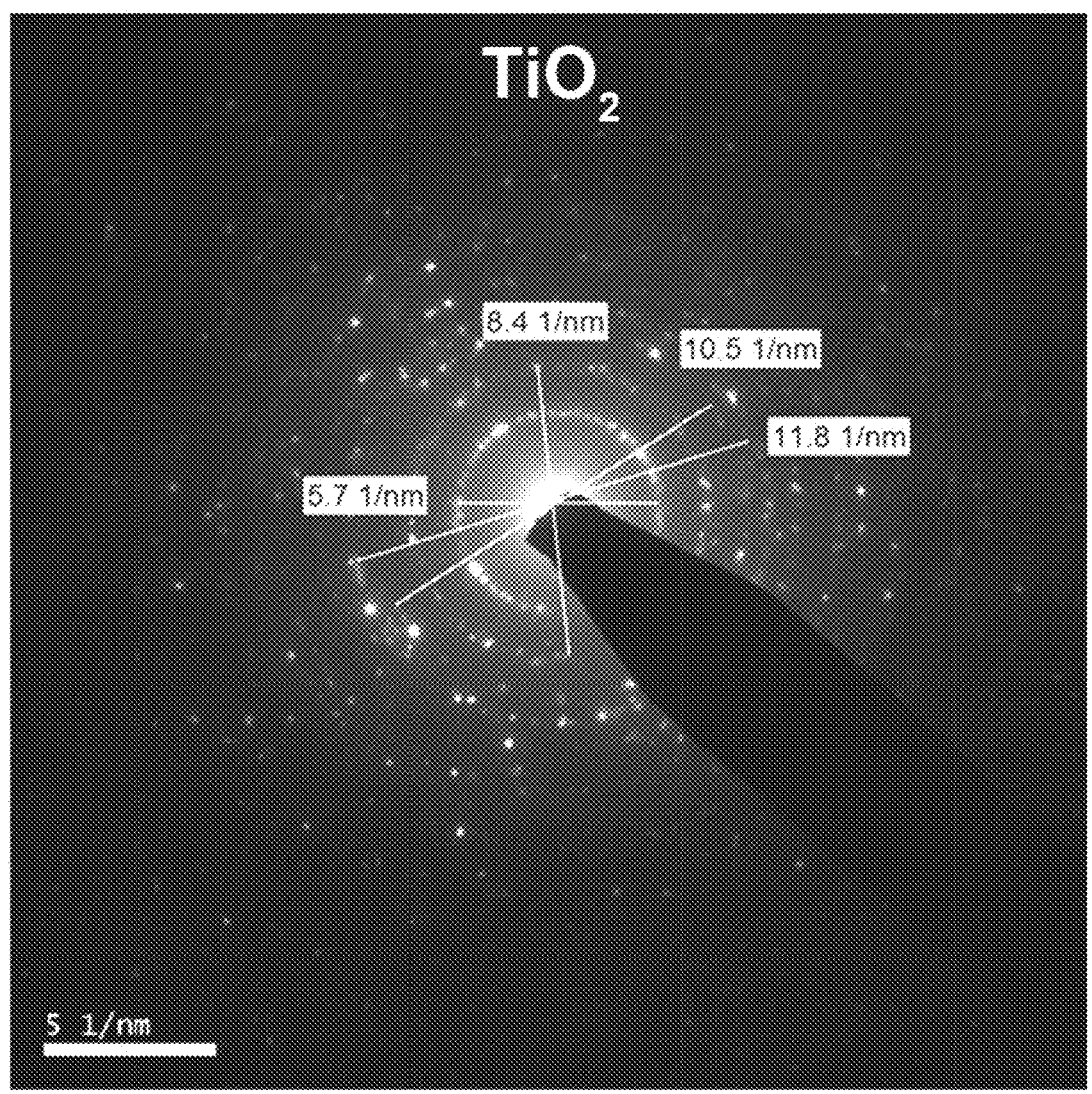
Figure 24D:
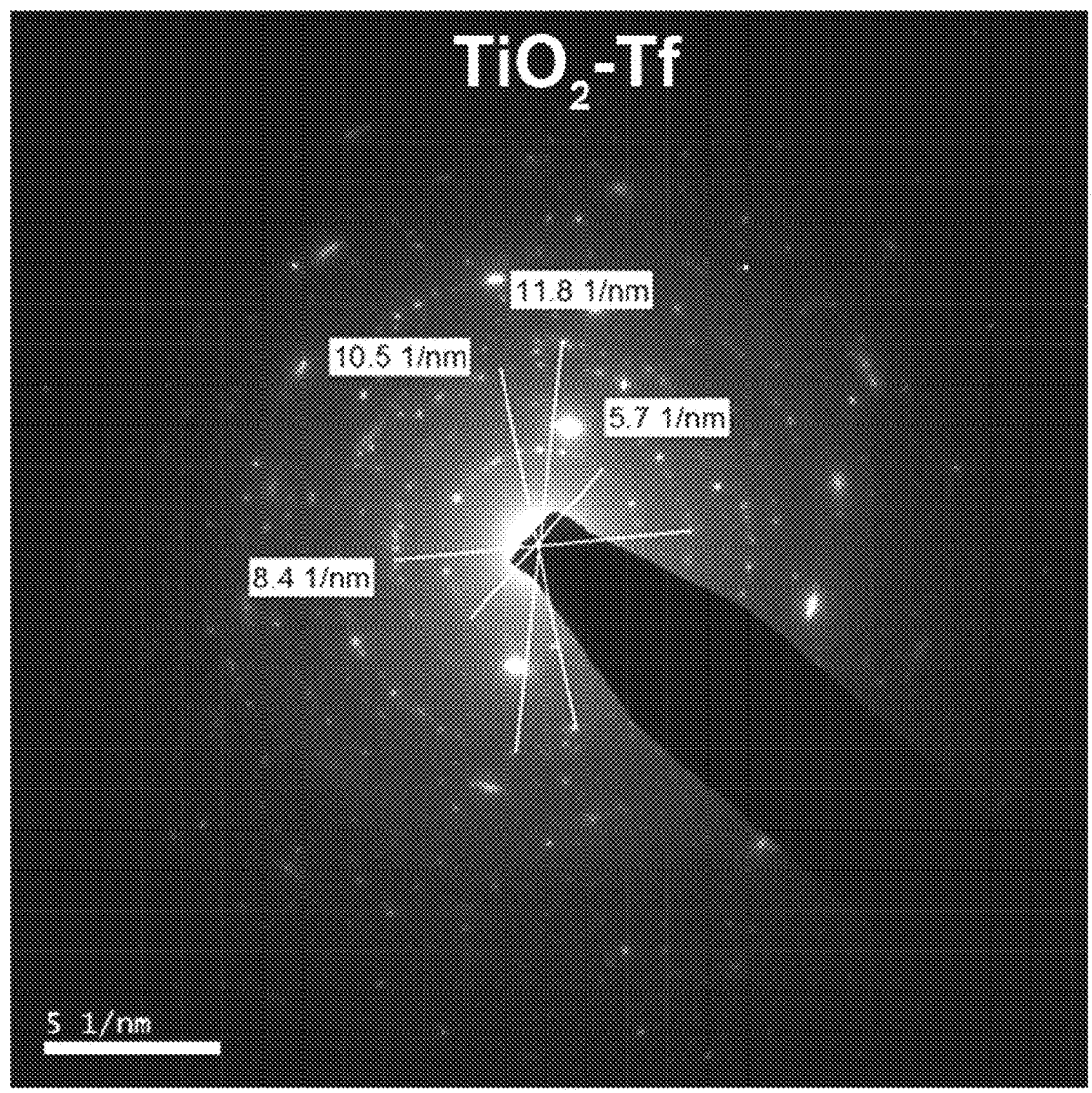

A strong signature of carbon in the Energy-dispersive X-ray spectroscopy (EDX) spectrum of TiO$_2$-Tf compared to TiO$_2$ alone (FIG. 24A) confirmed the presence of Tf on the surface of TiO$_2$ (FIG. 24B). Electron diffraction analysis confirmed that the crystal lattice structure of anatase TiO$_2$ remained unchanged as a result of processing with Tf (FIG. 24C,D). Phase transformation between anatase and rutile forms of TiO$_2$ typically occur at temperatures exceeding 700° C. Due to the relatively mild nature of the processing used to generate TiO$_2$-Tf adducts, the photocatalytic properties of anatase TiO$_2$ employed in this study was thus maintained. The ring measurements are as follows:

TiO$_2$—
5.7 1/nm/2=0.351 nm=3.51 A
8.4 1/nm/2=0.238 nm=2.38 A
10.51/nm/2=0.189 nm=1.89 A
11.81/nm/2=0.169 nm=1.69 A

TiO$_2$-Tf—
5.7 1/nm/2=0.351 nm=3.51 A
8.4 1/nm/2=0.238 nm=2.38 A
10.5 1/nm/2=0.190 nm=1.90 A
11.8 1/nm/2=0.169 nm=1.69 A

Example 17: Serum Stability of TiO$_2$-Tf

Figure 25A:
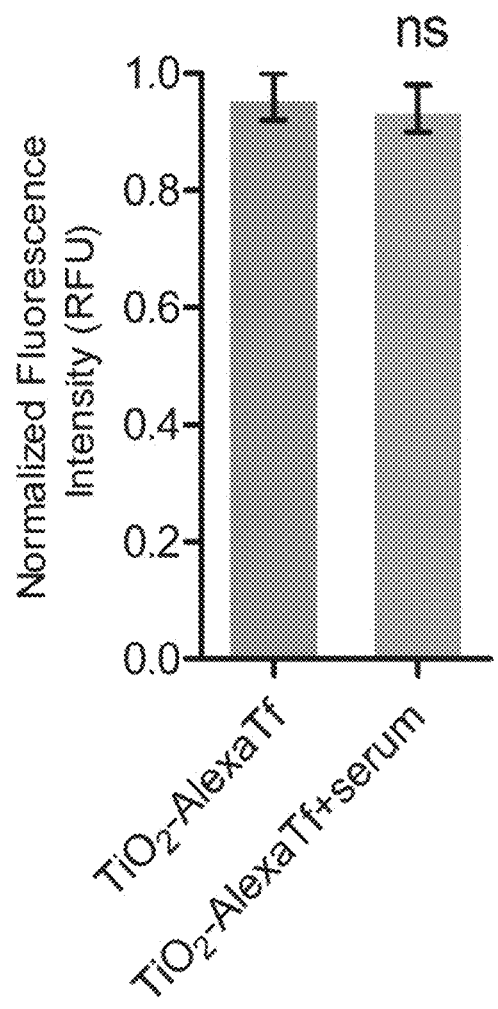
FIG. 25A and FIG. 25B depict graphs showing the serum stability of TiO$_2$-Tf NPS.
Figure 25B:
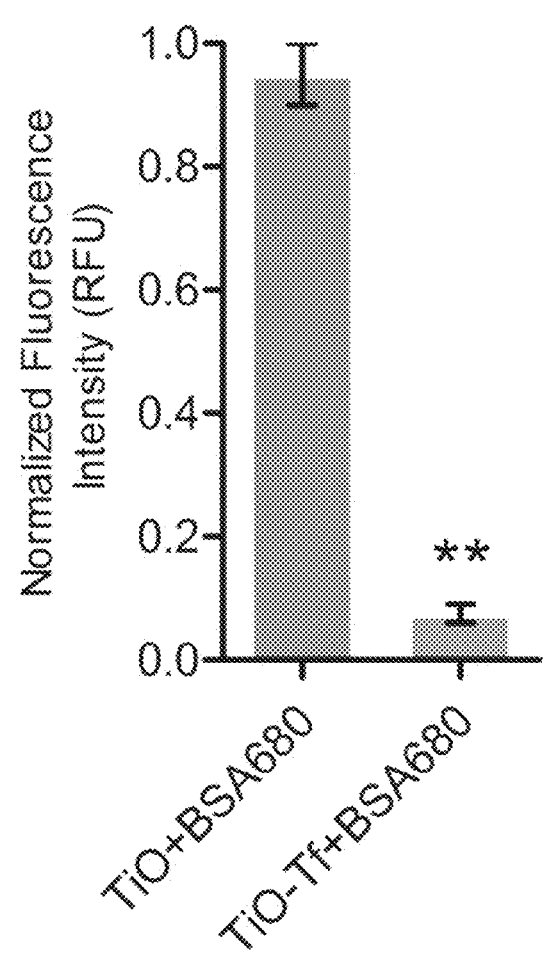

To determine the serum stability of the TiO$_2$-Tf interaction, we incubated the nanoparticles in fetal bovine serum for 24 h. We found that the amount of bound AlexaTf to TiO$_2$ surface did not significantly change with time (FIG. 25A). Further analysis of data showed that serum components such as albumin, using Alexa 680 labelled BSA, did not form appreciable protein corona on the TiO$_2$-Tf surface relative to pristine TiO$_2$ (FIG. 25B), confirming that Tf does not readily exchange with serum proteins.

Example 18: In Vitro and In Vivo Blocking Study Using TiO$_2$-Tf Labelled with Alexa 680

Figure 26A:
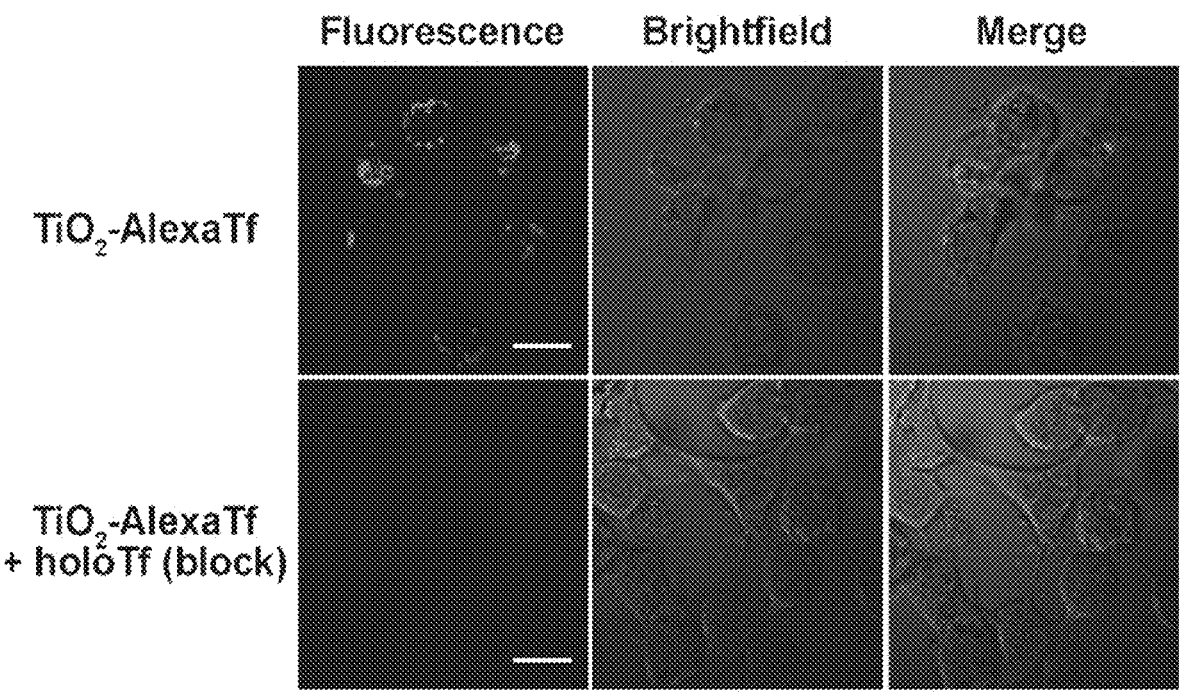
FIG. 26A and FIG. 26B depict images and a graph showing the cellular uptake of NPS.
Figure 26B:
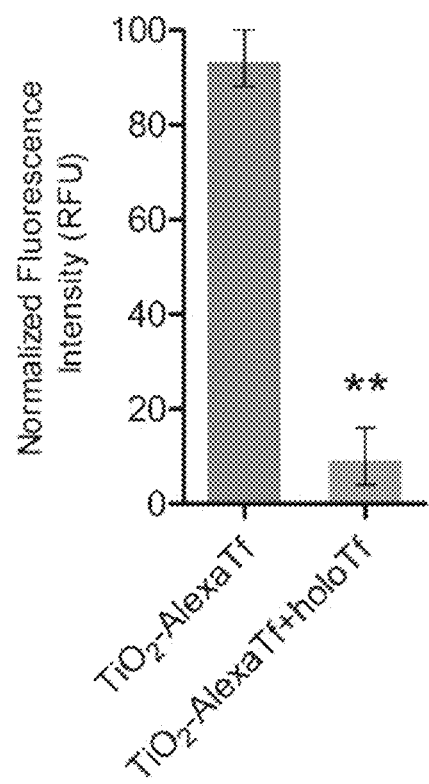
Figure 27A:
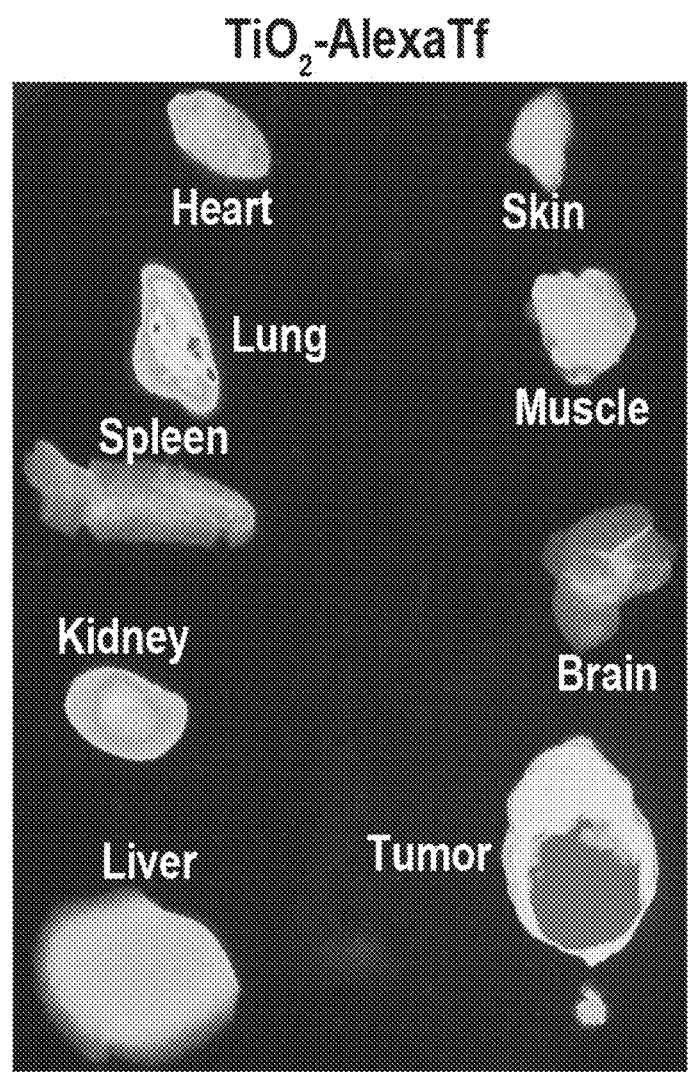
FIG. 27A, FIG. 27B and FIG. 27C depict images and a graph showing the In vivo blocking of TiO$_2$-Tf uptake by HT1080 tumours.
Figure 27B:
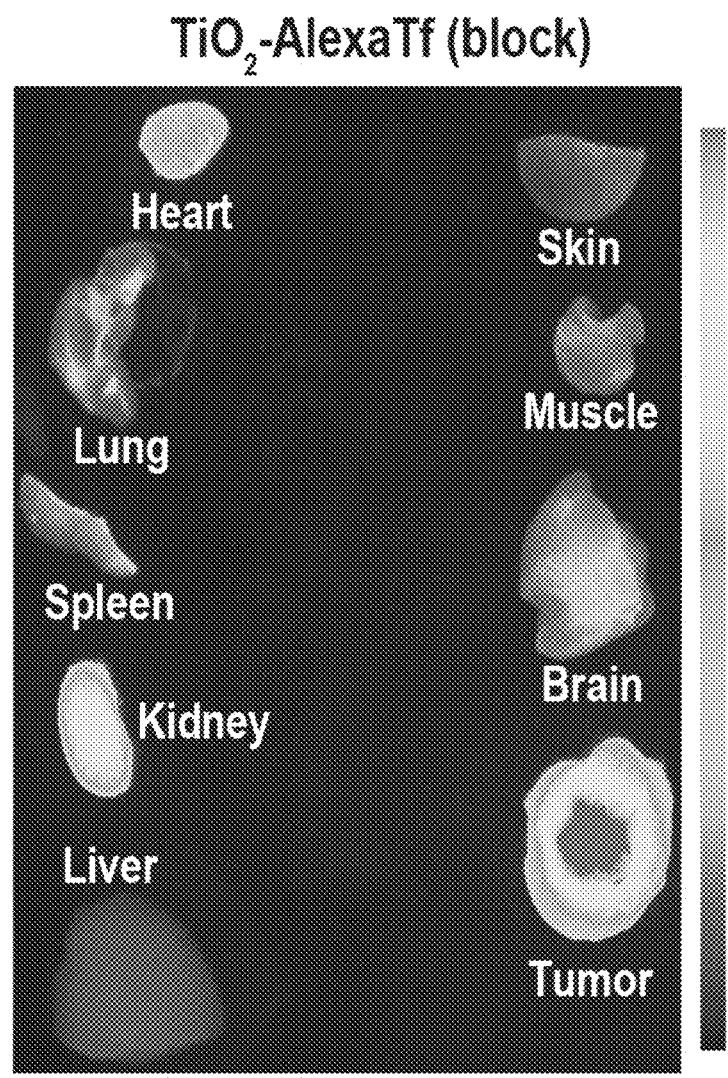
Figure 27C:
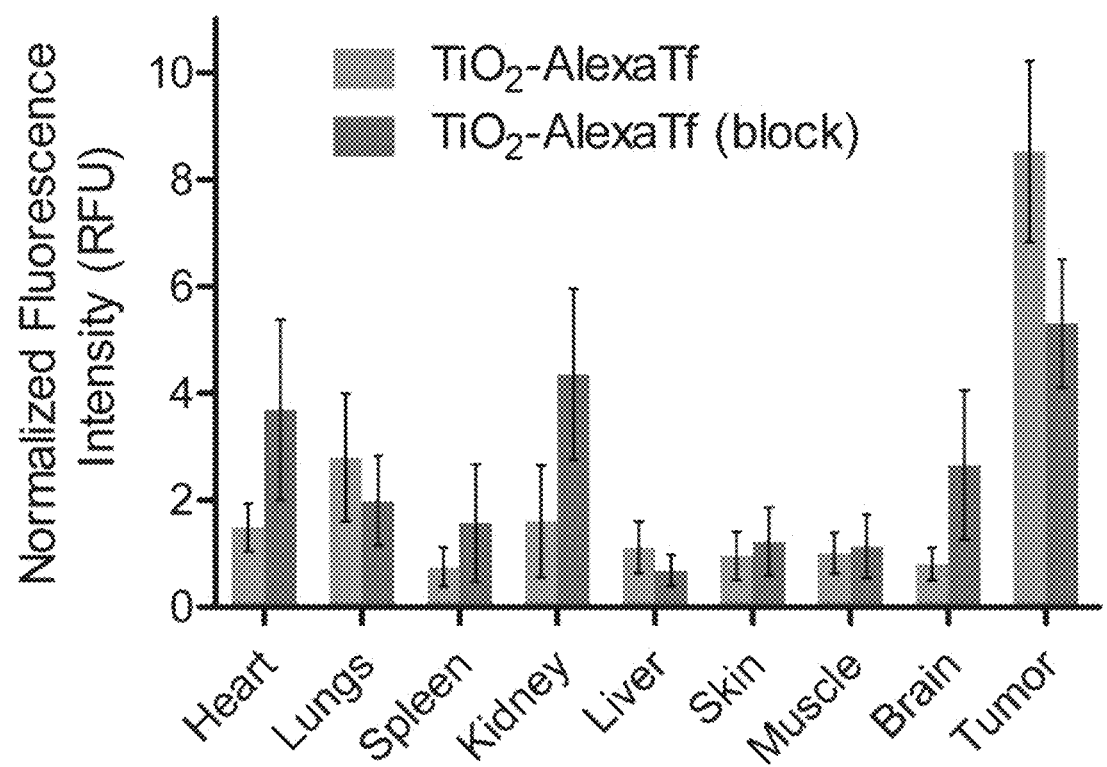

Competitive inhibition of TiO$_2$-Tf internalization in tumour cells using saturating amounts of holo-Tf (iron-chelated Tf; FIG. 26) demonstrates specific Tf-mediated endocytosis. However, attempts to reproduce this result in vivo only showed noticeable but statistically insignificant reduction in tumour uptake of the NPS (FIG. 27). We attribute this finding to several factors, including the high turnover rate of Tf receptor after endocytosis, difficulty in saturating Tf receptor in vivo with saturating dose of Tf, and the high avidity of the TiO$_2$-Tf adduct.

Figure 28:
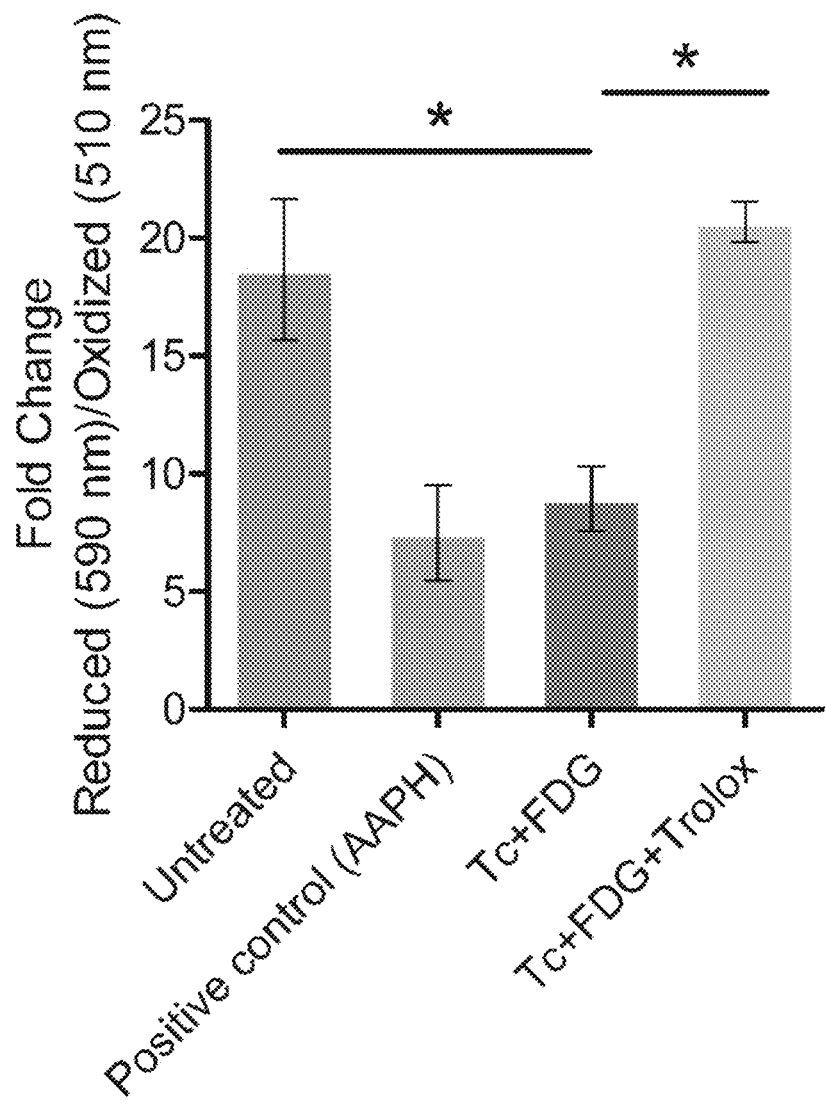
FIG. 28 depicts a lipid peroxidation assay using BODIPY 581i591 C11 reagent on HT1080 cells showing a higher degree of lipid peroxidation in cells treated with Tc and FDG. Values are means±s.e.m. *P<0.05, P<0.01 *P<0.001.

Example 19: In Vitro Assay to Determine Peroxyl Radical Generation from Photofragmentation of Titanocene Earlier reports have suggested the formation of peroxyl radicals by the photofragmentation products. To determine if the peroxyl radicals cause peroxidation of cellular lipids, a BODIPY® 581i591 C11 reagent was employed. While Tc and FDG induced significant peroxidation and degradation of cellular lipids through the free radicals, addition of peroxyl radical scavengers, such as Trolox, adequately inhibited this process (FIG. 28). This suggests a strong correlation between lipid peroxidation and photofragmentation of Tc through CR from FDG, implicating peroxyl radicals as the affector. Treatment with 2,2'-Azobis(2-methylpropionamidine) dihydrochloride (AAPH) was used as the positive control.

Figure 29:
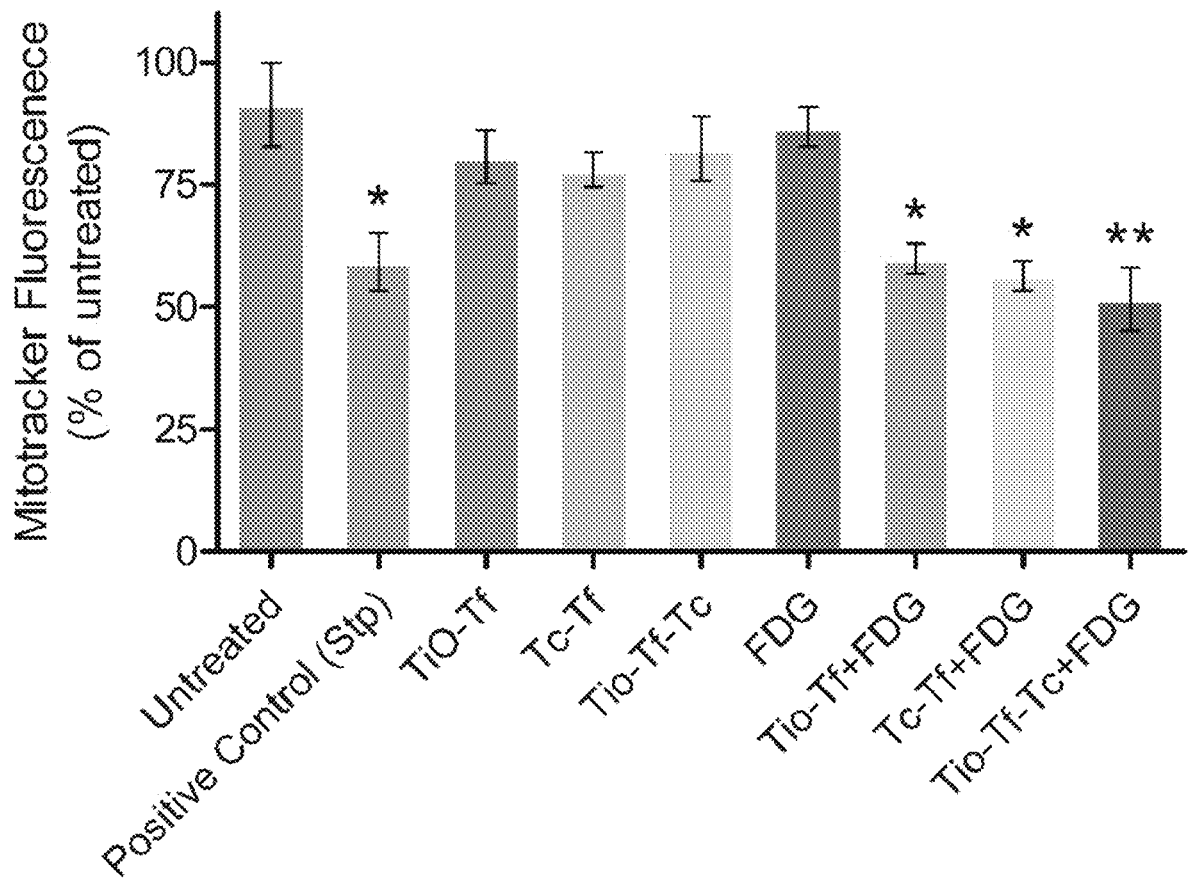
FIG. 29 depicts a graph showing loss of mitochondrial membrane potential due to CRIT. Mitochondrial membrane potential changes detected by Mitotracker Green dye as a result of CRIT. Values are means±s.e.m. *P<0.05, **P<0.01.

Example 20: In Vitro Assessment of Mitochondrial Membrane Potential as a Result of CRIT To further understand the role of free radicals and the mechanism of cell death, we evaluated whether CRIT induces alterations in mitochondrial membrane potential. There was a significant decrease in mitochondrial membrane potential in cells treated with both $TiO_2$ and Tc coincubated with FDG, indicating damaged and leaky membranes (FIG. 29). Typically, damage to mitochondrial membranes initiates the intrinsic signalling pathway for apoptosis, characterized by loss of membrane potential and a cascade of events involving caspases leading to nuclear fragmentation and cell death.

Example 21: TEM Analysis of Tumor Uptake of $TiO_2$-Tf-Tc

Figure 30A:
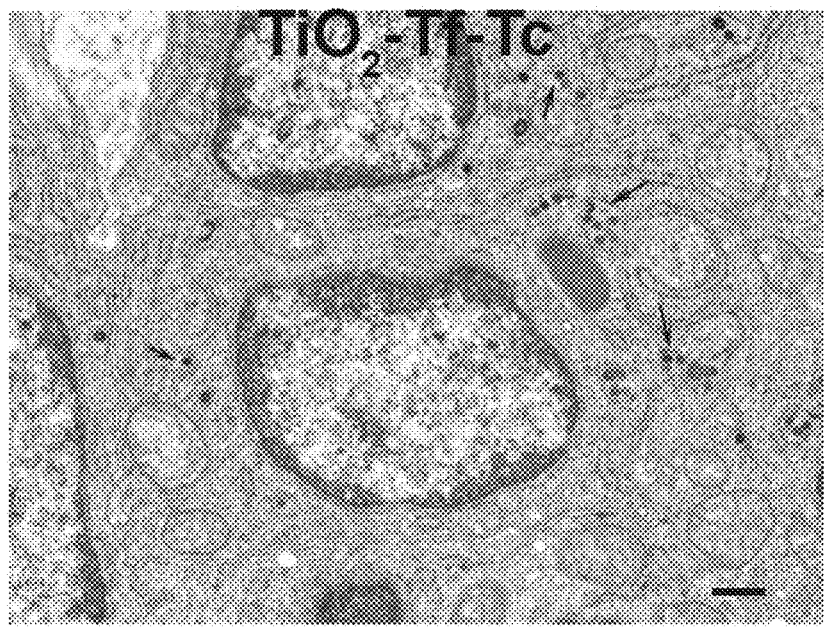
FIG. 30A and FIG. 30B depict TEM analysis of tumor uptake of TiO2-Tf-Tc.
Figure 30B:
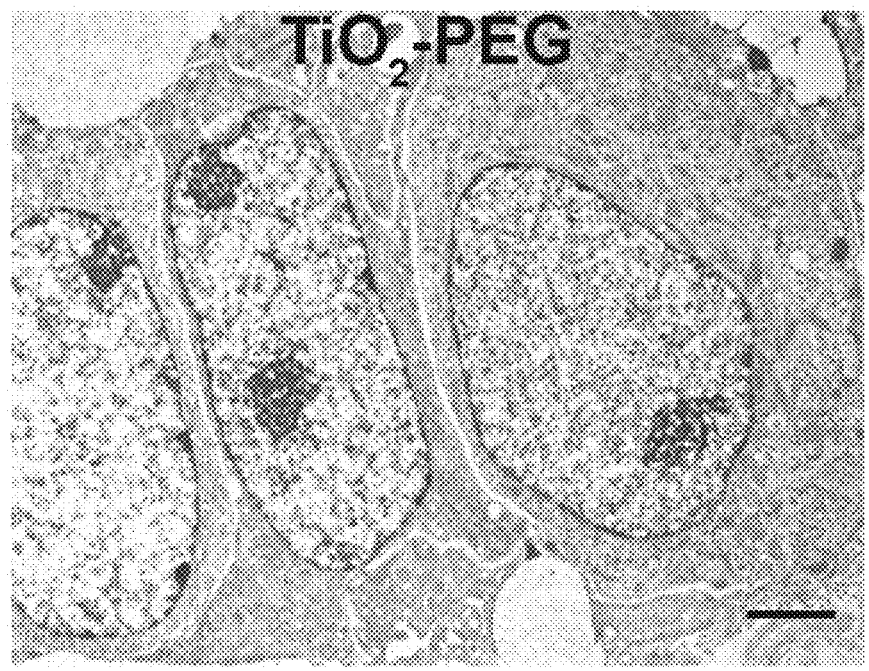

To determine internalization of the non-fluorescent $TiO_2$-Tf-Tc constructs in tumour cells after systemic administration, we employed TEM for the ex vivo analysis of tumour sections The TEM images of tumour sections clearly show $TiO_2$ nanoparticles as dark spots in the cells, demonstrating the tumour uptake of the $TiO_2$-Tf-Tc NPS in majority of the cells and the retention of monodispersity in vivo (FIG. 30A). In addition to Tf-mediated endocytosis, the monodisperse, small size, and favourable surface properties of the Tf adducts probably facilitated the tumour uptake via enhanced permeability and retention (EPR) effect. The fractional contribution of EPR and avidity effects could be gleaned from the differences in the tumour-to-muscle ratio of 5.3 for Tf alone, which is much lower than that of $TiO_2$-Tf. In contrast to Tf-facilitated endocytosis, the tumour cells did not appear to internalize $TiO_2$-PEG aggregates in vivo (FIG. 30B), suggesting that the observed peritumoural uptake of these particles was primarily mediated by EPR effect. Therefore, a combination of both extracellular (EPR) and intracellular (Tf) processes accounts for the higher accumulation of $TiO_2$-Tf-Tc in the tumour environment than $TiO_2$-PEG nanoparticles.

Example 22: Analysis of CRIT In Vivo

Figure 31A:
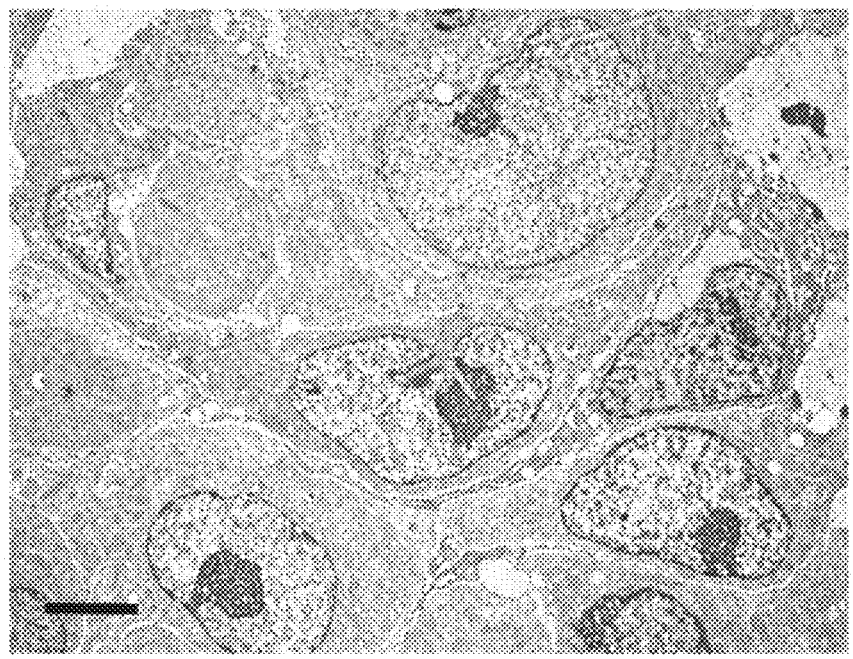
FIG. 31A, FIG. 31B, FIG. 31C and FIG. 31D depict TEM analysis of CRIT in vivo.
Figure 31B:
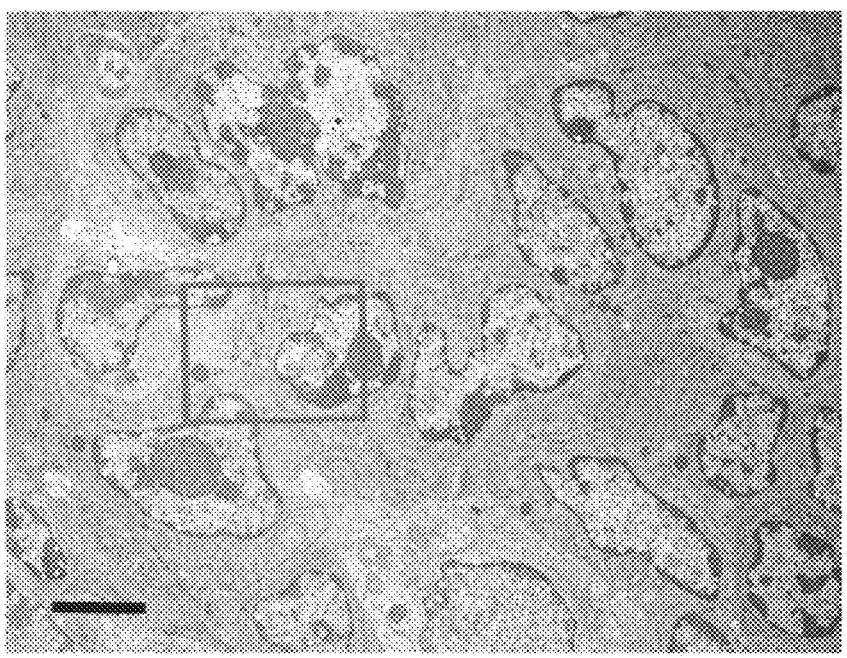
Figure 31C:
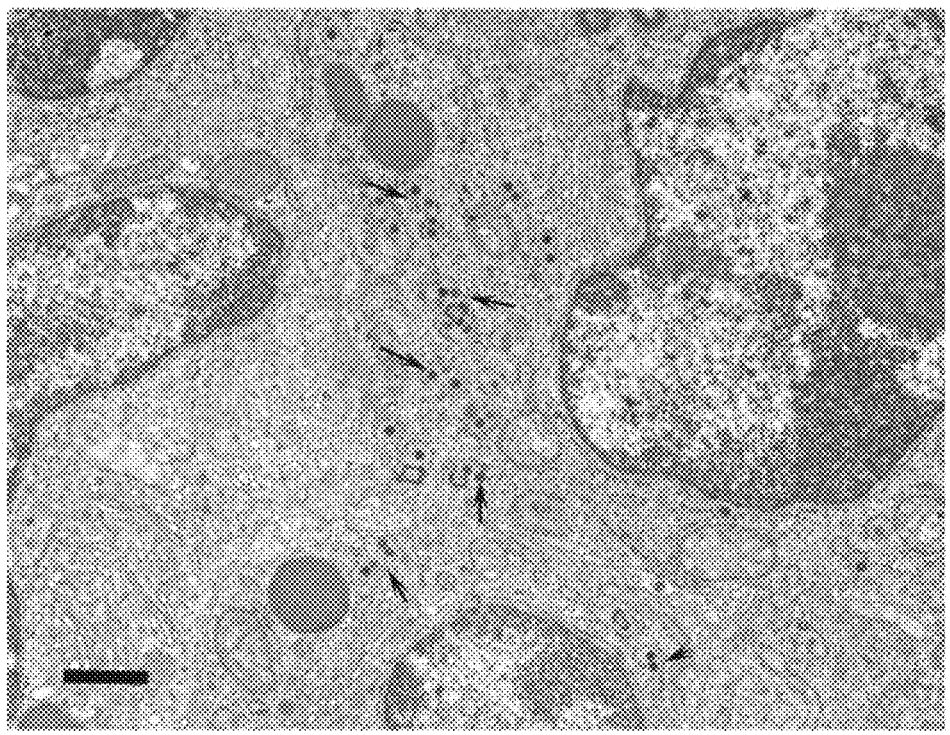
Figure 31D:
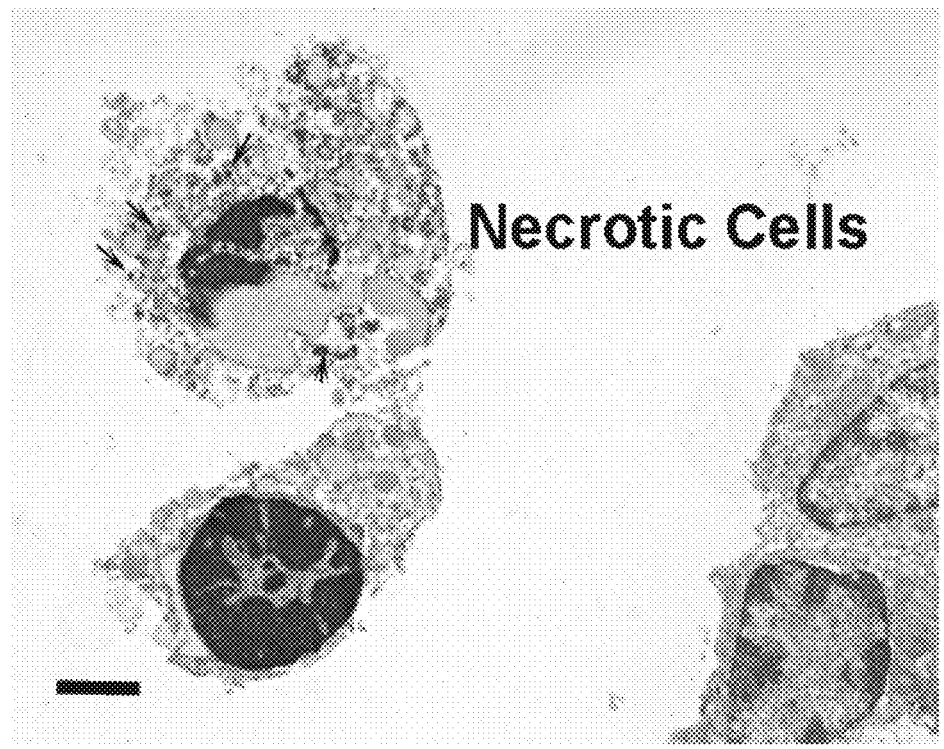

Comparison of untreated (FIG. 31A) and treated (FIG. 31B) tumour sections using TEM shows predominantly apoptotic cells in the latter. The localization of $TiO_2$-Tf based constructs in the apoptotic (FIG. 31C) and necrotic (FIG. 31D) cells also confirms the selectivity of the method.

Figure 32:
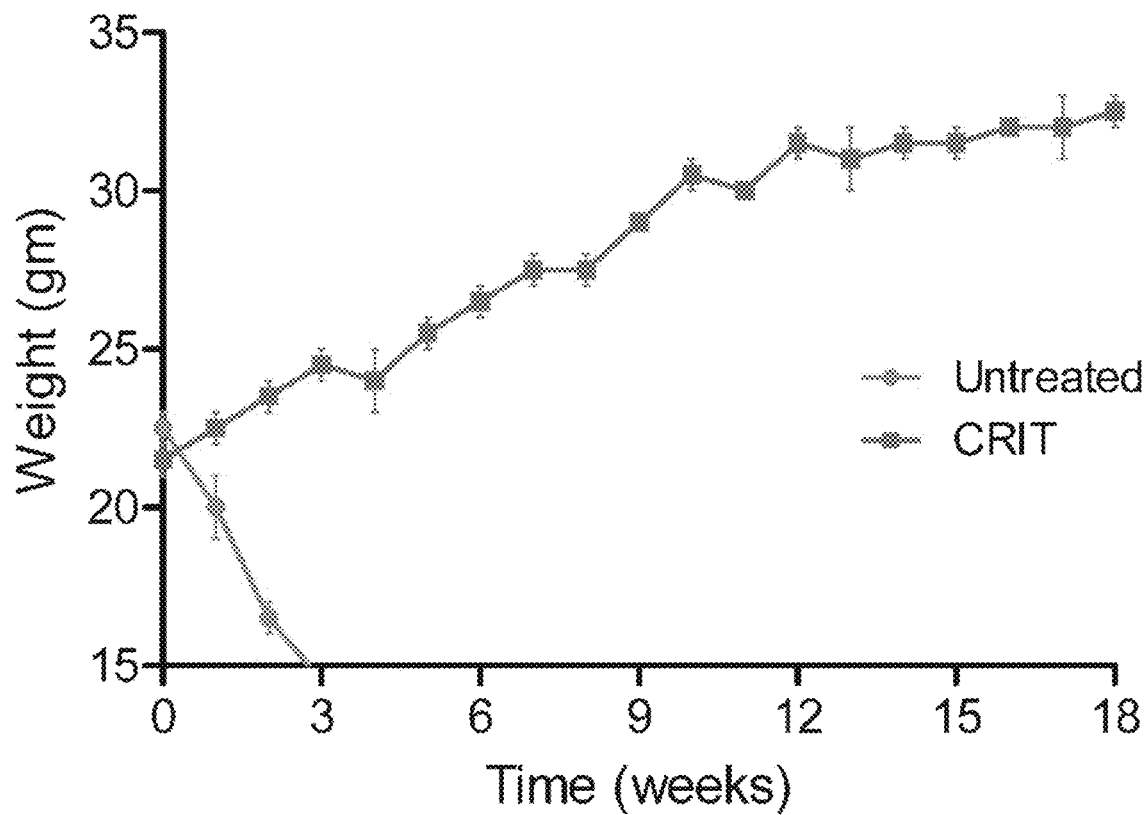
FIG. 32 depicts a graph showing the change in murine weights in untreated and treated groups of mice. TiO$_2$-PEG and chelated $^{64}$Cu were administered intratumourally and monitored over 4 months.

Assessment of body weight and remission after achieving CRIT induced regression of tumors revealed that CRIT-treated animal steadily gained weight whereas untreated animals quickly declined (FIG. 32).

Figure 33:
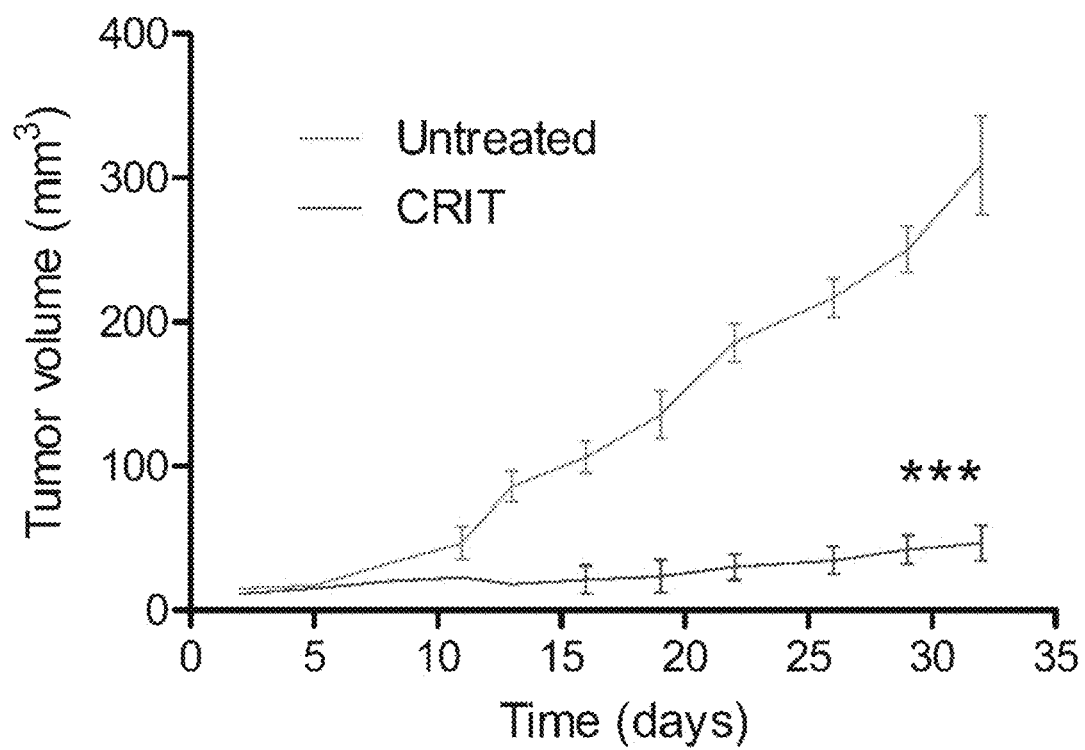
FIG. 33 depicts a graph showing in vivo CRIT in A549 tumour bearing Athymic nu/nu mice using TiO$_2$-Tf-Tc and FDG. Values are means±s.e.m. (n=4 mice per group). Experiments were replicated 2×. ***P<0.001.

Next, in vivo CRIT was evaluated in an A549 lung tumor model. Treated mice received $TiO_2$-Tf-Tc and FDG. There was a significant reduction in tumor burden in the treatment mice relative to the untreated mice (FIG. 33).

Figure 34A:
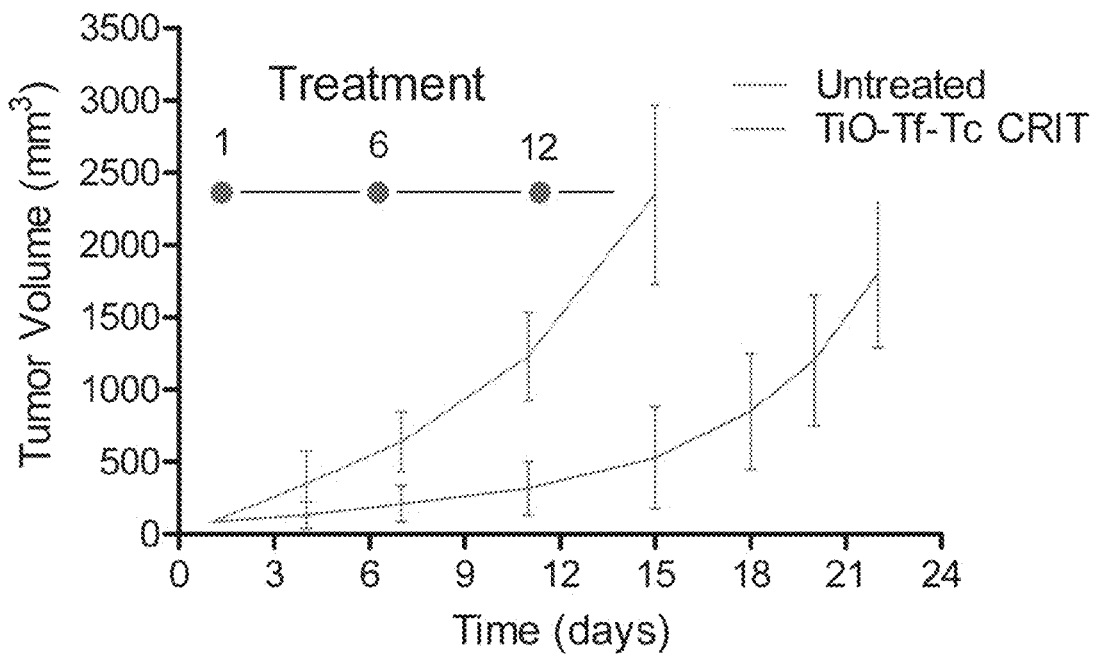
Figure 34B:
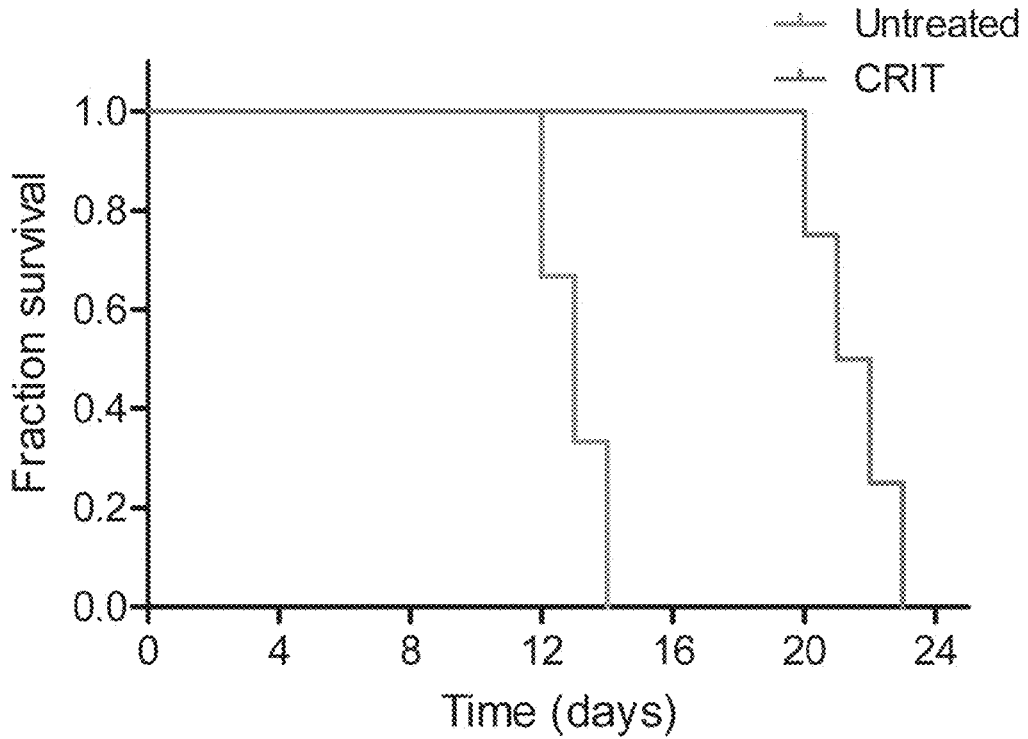

Additionally, in vivo CRIT was evaluated in the U266 multiple myeloma tumor model. U266 subcutaneous xenograft tumors were grown in NSG mice and treatment was initiated once the tumors became palpable. An i.v. dose 1 mg/kg of nanoparticle construct was administered, followed by an i.v. dose of 31 MBq/0.1 mL of $^{18}$FDG after 24 h. The mice received repeat injections on day 6 and 12. We observed that the tumor growth rate for the mice undergoing CRIT was considerably lower than in untreated mice. Median survival increased from 13±2 d, for the untreated and control groups, to 21.5±3 d for mice treated with construct and $^{18}$FDG (FIG. 34A,B). SPEP analysis revealed considerably lower γ-globulins in mice undergoing CRIT (FIG. 34C), compared to untreated mice, suggesting a decrease in tumor burden. CRIT-treated tumors had a significantly lower GFP fluorescence (FIG. 34E) than untreated tumors (FIG. 34D), suggesting the presence of predominantly dead cells in the tumor matrix. Although none of the experimental protocols were optimized at the time, the results clearly demonstrate the efficacy of CRIT in inhibiting MM proliferation and extending survival. We now plan to optimize the treatment protocol and nanoparticle size for clinical translation.

Methods for Examples 16-22

Synthesis of $TiO_2$-PEG, $TiO_2$-Tf, Tc-Tf and $TiO_2$-Tf-Tc: Anatase $TiO_2$ (1 mg; Sigma Aldrich Co., St. Louis, USA) was suspended in deionized water (1 ml) to prepare working stock solution. PEG 400 (100 µl) was added to the $TiO_2$ solution and sonicated using a probe sonicator for 10 min at room temperature (RT). The mixture was then dialyzed overnight against Dulbecco's Phosphate Buffered Saline (DPBS) using a 3000 Da molecular weight cutoff Slide-A-Lyzer MINI Dialysis Devices (Thermo Fisher Scientific Inc., Waltham, USA) to remove excess PEG. Working stock solutions of Tf were prepared by dissolving 5 mg of human apo-Tf (Sigma Aldrich Co.) in 1 ml DPBS, pH 7.4. To prepare $TiO_2$-Tf, a 1:1 (v/v) solution of $TiO_2$ and Tf was mixed and probe sonicated in continuous mode for ~2 min. It is important to ensure the temperature of the solution does not exceed 55° C. to prevent denaturation of Tf (60° C.). The solution was then immediately passed through a 0.45 µm syringe filter to isolate monodisperse nanoparticles. To prepare Tc-Tf, five-fold molar excess of Tc (Sigma Aldrich Co.) was added to human apo-Tf and incubated in a shaker for 2 h at room temperature (RT). A working stock of Tc was initially prepared in DMSO due to low solubility of Tc in water and aqueous buffers. The mixture was then dialyzed overnight against DPBS using a 3000 Da molecular weight cutoff Slide-A-Lyzer MINI Dialysis Devices to remove excess Tc. $TiO_2$-Tf-Tc was similarly prepared by incubating Tc with $TiO_2$-Tf conjugates and thereafter dialyzed to remove excess Tc.

Physicochemical Characterization:

TEM images of $TiO_2$ based constructs were acquired using a FEI Tecnai Spirit Transmission Electron Microscope (FEI, Hillsboro, USA) operating at an acceleration voltage of 200 kV. EDX and electron diffraction analysis was performed using a JEOL 2000FX TEM (JEOL USA Inc., Peabody, USA) and Philips EM420 TEM@120Kv (TEM Analysis Service Lab, Azle, USA). TEM grids coated with a layer of formvar were used throughout these studies. Dynamic light scattering measurements were acquired with a Malvern Zetasizer Nano ZS (Malvern Instruments Ltd., Malvern, UK) instrument equipped with a 633 nm laser. Three measurements were conducted for each sample with at least 10 runs and each run lasting 10 s. All sizes reported were based on intensity average. Absorption spectra of $TiO_2$ and Tc were recorded on a Beckman Coulter DU 640 UV-visible spectrophotometer (Beckman Coulter Inc., Brea, USA) and analysed using Graphpad Prism statistical software. Fluorescence spectra of $TiO_2$ were recorded on a Fluorolog-3 spectrofluorometer (Jobin Yvon Horiba, Kyoto, Japan). The sample was placed in a quartz cuvette and final measurements recorded in triplicates.

Cell Culture:

All cell lines were purchased from American Type Culture Collection (ATCC, Manassas, USA) that underwent STR profiling and tested for *mycoplasma* contamination. HT1080 fibrosarcoma cell line was cultured under recommended standard conditions. HT1080 cells were cultured in Dulbecco's Modified Eagle's Medium containing 10% foetal bovine serum (FBS), L-glutamine (2 mM), penicillin (100 units/rip, and streptomycin (100 pg/ml), incubated at 37° C. in a humidified atmosphere of 5% $CO_2$ and 95% air. For cytotoxicity studies, a concentration of 2.5 µg/ml of the $TiO_2$-Tf, Tc-Tf, and $TiO_2$-Tf-Tc constructs as well as 0.2, 0.4 and 0.85 mCi/0.1 ml of FDG; and 0.5 mCi/0.1 ml $^{64}Cu$ were used. Randomized block design was used for all in vitro experiments, which were run in triplicates, by dividing them into three blocks for all the treatment groups.

In Vitro Cell Viability Assays:

MTS (3-(4,5-dimethylthiazol-2-yl)-5-(3-carboxymethoxyphenyl)-2-(4-sulfophenyl)-2H-tetrazolium) assay, a calorimetric assay for assessing viability of cell culture, was performed using CellTiter 96® $AQ_{ueous}$ Non-Radioactive Cell Proliferation Assay kit (Promega Co., Madison, USA) according to the manufacturer's instructions. The cells were incubated with the constructs and FDG for 48 h before analysis.

Alkaline comet assays (Cell Biolabs Inc., San Diego, USA) were performed using the manufacturer's protocol. Briefly, treated and untreated control cells were removed from flask by scraping with a rubber policeman. The cell suspension was centrifuged and washed with ice-cold DPBS two times and re-suspended at $1 \times 10^5$ cells/ml in ice-cold DPBS. Cells were embedded in low melt Comet agarose and plated on provided microscope slides. The cells were then lysed with lysis buffer and treated with alkaline solution. The slides were electrophoresed in alkaline solution at 1 V/cm with a setting of 300 mAmp for 30 minutes. The slides were stained with Vista Green DNA dye after washing and drying. Fluorescence images were acquired using an Olympus BX51 epifluorescence microscope equipped with a charge coupled device camera. % Tail DNA was estimated using OpenComet (v1.3) plugin for Image J software.

TEM Analysis of Cells and Tissue with $TiO_2$-Tf and Tc-Tf:

For ultrastructural analysis, cells and tissue samples were fixed in 2% paraformaldehyde/2.5% glutaraldehyde (Polysciences Inc., Warrington, USA) in cacodylate buffer (100 mM, pH 7.2) for 1 h at room temperature. Samples were washed in cacodylate buffer and postfixed in 1% osmium tetroxide (Polysciences Inc.) for 1 h. Samples were then rinsed extensively in distilled water before en bloc staining with 1% aqueous uranyl acetate (Ted Pella Inc., Redding, USA) for 1 h. Following several rinses in water, samples were dehydrated in a graded series of ethanol and embedded in Eponate 12 resin (Ted Pella Inc.). Sections of 95 nm were cut with a Leica Ultracut UCT ultramicrotome (Leica Microsystems Inc., Buffalo Grove, USA), stained with uranyl acetate and lead citrate, and viewed on a JEOL 1200 EX transmission electron microscope (JEOL USA Inc.) equipped with an AMT 8 megapixel digital camera (Advanced Microscopy Techniques, Woburn, USA).

In Cellulo Receptor Binding:

We used Tf labelled with Alexa 680 (AlexaTf; Life Technologies, Carlsbad, USA) to prepare fluorescent $TiO_2$—AlexaTf construct, and the products were processed as described above. HT1080 cells were grown in 8 well chamber slides and incubated with $TiO_2$—AlexaTf, final concentration of 0.25 mg/ml, and incubated for 1 h at 37° C. For Tf blocking, 25 mg/ml (100×) of holo-Tf (Sigma Aldrich Co.) was added and incubated for 1 h before adding $TiO_2$—AlexaTf. The wells were washed 3× before imaging. Fluorescence images were acquired using an Olympus FV1000 confocal microscope. Fluorescence/brightfield cell images were taken with a 60× objective using a He:Ne 633 nm excitation laser and emission range of dichroic mirror set to 655-755 nm. Fluorescence and brightfield image overlay with false colour was performed using Fluoview FV10-ASW software from Olympus (Center Valley, USA). One hundred cells per well were counted to quantify fluorescence intensity.

In Cellulo Hydroxyl and Superoxide Radical Assay:

Hydroxyphenyl fluorescein (HPF) with an excitation and emission wavelength of 490 nm and 515 nm, respectively (Life Technologies Inc.) was used according to the manufacturer's instructions. Briefly, the 5 mM stock was diluted 1,000× to prepare 5 µM working stock solution in DPBS. The $TiO_2$-Tf, Tc-Tf and $TiO_2$-Tf-Tc and FDG treated HT1080 cells grown in 8 well culture slides were immersed in the HPF working stock 4 h post treatment. The cells were incubated for 1 h before the dye solution was removed and replaced with fresh DPBS. The cells were imaged byconfocal microscopy using the 488 nm Argon ion laser with emission set to 500-600 nm. Similarly, Mitosox Red (Life Technologies Inc.) with an excitation and emission wavelengths of 510 nm and 580 nm, respectively, was used to detect superoxide radicals according to the manufacturer's instructions.

Lipid Peroxidation and Mitochondrial Membrane Potential Assay:

BODIPY® 581i591 C11 reagent (Life Technologies Inc.) was used to quantitatively determine the degree of lipid peroxidation. It is a ratiometric fluorescence technique that relies on oxidation of lipids to shift fluorescence emission peak from 590 nm to 510 nm. HT1080 cells (~10,000) were grown in 96 well plate and incubated with Tc-Tf (2.5 µg/ml) and FDG (0.85 mCi/0.1 ml) for 6 h. Peroxyl radical scavenging was performed by coincubating Tc-Tf+FDG with Trolox (1 mM), a water soluble analogue of Vitamin E and a powerful antioxidant. As positive control, 2,2'-azobis-2-methyl-propanimidamide, dihydrochloride (AAPH; 100 µM) was used. All the compounds were incubated for 6 h at 37° C. Finally, the BODIPY-based dye (10 µM) was added and incubated for 30 min at 37° C. After washing the cells with PBS three times, the plate was analysed using a Synergy HT multimode plate reader (BioTek Instruments Inc., Winooski, USA) with excitation/emission of 581/591 nm for the reduced dye and at 488/510 nm for the oxidized dye. The ratio of the fluorescence intensities at 590/510 nm was plotted to derive the ratio of fluorescence change.

For measuring mitochondrial membrane potential, Mitotracker Green (Life Technologies Inc.) was used according to manufacturer's instructions. Staurosporine (2 µM; Sigma Aldrich Co.) was used as positive control.

Fluorescence readout was performed using a plate reader using excitation/emission wavelengths of 490/516 nm.

Matrigel Based Cell Studies:

Matrigel™ (BD Biosciences, San Jose, USA) was thawed at 4° C. For entrapment of NPS, we first mixed an equal volume of $TiO_2$ NPS solutions (3 mg/ml) with Matrigel, which was then plated on 8 well chamber culture slides. HT1080 cells were then introduced on the slides and allowed to grow in Matrigel. Since Matrigel solidifies at 3Tc, $TiO_2$ NPS remain suspended and immobilized in the gel and are not internalized by the surrounding cells. For the internalization model, Matrigel was omitted and cells were incubated with $TiO_2$ NPS to facilitate internalization. The cells were then washed to remove non-internalized $TiO_2$ NPS and reseeded on chamber slides. $^{64}Cu$ (0.5 mCi/0.1 ml) was then added to the respective chambers with (extracellular $TiO_2$) and without (intracellular $TiO_2$) matrigel and incubated for 48 h at 37° C. before performing the Live/Dead assay (Life Technologies Inc.) according to the manufacturer's instructions.

Chelation of $^{64}Cu$ to DOTA: For experiments with $^{64}Cu$, we prepared a stock solution (1 mg/ml) of DOTA (1,4,7,10-tetraazacyclododecane-1,4,7,10-tetraacetic acid; Macrocyclics Inc., Dallas, USA) in ammonium acetate buffer (50 mM) equilibrated to pH 5.5. Aliquots of DOTA stock solution (50 µl) was added to ammonium acetate buffer (450 µl), followed by $^{64}Cu$ (5 mCi; 185 MBq) in 0.1 M hydrochloric acid (5 µl). The reaction mixture was incubated at 45° C. for 1 h in a shaker. Non-chelated $^{64}Cu$ was removed from the chelated DOTA-$^{64}Cu$ using a Waters HPLC purification system. The flow rate was set to 1 ml/min. The solvents were A: 0.1% trifluoroacetic acid (TFA) in water, and B: 0.1% TFA in acetonitrile. After 5 min hold at 5% B, the gradient was programmed linearly to 100% B at 40 min. The sample eluted at 6 min post injection, corresponding to the peak in the radiometer and UV detector. The sample was then dried in a rotary shaker to remove TFA and acetonitrile before re-suspending the residue in DPBS.

In Vivo Tumour Model:

Athymic nu/nu mice (8 week, female) were purchased from Frederick Cancer Research and Development Center (Frederick, USA). All studies were conducted in compliance with Washington University Animal Welfare Committee's requirements for the care and use of laboratory animals in research. The HT1080 xenografts were generated by subcutaneous injection of $4 \times 10^6$ cells in DPBS (100 µl) in both flanks of Athymic nude mice. Likewise, a bilateral subcutaneous tumour model of A549 was developed using $5 \times 10^6$ cells in DPBS.

In Vivo Biodistribution Studies:

Athymic nude mice (8 week, female) with a tumour volume of ~300 mm$^3$, were injected with 3.2 mg/ml (12.8 mg/kg) of $TiO_2$—AlexaTf (n=5) and AlexaTf (n=5) (Life Technologies Inc.) in DPBS (100 µl) intravenously through the lateral tail vein. Fluorescence imaging was performed using excitation and emission wavelengths of 685 nm and 720 nm, respectively, in a Pearl whole animal imager (Li-Cor Biosciences Inc., Lincoln, USA). The mice were euthanized 24 h post-injection and the major organs were dissected and imaged. Mean fluorescence intensity for each tissue was estimated by region of interest analysis using Pearlcam software (Li-Cor Biosciences Inc.). The intensity was normalized to equalize muscle fluorescence levels and plotted for all the organs. For $TiO_2$ alone, the mice were injected with 250 µg/ml of $TiO_2$-PEG in DPBS (100 µl) intravenously through tail vein. The organs were dissected and fluorescence imaging was performed using Kodak IS4000MM multimodal imaging system (Carestream Health Inc., Rochester, USA) with excitation/emission wavelength set to 640/700 nm, 60 s exposure with 2×2 binning, for detecting $TiO_2$ using its inherent fluorescence.

In Vivo Blocking Studies:

In Athymic nu/nu mice (8 week, female) bearing HT1080 tumours, 200 mg/kg of holo-Tf (Sigma Aldrich Co.) was administered i.v. After 45 min, $TiO_2$-AlexaTf (10 mg/kg) was administered, and imaging was performed as described above. The animals were euthanized 24 h post injection for ex vivo biodistribution analysis of the organs.

CRIT of Solid Tumours:

For intratumoural administration, a cocktail of 2.5 µg/ml of $TiO_2$-PEG and 0.5 mCi/0.1 ml chelated $^{64}Cu$ in 50 µl of DPBS was injected directly into the tumour mass, after the tumour volume reached 200 mm$^3$. Two diametrically opposite injection sites were chosen and 25 µl of the cocktail was delivered at each site. Four groups (n=4), $TiO_2$-PEG treated mice, $^{64}Cu$ treated mice, non-radioactive Cu (1 µM $CuCl_2$) treated mice and untreated mice, served as controls.

For systemic administration, when tumour volume reached 50 mm$^3$, the mice (n=6 per group) were injected with 1 mg/kg $TiO_2$-Tf, Tc-Tf, $TiO_2$-Tf-Tc in 100 µl of DPBS intravenously followed by 0.87 mCi/0.1 ml of FDG, also intravenously, 24 h later. Control mice (n=6 per group) were administered with DPBS, the constructs or FDG alone. Animals were randomly divided into three blocks of two animals each for different treatments. Food was withheld from mice for 6 h before administering FDG and kept in a dark, lead-shielded room post injection. A second administration of FDG (0.87 mCi/0.1 ml) was given 48 h after the first FDG injection. Similarly, two additional cohorts were administered with 0.14 mCi/0.1 ml and 0.43 mCi/0.1 ml FDG (n=4 per group), respectively, and monitored over 45 d. For mice undergoing treatment using external UV light irradiation, the tumours were irradiated directly by a mercury lamp (300-400 nm) for 1 h at 14-20 J/cm$^2$, 24 h after administration of $TiO_2$-Tf-Tc constructs. Irradiation was reapplied again after 48 h and the cycle repeated 2×. For both, systemic and intra-tumoural studies, the mice were monitored for 45 days and the growing tumours were measured with callipers every two days and tumour volume calculated using the equation: $=(length \times width^2)/2$. The tumour volume was plotted versus time to analyse CRIT effect on the different groups of mice. The weight and any physical signs for distress were also monitored closely. The mice were euthanized by cervical dislocation after anaesthesia with 5% isoflurane when the tumour size reached 2 cm or loss of >20% total body weight. The mice with regressing tumours were monitored for an additional four months to determine whether the cancer was in remission. Similarly, CRIT was performed on slow growing A549 xenograft models and tumor growth monitored for 35 days.

FDG-PET Imaging:

FDG-PET imaging was performed on untreated mice on day 15 and on treated mice on day 30. The mice were fasted for 6 h before each scan. After anesthetizing the mice with 1.5-2% Isoflurane and Oxygen, 0.19 mCi (7.03 MBq)/0.1 ml of FDG was administered through i.v. route. A ten-minute transition scan was performed just before the ten minute emission at 1 h post injection using a MicroPET-Inveon MultiModality scanner (Siemens Preclinical Solutions, Erlangen, Germany). The animals were placed on the microCT® in the same position to obtain anatomical imaging and co-registered to the microPET® image. The data were analysed using Inveon Research Workstation software, by manually drawing 3-dimensional regions of interest (ROI) from PET images using CT anatomical guidelines. The activity associated with tumour was measured and maximum standard uptake values (SUVs) were calculated using SUV=([nCi/mL]×[animal weight (g)]/[injected dose (nCi)]).

Histology:

The HT1080 tumour bearing mice in the control groups were euthanized 15 d post administration of $TiO_2$-Tf, Tc-Tf, $TiO_2$-Tf-Tc constructs or FDG, while mice treated with 1 mg/kg of $TiO_2$-Tf and Tc-Tf with FDG were euthanized 30 d post administration and the group treated with 1 mg/kg of $TiO_2$-Tf-Tc with FDG were euthanized at 45 d post administration. Similarly, mice treated by intratumoural administration of $TiO_2$-PEG and $^{64}Cu$ were euthanized for histology 3 d after treatment. The tumours were harvested and snap-frozen in Optimal Cutting Temperature (OCT) media for routine staining with haematoxylin and eosin (H&E). Brightfield images of H&E stained 10 μm tumour sections were obtained byepifluorescence microscopy at 4× and 20× magnifications and analysed by a pathologist.

Statistical Analysis:

Statistical significance was measured by Student's t-test using GraphPad Prism software (GraphPad, San Diego, Calif.).

Kaplan-Meir survival curves were plotted using Graph Pad Prism software. Unless noted otherwise, all values are means and error bars are standard deviations. For animal studies, sample size estimates depend on the effect size (mean difference between untreated and treatment groups/ SD) of outcome. For effect size of 2.1 and using two-sided t-test, typically 5 per group were needed with 80% power to detect a significant difference at a type I error rate of 0.05.

Example 23: CRIT in Multiple Myeloma

Figure 35A:
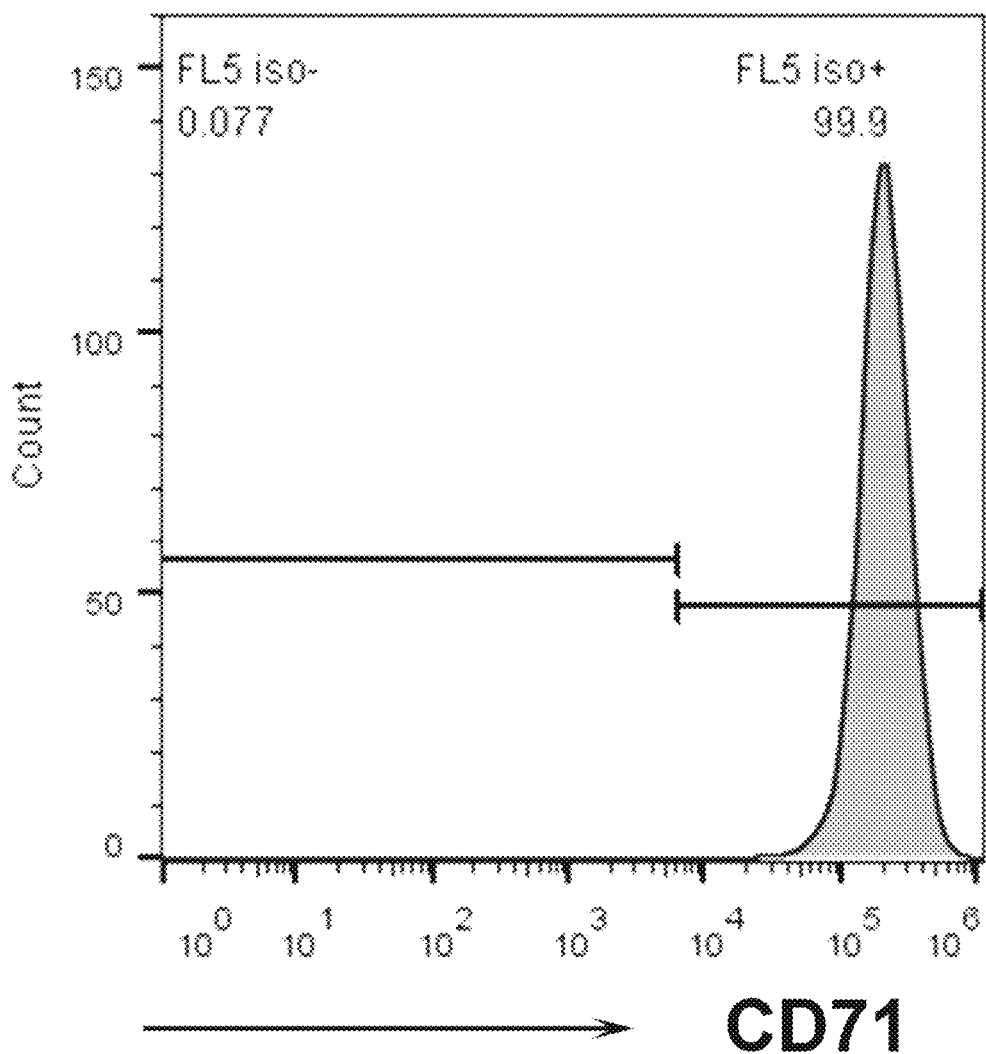
FIG. 35A, FIG. 35B and FIG. 35C depict flow cytometry plots of multiple myeloma cells.
Figure 35B:
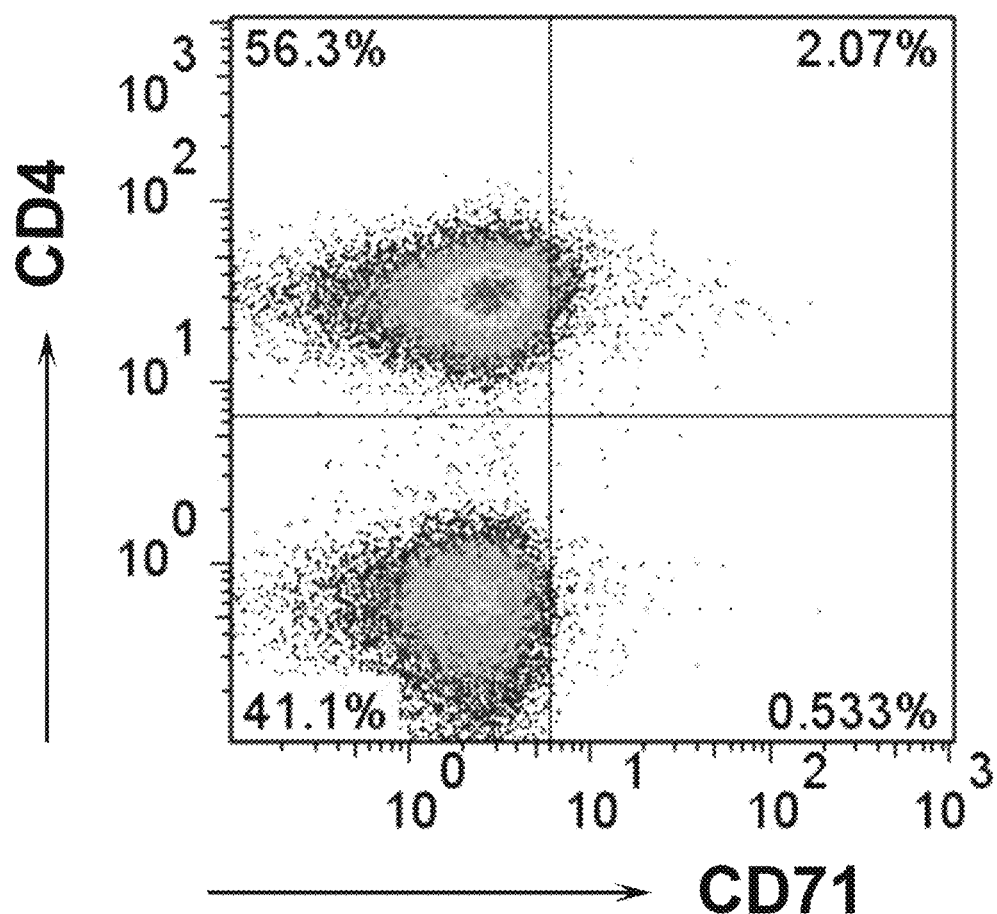
Figure 35C:
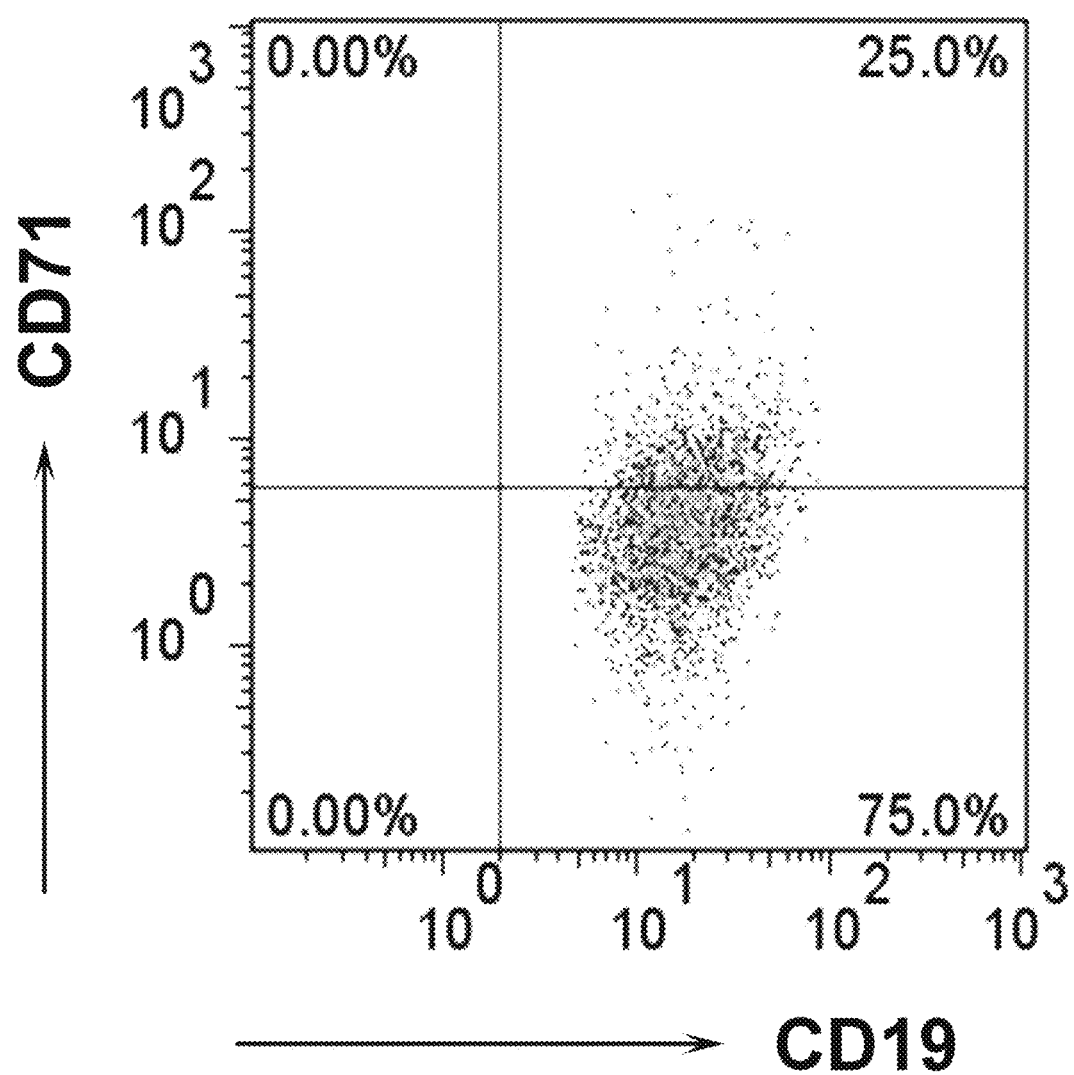

Transferrin receptor (TfR) is over expressed on highly proliferating cells, which includes most tumor types, due to the increased iron requirement for DNA synthesis. Moreover, in multiple myeloma, iron metabolism is significantly altered, which typically manifests as anemia in more than 73% of patients. Flow cytometry using anti-CD71 antibodies labeled with phycoerythrin show that TfR expression was upregulated in various MM cell lines, including STGM, U266, and MM1.S (>98%) compared to T cells (2%) and B cells (25%) (FIG. 35). T cells were identified using CD4 antibody and B cells using CD19 antibody. This demonstrates that the unexplored Tf is a viable homing ligand to MM cells.

Figure 36:
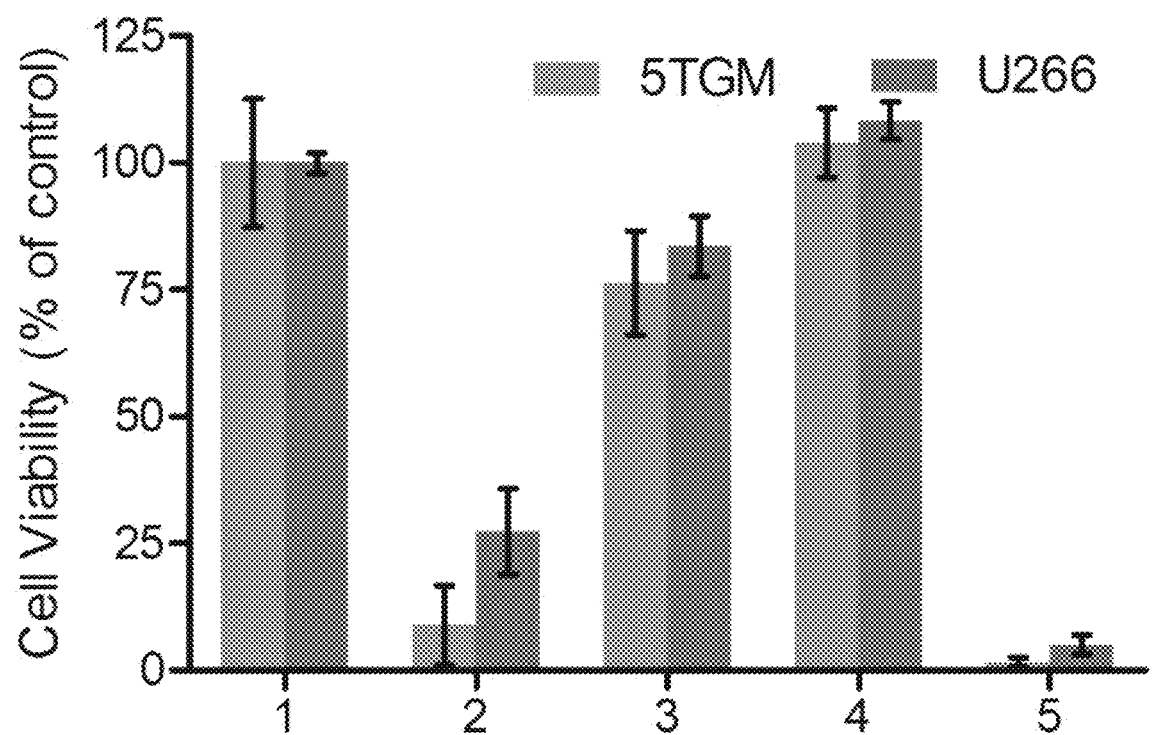
FIG. 36 depicts MTS cell viability assay (48 h) demonstrates higher degree of cell death when treated with TiO$_2$-Tf-Tc+FDG, in both MM cell lines. 1. Untreated. 2. Positive control (staurosporine). 3. TiO$_2$-Tf-Tc. 4. FDG 31 MBq/0.1 ml. 5. TiO$_2$-Tf-Tc+FDG.

Having demonstrated the complementary effects of Tc and $TiO_2$ nanoparticles in the HT1080 model, we applied the concept to MM. Cell viability studies of STGM and U266 using the MTS assay revealed that when cells were treated with both 10 μg/mL of $TiO_2$-Tf-Tc and 31 MBq/0.1 mL of $^{18}FDG$, significantly higher cell death occurred (FIG. 36). Minimal cell death was observed in untreated cells and the control groups. Staurosporine (2 μM) was used as a positive control.

Figure 37:
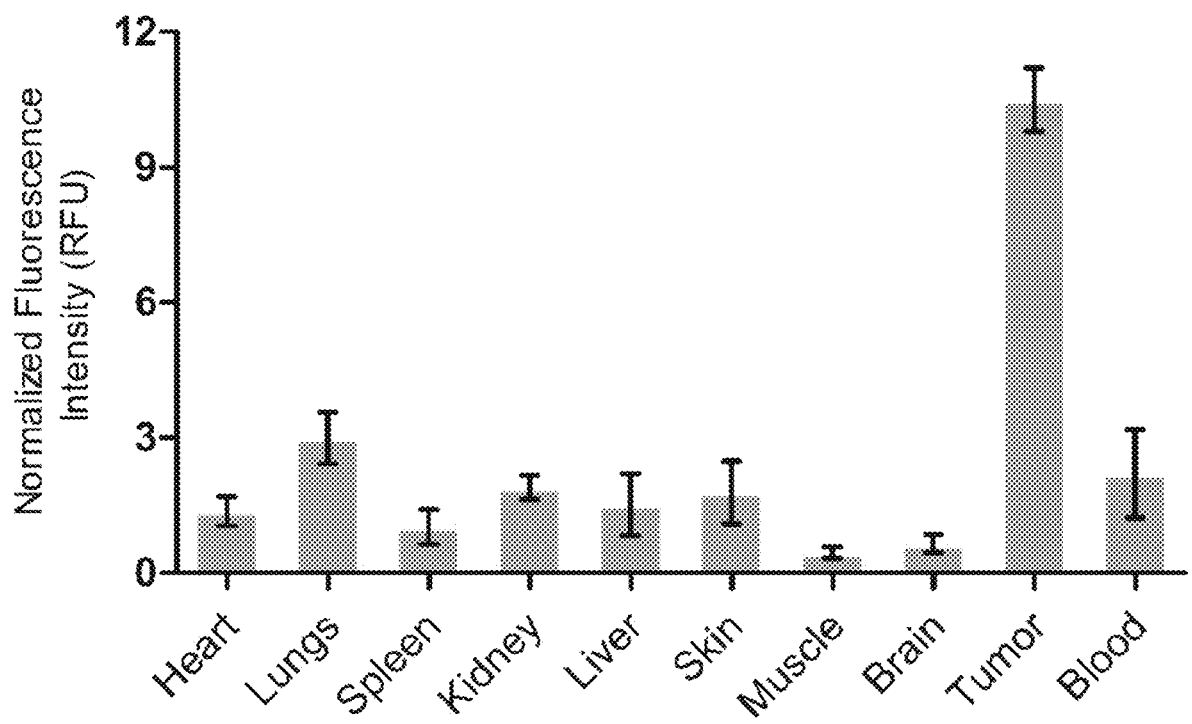
FIG. 37 depicts diodistribution of TiO$_2$-Tf showing excellent uptake in tumors 24 h post injection.

Biodistribution studies were carried out in NSG mice with U266 subcutaneous xenograft tumors using Alexa 680 labeled Tf conjugated to $TiO_2$. The fluorescence of Alexa 680 dye labeled Tf was used for non-invasive determination of the in vivo distribution and tumor-selective uptake of the nanoparticle construct (FIG. 37). $TiO_2$-Tf uptake was highest in tumors relative to other organs, an outcome that is rare for most nanoparticles. The high tumor-to-muscle ratio of 23.5 and low uptake by liver, kidney, and spleen could be attributed to Tf-mediated endocytosis. The Tf receptor has a fast turnover rate, enabling multiple cycles of nanoparticle endocytosis.

Example 24: CRIT Composition Comprising Micelles

Figure 38A:
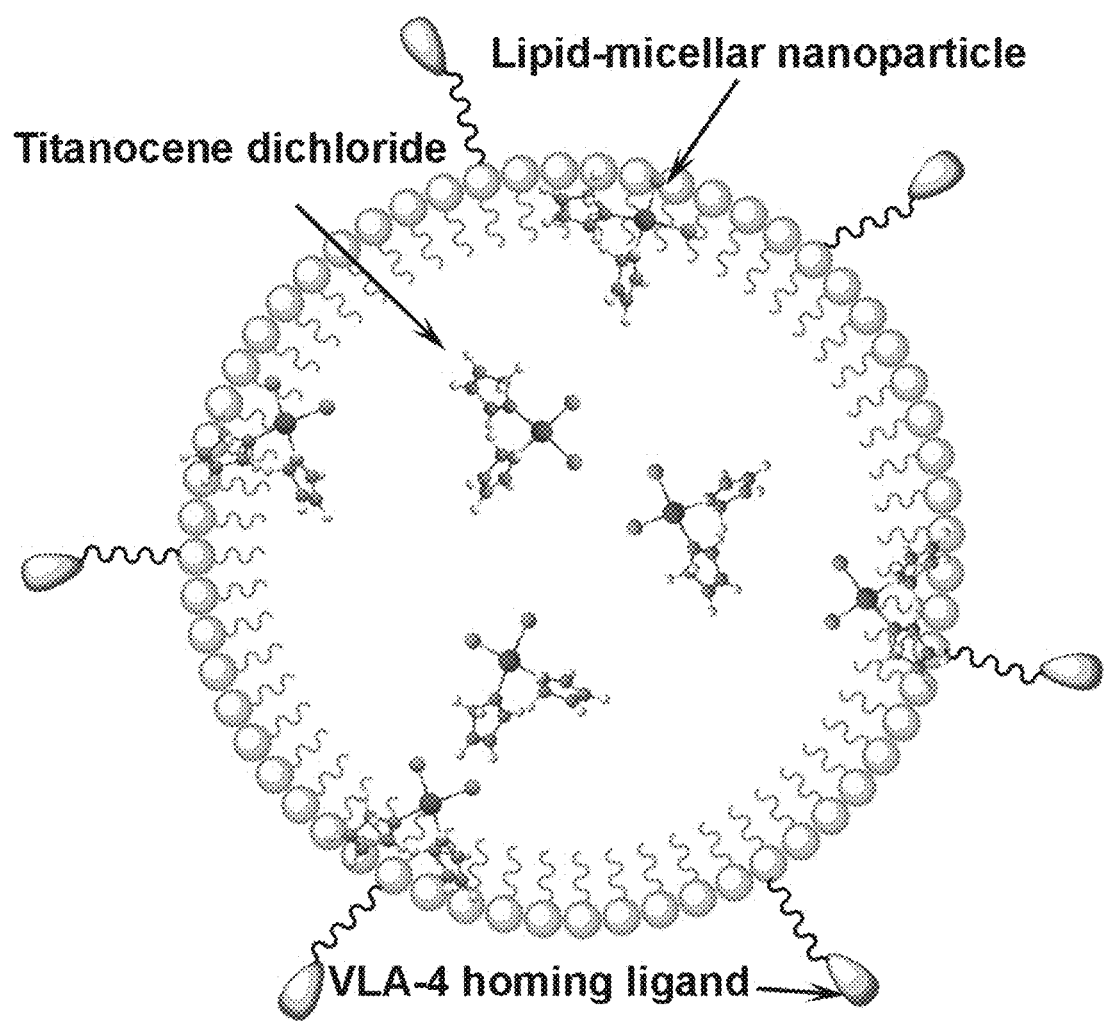
FIG. 38A, FIG. 38B and FIG. 38C depict a schematic and images of titanocene loaded lipid-micellar nanoparticles.
Figure 38B:
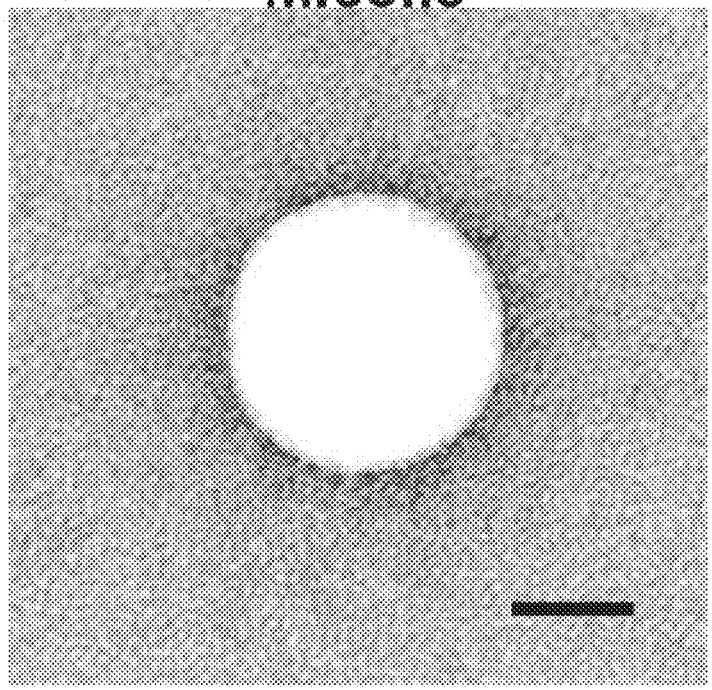
Figure 38C:
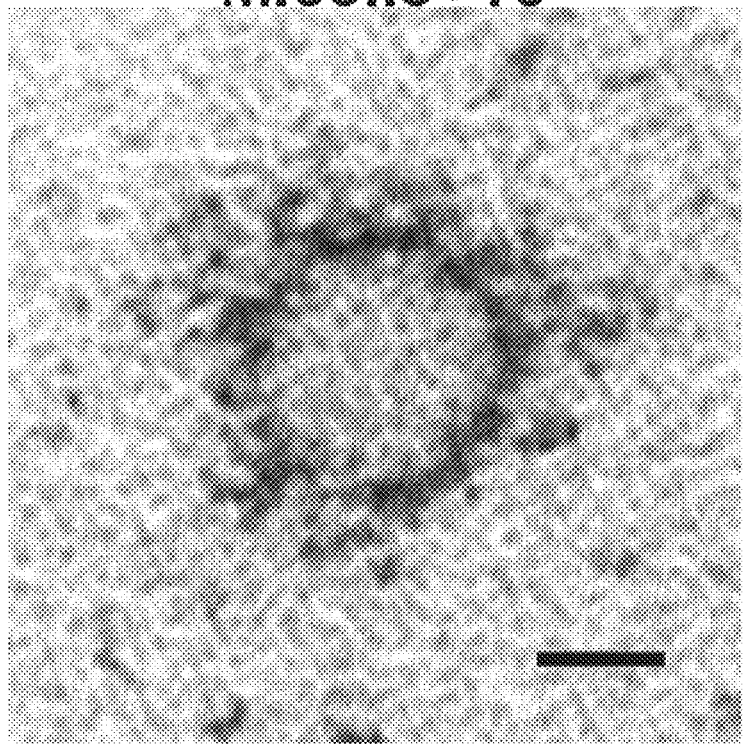

Development and Characterization of Titanocene Loaded Lipid-Micellar Nanoparticles:

For this project, the surfactant co-mixtures included 2 mole % of Tc, 0.15 mole % of VLA-4-homing ligand conjugated lipids, and ~96.5 mole % of lecithin (FIG. 38). Hydrodynamic particle size was 16±4 nm, with a narrow distribution (polydispersity indexes, PDI: ~0.1-0.2). The negative electrophoretic potential (ca.−20±6 mV) point to the colloidal stability and successful lipid encapsulation. TEM images of micelles alone confirmed a spherical shape in the anhydrous state (FIG. 38B). The electron dense signatures in the periphery and increase in opacity in the center compared to micelles alone demonstrates the successful incorporation of Tc in the lipid membrane and the center of the nanomicelles (FIG. 38C). These particles possess long shelf-life stability and retain the particle integrity (>5 months to date) over a broad pH range (pH 5.6-9.4). The UV-vis spectra of Tc ($\lambda_{max}$ 250 nm; plus another 322 nm peak) show an excellent overlap with the predominantly UV emission of CR for CRIT.

Figure 39:
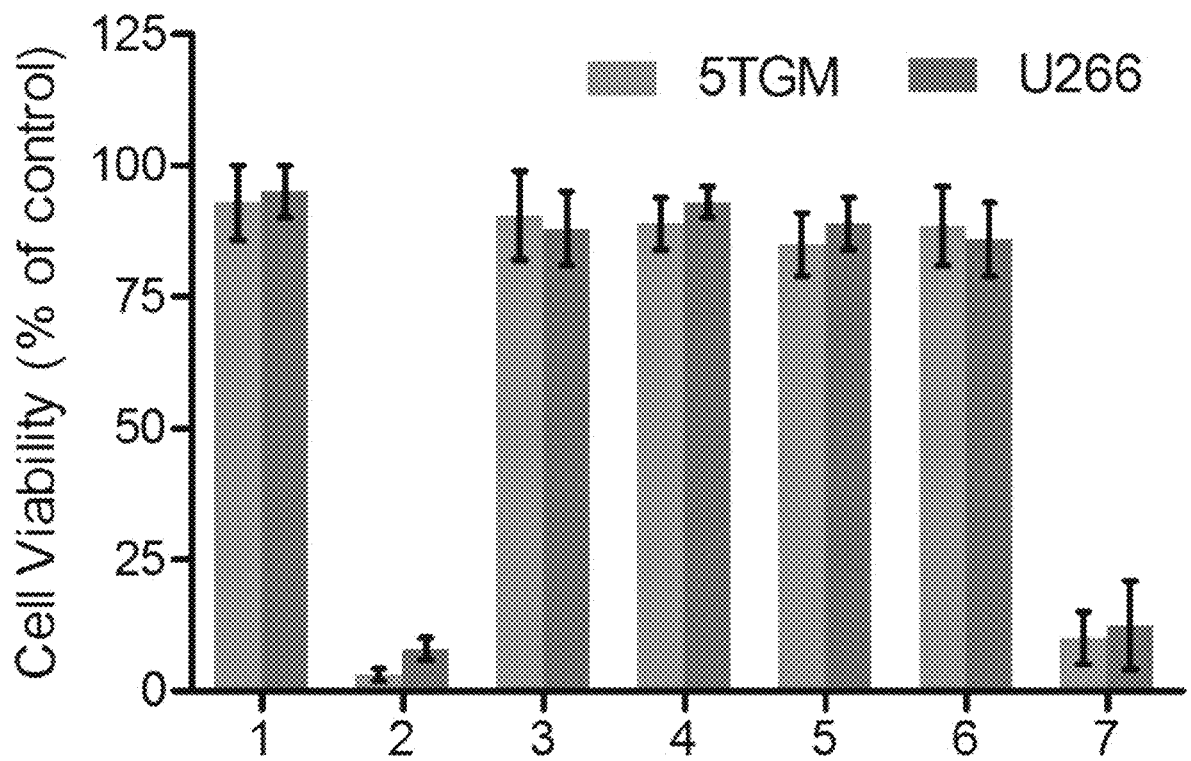
FIG. 39 depicts MTS cell viability assay (48 h) demonstrating higher degree of cell death when treated with micelle+Tc+FDG, in both STGM and U266 MM cell lines. 1. Untreated. 2. Positive control (Staurosporine). 3. FDG 31 MBq/0.1 ml. 4. Micelle. 5. Micelle+Tc. 6. Micelle+FDG. 7. Micelle+Tc+FDG.

Demonstration of In Vitro CRIT in MM Cells:

To delineate intrinsic from CR-mediated toxicity, we carried out toxicity analysis on micelles+Tc or $^{18}FDG$ alone using STGM and U266 MM cell lines. A tetrazolium dye based MTS cell viability assay shows that cells treated with 5 μg/mL of micelles+Tc or 31 MBq/0.1 mL of $^{18}FDG$ were >95% viable. When treated with $^{18}FDG$, the viability of MM cells pretreated with micelle+Tc significantly decreased (FIG. 39), suggesting low metabolic activity and attenuated proliferation. We used Staurosporine (2 μM) as a positive control.

Establishment of Animal Models and Development of Imaging Agents for Noninvasive Imaging and Monitoring of Treatment Response:

We have established both GFP and luciferase-expressing MM in KaLwRij mice (FIG. 40A,C). These models will be used to monitor treatment response noninvasively and longitudinally. We have also demonstrated the metabolic and VLA-4 targeted PET imaging of MM in orthotopic mouse models with $^{18}FDG$ and $^{64}Cu$-labeled VLA-4 ligand (FIG. 40). These data demonstrate the availability of realistic animal models and radiopharmaceuticals for imaging, treating, and monitoring treatment response of MM to CRIT.

Figure 41A:
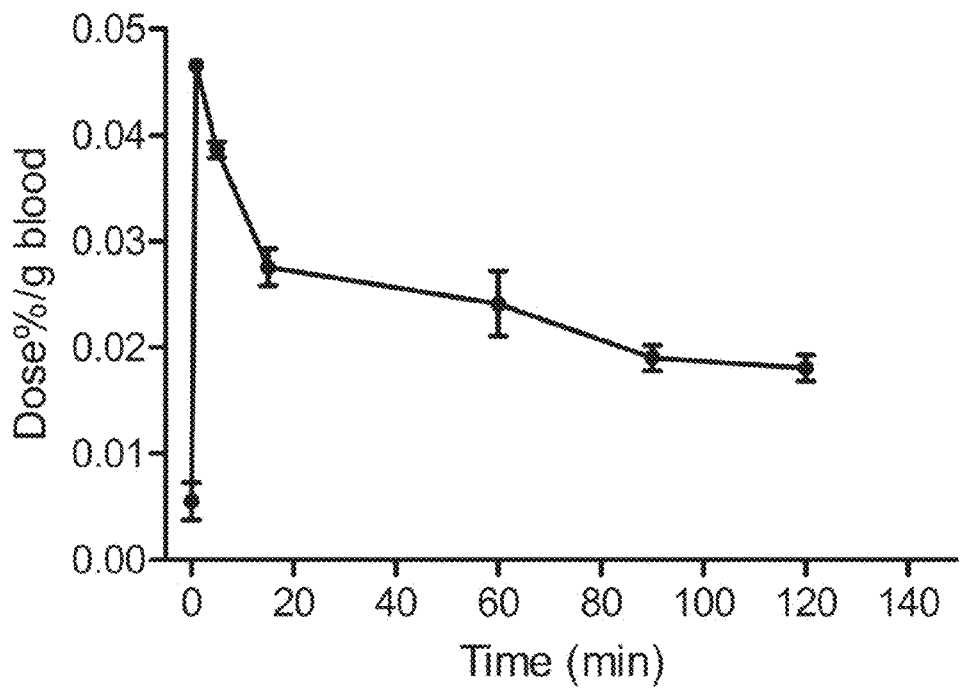
FIG. 41A and FIG. 41B depict graphs showing the pharmacokinetics and biodistribution of Tc loaded VLA-4 targeted nanomicelles.
Figure 41B:
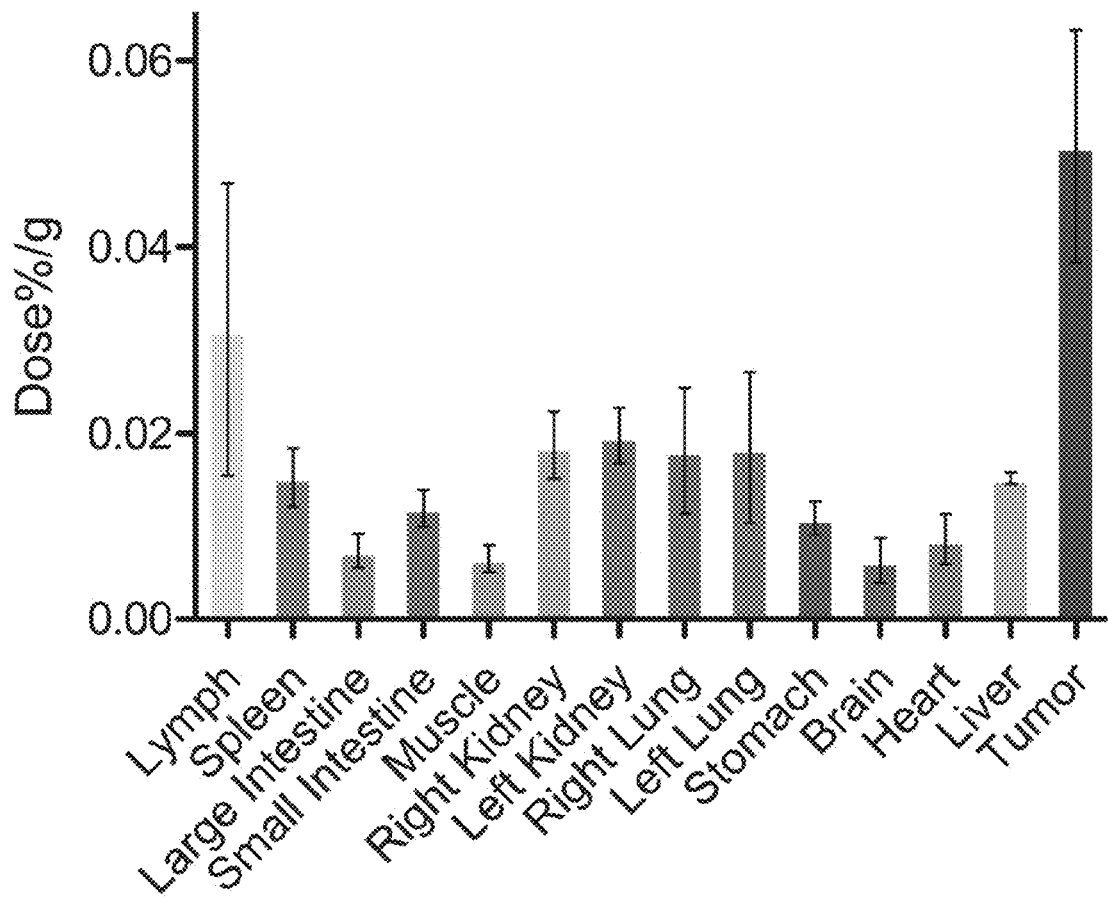

Pharmacokinetics and Biodistribution of Tc Loaded VLA-4 Targeted Nanomicelles:

Pharmacokinetics of targeted micelle+Tc (25 4/kg) was evaluated in rats by inductively coupled plasma optical emission spectrometry (ICP OES) using the Ti signal from Tc. A half-life of 123 min was obtained (FIG. 41A), which is consistent with previous data using similar nanomicelles loaded with gadolinium (122 min). ICP OES biodistribution analysis of the targeted micelle+Tc revealed significantly higher uptake and retention in MM than other organs 24 h post injection (FIG. 41B).

Figure 42A:
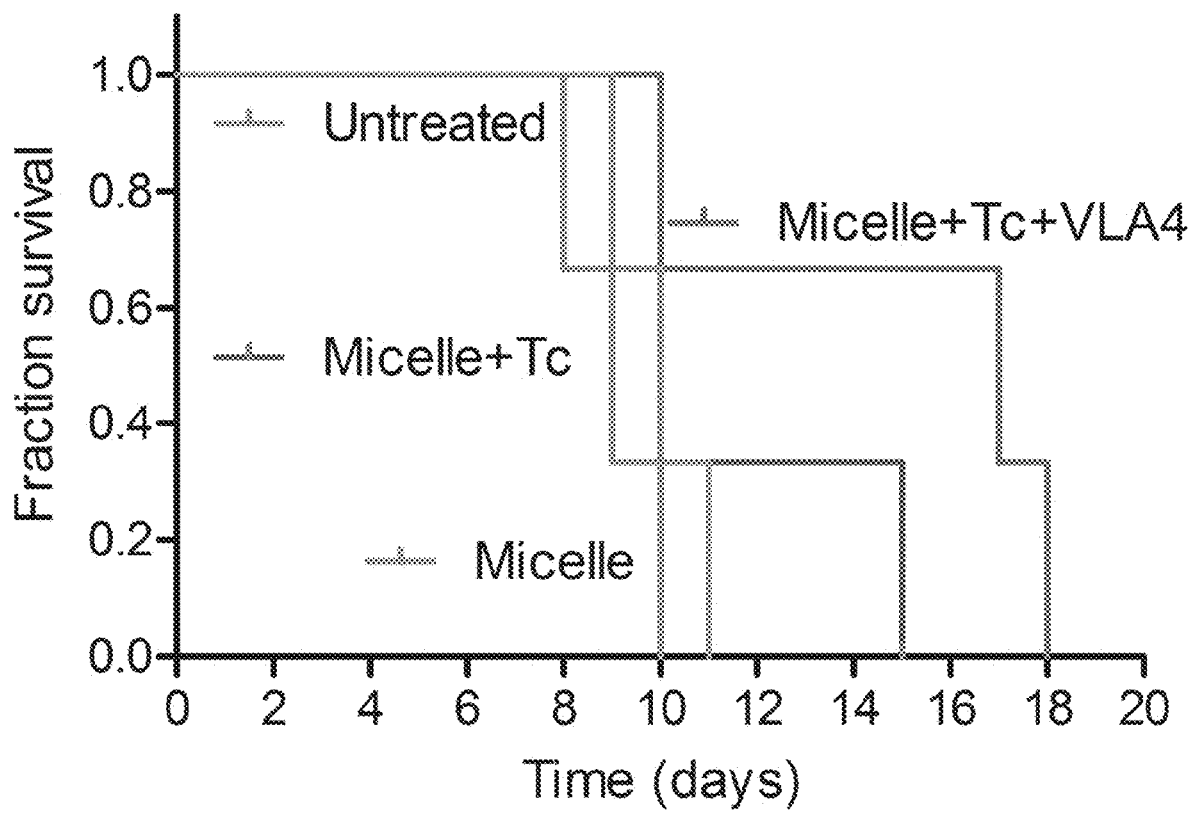
FIG. 42A, FIG. 42B and FIG. 42C depict in vivo CRIT using 5tGM xenograft MM mouse model.
Figure 42B:
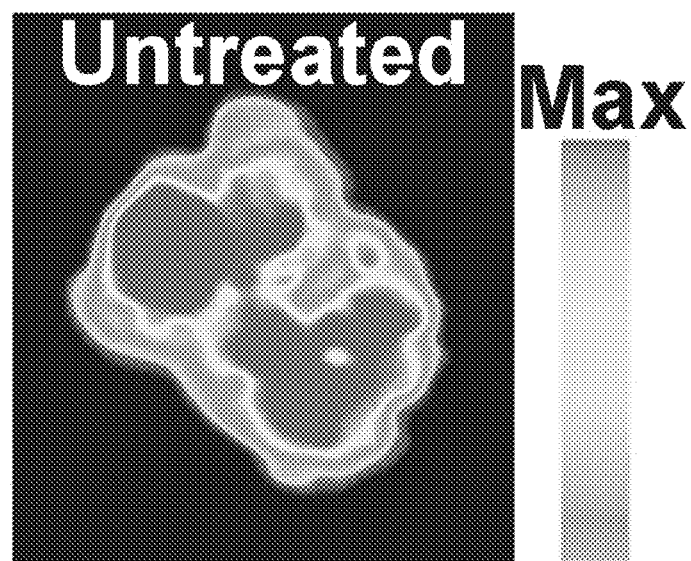
Figure 42C:
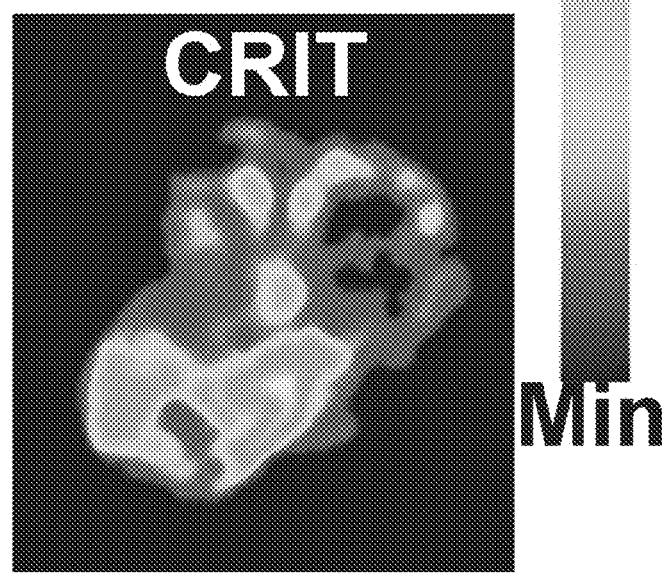

Demonstration of in vivo CRIT using 5TGM xenograft MM mouse model: 5TGM subcutaneous xenograft tumors were grown in KaLwRij mice and treatment was initiated once the tumors became palpable. An intravenous (i.v.) dose (50 μL) of micelle+Tc containing 0.3 mg/kg of Tc was administered, followed by an i.v. dose of 31 MBq/0.1 mL of $^{18}$FDG after 6 h. The same dosing schedule was followed for non-targeted micelle+Tc and micelles alone. Median survival increased from 10±2 d, for the untreated and control groups, to 17±2 d for mice treated with targeted micelle+Tc with $^{18}$FDG (FIG. 42A), a vast improvement for MM therapy. We evaluated if the expression of GFP in 5TGM cells is altered as a result of cells undergoing apoptosis in ex vivo tumor samples. The tumors that underwent CRIT with targeted micelle+Tc (FIG. 42C) had significantly lower GFP fluorescence compared to untreated tumors (FIG. 42B), suggesting perturbation in protein expression as a result of either free radical damage or a direct consequence of cells undergoing apoptosis.

What is claimed is:

1. A composition, the composition comprising a biocompatible inorganic nanoparticle comprised of at least one of ZnO, Si, TiO$_2$, CdSe, CdS, InP, PbS, or PbSe, wherein the nanoparticle is coated with a target agent, wherein the target agent is further bound to a photoinitiator.

2. The composition of claim 1, wherein the nanoparticle is further coated with polyethylene glycol (PEG), dextran, pullulan, glycolipid, hyaluronic acid, orosomucoid, heparin, chitosan, pectin, a polysaccharide, or a combination thereof.

3. The composition of claim 1, where in the target agent is a polypeptide, an antigen, a nucleic acid, a polysaccharide, a sugar, a fatty acid, a steroid, a purine, a pyrimidine, a ligand, an aptamer, a small molecule, albumin, or combinations thereof.

4. The composition of claim 3, where in the target agent is transferrin.

5. The composition of claim 1, where the photoinitiator comprises acetophenone, benzyl and benzoin compounds, benzophenone, cationic photoinitiators, thioxanthones, or a combination thereof.

6. The composition of claim 5, where the photoinitiator is a biocompatible photoinitiator comprised of at least one of titanocene, titanocene dichloride, 2 hydroxy-1-[4-(hydroxyethoxy)phenyl]-2-methyl-1-propanone, 2 hydroxy-1-[4-(hydroxyethoxy)phenyl]-1-propanone, 1 hydroxycyclohexane acetophenone, 2,2-dymethoxy-2-phenyl acetophenone, THX (thioxanthone), Eosin Y, camphorquinone, camphorquinone derivatives, BAPO (bisacylphosphine oxide bis(2,4,6-trimethylbenzoyl) phenylphosphineoxide), and HAP (hydroxyalkylphenone).

7. The composition of claim 6, where the biocompatible photoinitiator is titanocene.

8. The composition of claim 1, comprising a biocompatible inorganic TiO$_2$ nanoparticle coated with transferrin, wherein the transferrin is further bound to titanocene.

9. The composition of claim 8, wherein the composition is capable of being activated by Cerenkov radiation (CR)-emitting radionuclides.

10. The composition of claim 9, wherein the CR-emitting radionuclides are selected from the group consisting of $^{18}$F, $^{18}$F-FDG, $^{64}$Cu, $^{90}$Y, $^{124}$I, and $^{89}$Zr.

11. The composition of claim 1, wherein the composition is capable of being activated by Cerenkov radiation (CR)-emitting radionuclides.

12. The composition of claim 11, wherein the CR-emitting radionuclides are selected from the group consisting of $^{18}$F, $^{18}$F-FDG, $^{64}$Cu, $^{90}$Y, $^{124}$I, and $^{89}$Zr.

13. A method for administering Cerenkov radiation (CR)-induced therapy (CRIT) to a target tissue in a subject, the method comprising:
   a. administering to the subject a composition of claim 1 and
   b. administering to the subject an amount of a CR-emitting radionuclide effective to activate the composition of claim 1, thereby administering CRIT to the target tissue in the subject.

14. The method of claim 13, wherein administering CRIT to a target tissue is used to treat a disease associated with the target tissue.

15. A method for treating a tumor in a subject, the method comprising:
   a. administering to the subject a composition of claim 1; and
   b. administering to the subject an amount of a Cerenkov radiation (CR)-emitting radionuclide effective to activate the composition of claim 1, thereby treating the tumor.

* * * * *